United States Patent
Hagel et al.

(10) Patent No.: US 11,891,359 B2
(45) Date of Patent: Feb. 6, 2024

(54) PRENYLATED PSILOCYBIN DERIVATIVES AND METHODS OF USING

(71) Applicant: ENVERIC BIOSCIENCES CANADA INC., Calgary (CA)

(72) Inventors: Jillian M. Hagel, Calgary (CA); Peter J. Facchini, Calgary (CA); Xue Chen, Calgary (CA)

(73) Assignee: ENVERIC BIOSCIENCES CANADA INC., Calgary (CA)

( * ) Notice: Subject to any disclaimer, the term of this patent is extended or adjusted under 35 U.S.C. 154(b) by 0 days.

(21) Appl. No.: 17/955,922

(22) Filed: Sep. 29, 2022

(65) Prior Publication Data

US 2023/0219888 A1    Jul. 13, 2023

Related U.S. Application Data

(63) Continuation of application No. PCT/CA2022/050091, filed on Jan. 21, 2022.

(60) Provisional application No. 63/247,926, filed on Sep. 24, 2021, provisional application No. 63/140,322, filed on Jan. 22, 2021.

(51) Int. Cl.
   *C07D 209/16* (2006.01)
(52) U.S. Cl.
   CPC .................... *C07D 209/16* (2013.01)
(58) Field of Classification Search
   CPC ...................................................... C07D 209/16
   See application file for complete search history.

(56) References Cited

FOREIGN PATENT DOCUMENTS

| WO | WO2007070892 A2 | 6/2007 |
| WO | WO2018148605 A1 | 8/2018 |
| WO | WO2021155470 A1 | 8/2021 |
| WO | WO20211248087 A1 | 12/2021 |

OTHER PUBLICATIONS

Steffan et al. ChemBioChem 2007, 8, 1298-1307.*
Registry No. 1009361-14-1, File Registry on STN, Mar. 21, 2008.*
Rudolf and Poulter, ACS Chem. Biol, 2013, 8, 2707-2714.*
Kremer and Li, Appl Microbiol Biotechnol (2008) 79, 951-961.*
Registry No. 14599-60-1, File Registry on STN, Nov. 16, 1984.*
Registry No. 1049019-47-7, File Registry on STN, Sep. 12, 2008.*
Registry No. 1470023—19-8, File Registry on STN, Nov. 7, 2013s.*
Daniel, J. et al. Clinical potential of psilocybin as a treatment for mental health conditions. Mental Health Clin/, 2017;7(1): 24-28.
Grob, C. et al. Pilot study of psilocybin treatment for anxiety in patients with advanced-stage cancerArch. Gen. Psychiatry, 2011, 68(1) 71-78.
Cathart-Harris, R.L. et al. Psilocybin with psychological support for treatment-resistant depression: an open-label feasibility study. Lancet Psychiatry, 2016, 3: 619-627.
Inserra et al., Psychedelics in Psychiatry: Neuroplastic, Immunomodulatory, and Neurotransmitter Mechanisms. 2020, Pharmacol Rev 73: 202.
Terrasso et al., Human neuron-astrocyte 3D co-culture-based assay for evaluation of neuroprotective compounds. 2017, J Pharmacol Toxicol Methods 83: 72.
Pyrgiotakis G. et al., Cell death discrimination with Raman spectroscopy and support vector machines. 2009, Ann. Biomed. Eng. 37: 1464-1473.
Weaver et al., Test systems in drug discovery for hazard identification and risk assessment of human drug-induced liver injury. 2017, Expert Opin Drug Metab Toxicol 13: 767.
Donato et al., Culture and Functional Characterization of Human Hepatoma HepG2 Cells. 2015, Methods Mol Biol 1250: 77.
Núñez et al., Target-drug interactions: first principles and their application to drug discovery. 2012, Drug Disc Today 17: 10.
Maguire et al.,Radioligand binding assays and their analysis. 2012, Methods Mol Biol 897: 31.
Kim K. et al.,Structure of a Hallucinogen-Activated Gq-Coupled 5-HT 2A Serotonin Receptor. 2020, Cell 182: 1574-1588.
Finnin, B. and Morgan, T.M., Transdermal penetration enhancers: applications, limitations, and potential J Pharm Sci. Oct. 1999;88(10):955-8.
Cameron and Olson 2018, ACS Chem Neurosci 9: 2344.
Devereux et al., Nucleic Acids Res., 1984, 12: 387.
Henikoff S & Henikoff, J G, 1992, Proc. Natl. Acad. Sci. USA 89: 10915-10919.
Altschul et al., J. Mol. Biol., 1990:215:403.
Thompson, J D, Higgines, D G and Gibson T J, 1994, Nucleic Acid Res 22(22): 4673-4680.
Niedz et al., 1995, Plant Cell Rep., 14: 403.
Mattanovich et al., Methods Mol. Biol., 2012, 824:329-58.
Romanos et al., 1992, Yeast 8: 423-488.
Cregg et al., Mol Biotechnol. (2000) 16(1): 23-52.
S. Kawai et al., 2010, Bioeng. Bugs 1(6): 395-403.
Donato et al., 2015, Methods Mol Biol 1250: 77.
Rojas and Fiedler 2016, Front Cell Neurosci 10: 272.
Menéndez-Perdomo et al., 2021, Mass Spectrom 56: 34683.
Chang et al., 2015, Plant Physiol. 169: 1127-1140.
Lack, A. and Fuchs, G., 1992, J. Bacteriol. 174 (11) 3629-3636.
Sikorski and Hieter, 1989, Genetics 122(1): 19-27.
Yu, X. et al. Biochemical Characterization of Indole Prenyltransferases vol. 287, No. 2, pp. 1371-1380, Jan. 6, 2012.

(Continued)

*Primary Examiner* — Rebecca L Anderson
(74) *Attorney, Agent, or Firm* — BERESKIN & PARR LLP/S.E.N.C.R.L., s.r.l.; Michael Fenwick

(57) ABSTRACT

Disclosed are novel prenylated psilocybin derivative compounds and pharmaceutical and recreational drug formulations containing the same. The compounds may be produced in vitro or in vivo using a biosynthetic system which comprises cells comprising a prenyl transferase, and, optionally, additional enzymes, including a decarboxylase, and an N-acetyl transferase.

12 Claims, 29 Drawing Sheets

Specification includes a Sequence Listing.

(56) References Cited

OTHER PUBLICATIONS

Perez, G.P. et al. Synthesis and evaluation of N1-alkylindole-3-ylalkylammonium compounds as nicotinic acetylcholine receptor ligands. Bioorganic & Medicinal Chemistry 20 (2012) 3719-3727.

Sherwood, A.M. et al. Synthesis and Biological Evaluation of Tryptamines Found in Hallucinogenic Mushrooms: Norbaeocystin, Baeocystin, Norpsilocin, and Aeruginascin. J. Nat. Prod. 2020, 83, 461-46.

Alda, S.K. et al. Doubly prenylated tryptamines: cytotoxicity, antimicrobial activity and cyclisation to the marine natural product flustramine A†. Org. Biomol. Chem., 2013, 11, 6119.

Cardoso, A.S.P. et al. Studies in sigmatropic rearrangements of N-prenylindole derivatives—a formal enantiomerically pure synthesis of tryprostatin B†. Org. Biomol. Chem., 2006, 4, 3966-3972.

Kremer A. et al. Potential of a 7-dimethylallyltryptophan synthase as a tool for production of prenylated indole derivatives. Appl Microbiol Biotechnol (2008) 79:951-961.

Miyamoto, K. et al. A7-dimethylallyl tryptophan synthase from a fungal *Neosartorya* sp.: Biochemical characterization and structural insight into the regioselective prenylation. Bioorganic & Medicinal Chemistry 22 (2014) 2517-2528.

Muthusubramanian, P. et al. Marine Alkaloids. 7. Synthesis of Debromoflustramine B and Related Compounds. Acta Chemica Scandinavica B 37 (1983) 803-807.

Ruan, H-L. et al. Production of diprenylated indole derivatives by tandem incubation of two recombinant dimethylallyltryptophan synthases. Arch Microbiol (2009) 191:791-795.

Steffan, N. et al. Chemoenzymatic Synthesis of Prenylated Indole Derivatives by Using a 4-Dimethylallyltryptophan Synthase from Aspergillus fumigatus. ChemBioChem 2007, 8, 1298-1307.

Romeo, B. et al., J Psychiatr Res 137: 273-282, 2021.

Ross, S. et al. ACS Pharmacol. Transl. Sci. 4: 553-562, 2021.

Servillo L. et al., 2013, J. Agric. Chem. 61: 5156-5162.

Sleight et al., 1996, Biochem Pharmacol 51: 71.

\* cited by examiner

Geranyl-pyrophosphate (GPP)

Dimethylallyl pyrophosphate (DMAPP)

Farnesyl pyrophosphate (FPP)

geranylgeranyl pyrophosphate (GGPP)

[IV]

SEQUENCE LISTING

```
Sequence total quantity: 32
SEQ ID NO: 1           moltype = DNA  length = 1320
FEATURE                Location/Qualifiers
source                 1..1320
                       mol_type = genomic DNA
                       organism = Psilocybe cubensis
SEQUENCE: 1
atgcaggtga tacccgcgtg caactcggca gcaataagat cactatgtcc tactcccgag   60
tcttttagaa acatgggatg gctctctgtc agcgatgcgg tctacagcga gttcatagga  120
gagttggcta cccgcgcttc caatcgaaat tactccaacg agttcggcct catgcaacct  180
atccaggaat tcaaggcttt cattgaaagc gacccggtgg tgcaccaaga atttattgac  240
atgttcgagg gcattcagga ctctccaagg aattatcagg aactatgtaa tatgttcaac  300
gatatctttc gcaaagctcc cgtctacgga gaccttggcc ctcccgttta tatgattatg  360
gccaaattaa tgaacacccg agcgggcttc tctgcattca cgagacaaag gttgaaccttt  420
cacttcaaaa aacttttcga tacctgggga ttgttcctgt cttcgaaaga ttctcgaaat  480
gttcttgtgg ccgaccagtt cgacgacaga cattgcggct ggttgaacga gcgggccttg  540
tctgctatgg ttaaacatta caatggacgc gcatttgatg aagtcttcct ctgcgataaa  600
aatgccccat actacggctt caactcttac gacgacttct taatcgcag atttcgaaac  660
cgagatatcg accgacctgt agtcggtgga gttaacaaca ccaccctcat ttctgctgct  720
tgcgaatcac tttcctacaa cgtctcttat gacgtccagt ctctcgacac tttagttttc  780
aaaggagaga cttattcgct taagcatttg ctgaataatg acccttttcac cccacaattc  840
gagcatggga gtattctaca aggattcttg aacgtcaccg cttaccaccg atggcacgca  900
cccgtcaatg ggacaatcgt caaaatcatc aacgttccag gtacctactt tgcgcaagcc  960
ccgagcacga ttggcgaccc tatcccggat aacgattacg acccacctcc ttaccttaag 1020
tctcttgtct acttctctaa tattgccgca aggcaaatta tgtttattga agccgacaac 1080
aaggaaattg gcctcatttt ccttgtgttc atcggcatga ccgaaatctc gacatgtgaa 1140
```

```
gccacggtgt ccgaaggtca acacgtcaat cgtggcgatg acttgggaat gttccatttc   1200
ggtggttctt cgttcgcgct tggtctgagg aaggattgca gggcagagat cgttgaaaag   1260
ttcaccgaac ccggaacagt gatcagaatc aacgaagtcg tcgctgctct aaaggcttag   1320

SEQ ID NO: 2             moltype = AA   length = 439
FEATURE                  Location/Qualifiers
source                   1..439
                         mol_type = protein
                         organism = Psilocybe cubensis
SEQUENCE: 2
MQVIPACNSA AIRSLCPTPE SFRNMGWLSV SDAVYSEFIG ELATRASNRN YSNEFGLMQP    60
IQEFKAFIES DPVVHQEFID MFEGIQDSPR NYQELCNMFN DIFRKAPVYG DLGPPVYMIM   120
AKLMNTRAGF SAFTRQRLNL HFKKLFDTWG LFLSSKDSRN VLVADQFDDR HCGWLNERAL   180
SAMVKHYNGR AFDEVFLCDK NAPYYGFNSY DDFFNRRFRN RDIDRPVVGG VNNTTLISAA   240
CESLSYNVSY DVQSLDTLVF KGETYSLKHL LNNDPFTPQF EHGSILQGFL NVTAYHRWHA   300
PVNGTIVKII NVPGTYFAQA PSTIGDPIPD NDYDPPPYLK SLVYFSNIAA RQIMFIEADN   360
KEIGLIFLVF IGMTEISTCE ATVSEGQHVN RGDDLGMFHF GGSSFALGLR KDCRAEIVEK   420
FTEPGTVIRI NEVVAALKA                                                439

SEQ ID NO: 3             moltype = DNA   length = 2155
FEATURE                  Location/Qualifiers
source                   1..2155
                         mol_type = genomic DNA
                         organism = Psilocybe cubensis
SEQUENCE: 3
atgatcgctg tactattctc cttcgtcatt gcaggatgca tatactacat cgtttctcgt    60
agagtgaggc ggtcgcgctt gccaccaggg ccgcctggca ttcctattcc cttcattggg   120
aacatgtttg atatgcctga agaatctcca tggttaacat ttctacaatg gggacgggat   180
tacagtctgt cttgccgcgt tgacttctaa tatatgaaca gctaatatat tgtcagacac   240
cgatattctc tacgtggatg ctggagggac agaaatggtt attcttaaca cgttggagac   300
cattaccgat ctattagaaa agcgagggtc catttattct ggccggtgag ctgatgttga   360
gtttttttgca attgaatttg tggtcacacg tttccagact tgagagtaca atggtcaacg   420
aacttatggg gtgggagttt gacttagggt tcatcacata cggcgacagg tggcgcgaag   480
aaaggcgcat gttcgcaaag gagttcagtg agaagggcat caagcaattt cgccatgctc   540
aagtgaaagc tgcccatcag cttgtccaac agcttaccaa aacgccagac cgctgggcac   600
aacatattcg ccagtaagta ctacttgagg aaaatagcgt acgcttcgct gaccggtccg   660
tacatcaaag tcagatagcg gcaatgtcac tggatattgg ttatggaatt gatcttgcag   720
aagacgaccc ttggctggaa gcgacccatt tggctaatga aggcctgcc atagcatcag   780
tgccgggcaa attttgggtc gattcgttcc cctctcgtga gcatccttct tctatgtagg   840
aagggaagga gtctaacaag tgttagtaaa ataccttcct gcttggttcc caggtgctgt   900
cttcaagcgc aaagcgaagg tctggcgaga agccgccgac catatggttg acatgcctta   960
tgaaactatg aggaaattag cagttagtca aatgcgttct ccccgtattt tttcaatact  1020
ctaacttcag ctcacagcct caaggattga ctcgtccgtc gtatgcttca gctcgtctgc  1080
aagccatgga tctcaacggt gaccttgagc atcaagaaca cgtaatcaag aacacagccg  1140
cagaggttaa tgtcggtaag tcaaaagcgt ccgtcggcaa ttcaaaattc aggcgctaaa  1200
gtgggtcttc tcaccaaggt ggaggcgata ctgtaaggat ttctcaatcg ttagagtata  1260
agtgttctaa tgcagtacat actccaccaa ccagactgtc tctgctatgt ctgcgttcat  1320
cttggccatg gtgaagtacc ctgaggtcca gcgaaaggtt caagcggagc ttgatgctct  1380
gaccaataac ggccaaattc ctgactatga cgaagaagtt gactccttgc cataccttac  1440
cgcatgtatc aaggagcttt tccggtgaa tcaaatcgca ccctcgcta taccgcacaa  1500
attaatgaag gacgacgtgt accgcgggta tctgattccc aagaacactc tagtcttctg  1560
aaacacctgg tgaggctgtc cattcattcc tagtacatcc gttgcccac taatagcatc  1620
ttgataacag ggcagtatta aacgatccag aagtctatcc agatccctct gtgttccgcc  1680
cagaaagata tcttggtcct gacgggaagc ctgataacac tgtacgcgac ccacgtaaag  1740
cggcatttgg ctatggacga cgaaattggt aagtgcgctt tcagaacccc cccttccgtt  1800
gactagtgcc atgcgcgcat acaatatcgc tattgatctg atataacttc cctgcggcat  1860
ttattttggc attcctttag tcccggaatt catctagcgc agtcgacggt ttggattgca  1920
ggggcaaccc tcttatcagc gttcaatatc gagcgacctg tcgatcagaa tgggaagccc  1980
attgacatac cggctgattt tacttacagga ttcttcaggt agctaatttc cgtctttgtg  2040
tgcataatac ccctaacgac gcacgtttac cttttttgtaa agacacccag tgcctttcca  2100
gtgcaggttt gttcctcgaa cagagcaagt ctcacgtcg gtatccggac cctga       2155

SEQ ID NO: 4             moltype = AA   length = 508
FEATURE                  Location/Qualifiers
source                   1..508
                         mol_type = protein
                         organism = Psilocybe cubensis
SEQUENCE: 4
MIAVLFSFVI AGCIYYIVSR RVRRSRLPPG PPGIPIPFIG NMFDMPEESP WLTFLQWGRD    60
YNTDILYVDA GGTEMVILNT LETITDLLEK RGSIYSGRLE STMVNELMGW EFDLGFITYG   120
DRWREERRMF AKEFSEKGIK QFRHAQVKAA HQLVQQLTKT PDRWAQHIRH QIAAMSLDIG   180
YGIDLAEDDP WLEATHLANE GLAIASVPGK FWVDSFPSLK YLPAWFPGAV FKRKAKVWRE   240
AADHMVDMPY ETMRKLAPQG LTRPSYASAR LQAMDLNGDL EHQEHVIKNT AAEVNVGGGD   300
TTVSAMSAFI LAMVKYPEVQ RKVQAELDAL TNNGQIPDYD EEDDSLPYLT ACIKELFRWN   360
QIAPLAIPHK LMKDDVYRGY LIPKNTLVFA NTWAVLNDPE VYPDPSVFRP ERYLGPDGKP   420
DNTVRDPRKA AFGYGRRNCP GIHLAQSTVW IAGATLLSAF NIERPVDQNG KPIDIPADFT   480
TGFFRHPVPF QCRFVPRTEQ VSQSVSGP                                      508

SEQ ID NO: 5             moltype = DNA   length = 1089
```

```
FEATURE                 Location/Qualifiers
source                  1..1089
                        mol_type = genomic DNA
                        organism = Psilocybe cubensis
SEQUENCE: 5
atggcgttcg atctcaagac tgaagacggc ctcatcacat atctcactaa acatctttct    60
ttggacgtcg acacgagcgg agtgaagcgc cttagcggag gctttgtcaa tgtaacctgg   120
cgcattaagc tcaatgctcc ttatcaaggt catacgagca tcatcctgaa gcatgctcag   180
ccgcacatgt ctacggatga ggattttaag ataggtgtga aacgttcggt ttacgaatac   240
caggctatca agctcatgat ggccaatgga gaggttctga gaggcgtgga tggcatagtt   300
tctgtgccag aaggcctgaa ctacgactta gagaataatg cattgatcat gcaagatgtc   360
gggaagatga agaccctttt agattatgtc accgccaaac cgccacttgc gacggatata   420
gcccgccttg ttgggacaga aattgggggg tcgttgcca  gactccataa cataggccgc   480
gagaggcgag acgatcctga gttcaaattc ttctctgaaa atattgtcgg aaggacgact   540
tcagaccagc tgtatcaaac catcataccc aacgcagcga aatatggcgt cgatgacccc   600
ttgctgccta ctgtggttaa ggaccttgtg acgatgtca  tgcacagcga agaccctt     660
gtcatggcgg acctgtggag tggaaatatt cttctccagt tggaggaggg aaacccatcg   720
aagctgcaga agatatatat cctggattgg aacttgtca  agtacggccc agcgtcgttg   780
gacctgggct atttcttggg tgactgctat ttgatatccc gctttcaaga cgagcaggtc   840
ggtacgacga tgcggcaagc ctacttgcaa agctatgcgc gtacgagcaa gcattcgatc   900
aactacgcca aagtcactgc aggtattgct gctcatattg tgatgtggac cgactttatg   960
cagtgggggg gcgaggaaga aaggataaat tttgtgaaaa agggggtagc tgcctttcac  1020
gacgccaggg gcaacaacga caatgggaa  attacgtcta ccttactgaa ggaatcatcc  1080
actgcgtaa                                                         1089

SEQ ID NO: 6            moltype = AA   length = 309
FEATURE                 Location/Qualifiers
source                  1..309
                        mol_type = protein
                        organism = Psilocybe cubensis
SEQUENCE: 6
MHIRNPYRTP IDYQALSEAF PPLKPFVSVN ADGTSSVDLT IPEAQRAFTA ALLHRDFGLT    60
MTIPEDRLCP TVPNRLNYVL WIEDIFNYTN KTLGLSDDRP IKGVDIGTGA SAIYPMLACA   120
RFKAWSMVGT EVERKCIDTA RLNVVANNLQ DRLSILETSI DGPILVPIFE ATEEYEYEFT   180
MCNPPFYDGA ADMQTSDAAK GFGFGVGAPH SGTVIEMSTE GGESAFVAQM VRESLKLRTR   240
CRWYTSNLGK LKSLKEIVGL LKELEISNYA INEYVQGSTR RYAVAWSFTD IQLPEELSRP   300
SNPELSSLF                                                          309

SEQ ID NO: 7            moltype = DNA   length = 930
FEATURE                 Location/Qualifiers
source                  1..930
                        mol_type = genomic DNA
                        organism = Psilocybe cubensis
SEQUENCE: 7
atgcatatca gaaatcctta ccgtacacca attgactatc aagcactttc agaggccttc    60
cctcccctca agccatttgt gtctgtcaat gcagatggta ccagttctgt tgacctcact   120
atcccagaag cccagagggc gttcacggcc gctcttcttc atcgtgactt cgggctcacc   180
atgaccatac cagaagaccg tctgtgccca acagtcccca taggttgaa  ctacgttctg   240
tggattgaag atattttcaa ctacacgaac aaaaaccctc gcctgtcgga tgaccgtcct   300
attaaaggcg ttgatattgg tacaggagcc tccgcaattt atcctatgct tgcctgtgct   360
cggttcaagg catggtctat ggttggaaca gaggtcgaga ggaagtgcat tgacacggcc   420
cgcctcaatg tcgtcgcgaa caatctccaa gaccgtctct cgatattaga gacatccatt   480
gatggtccta ttctcgtccc cattttcgag gcgactgaag aatacgaata cgagtttact   540
atgtgtaacc ctccattcta cgacggtgct gccgatatgc agacttcgga tgctgccaaa   600
ggatttggat ttggcgtggg cgctccccat tctggaacag tcatcgaaat gtcgactgg   660
ggaggtgaat cggcttttgt cgctcagatg gtccgtgaga gcttgaagct tcgaacacga   720
tgcagatggt acacgagtaa cttgggaaag ctgaaatcct tgaaagaaat agtgggggctg  780
ctgaaagaac ttgagataag caactatgcc attaacgaat acgttcaggg gtccacacgt   840
cgttatgccg ttgcgtggtc tttcactgat attcaactgc ctgaggagct ttctcgtccc   900
tctaaccccg agctcagctc tctttttctag                                   930

SEQ ID NO: 8            moltype = AA   length = 309
FEATURE                 Location/Qualifiers
source                  1..309
                        mol_type = protein
                        organism = Psilocybe cubensis
SEQUENCE: 8
MHIRNPYRTP IDYQALSEAF PPLKPFVSVN ADGTSSVDLT IPEAQRAFTA ALLHRDFGLT    60
MTIPEDRLCP TVPNRLNYVL WIEDIFNYTN KTLGLSDDRP IKGVDIGTGA SAIYPMLACA   120
RFKAWSMVGT EVERKCIDTA RLNVVANNLQ DRLSILETSI DGPILVPIFE ATEEYEYEFT   180
MCNPPFYDGA ADMQTSDAAK GFGFGVGAPH SGTVIEMSTE GGESAFVAQM VRESLKLRTR   240
CRWYTSNLGK LKSLKEIVGL LKELEISNYA INEYVQGSTR RYAVAWSFTD IQLPEELSRP   300
SNPELSSLF                                                          309

SEQ ID NO: 9            moltype = DNA   length = 3042
FEATURE                 Location/Qualifiers
source                  1..3042
                        mol_type = genomic DNA
                        organism = Psilocybe cubensis
```

```
SEQUENCE: 9
atgccttcca gtcaccctca cattactcat cgctatcggg ttccttcgag tgacgaccat    60
gaacgtatat ctgctctgtt cttgggtccc aaagcagaaa atgccgcatt tctccagcaa   120
tggttgacca cggtcgtcgc acagcaaaag gctgcccgcg atgcatactt cccggatgac   180
aatgctttta ttactacaga catgcaaact tccccccgca ttgctcagac tactaaagta   240
atcgcctcca atctcaccga attattgact gcactcggtg aaaggtcgat tcctttcttc   300
tcacctcggt acagcggcca tatgtctgtg gaccaaagtc tacctgccat tctcggattc   360
ttatcgacca cattttataa tcctaacaat gttgccttcg aggctagtcc attcacgacc   420
ctcatcgagg aagaagttgg cttgcaactc tctgaaatgc tgggttataa tcggctaaat   480
aacaccgaga aacctctcgc ctggggacat attgcatcag gtggaactgt tgcaaacttg   540
gaagcgatgt gggcggcgcg aaacctcaag ttttaccctc tctcactccg tgatgcttca   600
gccgaaggcg cagagatgga attcattcgt gacacattct ccgtcaaaac ctgtgttggt   660
gacaaaaaat tattaaagga ttgcagccca tgggaactcc tcaatttgca tgtttctact   720
atcttagaca tgcccgaccg tctgcacgac gagtacaata tttcacctca gttcctcgaa   780
aaggttatgc gaaagtatat catccagtct accaacaaag acacgttgat gcagcgttgg   840
ggacttaccc aacaacctgt cgttttatcc ccgagcacaa accattattc ctggccaaag   900
gctgcagctg tgctcggtat tggctcagac aaccttcgca acgtcccagt agacatccaa   960
gcccacatgg acataaacga actcgatcgt atgttaaaaa tttgcttgga cgaggagacg  1020
ccagtatatc aagtagttgc tgtttatcgg accaccgaag agggcggtgt cgatcgcatt  1080
acggagatcc tgaagctgcg ccaaaagtat gaagctttgg ggctgtcttt tgccatccat  1140
gcagatgctg cttggggagg ctattttgca accatgctac ccaaagatac attgggtcga  1200
aaccggacta ggcttcccaa agaggacact acctcggcgt ttgtccctca cgtcggtctg  1260
cgcgaggaga gcgcgttaca actcagccat ataaagtatg ccgattctat tactatcgac  1320
ccgcacaagg caggctatgt tccttacccc gctgggcac tctgttatcg cgacggaaga   1380
atgaggtacc tgcttacatg gtccgcgccc taccttgccc aaggcaacga gggccaaagt  1440
atcggaatat acgggatcga aggaagcaaa cctggtcgac tgcatccgc ggtattcatg    1500
gcgcacgaaa ccattggcct gactccttct ggatacggga accttcttgg ccaggcaatg  1560
tttacatgtc gccgatacgc tgctcactgg tctgcaatgt caacggatac taccagtttc  1620
actgtccacc cgttcaatcc tatccctgct gacatcgacc caacgctga ccccgcaaag   1680
gtcgaaggac aaaaacagtt catcagagat cgtatcttgt tcaaatcgaa cgagaaata   1740
tacaacgatt ctgaggctat ggaactcttg caccaacttg ggtccgatct caatatcaac  1800
gtttcgcat gcaacttccg cgaccgcgat aataatctca caccgacgt cgaggaagcc   1860
aactggctca ataccgtat tttccaacgc ttttctgtta caagtgctga ggagaaccca   1920
ttggaaacgc cattcttcct cagctcaact acattgaaac aatccgaata cggcgtctgc  1980
gcaaccgaag taagagacg catgggactt gttggtgacc aggatgttat agtcctgagg  2040
aacgtcgtta tgtctccatt tactacaacg aacgactttg tgggaactct ggcaaacacc  2100
ttccaaaaga tcgttgagga ggaggtcgag tatgcacgga tccgcaacga tatgaaacct  2160
agcattcaca ccttccttct tcatggttca ggagagcaat actatcttgt ccacaccccca 2220
acgatccata tggccagcgg ccgtcgccaa atcatccttt cagttaatgt tgaaggccaa  2280
gttcggcagg cgatacatgc ccatgaaaga gttaagcag tgattgtaca taacactgtg   2340
cccctccgcc ttgacgaaat cgttgacgga ggatcatttg acggcatact caccatcgga  2400
aagaggaaaa ctagtttcaa agtgaagatt tcaaacatta aagtagtcaa gaagcgctct  2460
ctgatgactg aggacctgga atctcgctac ccatcgttga tgccattcta tttctacggg  2520
actcaaggac acgctcatct cgaccatgtc attactgtcg ttcctaacat ccatctgagt  2580
gctggcgaaa tacagtacaa attcgacgac gaggtgtcaa gcgaggacct cgccaagggc  2640
ctcattgttg ttgctgagaa cgtacacgag gcatccatgc agcccttccc gctcatgaaa  2700
gatttcaaga tcaccaacca atcttcttc agctccggac aaatactccg cgtcaaagtg  2760
tacagagatc cataccccggc atcgacaatg gatcccatcc ctctccacga catcaagaac  2820
cagcccgtcg tgacacaagg caccatcacg ctcgtcggaa atatttacgt cgattctgat  2880
gcgctcaacg tcgcttccga gcctactgcc gacgaagacg cggcgcatgt tcctcacgct  2940
cgcaacatgt acggcgagat gaccgctgga acgatcaaag gctggcaaaa cgctgttcgt  3000
catttccaca acaaattgga gactgttgct ccgacgaagt ag                     3042

SEQ ID NO: 10          moltype = AA  length = 1013
FEATURE                Location/Qualifiers
source                 1..1013
                       mol_type = protein
                       organism = Psilocybe cubensis
SEQUENCE: 10
MPSSHPHITH RYRVPSSDDH ERISALFLGP KAENAAFLQQ WLTTVVAQQK AARDAYFPDD    60
NAFITTDMQT SPAFAQTTKV IASNLTELLT ALGERSIPFF SPRYSGHMSV DQSLPAILGF   120
LSTTFYNPNN VAFEASPFTT LIEEEVGLQL SEMLGYNRLN NTEKPLAWGH IASGGTVANL   180
EAMWAARNLK FYPLSLRDAS AEGAEMEFIR DTFSVKTCVG DKKLLKDCSP WELLNLHVST   240
ILDMPDRLHD EYNISPQFLE KVMRKYIIQS TNKDTLMQRW GLTQQPVVLS PSTNHYSWPK   300
AAAVLGIGSD NLRNVPVDIQ AHMDINELDR MLKICLDEET PVYQVVAVIG TTEEGGVDRI   360
TEILKLRQKY EALGLSFAIH ADAAWGGYFA TMLPKDTLGR NRTRLPKEDT TSGFVPHVGL   420
REESALQLSH IKYADSITID PHKAGYVPYP AGALCYRDGR MRYLLTWSAP YLAQGNEGQS   480
IGIYGIEGSK PGAAASAVFM AHETIGLTPS GYGNLLGQAM FTCRRYAAHW SAMSTDTTSF   540
TVTPFNPIPA DIDPNADPAK VEEQKQFIRD RILFKSNEEI YNDSEAMELL HQLGSDLNIN   600
VFACNFRDRD NNLNTDVEEA NWLNNRIFQR FSVTSAEENP LETPFFLSST TLKQSEYGVC   660
ATEVKRRMGL VGDQDVIVLR NVVMSPFTTT NDFVGTLANT FQKIVEEEVE YARIRNDMKP   720
SIHTFLLHGS GEQYYLVHTP TIHMASGRRQ IILSVNVEGQ VRQAIHAHER VEAVIVHNTV   780
PLRLDEIVDG GSFDGILTIG KRKTSFKVKI SNIKVVKKRS LMTEDLESAY PSLMPFYFYG   840
TQGHAHLDHV ITVVPNIHLS AGEIQYKFDD EVSSEDLAKG LIVVAENVHE ASMQPFPLMK   900
DFKITNQFFF SSGQILRVKV YRDPYPASTM DPIPLHDIKN QPVVTQGTIT LVGNIYVDSD   960
ALNVASEPTA DEDAAHVPHA RNMYGEMTAG TIKGWQNAVR HFHNKLETVA PTK         1013

SEQ ID NO: 11          moltype = DNA  length = 2103
FEATURE                Location/Qualifiers
```

-continued

```
source               1..2103
                     mol_type = genomic DNA
                     organism = Psilocybe cubensis
SEQUENCE: 11
atggaggcta tcaaaaaggt ttttgagaac aaaaaggcgg agggcattcc tgtgttggtg      60
acctttgtta ctgcaggata tcctcgtccc gaagatactg ttcccatctt gctggccatg     120
gaggccggtg gtgctgatat catcgagctt ggtatgccat tttcagaccc aattgcagat     180
ggtcctgtca tccaggaaac gaacacaatc gccgttgcaa accaggtaga ttataccact     240
gttctcggac aacttcggga agcccgcaaa caagggctca aggcaccccgt tcttctgatg     300
ggatattata accccatatt ggcttacgga gaagacagat ctattccaga tgccggctgaa    360
gctggagcca atgggtttat tatggtcgac cttccacccg aggaggctgt cgcttttcga     420
gagaaatgta tcaaatccaa cctctcatat gttcctctaa ttgcaccctc aacgactctg     480
tcgcgtataa agttcctctc aacaattgca gacacgttca tctatgtcgt gtctaaaatg     540
ggaaccaccg gatcctcaga aaggttgcc atgaataacg cccttcccac catcatcgat     600
cgtattcgcg agtacgctga agttccttta gcagtcggat ttggagtcgc cactcgggct     660
cacttcaact acgtcgccga ttccggtgct gatggtgtcg ttattggcac caaactcgtt     720
aacgttatta aagagtcacc gcaagggaa gcacccaaaa atgttgaggc atactgccgt     780
gagatgagcc aaaagggaga aacaaatcgc gtcaaatctc caccaactgc ccgtgctgcc     840
agctccgaat caattcctgt tgttgttcct tctgttctcc ccgcacgttt cggagaattc     900
ggaggacaat acgttcccga agctcttgtc gattgtctgg ttgaactaga agaagctcac     960
aaatctgcca tggctgatcc tgaattccag aaggaactac aatcgcatgc cggatatgca    1020
aatcgtcctt cacaaatata cctcgccgaa aatctcacca aggatgctgg gggtgcaaat    1080
atttggttga aacgtgaaga tttgaaccac acaggttccc acaaaatcaa taacgctttg    1140
ggacaaattc tgcttgcccg gagaatcgga aagaccagaa ttatcgcaga aacaggtgcc    1200
ggccagcatg gtgttgcaac agcgactgtt tgcgctaagt ttggaatgga atgtgttatc    1260
tacatgggcg cagaaatgt gcgacggcaa gctctataa tattcaggat tgagatgcta    1320
ggagcaaaag ttgttcctgt tacttcagga tcatgcact tgaaggacgc tgtaaacgag    1380
gccttccgtg actgggtgac aaaccttttct acgacgcatt atttggttgg ctctgtaatt    1440
ggacctcatc ccttccccac cattgtccga gatttccaaa aggtcattgg tcaagagatc    1500
aaggctcaga tgttggccgc ccgcggcaaa cttcctgatg tcgtcgtcgc ttgtgttggt    1560
ggaggaagca atgctatcgg tacgttctat gattttattg gcgacaagag tgtacgtcta    1620
gttggggtgg aagcaggagg agaaggtatt gacggagacc gacatagcgc cacactttcg    1680
atggggcaac cggagtact tcacggtgtt agaacatata ttctacaaga caaggccggt    1740
caaatcatcg agacgcactc aatcagcgct ggattggatt atccggcgt tggaccagaa    1800
catgcttggc taaaggactc taaaagagca gaatatgttg tcgccacaga cgaagaagaa    1860
cttcgcggtt tccgtatgct aacacaaagg gagggaatta ttcctgccct tgaatcttcc    1920
catgcgatct gggaggctgt caggattgcc cgcaccatgt cgaaggacca ggatcttgtt    1980
gtgtgtttgt ctggccgagg tgataaagac gttgagcaaa tttctcaact tcttcccaag    2040
tgggcggata ttctagactg gcatgtttct tcccatgccg ttgacacac aacaaaattc    2100
taa                                                                   2103

SEQ ID NO: 12        moltype = AA  length = 700
FEATURE              Location/Qualifiers
source               1..700
                     mol_type = protein
                     organism = Psilocybe cubensis
SEQUENCE: 12
MEAIKKVFEN KKAEGIPVLV TFVTAGYPRP EDTVPILLAM EAGGADIIEL GMPFSDPIAD      60
GPVIQETNTI AVANQVDYTT VLGQLREARK QGLKAPVLLM GYYNPILAYG EDRSIQDAAE     120
AGANGFIMVD LPPEEAVAFR EKCIKSNLSY VPLIAPSTTL SRIKFLSTIA DTFIYVVSKM     180
GTTGSSEKVA MNNALPTIID RIREYAEVPL AVGFGVATRA HFNYVADSGA DGVVIGTKLV     240
NVIKESPQGE APKNVEAYCR EMSQKGETNR VKSPPTARAA SSESIPVVVP SVLPARFGEF     300
GGQYVPEALV DCLVELEEAH KSAMADPEFQ KELQSHAGYA NRPSQIYLAE NLTKDAGGAN     360
IWLKREDLNH TGSHKINNAL GQILLARRIG KTRIIAETGA GQHGVATATV CAKFGMECVI     420
YMGAEDVRRQ ALNVFRIEML GAKVVPVTSG SCTLKDAVNE AFRDWVTNLS TTHYLVGSVI     480
GPHPFPTIVR DFQKVIGQEI KAQMLAARGK LPDVVVACVG GGSNAIGTFY DFIGDKSVRL     540
VGVEAGGEGI DGDRHSATLS MGQPGVLHGV RTYILQDKAG QIIETHSISA GLDYPGVGPE     600
HAWLKDSKRA EYVVATDEEA LRGFRMLTQR EGIIPALESS HAIWEAVRIA RTMSKDQDLV     660
VCLSGRGDKD VEQISQLLPK WADILDWHVS SHAVGHTTKF                           700

SEQ ID NO: 13        moltype = DNA  length = 1122
FEATURE              Location/Qualifiers
source               1..1122
                     mol_type = genomic DNA
                     organism = Salinispora arenicola
SEQUENCE: 13
atgaccgagg agttgacgac ggtccgagac gcctgcgcca gaacgttgga gaacacggca      60
cggacactgc acctgggagc cagcggtacg gaattcgtcg cggcgttccg ggccatgacc     120
gaccactggg gcgcccccg ccccacgat ctaccccgtg cggacgtgtc ccgacgtgg      180
tcgccggtgg agtacgccgt cgacctcggc gggctcgcgc ccgcactcca gttcgccatg     240
gagccgctga ccgcgggcgt gccggctcgt gatcccctcg cggcgcgggc catcatgccg     300
ctgctggccg gcggtacgg cgccgacgcg accggtggt cggccctcgc ggaccggctc     360
ctgccagacg acgcgcacgg cccgcacgtc tccatgtacg gcgccgaggt cgggcgggt     420
gccccgatcc ggttcaaggc ctggttctac ctgaacgtca ccggcccgga cggcccttc     480
aacctgctgt actccgcctt ggaacggatg gtacgacgc acctgtgcc ggtcgtccaa     540
gcgcacgtgc accgcgctgg ggaggacgtg ccgttcctgc tgtcgctgga cctgtcggac     600
gacccggcgg cccgggtgaa ggtgtacttc cggcacttcg cggcggatgt cgaggaggtc     660
gcggccgtgc tcaaggcgta cccaggtttc gagccggggca aggtgcgggc cttctgcaag     720
gtcatgatgg gcggtcggcg ccgcttcagc gaccagccgg ccgtcacctg cgtatcactg     780
```

```
ctcgacgcgc agaccttcga tcgcactgcg gccaccctct acgttccgct gtggacgtac   840
gccgagcacg acggcgaagt gcggcagcgg gtgcaccgga ccctggctgc gtggccggag   900
gcgctgtacc gctacgacag cgtgctcgcc ggcatcgcgc accgcgggct ggacgccgga   960
accgggatcc acaactacat ctcctggcaa cccggccgga cccgcccgcg gatgaaggtc  1020
tacctgtcac cggagatgca cgacgtcact cctccgccgc tcggcgtaag ccaacagcat  1080
cacctcagtg gccagaccac tgcgagaggg agaaccgaat ga                    1122

SEQ ID NO: 14           moltype = AA  length = 373
FEATURE                 Location/Qualifiers
source                  1..373
                        mol_type = protein
                        organism = Salinispora arenicola
SEQUENCE: 14
MTEELTTVRD ACARTLENTA RTLHLGASGT EFVAAFRAMT DHWGAARPHD LPLSDVSPDG    60
SPVEYAVDLG GLAPALQFAM EPLTAGVPAR DPLAARAIMP LLAGRYGADA TRWSALADRL   120
LPDDAHGPHV SMYGAEVRAG APIRFKAWFY LNVTGPDGAF NLLYSALERM GTTHLWPVVQ   180
AHVHRAGEDV PFLLSLDLSD DPAARVKVYF RHFAADVEEV AAVLKAYPGF EPGEVRAFCK   240
VMMGGRRRFS DQPAVTCVSL LDAQTFDRTA ATLYVPLWTY AEHDGEVRQR VHRTLAAWPE   300
ALYRYDSVLA GIAHRGLDAG TGIHNYISWQ PGRTRPRMKV YLSPEMHDVT PPPLGVSQQH   360
HLSGQTTARG RTE                                                     373

SEQ ID NO: 15           moltype = DNA  length = 1380
FEATURE                 Location/Qualifiers
source                  1..1380
                        mol_type = genomic DNA
                        organism = Aspergillus fumigatus
SEQUENCE: 15
atgaaggcag ccaatgcctc cagtgcggag gcctatcgag ttcttagtcg cgcctttaga    60
ttcgataatg aagatcagaa gctgtggtgg cacagcactg cccgatgtt tgcaaaaatg    120
ctggaaactg ccaactacac cacaccttgt cagtatcaat acctcatcac ctataaggag   180
tgcgtaattc ccagtctcgg atgctatccg accaacagcg ccccccgctg gttgagcatc   240
ctcactcgat acggcactcc gttcgaattg agcctaaatt gctctaattc aatagtgaga   300
tacacattcg agccgatcaa tcaacatacc ggaacagata agacccatt caatacgcac   360
gccatctggg agagcctgca gcacctgctt ccactggaga agagcattga tctggagtgg   420
ttccgccact tcaagcacga tctcacctc aacagtgaag aatctgcttt tctggctcat   480
aatgatcgcc tcgtgggcgg cactatcagg acgcagaaca agctcgcgct cgatctgaag   540
gatggccgct ttgcacttaa gacgtacata taccccggctc tcaaagctgt cgtcaccggc   600
aagacaattc atgagttggt cttttggctca gtccgccggc tggcagtgag ggagcccga   660
atcttgcccc cactcaacat gctggaggaa tacatccgat cacgcggttc caagagcact   720
gccagtcccc gcctagtgtc ctgtgatctg accagtcctg ccaagtcgag aatcaagatc   780
tacctgctgg agcagatggt ttcactagaa gccatggagg acctgtggac tctgggcgga   840
cggcgccgag acgcttccac tttagagggg ctctctctgg tgcgtgagct ttgggatctg   900
atccaactgt cgccgggatt gaagtcctat ccggcgcgat atcgcctct cggggttatc   960
ccagacgaga ggctgccgct tatggccaat ttcaccctgc accagaatga cccggtccca  1020
gagccgcaag tatatttcac aaccttcggc atgaacgaca tggcggtggc ggatgccctg  1080
acgacgttct tcgagcgccg gggttggagt gaaatggccc gcacctacga aactactttg  1140
aagtcgtact accccatgc ggatcatgac aaacttacct acctacatatcc             1200
ttctcctaca gggaccgtac cccttatctg agtgtctatc ttcaatcctt cgagacaggg  1260
gactgggcag ttgcaaactt atccgaatca aaggtcaagt gtcaggatgc ggcctgtcaa  1320
cccacagctt tacctccaga tctgtcaaag acaggggtat attattccgg tctccactga  1380

SEQ ID NO: 16           moltype = AA  length = 459
FEATURE                 Location/Qualifiers
source                  1..459
                        mol_type = protein
                        organism = Aspergillus fumigatus
SEQUENCE: 16
MKAANASSAE AYRVLSRAFR FDNEDQKLWW HSTAPMFAKM LETANYTTPC QYQYLITYKE    60
CVIPSLGCYP TNSAPRWLSI LTRYGTPFEL SLNCSNSIVR YTFEPINQHT GTDKDPFNTH   120
AIWESLQHLL PLEKSIDLEW FRHFKHDLTL NSEESAFLAH NDRLVGGTIR TQNKLALDLK   180
DGRFALKTYI YPALKAVVTG KTIHELVFGS VRRLAVREPR ILPPLNMLEE YIRSRGSKST   240
ASPRLVSCDL TSPAKSRIKI YLLEQMVSLE AMEDLWTLGG RRRDASTLEG LSLVRELWDL   300
IQLSPGLKSY PAPYLPLGVI PDERLPLMAN FTLHQNDPVP EPQVYFTTFG MNDMAVADAL   360
TTFFERRGWS EMARTYETTL KSYYPHADHD KLNYLHAYIS FSYRDRTPYL SVYLQSFETG   420
DWAVANLSES KVKCQDAACQ PTALPPDLSK TGVYYSGLH                         459

SEQ ID NO: 17           moltype = DNA  length = 1128
FEATURE                 Location/Qualifiers
source                  1..1128
                        mol_type = genomic DNA
                        organism = Streptomyces coelicolor
SEQUENCE: 17
atgagggccg cgtcgacggg cgcggaccga caggacgcat ccacgctcgg ctctttcacc    60
ggcggccagt tgcgaagact cggtccggtc gccggtcggg cccgcgcgg cgtcgagacc   120
tacgcacagg tcctgaccga cgcattgggc ccggtggccc agcggccgct gagcctggcg   180
ccgcccaccc gcaccttcct gtcggacgac cacaccccg tggagttctc cctctccttc   240
cggcccgggg cggcgcccgc catgcgggtc ctcgtggaac cggctgcgg tgcgaccagc   300
ctggccgaca acgccgtgc cggtcttgag gcggtccgca cgatgcgcg cgctggcac   360
ttcaccaccg acgccctcga cgaactcctg gacctgttcc tgccgcccgc tccgcagggc   420
```

```
cccctcgccc tgtggtgcgc cctggaactc aggcccgggg gtgtaccggg cgtcaaggtc    480
tatctgaacc ctgcggtggg cggggaggaa cgttccgccg cgacggtgcg cgaggccctg    540
cgccggctcg ggcaccacca ggccttcgac agcctccccc agggcagtgg ataccgttc     600
ctcgccctgg acctcgggaa ctggacggag ccccgggcga aggtctacct gcgccacgac    660
aacctcacgg ccggtcgggc cgcacggctg tcccggacgg actcgggcct cgtgccgacc    720
gcggtcgagg gttttcttccg caccgccgcg ggtcccggct ccgacgcggg tgggctcgac    780
gggcggcctg ctcagtcctg ccactccttc accgaccccg gcgcggagcg gccgagcggc    840
ttcacccctgt acatcccggt tcgtgactac gtccggcatg acggggaggc cctggcgcgg    900
gcgtccaccg tgctgcacca ccaggcatg gacgcctccg tgctccaccg cgccctggcc     960
gccctcaccg agcggcggcc cgaggacggg gtgggcctga tcgcctacct ggccctggcc   1020
ggccaacggg accagccgcc gcgggtgacg gcctacctct cctcggaggc ctacacggtc   1080
cggccgccgt cgtggagac cgtccgccaa ccgctgtcgg tcggctga                1128

SEQ ID NO: 18        moltype = AA  length = 375
FEATURE              Location/Qualifiers
source               1..375
                     mol_type = protein
                     organism = Streptomyces coelicolor
SEQUENCE: 18
MRAASTGADP QDASTLGSFT GGQLRRLGSV AGLSRADVET YAQVLTDALG PVAQRPLSLA   60
PPTRTFLSDD HTPVEFSLSF RPGAAPAMRV LVEPGCGATS LADNGRAGLE AVRTMARRWH  120
FTTDALDELL DLFLPPAPQG PLALWCALEL RPGGVPGVKV YLNPAVGGEE RSAATVREAL  180
RRLGHHQAFD SLPQGSGYPF LALDLGNWTE PRAKVYLRHD NLTAGRAARL SRTDSGLVPT  240
AVEGFFRTAA GPGSDAGGLD GRPAQSCHSF TDPGAERPSG FTLYIPVRDY VRHDGEALAR  300
ASTVLHHHGM DASVLHRALA ALTERRPEDG VGLIAYLALA GQRDQPPRVT AYLSSEAYTV  360
RPPVVETVRQ PLSVG                                                  375

SEQ ID NO: 19        moltype = DNA  length = 1158
FEATURE              Location/Qualifiers
source               1..1158
                     mol_type = genomic DNA
                     organism = Streptomyces sp.
SEQUENCE: 19
atgggaggtc cgatgagcgg tttccattcg ggggaggcgc tgctcggtga ccctcgccacc    60
ggtcagctga ccaggctgtg cgaggtggcg gggctgaccg aggccgacac ggcggcctac   120
acgggggtgc tgatcgaaag tctggggacg tcggccggac ggccgttgtc cctgccaccc   180
ccgtcgcgga ccttctctc cgacgaccac accccgtgg agttctccct ggccttcctg     240
ccgggacgcg caccgcacct gcgggtcctg gtggaaccgg gctgctccag cggcgacgac   300
ctggcggaaa acggccgggc cggtctgcgg gcggtccaca ccatgcggga ccgctgggga   360
ttctccaccg agcaactcga ccggctggag gacctgttct tcccctcctc ccccgagggc   420
ccgctgcgcc tgtggtgcgc cctggagctc cgctccggtg gggtgccggg ggtgaaggtc   480
tacctcaacc ccgcggcgaa tggcgccgac cgggccgccg agacggtacg cgaggcgctg   540
gccaggctgg gccacctgca ggcgttcgac gcgctgccgc gggacggacgg cttcccgttc   600
ctcgccctgg acctcggcga ctgggacgcc ccgggtgaa gatctacct caaacacctc    660
ggcatgtccg ccgccgacgc gggctccctc ccccggatgt cgcccgcacc gagcgggag    720
cagctggagg agttcttccg caccgccggt gacctcccgg ccccgggaga cccggggccc   780
accgaggaca ccggccggct cgccggggcg cccgccctca ggtgccactc cttcacggag   840
acggcgaccg ggcggcccag cggctacacc ctccacgtgc cggtccgcga ctacgtccgg   900
cacgacggcg aggcacggga ccgggcggtg gccgtgctgc gcgaacatga catggacagt   960
gcggcactgg accgggcgct ggccgccgtg agccccgcc cgctgagtga cggggtgggc   1020
ctgatcgcct atctggccct ggtccaccag cgcggccggc cgacacgggt gaccgtctac   1080
gtctcctccg aggcgtacga ggtgcggccg ccccgcgaga cggtccccac ccgcgaccgg   1140
gcgcgggcac ggctgtga                                                1158

SEQ ID NO: 20        moltype = AA  length = 385
FEATURE              Location/Qualifiers
source               1..385
                     mol_type = protein
                     organism = Streptomyces sp.
SEQUENCE: 20
MGGPMSGFHS GEALLGDLAT GQLTRLCEVA GLTEADTAAY TGVLIESLGT SAGRPLSLPP    60
PSRTFLSDDH TPVEFSLAFL PGRAPHLRVL VEPGCSSGDD LAENGRAGLR AVHTMADRWG   120
FSTEQLDRLE DLFFPSSPEG PLALWCALEL RSGGVPGVKV YLNPAANGAD RAAETVREAL   180
ARLGHLQAFD ALPRADGFPF LALDLGDWDA PRVKIYLKHL GMSAADAGSL PRMSPAPSRE   240
QLEEFFRTAG DLPAPGDPGP TEDTGRLAGR PALTCHSFTE TATGRPSGYT LHVPVRDYVR   300
HDGEARDRAV AVLREHDMDS AALDRALAAV SPRPLSDGVG LIAYLALVHQ RGRPTRVTVY   360
VSSEAYEVRP PRETVPTRDR ARARL                                       385

SEQ ID NO: 21        moltype = DNA  length = 1419
FEATURE              Location/Qualifiers
source               1..1419
                     mol_type = genomic DNA
                     organism = Aspergillus fumigatus
SEQUENCE: 21
atgtccatcg agccgagat cgattcgctg gttcctgctc caccgggcct caacggcacc       60
gctgcgggct atccagccaa gacgcagaag gagttaagca acggagactt tgacgcgcac    120
gatggtctttt ctcttgcaca actgacaccg tacgatgtct tgacggctgc acttccgctg   180
ccggctccgg cttcgagcac agggttctgg tggcgggaga cgggcccctgt tatgagcaag   240
cttttggcca aggcgaacta ccctctttac actcattaca agtaccttat gttataccat    300
```

```
acccatattc tcccattgtt gggacctcga ccgccgctcg agaactcgac gcacccgtcg    360
ccgagtaacg cgccgtggag gtccttcctg acagacgact tcactccgct cgagccgagc    420
tggaacgtga acgggaactc ggaagcacag agcacaatcc gtcttggtat tgaacctata    480
ggctttgaag ccggggctgc agcggaccca ttcaaccaag ctgccgtgac gcagttcatg    540
cactcatacg aggcaaccga agtcggtgcc acgctggcga tgttcgagca cttccgcaac    600
gacatgtttg ttggcccaga aacgtacgct gcgttaagag cgaagatacc agaaggcgag    660
cataccacac agagtttcct ggcgttcgac ctggacgcgg tcgtgtcac cacaaaggcg    720
tacttttttcc cgattctcat gtcgttgaaa actggacaga gcacaacaaa ggtggtctct    780
gattccattc tgcatctagc gctgaagagt gaggtgtggg gtgtgcagac catcgccgcg    840
atgtcggtca tggaggcgtg gataggtagc tacggtgccg cggcaaagac ggagatgatc    900
agcgtcgatt gcgtgaacga ggcagactct cggatcaaga tatacgtgcg gatgccacat    960
acatccttgc ggaaggtaaa agaggcgtac tgcttaggtg ggcggttgac agacgagaac   1020
acaaaggagg gcctgaagct gctggacgag ctgtggagga cggtcttcgg catcgacgac   1080
gaggacggca agctgccaca gaatagccat cgcaccgcag gcacaatatt caatttcgag   1140
ctgaggccag ggaaatggtt ccccgagccc aaggtatacc tgcccgtccg acactactgt   1200
gaaagtgata tgcagattgc tagtcggcta caaacgttct ttggaaggct cggatggcac   1260
aacatggaga agattattg caagcatctg gaagatttgt ttccccatca tccactgtcc   1320
tcgtcaacgg gcacacacac cttcctctca ttttcgtata agaagcagaa gggggtctat   1380
atgaccatgt attataatct ccgggtgtac agcacctaa                          1419

SEQ ID NO: 22             moltype = AA  length = 472
FEATURE                   Location/Qualifiers
source                    1..472
                          mol_type = protein
                          organism = Aspergillus fumigatus
SEQUENCE: 22
MSIGAEIDSL VPAPPGLNGT AAGYPAKTQK ELSNGDFDAH DGLSLAQLTP YDVLTAALPL    60
PAPASSTGFW WRETGPVMSK LLAKANYPLY THYKYLMLYH THILPLLGPR PPLENSTHPS   120
PSNAPWRSFL TDDFTPLEPS WNVNGNSEAQ STIRLGIEPI GFEAGAAADP FNQAAVTQFM   180
HSYEATEVGA TLTLFEHFRN DMFVGPETYA ALRAKIPEGE HTTQSFLAFD LDAGRVTTKA   240
YFFPILMSLK TGQSTTKVVS DSILHLALKS EVWGVQTIAA MSVMEAWIGS YGGAAKTEMI   300
SVDCVNEADS RIKIYVRMPH TSLRKVKEAY CLGGRLTDEN TKEGLKLLDE LWRTVFGIDD   360
EDAELPQNSH RTAGTIFNFE LRPGKWFPEP KVYLPVRHYC ESDMQIASRL QTFFGRLGWH   420
NMEKDYCKHL EDLFPHHPLS SSTGTHTFLS FSYKKQKGVY MTMYYNLRVY ST           472

SEQ ID NO: 23             moltype = DNA  length = 1158
FEATURE                   Location/Qualifiers
source                    1..1158
                          mol_type = genomic DNA
                          organism = Streptomyces sp.
SEQUENCE: 23
atgggaggtc cgatgagcgg tttccattcg ggggaggcgc tgctcggtga cctcgccacc    60
ggtcagctga ccaggctgtg cgaggtgcg gggctgacag aggccgacac ggcggcctac   120
acggggggtgc tgatcgaaag tctggggacg tcggccggac ggcgtttgtc cctgccaccc   180
ccgtcgcgga cctttctctc cgacgaccac accccgtgg agttctccct ggccttcctg   240
ccgggacgcg caccgcacct gcgggtcctg gtggaaccgg gctgctccag cggcgacgac   300
ctggcggaaa acgccgggc cggtctgcgg gcggtccaca ccatgcggcgga ccgctgggga   360
ttctccaccg agcaactcga ccggctggag gacctgttct tccccctctc ccccgagggc   420
ccgctgccc tgtggtgcgc cctggagctc cgctccggtg gggtgccggg ggtgaaggtc   480
tacctcaacc ccgcggcgaa tggcgccgac cgggccgccg agacggtacg cgaggcgctg   540
gccaggctgg gccaccttgca ggcgttcgac gcgctgcccc gggccgacgg cttcccgttc   600
ctcgccctgg acctcggcga ctgggacgcc ccgcgggtga agatctacct caaacacctc   660
ggcatgtccg ccgccgacgc gggctccctc cccggaatgt cgcccgcacc gagccggagc   720
cagctggagg agttcttccg caccgccggt gacctccccgg gccccgggag acccggggccc   780
accggagaca ccggccggct gccgggggcg cccgccctca cctgccactc cttcacggag   840
acggcgaccg gcggggccag cggctacacc ctccacgtgc cggtccgcga ctacgtccgg   900
cacgacggcg aggcacggga ccgggcggtg gccgtgctgc gcgaacatga catggacagt   960
gcggcactgg accgggcgct ggccgccgtg agccccgcc cgctgagtga cggggtgggc  1020
ctgatcgcct atctggcact ggtccaccag cgcggccggc cgacacgggt gaccgtctac  1080
gtctcctccg aggcgtacga ggtgcggcgg cccccgcgaga cggtccccac cgcgaccggg  1140
gcgcgggcac ggctgtga                                                 1158

SEQ ID NO: 24             moltype = AA  length = 385
FEATURE                   Location/Qualifiers
source                    1..385
                          mol_type = protein
                          organism = Streptomyces sp.
SEQUENCE: 24
MGGPMSGFHS GEALLGDLAT GQLTRLCEVA GLTEADTAAY TGVLIESLGT SAGRPLSLPP    60
PSRTFLSDDH TPVEFSLAFL PGRAPHLRVL VEPGCSSGDD LAENGRAGLR AVHTMADRWG   120
FSTEQLDRLE DLFFPSSPEG PLALWCALEL RSGGVPGVKV YLNPAANGAD RAAETVREAL   180
ARLGHLQAFD ALPRADGFPF LALDLGDWDA PRVKIYLKHL GMSAADAGSL PRMSPAPSRE   240
QLEEFFRTAG DLPAPGDPGP TEDTGRLAGR PALTCHSFTE TATGRPSGYT LHVPVRDYVR   300
HDGEARDRAV AVLREHDMDS AALDRALAAV SPRPLSDGVG LIAYLALVHQ RGRPTRVTVY   360
VSSEAYEVRP PRETVPTRDR ARARL                                          385

SEQ ID NO: 25             moltype = DNA  length = 1461
FEATURE                   Location/Qualifiers
source                    1..1461
```

```
                        mol_type = genomic DNA
                        organism = Bacillus atrophaeaus
SEQUENCE: 25
atgtctgaaa atttgcaatt gtcagctgaa gaaatgagac aattgggtta ccaagcagtt    60
gatttgatca tcgatcacat gaaccatttg aagtctaagc cagtttcaga aacaatcgat   120
tctgatatct tgagaaataa gttgactgaa tctatcccag aaaatggttc agatccaaag   180
gaattgttgc atttcttgaa cagaaacgtt tttaatcaaa ttacacatgt tgatcatcca   240
catttcttgg cttttgttcc aggtccaaat aattacgttg gtgttgttgc agatttcttg   300
gcttctggtt ttaatgtttt tccaactgca tggattgctg gtgcaggtgc tgaacaaatc   360
gaattgacta caattaattg gttgaaatct atgttgggtt ttccagattc agctgaaggt   420
ttatttgttt ctggtggttc aatggcaaat ttgacagctt tgactgttgc aagacaggct   480
aagttgaaca acgatatcga aaatgctgtt gtttacttct ctgatcaaac acatttctca   540
gttgatagag cattgaaggt tttaggtttt aaacatcatc aaatctgtag aatcgaaaca   600
gatgaacatt tgagaatctc tgtttcagct ttgaagaaac aaattaaaga agatagaact   660
aagggtaaaa agccattctg tgttattgca aatgctggta ctacaaattg tggtgctgtt   720
gattctttga acgaattagc agatttgtgt aacgatgaag atgtttggtt gcatgctgat   780
ggttcttatg gtgctccagc tatcttgtct gaaaagggtt cagctatgtt gcaaggtatt   840
catagagcag attcttttgac tttagatcca cataagtggt tgttccaacc atacgatgtt   900
ggttgtgttt tgatcagaaa ctctcaatat ttgtcaaaga cttttagaat gatgccagaa   960
tacatcaagg attcagaaac taacgttgaa ggtgaaatta atttcggtga atgtggtatc  1020
gaattgtcaa gaagattcag agctttgaag gtttggttgt cttttaaagt tttcggtgtt  1080
gctgcttttta gacaagcaat cgatcatggt atcatgttag aagaacaagt tgaagcattt  1140
ttgggtaaag caaaagattg ggaagttgtt acaccagctc aattgggtat cgttactttt  1200
agatacattc catctgaatt ggcatcaaca gatactatta tgaaattaa taagaaattg   1260
gttaaggaaa tcacacatag aggtttcgct atgttatcta ctacagaatt gaaggaaaag  1320
gttgttatta gattgtgttc aattaatcca agaactacaa ctgaagaaat gttgcaaatc  1380
atgatgaaga ttaaagcatt ggctgaagaa gtttctattt catacccatg tgttgctgaa  1440
catcatcatc atcatcatta a                                            1461

SEQ ID NO: 26           moltype = AA  length = 486
FEATURE                 Location/Qualifiers
source                  1..486
                        mol_type = protein
                        organism = Bacillus atrophaeaus
SEQUENCE: 26
MSENLQLSAE EMRQLGYQAV DLIIDHMNHL KSKPVSETID SDILRNKLTE SIPENGSDPK    60
ELLHFLNRNV FNQITHVDHP HFLAFVPGPN NYVGVVADFL ASGFNVFPTA WIAGAGAEQI   120
ELTTINWLKS MLGFPDSAEG LFVSGGSMAN LTALTVARQA KLNNDIENAV VYFSDQTHFS   180
VDRALKVLGF KHHQICRIET DEHLRISVSA LKKQIKEDRT KGKKPFCVIA NAGTTNCGAV   240
DSLNELADLC NDEDVWLHAD GSYGAPAILS EKGSAMLQGI HRADSLTDP HKWLFQPYDV    300
GCVLIRNSQY LSKTFRMMPE YIKDSETNVE GEINFGECGI ELSRRFRALK VWLSFKVFGV   360
AAFRQAIDHG IMLAEQVEAF LGKAKDWEVV TPAQLGIVTF RYIPSELAST DTINEINKKL   420
VKEITHRGFA MLSTTELKEK VVIRLCSINP RTTTEEMLQI MMKIKALAEE VSISYPCVAE   480
HHHHHH                                                              486

SEQ ID NO: 27           moltype = DNA  length = 573
FEATURE                 Location/Qualifiers
source                  1..573
                        mol_type = genomic DNA
                        organism = Streptomyces griseofuscus
SEQUENCE: 27
atgaacacct tcagaacagc cactgccaga gacatacctg atgtagcagc aactcttacg    60
gaagccttcg caactgatcc acccacgcag tgggtgttcc ccgacggtac tgccgccgtc   120
agcaggttct ttacacatgt tgcagatagg gttcacacgg ccggtggtat tgttgagcta   180
ctaccagaca gagccgccat gattgcattg ccaccacacg tgaggctgcc aggagaagct   240
gccgacggaa ggcaggcgga aattcagaga aggctggcag acaggcaccc gctgacacct   300
cactactacc tgctgtttta cggagttaga acggcacacc agggtccggg attgggcgga   360
agaatgctgg ccagattaac tagcagagct gataggaca gggtgggtac atatactgag   420
gcatccacct ggcgtggcgc tagactgatg ctgagacatg gattccatgc tacaaggcca   480
ctaagattgc cagatggacc cagcatgttt ccacttgga gagatccaat ccatgatcat   540
tctgatcatcg agcaccacca ccaccaccac tga                              573

SEQ ID NO: 28           moltype = AA  length = 182
FEATURE                 Location/Qualifiers
source                  1..182
                        mol_type = protein
                        organism = Streptomyces griseofuscus
SEQUENCE: 28
MNTFRTATAR DIPDVAATLT EAFATDPPTQ WVFPDGTAAV SRFFTHVADR VHTAGGIVEL    60
LPDRAAMIAL PPHVRLPGEA ADGRQAEIQR RLADRHPLTP HYYLLFYGVR TAHQGSGLGG   120
RMLARLTSRA DRDRVGTYTE ASTWRGARLM LRHGFHATRP LRLPDGPSMF PLWRDPIHDH   180
SD                                                                  182

SEQ ID NO: 29           moltype = DNA  length = 795
FEATURE                 Location/Qualifiers
source                  1..795
                        mol_type = genomic DNA
                        organism = Xanthomonas translucens
SEQUENCE: 29
```

```
atgacacaca cgctgccggc ctcaacctcg accagtacca gcactccggc aacggcagca    60
gctgctgcgg gcaaagcatc gggttacctg gcaccggcgg caattccagc tagcctgcag   120
ttactgccgc cccaccagcc ggaaggctca ccgggacaag ctttagacct ggcggtaaat   180
cgtgaggcgc tggcgatgcg cggctctgct cgctggcaac aagcaacacg tgacgccgac   240
ttaagcttcc cggcaggtgc cggtcatttc gcttgcgcgc ttggtgtggc aattgacgcc   300
caacgtactc ctcacttata cgctttactt gaacgttcac gcattgacgc ttcggcagcg   360
actaaggcca caagaatca ttaccgccgt ccacgccctt tcatgctgaa ccaacaaccg   420
agctgcaccc tcaggacga agaacaatta cgccataacg ttcatatcc ctcggggcat   480
tcggctattg gttggacatg gctcttatt cttagcgaga tcgcgccaga ccgtgcagat   540
gccttgattt tacgtgggcg tagtttcagt gagtcgcgcc tggtgtgcaa tgttcattgg   600
cacagcgatg tgttagcggg ccgcctgatg ggcgcggcga cagttgcccg tctgcacgcg   660
gatcctacct ttcgtgccga tttggatgca gcccgtgggg aaattgcacg tgcgcaggcc   720
cagggcgcga tgcctggaga ggactgcgct gcgcaagcac agacgctcca agtccgtcca   780
gcgagtgcat tataa                                                    795

SEQ ID NO: 30           moltype = AA  length = 264
FEATURE                 Location/Qualifiers
source                  1..264
                        mol_type = protein
                        organism = Xanthomonas translucens
SEQUENCE: 30
MTHTLPASTS TSTSTPATAA AAAGKASGYL APAAIPASLQ LLPPPPAEGS PGQALDLAVN    60
REALAMRGSA RWQQATRDAD LSFPAGAGHF ACALGVAIDA QRTPHLYALL ERSRIDASAA   120
TKAAKNHYRR PRPFMLNQQP SCTPQDEEQL RHNGSYPSGH SAIGWTWALI LSEIAPDRAD   180
ALILRGRSFS ESRLVCNVHW HSDVLAGRLM GAATVARLHA DPTFRADLDA ARGEIARAQA   240
QGAMPGEDCA AQAQTLQVRP ASAL                                         264

SEQ ID NO: 31           moltype = DNA  length = 777
FEATURE                 Location/Qualifiers
source                  1..777
                        mol_type = genomic DNA
                        organism = Methanolobus tindarius
SEQUENCE: 31
atggataata acaacatcac aattttgaag attggtggaa gcgtgatcac cgataagtct    60
gccgatgacg gcaccgctag actctcggag atagaaagaa tcgcagctga atctccggt   120
tttgagggca aacttatcat cgttcatggt gccggttctt tcggacaccc tcaagttaaa   180
agattcggcc tgaccgggaa atttgaccac gagggcagca tcatcacaca catgtctgtg   240
cgaaaattga cactatggt ggtggaaact ttaaacagtg ctggtatcaa tgctttacca   300
gtccacccta tggcgtgcgc tatttcaagt aattcacgca ttaagagtat gtttcgggag   360
caaatagagg aaatgttagc caatggattt gttccggtat tacaccggcga catggttatg   420
gatactgacc ttgggacgtc tgtacttagc ggcgaccaga tcgtgccgta cctggcaata   480
caaatgaaag cctcaagaat cggtatcggc agtgccgagg aaggagttct ggatgataag   540
ggcggtgtta tccctctgat aaataacgag aacttcgatg agattaaggc ttatctgtcc   600
ggttccgcaa acactgatgt tacgggtggg atgttaggga agttttaga attattggag   660
ttgagcgagc aaagtaacag tacctcatac atatttaatg ctggtaacac cggtaacatt   720
agtgatttcc tttccggcaa gaatatcggg accgctattg cgccggcac gatataa     777

SEQ ID NO: 32           moltype = AA  length = 258
FEATURE                 Location/Qualifiers
source                  1..258
                        mol_type = protein
                        organism = Methanolobus tindarius
SEQUENCE: 32
MDNNNITILK IGGSVITDKS ADDGTARLSE IERIAAEISG FEGKLIIVHG AGSFGHPQVK    60
RFGLTGKFDH EGSIITHMSV RKLNTMVVET LNSAGINALP VHPMACAISS NSRIKSMFRE   120
QIEEMLANGF VPVLHGDVVM DTDLGTSVLS GDQIVPYLAI QMKASRIGIG SAEEGVLDDK   180
GGVIPLINNE NFDEIKAYLS GSANTDVTGG MLGKVLELLE LSEQSNSTSY IFNAGNTGNI   240
SDFLSGKNIG TAIGAGTI                                                258
```

PRENYLATED PSILOCYBIN DERIVATIVES AND METHODS OF USING

RELATED APPLICATIONS

This application is a continuation of PCT Application No. PCT/CA2022/050091 filed Jan. 21, 2022, which claims the benefit of U.S. Provisional Application No. 63/140,322 filed Jan. 22, 2021 and U.S. Provisional Application No. 63/247,926 filed Sep. 24, 2021; the entire contents of Patent Application Nos. PCT/CA2022/050091, 63/140,322 and 63/247,926 are hereby incorporated by reference.

INCORPORATION OF SEQUENCE LISTING

A computer readable form of the Sequence Listing "29664-P63865US02_SequenceListing.xml" (57,159 bytes), submitted via EFS-WEB and created on Sep. 28, 2022, is herein incorporated by reference.

FIELD OF THE DISCLOSURE

The compositions and methods disclosed herein relate to a chemical compound known as psilocybin. Furthermore, the compositions and methods disclosed herein relate, in particular, to prenylated forms of psilocybin.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Psilocybin, for example, is a secondary metabolite that is naturally produced by certain mushrooms which taxonomically can be classified as belonging the Basidiomycota division of the fungi kingdom. Mushroom species which can produce psilocybin include species belonging to the genus *Psilocybe*, such as *Psilocybe azurescens, Psilocybe semilanceata, Psilocybe serbica, Psilocybe mexicana*, and *Psilocybe cyanescens*, for example. The interest of the art in psilocybin is well established. Thus, for example, psilocybin is a psychoactive compound and is therefore used as a recreational drug. Furthermore, psilocybin is used as a research tool in behavioral and neuro-imaging studies in psychotic disorders, and has been evaluated for its clinical potential in the treatment of mental health conditions (Daniel, J. et al., Mental Health Clin/, 2017; 7(1): 24-28), including to treat anxiety in terminal cancer patients (Grob, C. et al., Arch. Gen. Psychiatry, 2011, 68(1) 71-78) and to alleviate symptoms of treatment-resistant depression (Cathart-Harris, R.L. et al., Lancet Psychiatry, 2016, 3: 619-627).

Although the toxicity of psilocybin is low, adverse side effects, including, for example, panic attacks, paranoia, and psychotic states, sometimes together or individually referred to as "a bad trip", are not infrequently experienced by recreational psilocybin users.

There exists therefore a need in the art for improved psilocybin compounds.

SUMMARY OF THE DISCLOSURE

The following paragraphs are intended to introduce the reader to the more detailed description, not to define or limit the claimed subject matter of the present disclosure.

In one aspect, the present disclosure relates to psilocybin and derivative compounds.

In another aspect, the present disclosure relates to prenylated psilocybin derivative compounds and methods of making and using these compounds.

Accordingly, in one aspect, the present disclosure provides, in at least one embodiment, a chemical compound or salt thereof having formula (I):

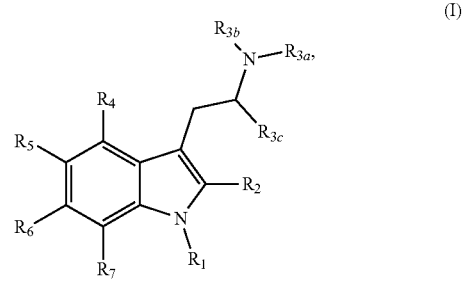

(I)

wherein, at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, O-alkyl group, an O-acyl group, a hydroxy group, a phosphate group, a glycosyloxy group, or a hydrogen atom, and wherein $R_{3a}$ and $R_{3b}$ are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

In at least one embodiment, in an aspect, one or at least one of $R_4$, $R_6$ or $R_7$ can be prenylated.

In at least one embodiment, in an aspect, one or at least one of $R_4$, $R_6$ or $R_7$ can be prenylated, and one or at least one of $R_4$, $R_6$ or $R_7$ which is not prenylated can be an alkyl group.

In at least one embodiment, in an aspect, one or at least one of $R_4$, $R_6$ or $R_7$ can be prenylated, and all of $R_4$, $R_6$ or $R_7$ which are not prenylated can be a hydrogen atom.

In at least one embodiment, in an aspect, $R_4$ can be prenylated, and one or at least one of $R_5$, $R_6$ or $R_7$ can be an alkyl group, wherein $R_5$, $R_6$ and $R_7$ which are not an alkyl group are a hydrogen atom.

In at least one embodiment, in an aspect, $R_6$ can be prenylated, and one or at least one of $R_4$, $R_5$ or $R_7$ can be an alkyl group, wherein $R_4$, $R_5$ and $R_7$ which are not an alkyl group are a hydrogen atom.

In at least one embodiment, in an aspect, $R_7$ can be prenylated, and one or at least one of $R_4$, $R_5$ or $R_6$ can be an alkyl group, wherein $R_4$, $R_5$ and $R_6$ which are not an alkyl group are a hydrogen atom.

In at least one embodiment, in an aspect, $R_4$ can be prenylated, and $R_7$ can be an alkyl group.

In at least one embodiment, in an aspect, $R_7$ can be prenylated, and $R_5$ can be an alkyl group.

In at least one embodiment, in an aspect, the alkyl group can be a $C_1$-$C_6$ alkyl group.

In at least one embodiment, in an aspect, the alkyl group can be an ethyl or methyl group.

In at least one embodiment, in an aspect, $R_1$ can be a hydrogen atom, and $R_2$ can be an alkyl group.

In at least one embodiment, in an aspect, $R_1$ and $R_2$ can each be a hydrogen atom.

In at least one embodiment, in an aspect, at least two of $R_1$, $R_2$, $R_4$, $R_5$, $R_6$, or $R_7$ can be a prenyl group, and wherein each non-prenylated $R_1$, $R_2$, $R_5$, $R_6$, or $R_7$ is a hydrogen atom, wherein $R_4$, when not prenylated, is an O-alkyl group, an O-acyl group, a hydroxy group, a phosphate group, a glycosyloxy group, or a hydrogen atom, and wherein $R_{3a}$ and $R_{3b}$ are a hydrogen atom, an alkyl group, acyl group or an aryl group.

In at least one embodiment, in an aspect, at least three of $R_1$, $R_2$, $R_4$, $R_5$, $R_6$, or $R_7$ can be a prenyl group, and wherein each non-prenylated $R_1$, $R_2$, $R_5$, $R_6$, or $R_7$ is a hydrogen atom, wherein $R_4$, when not prenylated, is an O-alkyl group, an O-acyl group, a hydroxy group, a phosphate group, a glycosyloxy group, or a hydrogen atom, and wherein $R_{3a}$ and $R_{3b}$ are a hydrogen atom, an alkyl group, acyl group or an aryl group.

In at least one embodiment, in an aspect, at least four of $R_1$, $R_2$, $R_4$, $R_5$, $R_6$, or $R_7$ can be a prenyl group, and wherein each non-prenylated $R_1$, $R_2$, $R_5$, $R_6$, or $R_7$ is a hydrogen atom, wherein $R_4$, when not prenylated, is an O-alkyl group, an O-acyl group, a hydroxy group, a phosphate group, a glycosyloxy group, or a hydrogen atom, and wherein $R_{3a}$ and $R_{3b}$ are a hydrogen atom, an alkyl group, acyl group or an aryl group.

In at least one embodiment, in an aspect, at least five of $R_1$, $R_2$, $R_4$, $R_5$, $R_6$, or $R_7$ can be a prenyl group, and wherein each non-prenylated $R_1$, $R_2$, $R_5$, $R_6$, or $R_7$ is a hydrogen atom, wherein $R_4$, when not prenylated, is an O-alkyl group, an O-acyl group, a hydroxy group, a phosphate group, a glycosyloxy group, or a hydrogen atom, and wherein $R_{3a}$ and $R_{3b}$ are each independently a hydrogen atom, an alkyl group, acyl group or an aryl group.

In at least one embodiment, all six of $R_1$, $R_2$, $R_4$, $R_5$, $R_6$, or $R_7$ can be a prenyl group.

In at least one embodiment, in an aspect, $R_{3a}$ and $R_2$ can be joined together, along with the nitrogen atom to which $R_{3a}$ is attached, to form an optionally substituted 5-7-membered heterocyclic ring, wherein the optional substituent on the heterocyclic ring is an alkyl group.

In at least one embodiment, in an aspect, the optionally substituted heterocyclic ring can be an optionally substituted 6-membered heterocyclic ring.

In at least one embodiment, in an aspect, the optional substituents can be methyl, ethyl or propyl.

In at least one embodiment, in an aspect, the chemical compound can be selected from the group consisting of compounds having formulas:

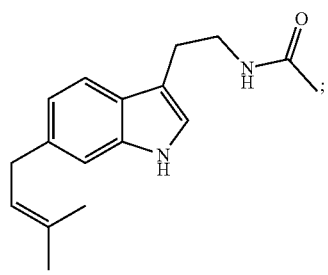
(IV)

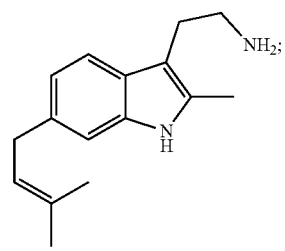
(V)

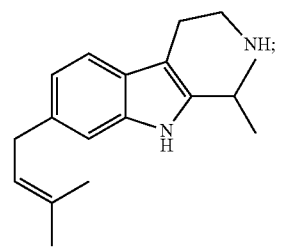
(VI)

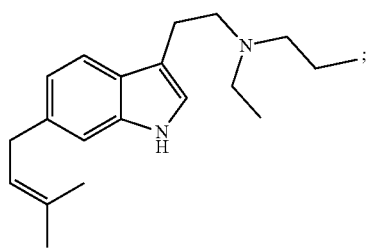
(VII)

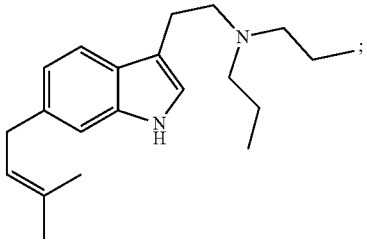
(VIII)

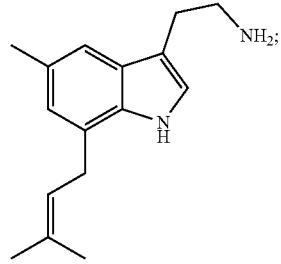
(IX)

-continued

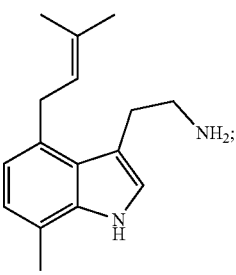
(X)

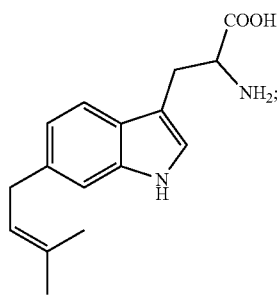
(XI)

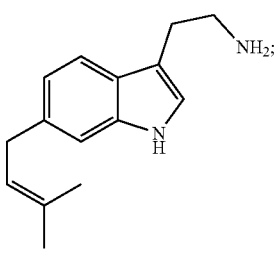
(XII)

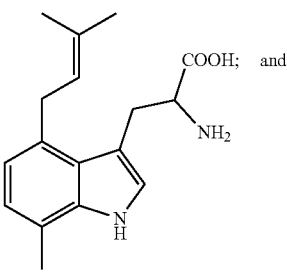
(XIII)

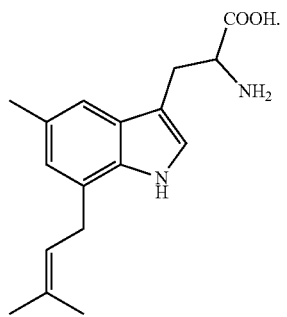
(XIV)

In another aspect, the present disclosure relates to pharmaceutical and recreational drug formulations comprising prenylated psilocybin derivatives. Accordingly, in one aspect, the present disclosure provides in at least one aspect, a pharmaceutical or recreational drug formulation comprising an effective amount of a chemical compound having formula (I):

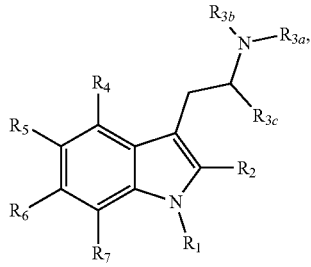
(I)

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and Rab are a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

In another aspect, the present disclosure relates to methods of treatment of psychiatric disorders. Accordingly, the present disclosure further provides a method for treating a psychiatric disorder, the method comprising administering to a subject in need thereof a pharmaceutical formulation comprising a chemical compound having formula (I):

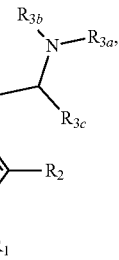
(I)

wherein at least one of $R_1$, $R_2$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and Rab are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

In at least one embodiment, in an aspect, the disorder can be a 5-$HT_{2A}$ receptor mediated disorder, or a 5-$HT_{1A}$ receptor mediated disorder.

In at least one embodiment, in an aspect, a dose can be administered of about 0.001 mg to about 5,000 mg.

In another aspect, the present disclosure provides, in at least one embodiment, a method for modulating a 5-$HT_{2A}$ receptor or a 5-HT$_{1A}$ receptor, the method comprising contacting a 5-HT$_{2A}$ receptor or a 5-HT$_{1A}$ receptor with a chemical compound or salt thereof having formula (I):

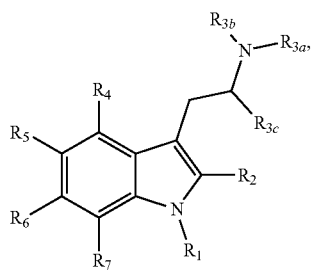

(I)

wherein, at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and Rab are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

In some embodiments, in an aspect, the reaction conditions can be in vitro reaction conditions.

In some embodiments, in an aspect, the reaction conditions can be in vivo reaction conditions.

In another aspect, the present disclosure relates to methods of making prenylated psilocybin derivatives. Accordingly, in one aspect, the present disclosure provides, in at least one embodiment, a method of making a prenylated psilocybin derivative, the method comprising contacting a psilocybin derivative precursor compound having formula (XXII):

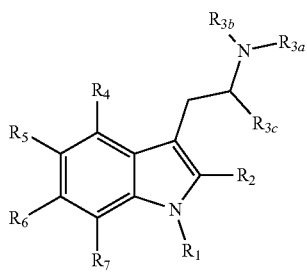

(XXII)

wherein each of $R_1$, $R_2$, $R_4$, $R_5$, $R_6$, or $R_7$ is independently a hydrogen atom or an alkyl group, wherein $R_4$ is an alkyl group, an O-alkyl group, an O-acyl group, a hydroxy group, a phosphate group, a glycosyloxy group, or a hydrogen atom, and wherein $R_{3a}$ and $R_{3b}$ are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group, with sufficient quantities of a prenyl compound and a catalytic quantity of a prenyl transferase under reaction conditions permitting an enzyme catalyzed conversion of the psilocybin derivative precursor compound to form a prenylated psilocybin derivative compound having formula (I):

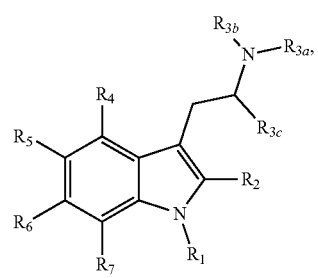

(I)

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and $R_{3b}$ are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

In at least one embodiment, in an aspect, the reaction conditions can be in vitro reaction conditions.

In at least one embodiment, in an aspect, the reaction conditions can be in vivo reaction conditions.

In at least one embodiment, in an aspect, the psilocybin derivative precursor compound and the prenyl compound can be contacted with the prenyl transferase in a host cell, wherein the host cell comprises a chimeric nucleic acid sequence comprising as operably linked components:
  (i) a nucleic acid sequence controlling expression in the host cell; and
  (ii) a nucleic acid sequence encoding a prenyl transferase, and the host cell is grown to express the prenyl transferase and to produce the prenylated psilocybin derivative compound.

In at least one embodiment, in an aspect, the prenyl compound can be a phosphorylated prenyl compound.

In at least one embodiment, in an aspect, the phosphorylated prenyl compound can be selected from the group consisting of dimethylallyl pyrophosphate (DMAPP), geranyl pyrophosphate (GPP), farnesyl pyrophosphate (FPP), and geranylgeranyl pyrophosphate (GGPP).

In at least one embodiment, in an aspect, the prenyl transferase can be an enzyme encoded by a nucleic acid selected from:
  (a) SEQ.ID NO: 13, SEQ.ID NO: 15, SEQ. ID NO: 17, SEQ.ID NO: 19, SEQ.ID NO: 21 and SEQ.ID NO: 23;
  (b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ.ID NO: 14, SEQ.ID NO: 16, SEQ. ID NO: 18, SEQ.ID NO: 20, SEQ.ID NO: 22 and SEQ.ID NO: 24;

(f) a nucleic acid sequence that encodes a functional variant of any one of the amino acid sequences set forth in SEQ.ID NO: 14, SEQ.ID NO: 16, SEQ. ID NO: 18, SEQ.ID NO: 20, SEQ.ID NO: 22, and SEQ.ID NO: 24; and (g) a nucleic acid sequence that hybridizes under stringent conditions to any one of the nucleic acid sequences set forth in (a), (b), (c), (d), (e) or (f).

In at least one embodiment, the host cell can comprise a psilocybin biosynthetic enzyme complement.

In at least one embodiment, in an aspect, the psilocybin biosynthetic enzyme complement can comprise at least one enzyme encoded by a nucleic acid selected from:

(a) SEQ.ID NO: 1, SEQ.ID NO: 3, SEQ.ID NO: 5, SEQ.ID NO: 7, SEQ.ID NO: 9, and SEQ.ID NO 11;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ.ID NO: 2, SEQ.ID NO: 4, SEQ.ID NO: 6, SEQ.ID NO: 8, SEQ.ID NO: 10, and SEQ.ID NO 12;

(f) a nucleic acid sequence that encodes a functional variant of any one of the amino acid sequences set forth in SEQ.ID NO: 2, SEQ.ID NO: 4, SEQ.ID NO: 6, SEQ.ID NO: 8, SEQ.ID NO: 10, and SEQ.ID NO 12; and (g) a nucleic acid sequence that hybridizes under stringent conditions to any one of the nucleic acid sequences set forth in (a), (b), (c), (d), (e) or (f).

In at least one embodiment, in an aspect, the prenyl compound can be exogenously supplied in the host cell's growth medium.

In at least one embodiment, in an aspect, the precursor psilocybin derivative compound can be exogenously supplied in the host cell's growth medium.

In at least one embodiment, in an aspect, the method can further include a step comprising isolating the prenylated psilocybin derivative compound, from the host cell and/or a host cell medium.

In at least one embodiment, in an aspect, the host cell can be a microorganism.

In at least one embodiment, in an aspect, the host cell can be a bacterial cell or a yeast cell.

In at least one embodiment, in an aspect, the psilocybin derivative precursor compound can be a chemical compound selected from the group having formula (XV); (XVI); (XVII); (XVIII); (XIX); (XX); and (XXI):

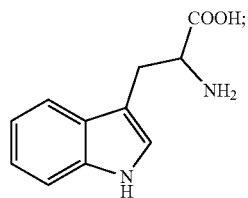
(XV)

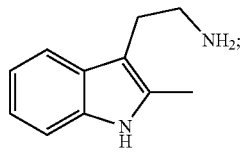
(XVI)

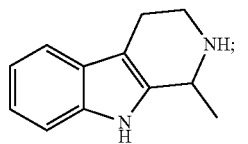
(XVII)

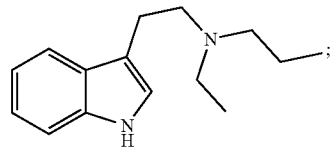
(XVIII)

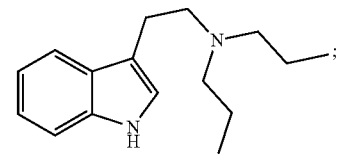
(XIX)

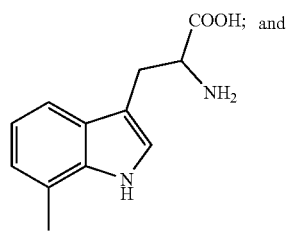
(XX)

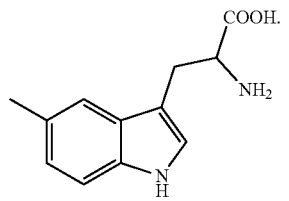
(XXI)

In at least one embodiment, in an aspect, the psilocybin derivative precursor compound can be a chemical compound having formula (XV):

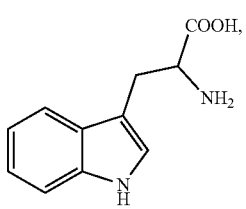

(XV)

the prenyl compound can be dimethylallyl pyrophosphate (DMAPP), and the formed prenylated psilocybin derivative compound can have formula (XI):

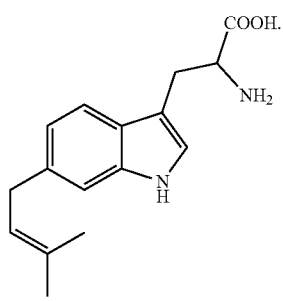

(XI)

In at least one embodiment, in an aspect, the prenylated psilocybin derivative compound having formula (XI) can further be reacted with a decarboxylase to form a second prenylated psilocybin derivative compound having formula (XII):

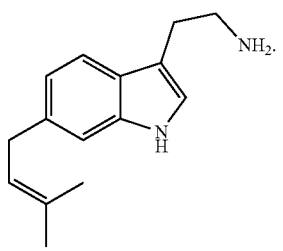

(XII)

In at least one embodiment, in an aspect, the decarboxylase can be an enzyme encoded by a nucleic acid selected from:
(a) SEQ.ID NO: 25;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 26;
(f) a nucleic acid sequence that encodes a functional variant of any one of the amino acid sequence set forth in SEQ.ID NO: 26; and
(g) a nucleic acid sequence that hybridizes under stringent conditions to any one of the nucleic acid sequences set forth in (a), (b), (c), (d), (e) or (f).

In at least one embodiment, in an aspect, the second prenylated psilocybin derivative compound having formula (XII) can further be reacted with an N-acetyl transferase to form a third prenylated psilocybin derivative compound having formula (IV):

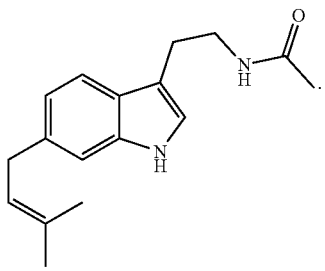

(IV)

In at least one embodiment, in an aspect, the N-acetyl transferase can be an enzyme encoded by a nucleic acid selected from:
(a) SEQ.ID NO: 27;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 28;
(f) a nucleic acid sequence that encodes a functional variant of any one of the amino acid sequence set forth in SEQ.ID NO: 28; and
(g) a nucleic acid sequence that hybridizes under stringent conditions to any one of the nucleic acid sequences set forth in (a), (b), (c), (d), (e), or (f).

In at least one embodiment, in an aspect, the psilocybin derivative precursor compound can be a chemical compound having formula (XVI):

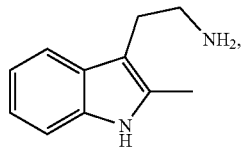

(XVI)

the prenyl compound can be dimethylallyl pyrophosphate (DMAPP), and the formed prenylated psilocybin derivative compound can have formula (V):

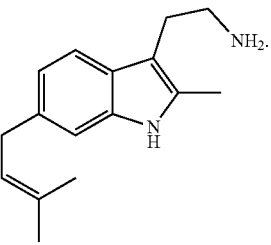

(V)

In at least one embodiment, in an aspect, the psilocybin derivative precursor compound can be a chemical compound having formula (XVII):

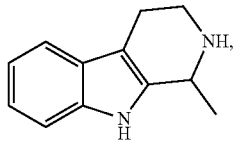

(XVII)

the prenyl compound can be dimethylallyl pyrophosphate (DMAPP), and the formed prenylated psilocybin derivative compound can have formula (VI):

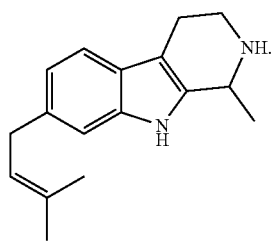

(VI)

In at least one embodiment, in an aspect, the psilocybin derivative precursor compound can be a chemical compound having formula (XVIII):

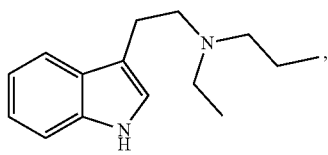

(XVIII)

the prenyl compound can be dimethylallyl pyrophosphate (DMAPP), and the formed prenylated psilocybin derivative compound can have formula (VII):

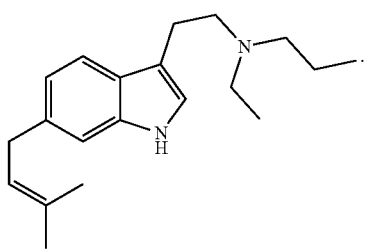

(VII)

In at least one embodiment, in an aspect, the psilocybin derivative precursor compound can be a chemical compound having formula (XIX):

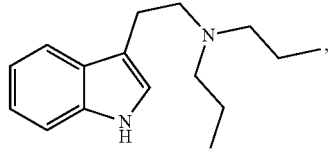

(XIX)

the prenyl compound can be dimethylallyl pyrophosphate (DMAPP), and the formed prenylated psilocybin derivative compound can have formula (VIII):

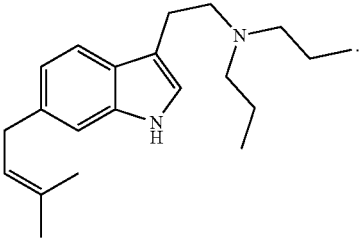

(VIII)

In at least one embodiment, in an aspect, the psilocybin derivative precursor compound can be a chemical compound having formula (XX):

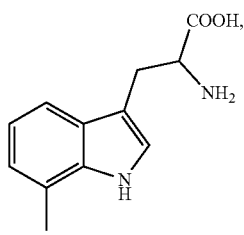

(XX)

the prenyl compound can be dimethylallyl pyrophosphate (DMAPP), and the formed prenylated psilocybin derivative compound can have formula (XIII):

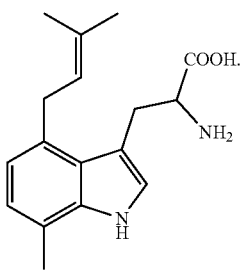

(XIII)

In at least one embodiment, in an aspect, the prenylated psilocybin derivative having formula (XIII) can further be reacted with a decarboxylase to form a second prenylated psilocybin derivative compound having formula (X):

(X)

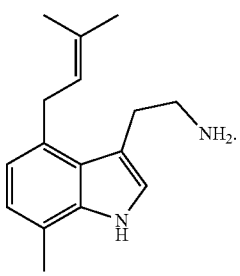

In at least one embodiment, in an aspect, the psilocybin derivative precursor compound can be a chemical compound having formula (XXI):

(XXI)

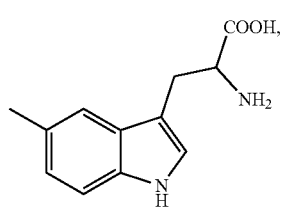

the prenyl compound can be dimethylallyl pyrophosphate (DMAPP), and the formed prenylated psilocybin derivative compound can have formula (XIV):

(XIV)

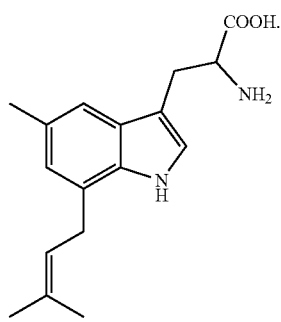

In at least one embodiment, in an aspect, the prenylated psilocybin derivative having formula (XIV) can further be reacted with a decarboxylase to form a second prenylated psilocybin compound derivative having formula (IX):

(IX)

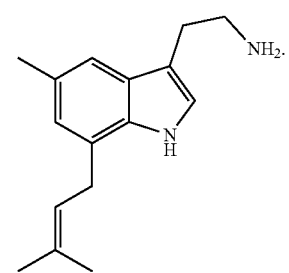

In at least one embodiment, in an aspect, the formed prenylated psilocybin derivative compound can subsequently be converted under in vivo or in vitro reaction conditions to form a second prenylated psilocybin derivative compound.

In at least one embodiment, in an aspect, the formed prenylated psilocybin derivative compound can be a compound selected from a compound having formula (XI), (XIII) or (XIV):

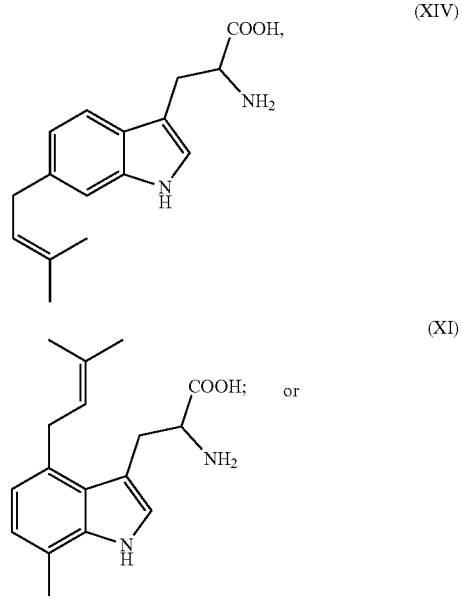

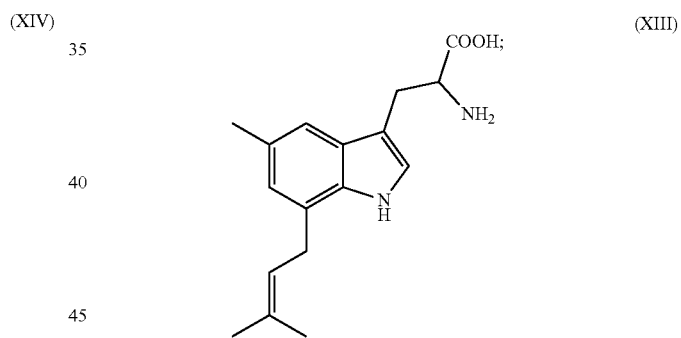

and can subsequently be converted under in vivo or in vitro reaction conditions, wherein the formed prenylated psilocybin derivative compound having formula (XI), (XIII) or (XIV) is contacted with a decarboxylase to form a second prenylated psilocybin derivative compound selected from a chemical compound having formula (XII); (X); or (IX):

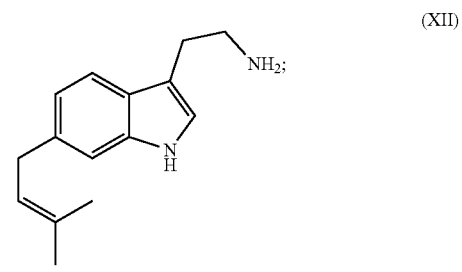

-continued

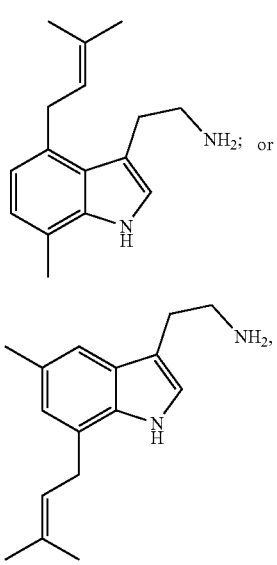

(X)

(IX)

respectively.

In at least one embodiment, in an aspect, the formed second prenylated psilocybin derivative compound can subsequently be converted under in vivo or in vitro reaction conditions to form a third prenylated psilocybin derivative compound.

In at least one embodiment, in an aspect, the second prenylated psilocybin derivative compound having formula (XII) can subsequently be converted under in vivo or in vitro reaction conditions wherein the second prenylated psilocybin derivative compound is contacted with an N-acetyl transferase to form a third prenylated psilocybin derivative compound having formula (IV):

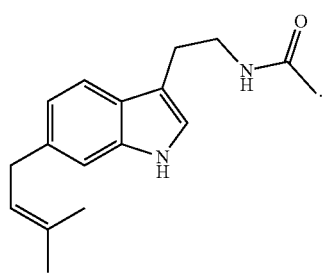

(IV)

In at least one embodiment, in an aspect, the subsequent conversion under in vivo reaction conditions can comprise growing a host cell expressing a decarboxylase, wherein the host cell is grown to produce the second prenylated psilocybin derivative compound.

In at least one embodiment, in an aspect, the subsequent conversion under in vivo reaction conditions can further comprise growing a host cell expressing a decarboxylase and an N-acetyl transferase, wherein the host cell is grown to produce the second prenylated psilocybin derivative compound and the third prenylated psilocybin derivative compound.

In at least one embodiment, in an aspect, the formed prenylated psilocybin derivative compound can subsequently be converted under in vivo reaction conditions to form a second prenylated psilocybin derivative compound.

In at least one embodiment, in an aspect, the formed prenylated psilocybin derivative compound can be a compound selected from a compound having formula (XI), (XIII) or (XIV):

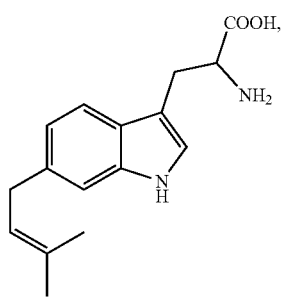

(XIV)

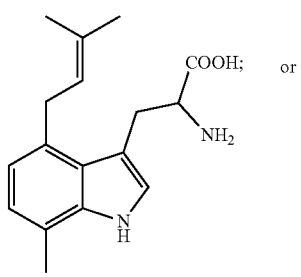

(XI)

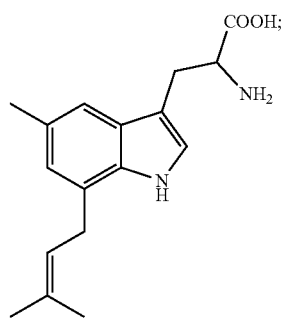

(XIII)

and subsequently be converted under in vivo reaction conditions wherein the host cell further expresses a decarboxylase to form a second prenylated psilocybin derivative compound selected from a chemical compound having formula (XII); (X); or (IX):

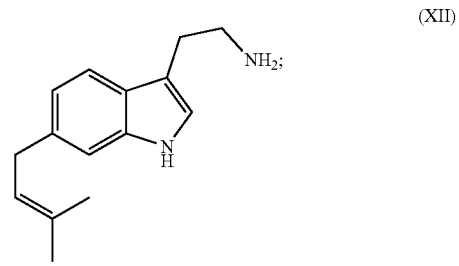 [SMILES: CC(C)=CCc1ccc2c(CCN)c[nH]c2c1]

(XII)

-continued

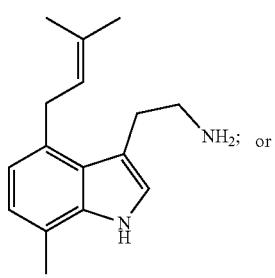

(X)

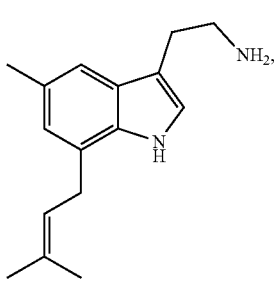

(IX)

respectively, and wherein the host cell is grown to produce the second prenylated psilocybin derivative compound.

In at least one embodiment, in an aspect, the formed second prenylated psilocybin derivative compound can subsequently be converted under in vivo or in vitro reaction conditions to form a third prenylated psilocybin derivative compound.

In at least one embodiment, in an aspect, the second prenylated psilocybin derivative compound having formula (XII) can subsequently be converted under in vivo reaction conditions, the host cell further comprising a N-acetyl transferase to form a third prenylated psilocybin derivative compound having formula (IV):

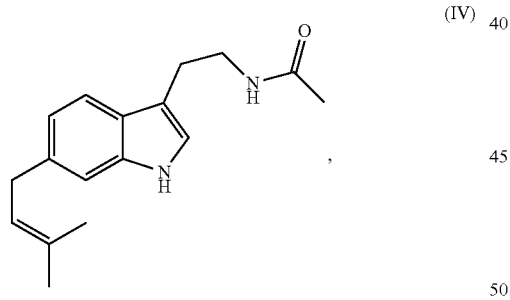

(IV)

and wherein the host cell is grown to produce the third prenylated psilocybin derivative compound.

In at least one embodiment, in an aspect, the prenyl compound can be formed by reacting dimethylallyl alcohol (DMAOH) in the presence of adenosine tri-phosphate (ATP) of an acid phosphatase and an isopentenyl phosphate kinase, wherein the acid phosphatase is an enzyme encoded by a nucleic acid sequence selected from:
(a) SEQ.ID NO: 29;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 30;
(f) a nucleic acid sequence that encodes a functional variant of any one of the amino acid sequence set forth in SEQ.ID NO: 30; and
(g) a nucleic acid sequence that hybridizes under stringent conditions to any one of the nucleic acid sequences set forth in (a), (b), (c), (d), (e) or (f); and wherein the isopentenyl phosphate kinase is an enzyme encoded by a nucleic acid sequence selected from:
(a) SEQ.ID NO: 31;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 32;
(f) a nucleic acid sequence that encodes a functional variant of any one of the amino acid sequence set forth in SEQ.ID NO: 32; and
(g) a nucleic acid sequence that hybridizes under stringent conditions to any one of the nucleic acid sequences set forth in (a), (b), (c), (d), (e) or (f).

In another aspect, the present disclosure provides, in at least one embodiment, a host cell comprising a chimeric nucleic acid sequence comprising as operably linked components:
(i) a nucleic acid sequence controlling expression in the host cell; and
(ii) a nucleic acid sequence encoding a prenyl transferase, the host cell capable of being grown to express the prenyl transferase and produce a prenylated psilocybin derivative compound having the formula (I):

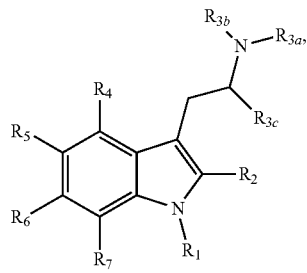

(I)

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and Rab are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

In at least one embodiment, in an aspect, the prenyl transferase can be an enzyme encoded by a nucleic acid selected from:

(a) SEQ.ID NO: 13, SEQ.ID NO: 15, SEQ. ID NO: 17, SEQ.ID NO: 19, SEQ.ID NO: 21 and SEQ.ID NO: 23;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 14, SEQ.ID NO: 16, SEQ. ID NO: 18, SEQ.ID NO: 20, SEQ.ID NO: 22 and SEQ.ID NO: 24;
(f) a nucleic acid sequence that encodes a functional variant of any one of the amino acid sequences set forth in SEQ.ID NO: 14, SEQ.ID NO: 16, SEQ. ID NO: 18, SEQ.ID NO: 20, SEQ.ID NO: 22, and SEQ.ID NO: 24; and
(g) a nucleic acid sequence that hybridizes under stringent conditions to any one of the nucleic acid sequences set forth in (a), (b), (c), (d), (e), or (f).

In at least, one embodiment, in an aspect, the host cell can further heterologously express a decarboxylase encoded by a nucleic acid selected from:
(a) SEQ.ID NO: 25;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 26;
(f) a nucleic acid sequence that encodes a functional variant of any one of the amino acid sequence set forth in SEQ.ID NO: 26; and
(g) a nucleic acid sequence that hybridizes under stringent conditions to any one of the nucleic acid sequences set forth in (a), (b), (c), (d), (e) or (f).

In at least, one embodiment, in an aspect, the host cell can further heterologously express an N-acetyl transferase encoded by a nucleic acid selected from:
(a) SEQ.ID NO: 27;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 28;
(f) a nucleic acid sequence that encodes a functional variant of any one of the amino acid sequence set forth in SEQ.ID NO: 28; and
(g) a nucleic acid sequence that hybridizes under stringent conditions to any one of the nucleic acid sequences set forth in (a), (b), (c), (d), (e) or (f).

In at least one embodiment, in an aspect, the host cell can further heterologously express an acid phosphatase encoded by a nucleic acid sequence selected from:
(a) SEQ.ID NO: 29;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 30;
(f) a nucleic acid sequence that encodes a functional variant of any one of the amino acid sequence set forth in SEQ.ID NO: 30; and
(g) a nucleic acid sequence that hybridizes under stringent conditions to any one of the nucleic acid sequences set forth in (a), (b), (c), (d), (e) or (f).

In at least one embodiment, in an aspect, the host cell can further heterologously express an isopentenyl phosphate kinase encoded by a nucleic acid sequence selected from:
(a) SEQ.ID NO: 31;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 32;
(f) a nucleic acid sequence that encodes a functional variant of any one of the amino acid sequence set forth in SEQ.ID NO: 32; and
(g) a nucleic acid sequence that hybridizes under stringent conditions to any one of the nucleic acid sequences set forth in (a), (b), (c), (d), (e) or (f).

In at least one embodiment, in an aspect, the prenylated psilocybin derivative compound produced by the host cell can be:

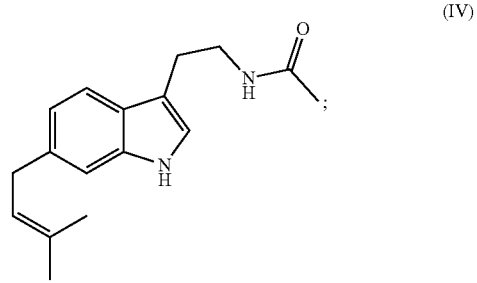 [SMILES: CC(=O)NCCc1c[nH]c2cc(CC=C(C)C)ccc12]

(IV)

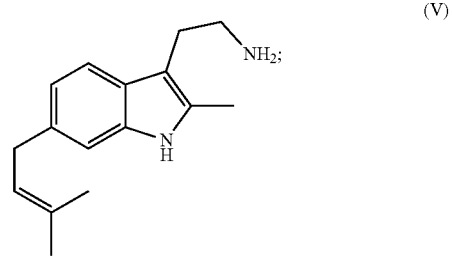 [SMILES: CC(C)=CCc1ccc2c(CCN)c(C)[nH]c2c1]

(V)

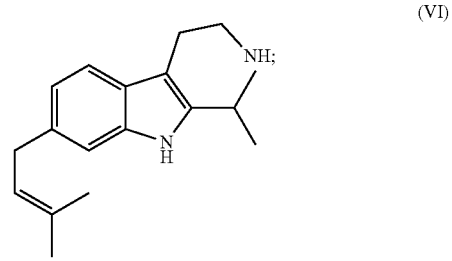

(VI)

(VII)
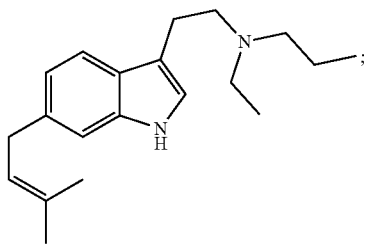

(VIII)
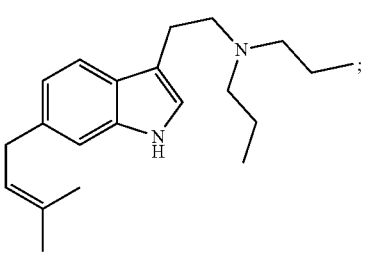

(IX)
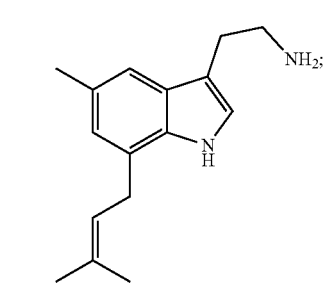

(X)
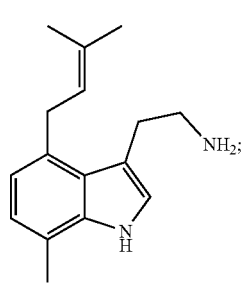

(XI)
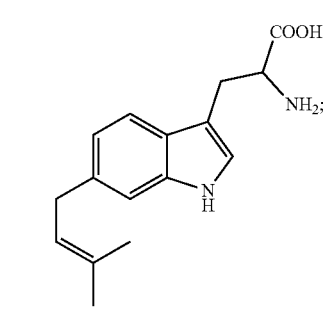

(XII)
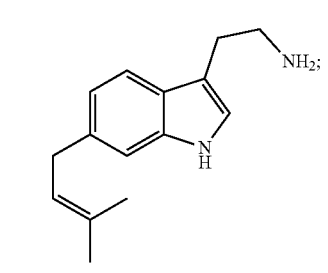

(XIII)
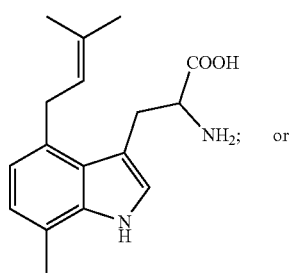

or (XIV)
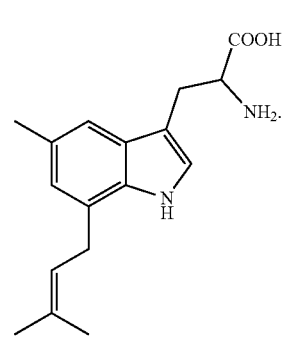

In another aspect the present disclosure provides, in at least one mbodiment, a use of a chemical compound having formula (I):

(I)
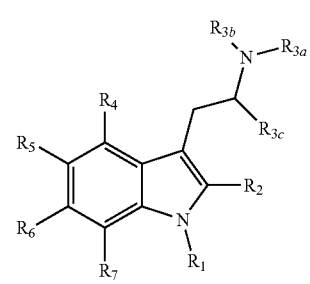

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and Rab are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group in the manufacture of a pharmaceutical or recreational drug formulation.

In at least one embodiment, in an aspect, the manufacture can comprise formulating the chemical compound with a pharmaceutically acceptable excipient, diluent or carrier.

In another aspect, the present disclosure provides, in at least one embodiment, a use of a chemical compound having formula (I):

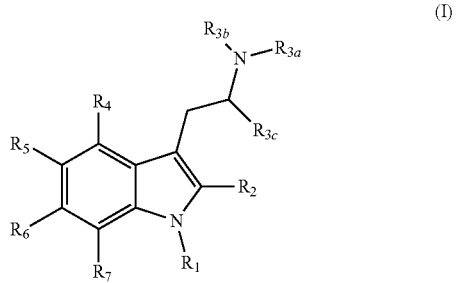

(I)

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and Rab are independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group, together with a pharmaceutically acceptable diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The FIGS. are not intended to limit the present disclosure.

Figure 1:
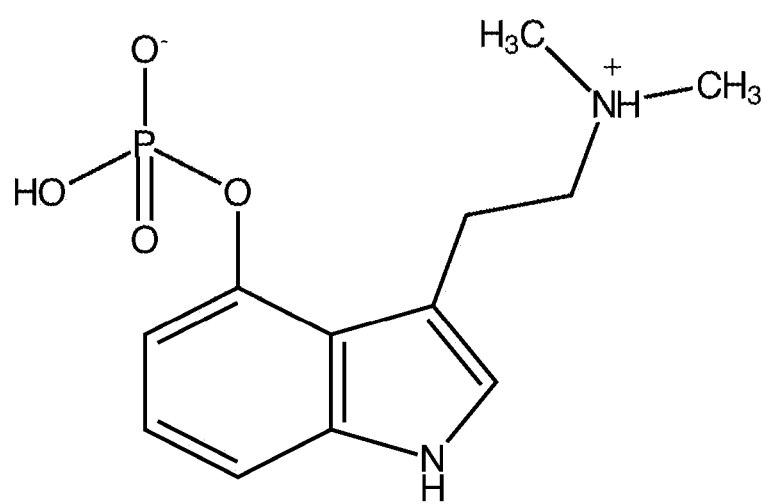
FIG. 1 depicts the chemical structure of psilocybin.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Sefinitions

The term "psilocybin", as used herein, refers to a chemical compound having the structure set forth in FIG. 1, and further includes salts, thereof, such as a sodium salt, a potassium salt, etc.

The terms "prenyl group", and "prenyl", as used herein, refers to a chemical group having the structure (II):

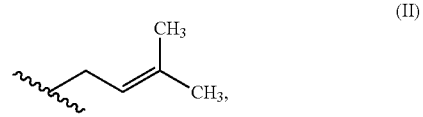 [SMILES: *CC=C(C)C]

and further includes poly-prenyl groups having the structure:

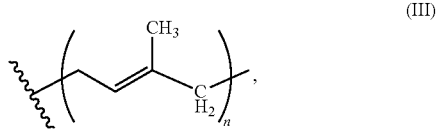

wherein n is an integer having a value of 2 or more, e.g., 2, 3, 4, 5, etc. Furthermore, the term "prenyl compound" refers to a chemical compound being, substantially being, or possessing a reactive prenyl group, i.e., a prenyl group that may be received by another entity. Prenyl compounds include, for example, geranyl pyrophosphate (GPP), dimethylallyl diphosphate (DMAPP), farnesyl pyrophosphate (FPP) and geranylgeranyl pyrophosphate (GGPP).

Figure 2:
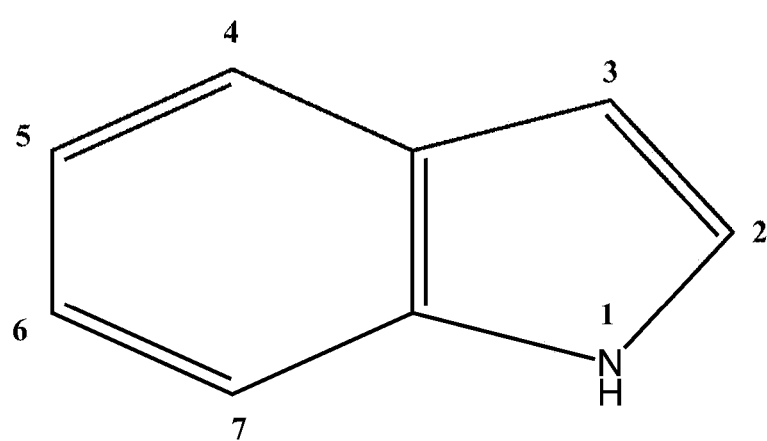
FIG. 2 depicts a certain prototype structure of a psilocybin derivative precursor compound, namely an indole. Certain carbon and nitrogen atoms may be referred herein by reference to their position within the indole structure, i.e., $N_1$, $C_2$, $C_3$ etc. The pertinent atom numbering is shown.

The term "indole prototype structure", as used herein, refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example $R_4$ and $R_6$ reference chemical groups attached to the $C_4$ and $C_6$ atom, respectively. In addition, $R_{3a}$, $R_{3b}$ and $R_{3c}$, in this respect, reference chemical groups extending from the ethyl-amino group extending in turn from the $C_3$ atom of the prototype indole structure.

The terms "prenylated psilocybin derivative" and "prenylated psilocybin derivative compound", as used herein, refer to a chemical compound comprising psilocybin modified in such a manner that it includes least one prenyl group, for example, by substituting a hydrogen atom at the $N_1$, $C_2$, $C_4$, $C_6$ or $C_7$ atoms with a prenyl group. It is noted that reference may be made to specific carbon or nitrogen atoms of the psilocybin derivative compound which may be prenylated, for example, 7-prenylated-psilocybin refers to a prenylated psilocybin in which carbon atom number 7 ($C_7$) (as identified in the indole prototype structure) is prenylated, or, similarly, 1-prenylated-psilocybin refers to a prenylated psilocybin in which nitrogen atom number 1 ($N_1$) (as identified in the indole prototype structure) is prenylated. The terms further includes psilocybin derivatives which are prenylated, for example, psilocybin derivatives in which the phosphate group bonded to carbon $C_4$ has been substituted by another group, such as a hydroxy group, or a hydrogen atom, for example. Prenylated psilocybin derivatives and prenylated psilocybin derivative compounds further include chemical compounds having formula (I):

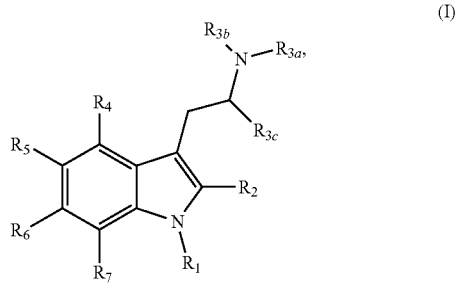

(I)

wherein, at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, O-alkyl group, an O-acyl group, a hydroxy group, a phosphate group, a glycosyloxy group, or a hydrogen atom, and wherein $R_{3a}$ and $R_{3b}$ are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

The term "psilocybin derivative precursor compound", as used herein, refers to a chemical compound that may serve as a precursor compound in the synthesis or biosynthesis of a prenylated psilocybin derivative, and includes compounds comprising an indole prototype structure, including, for example, tryptophan, tryptamine, 4-hydroxyindole, 4-hydroxytryptophan, 4-hydroxytryptamine, norbaeocystin, and baeocystin, and further includes compounds having the chemical formula (XXII):

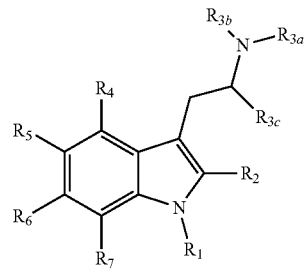

(XXII)

wherein each of $R_1$, $R_2$, $R_4$, $R_5$, $R_6$, or $R_7$ is independently a hydrogen atom or an alkyl group, wherein $R_4$ is an alkyl group, an O-alkyl group, an O-acyl group, a hydroxy group, a phosphate group, a glycosyloxy group, or a hydrogen atom, and wherein $R_{3a}$ and Rab are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

Figure 3A:
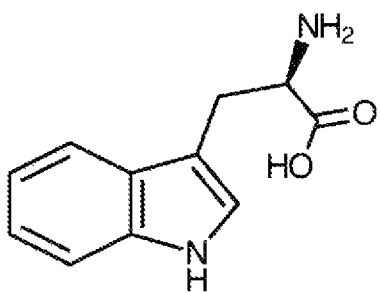
FIGS. 3A, 3B, 3C, 3D, 3E, 3F, and 3G depict the chemical structures of example psilocybin derivative precursor compounds, notably L-tryptophan (FIG. 3A), tryptamine (FIG. 3B), 4-hydroxytryptamine (FIG. 3C), L-4-hydroxytryptophan (FIG. 3D), 4-hydroxyindole (FIG. 3E), norbaeocystin (FIG. 3F), and baeocystin (FIG. 3G)

The term "tryptophan", as used herein, refers to a chemical compound having the structure set forth in FIG. 3A and further includes its D-enantiomeric form (not shown).

Figure 3B:
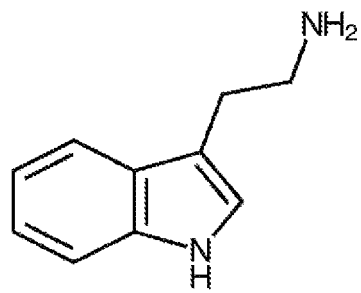

The term "tryptamine", as used herein, refers to a chemical compound having the structure set forth in FIG. 3B.

Figure 3C:
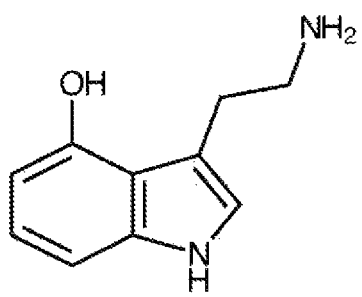

The term "4-hydroxytryptamine", as used herein, refers to a chemical compound having the structure set forth in FIG. 3C.

Figure 3D:
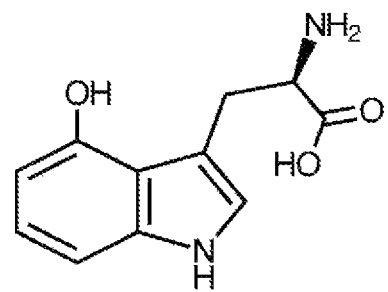

The term "4-hydroxytryptophan", as used herein, refers to a chemical compound having the structure set forth in FIG. 3D and further includes its D-enantiomeric form (not shown).

Figure 3E:
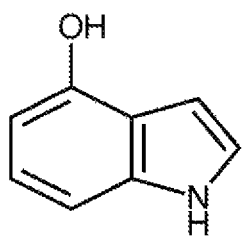

The term "4-hydroxyindole", as used herein, refers to a chemical compound having the structure set forth in FIG. 3E.

Figure 3F:
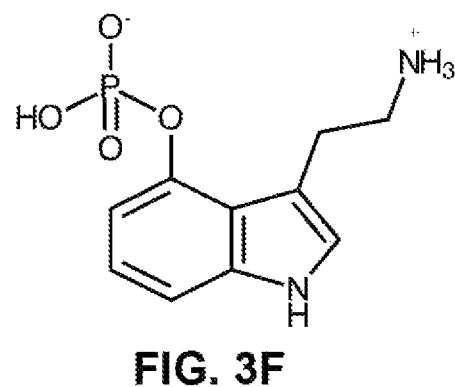

The term "norbaeocystin", as used herein, refers to a chemical compound having the structure set forth in FIG. 3F.

Figure 3G:
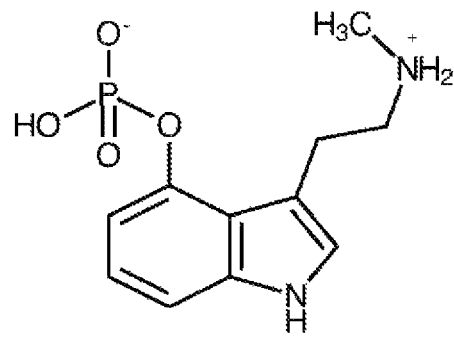

The term "baeocystin", as used herein, refers to a chemical compound having the structure set forth in FIG. 3G.

Figure 5A:
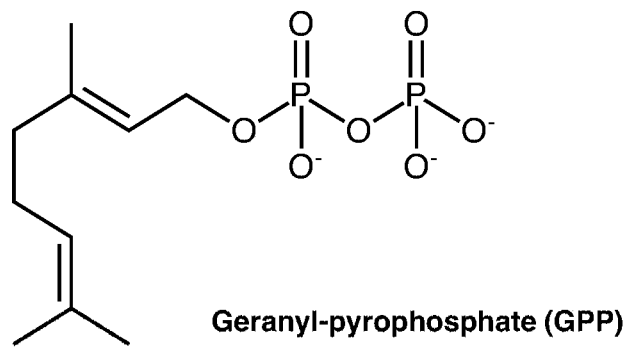
FIGS. 5A, 5B, 5C, and 5D depict the chemical structure of geranyl pyrophosphate (GPP), dimethylallyl pyrophosphate (DMAPP), farnesyl pyrophosphate (FPP), and geranylgeranyl pyrophosphate (GGPP), respectively.

The terms "geranyl pyrophosphate" or "GPP", as used herein, refer to a chemical compound having the structure set forth in FIG. 5A.

Figure 5B:
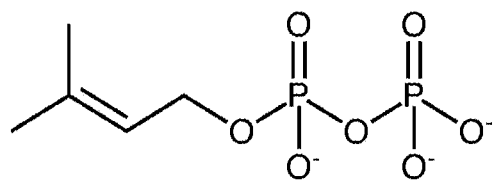

The terms "dimethylallyl diphosphate" or "DMAPP", as used herein, refer to a chemical compound having the structure set forth in FIG. 5B.

Figure 5C:
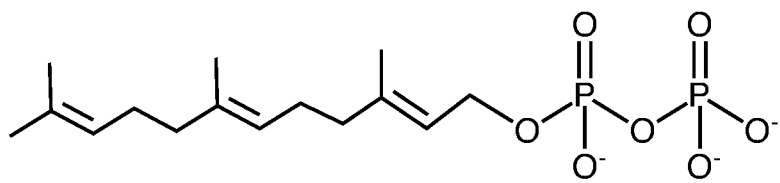

The terms "farnesyl pyrophosphate" or "FPP", as used herein, refer to a chemical compound having the structure set forth in FIG. 5C.

Figure 5D:
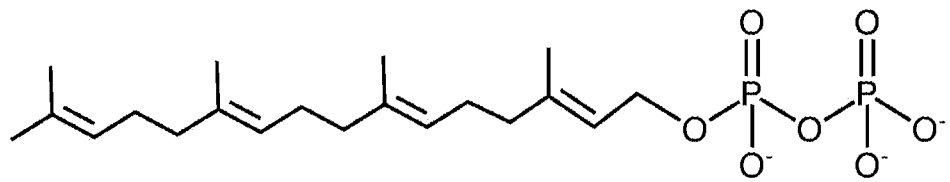
Figure 6A:
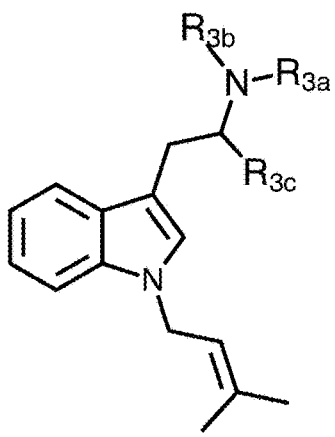
FIGS. 6A, 6B, 6C, 6D, 6E, and 6F depict certain example prenylated compounds, notably Ni prenylated compounds, and in particular a (N)1-prenyl psilocybin derivative (comprising a hydrogen atom at each of $C_2$, $C_4$, $C_5$, $_6$ and $C_7$) (FIG. 6A), a (N)1-prenyl-2-methyl psilocybin derivative (FIG. 6B), a (N)1-prenyl-4-methyl psilocybin derivative (FIG. 6C), a (N)1-prenyl-5-methyl psilocybin derivative (FIG. 6D), a (N)1-prenyl-6-methyl psilocybin derivative (FIG. 6E), and a (N)1-prenyl-7-methyl psilocybin derivative (FIG. 6F). It is noted that $R_{3a}$ and $R_{3b}$ are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, and $R_{3b}$ is a hydrogen atom, an alkyl group, acyl group or an aryl group, and wherein $R_{3c}$ is a hydrogen atom or a carboxy group.
Figure 6B:
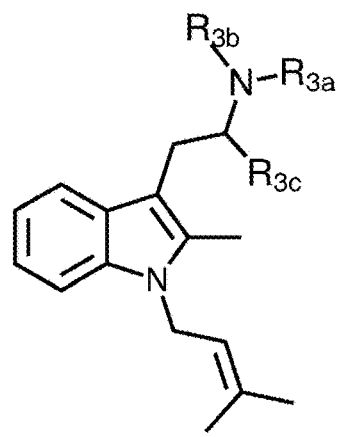
Figure 6C:
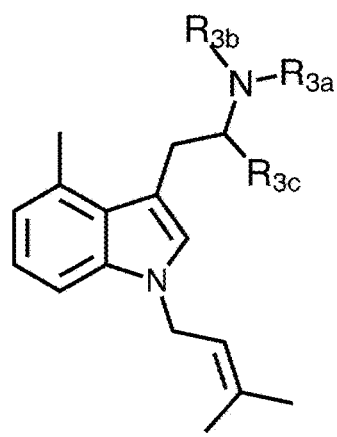
Figure 6D:
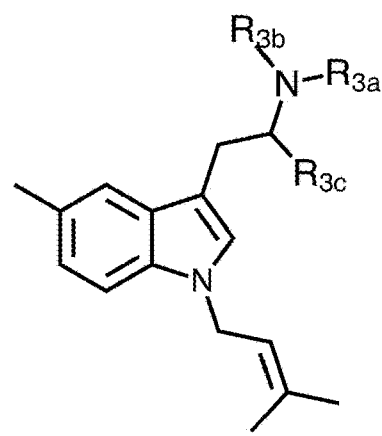
Figure 6E:
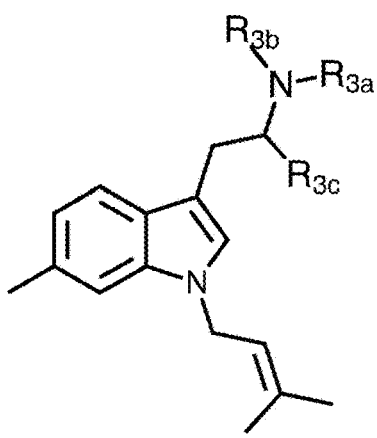
Figure 6F:
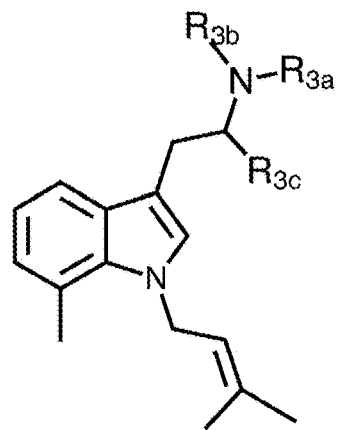
Figure 7A:
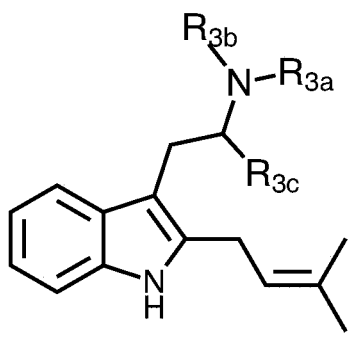
FIGS. 7A, 7B, 7C, 7D, 7E, and 7F depict certain example prenylated compounds, notably $C_2$ prenylated compounds, and in particular a $C_2$-prenyl psilocybin derivative (comprising a hydrogen atom at each of $N_1$, $C_4$, $C_5$, $C_6$ and $_7$) (FIG. 7A), a (N)1-methyl-2-prenyl psilocybin derivative (FIG. 7B), 2-prenyl-4-methyl psilocybin derivative (FIG. 7C), 2-prenyl-5-methyl psilocybin derivative (FIG. 7D), a 2-prenyl-6-methyl psilocybin derivative (FIG. 7E), and a 2-prenyl-7-methyl psilocybin derivative (FIG. 7F). It is noted that $R_{3a}$ and $R_{3b}$ are each independently a hydrogen atom, an alkyl group, acyl group or an aryl group.
Figure 7B:
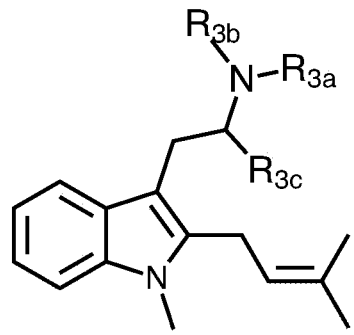
Figure 7C:
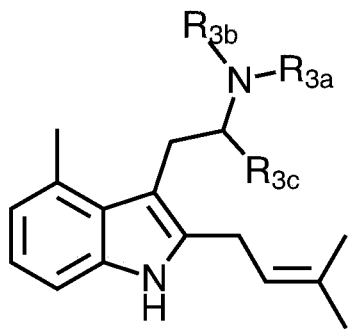
Figure 7D:
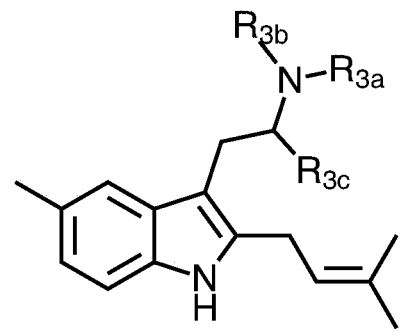
Figure 7E:
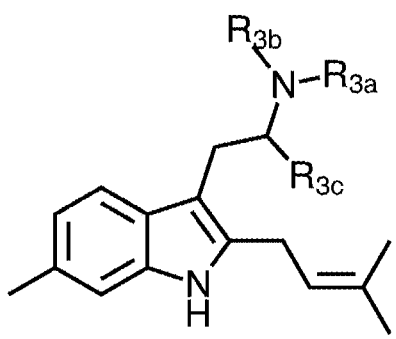
Figure 7F:
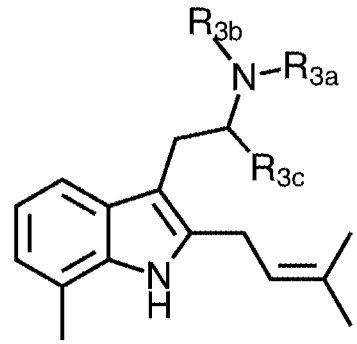
Figure 8A:
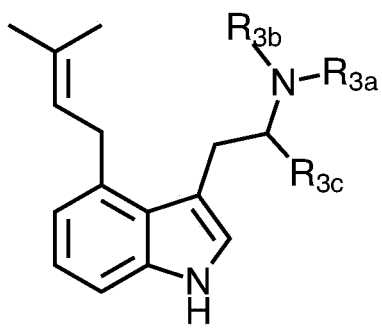
FIGS. 8A, 8B, 8C, 8D, 8E, and 8F depict certain example prenylated compounds, notably 04 prenylated compounds, and in particular a $C_4$-prenyl psilocybin derivative (comprising a hydrogen atom at each of $N_1$, $C_2$, $C_5$, $_6$ and $_7$) (FIG. 8A), a (N)1-methyl-4-prenyl psilocybin derivative (FIG. 8B), 2-methyl-4-prenyl psilocybin derivative (FIG. 8C), 4-prenyl-5-methyl psilocybin derivative (FIG. 8D), a 4-prenyl-6-methyl psilocybin derivative (FIG. 8E), and a 4-prenyl-7-methyl psilocybin derivative (FIG. 8F). It is noted that $R_{3a}$ and $R_{3b}$ are each independently a hydrogen atom, an alkyl group, acyl group or an aryl group, or $R_3$a and $R_2$ are joined together, along with the nitrogen atom to which $R_{3a}$ is attached, to form an optionally substituted heterocyclic ring, and $R_{3b}$ is a hydrogen atom, an alkyl group, acyl group or an aryl group, and wherein $R_{3c}$ is a hydrogen atom or a carboxy group.
Figure 8B:
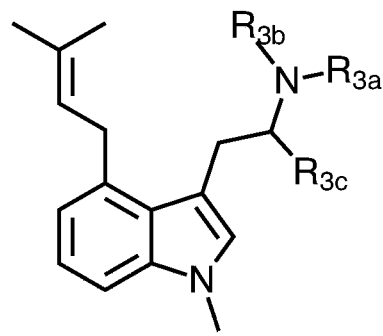
Figure 8C:
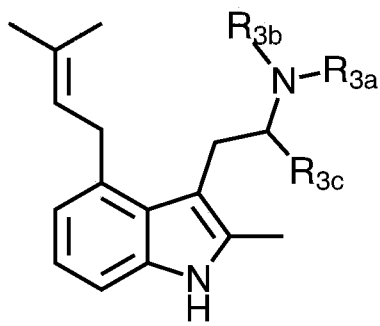
Figure 8D:
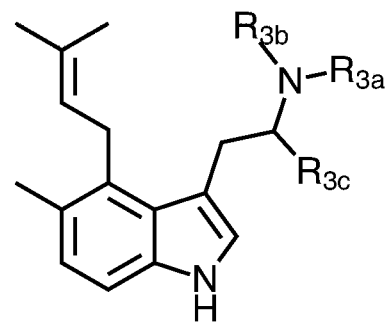
Figure 8E:
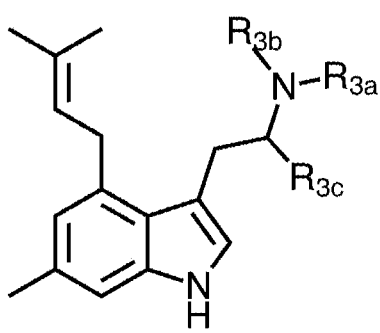
Figure 8F:
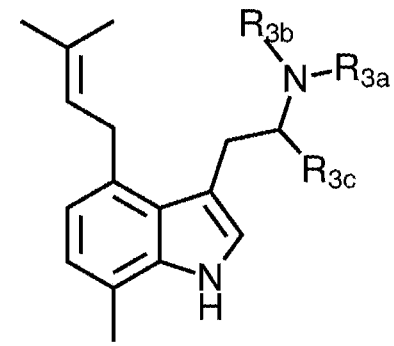
Figure 9A:
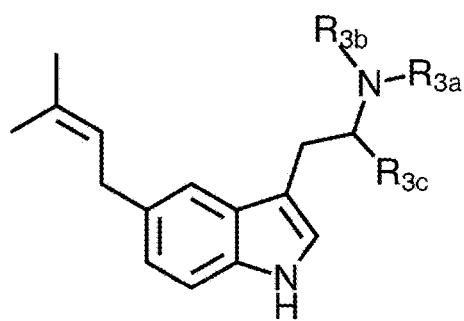
FIGS. 9A, 9B, 9C, 9D, 9E, and 9F depict certain example prenylated compounds, notably $C_5$ prenylated compounds, and in particular a $C_5$-prenyl psilocybin derivative (comprising a hydrogen atom at each of $N_1$, $C_2$, $C_4$, $C_6$ and $C_7$) (FIG. 9A), a (N)1-methyl-5-prenyl psilocybin derivative (FIG. 9B), 2-methyl-5-prenyl psilocybin derivative (FIG. 9C), 4-methyl-5-prenyl psilocybin derivative (FIG. 9D), a 5-prenyl-6-methyl psilocybin derivative (FIG. 9E), and a 5-prenyl-7-methyl psilocybin derivative (FIG. 9F). It is noted that $R_{3a}$ and $R_{3b}$ are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, and $R_{3b}$ is a hydrogen atom, an alkyl group, acyl group or an aryl group, and wherein $R_{3c}$ is a hydrogen atom or a carboxy group.
Figure 9B:
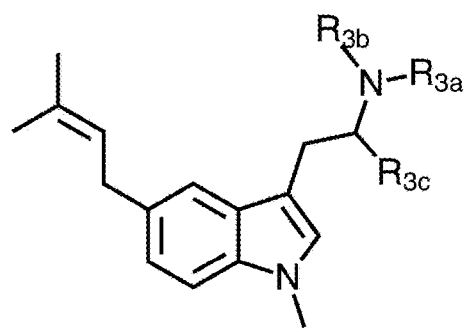
Figure 9C:
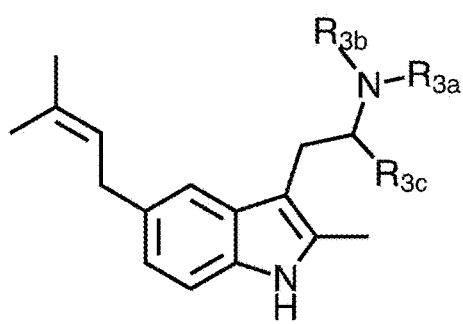
Figure 9D:
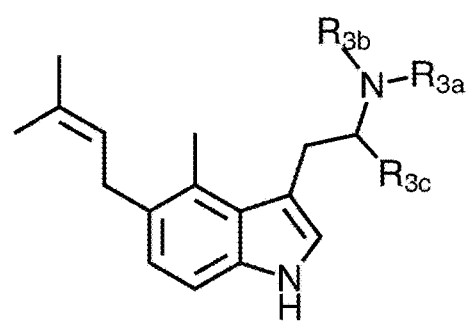
Figure 9E:
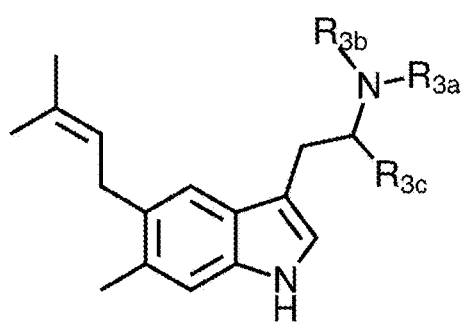
Figure 9F:
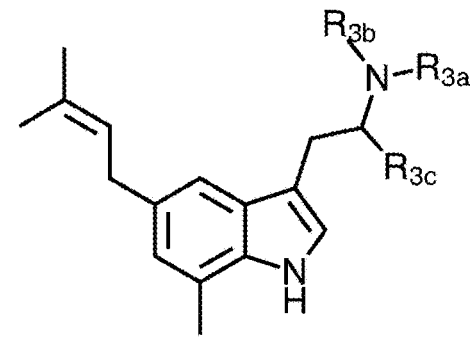
Figure 10A:
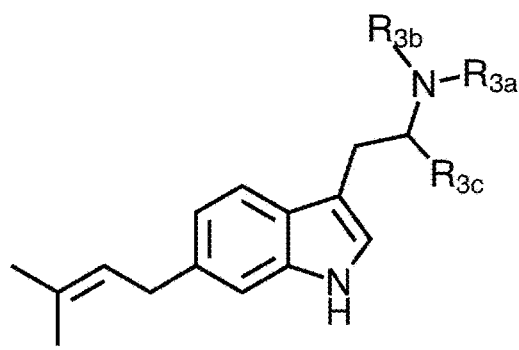
FIGS. 10A, 10B, 10C, 10D, 10E, and 10F depict certain example prenylated compounds, notably $C_6$ prenylated compounds, and in particular a $C_6$-prenyl psilocybin derivative (comprising a hydrogen atom at each of $N_1$, $C_2$, $C_4$, $C_5$ and $C_7$) (FIG. 10A), a 1-methyl-6-prenyl psilocybin derivative (FIG. 10B), 2-methyl-6-prenyl psilocybin derivative (FIG. 10C), 4-methyl-6-prenyl psilocybin derivative (FIG. 10D), a 5-methyl-6-prenyl psilocybin derivative (FIG. 10E), and a 6-prenyl-7-methyl psilocybin derivative (FIG. 10F). It is noted that $R_{3a}$ and $R_{3b}$ are each independently a hydrogen atom, an alkyl group, acyl group or an aryl group, or $R_{3a}$ and $R_2$ together form an alkyl group and $R_{3b}$ is a hydrogen atom, an alkyl group, acyl group or an aryl group, and wherein $R_{3c}$ is a hydrogen atom or a carboxy group.
Figure 10B:
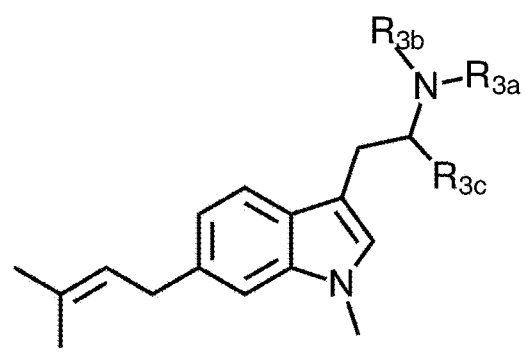
Figure 10C:
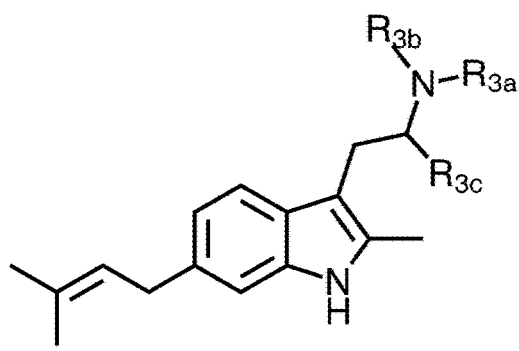
Figure 10D:
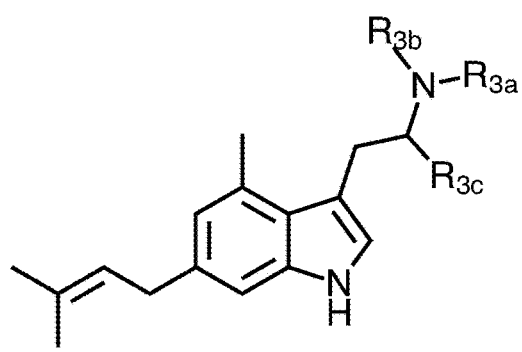
Figure 10E:
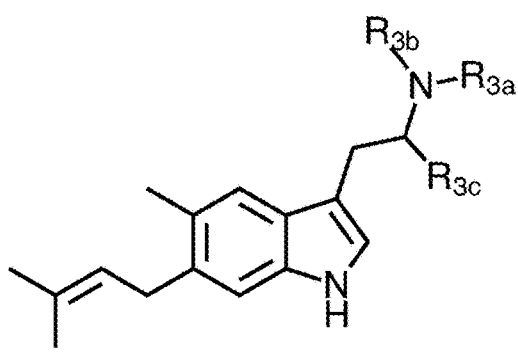
Figure 10F:
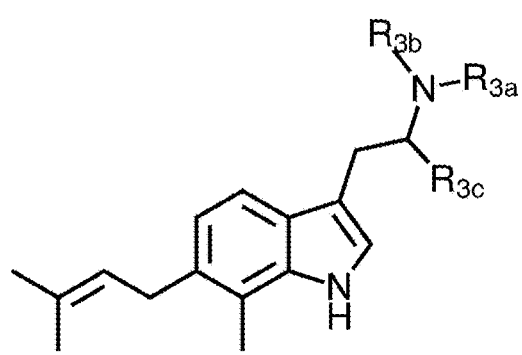
Figure 11A:
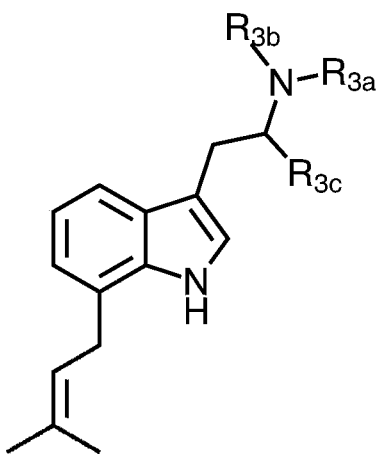
FIGS. 11A, 11B, 11C, 11D, 11E, and 11F depict certain example prenylated compounds, notably $C_7$ prenylated compounds, and in particular a $C_7$-prenyl psilocybin derivative (comprising a hydrogen atom at each of $N_1$, $C_2$, $C_4$, $C_5$ and $C_6$) (FIG. 11A), a (N)1-methyl-7-prenyl psilocybin derivative (FIG. 11B), 2-methyl-7-prenyl psilocybin derivative (FIG. 11C), 4-methyl-7-prenyl psilocybin derivative (FIG. 11D), a 5-methyl-7-prenyl psilocybin derivative (FIG. 11E), and a 6-methyl-7-prenyl psilocybin derivative (FIG. 11F). It is noted that $R_{3a}$ and $R_{3b}$ are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, and $R_{3b}$ is a hydrogen atom, an alkyl group, acyl group or an aryl group, and wherein $R_{3c}$ is a hydrogen atom or a carboxy group.
Figure 11B:
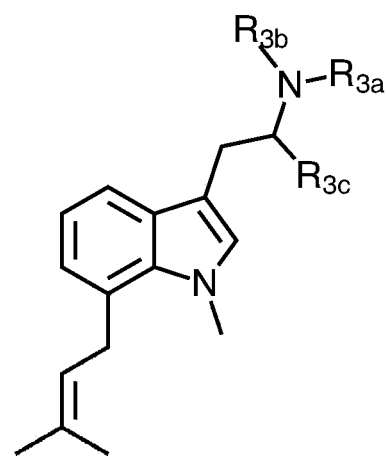
Figure 11C:
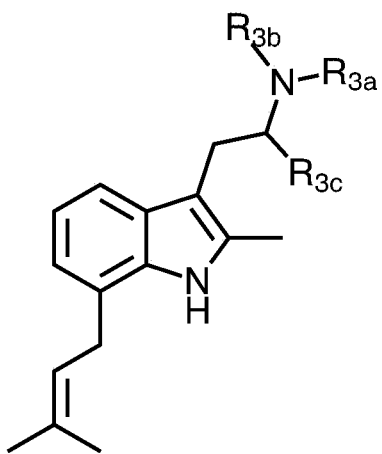
Figure 11D:
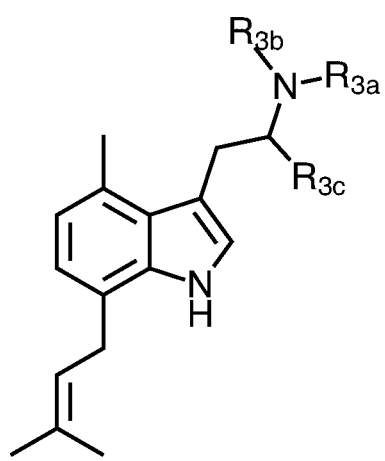
Figure 11E:
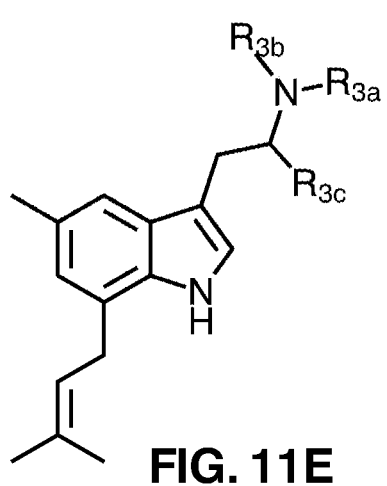
Figure 11F:
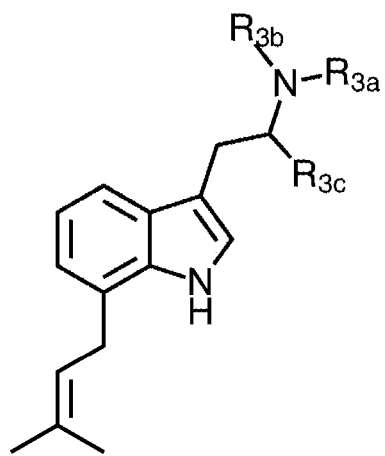

The terms "geranylgeranyl pyrophosphate" or "GGPP", as used herein, refer to a chemical compound having the structure set forth in FIG. 5D.

The term "phosphate group", as used herein, is a molecule containing one atom of phosphorus, covalently bound to four oxygen atoms (three single bonds and one double bond). Of the four oxygen atoms one oxygen atom may be a hydroxy group, and one of the non-hydroxylated oxygen atom may be chemically bonded to another entity.

The terms "hydroxy group", and "hydroxy", as used herein, refers to a molecule containing one atom of oxygen bonded to one atom of hydrogen, and having the chemical formula —OH. A hydroxy group through its oxygen atom may be chemically bonded to another entity.

The terms "glycosylated" or "glycosyl", as used herein, refer to a saccharide group, such as a mono-, di-, tri- oligo- or a poly-saccharide group, which can be or has been bonded from its anomeric carbon either in the pyranose or furanose form, either in the a or the β conformation. When bonded through its anomeric carbon via an oxygen atom to another entity, the bonded saccharide group, inclusive of the oxygen atom, may be referred to herein as a "glycosyloxy" group. Example monosaccharide groups include, but are not limited to, a pentosyl, a hexosyl, or a heptosyl group. The glycosyloxy group may also be substituted with various groups. Such substitutions may include lower alkyl, lower alkoxy, acyl, carboxy, carboxyamino, amino, acetamido, halo, thio, nitro, keto, and phosphatyl groups, wherein the substitution may be at one or more positions on the saccharide. Included in the term glycosyl are further stereoisomers, optical isomers, anomers, and epimers of the glycosyloxy group. Thus, a hexose group, for example, can be either an aldose or a ketose group, can be of D- or L-configuration, can assume either an α or β conformation, and can be a dextro- or levo-rotatory with respect to plane-polarized light. Example glycosyloxy groups further include, without limitation, glucosyl groups, glucuronic acid groups, galactosyl groups, fucosyl groups, xylose groups, arabinose groups, and rhamnose groups.

The term "alkyl group", as used herein, refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl, and the like, where the variable p is an integer representing the largest number of carbon atoms in the alkyl radical. Alkyl groups further include hydrocarbon groups arranged in a chain having the chemical formula —$C_nH_{2n+1}$, including, without limitation, methyl groups (—$CH_3$), ethyl groups (—$C_2H_5$), propyl groups (—$C_3H_7$), and butyl groups (—$C_4H_9$).

The term "aryl group", as used herein, refers to a hydrocarbon group arranged in an aromatic ring and can, for example, be a $C_6$-$C_{14}$-aryl, a $C_6$-$C_{10}$-aryl. Aryl groups further include phenyl, naphthyl, tetrahydronaphthyl, phenanthrenyl, biphenylenyl, indanyl, tolyl, xylyl, or indenyl groups, and the like.

The term "acyl group", as used herein, refers to a carbon atom double bonded to an oxygen and single bonded to an alkyl group. The carbon atom further can be bonded to another entity. An acyl group can be described by the chemical formula: —C(=O)—$C_nH_{2n+1}$.

The term "O-acyl group", as used herein, refers to an acyl group in which the carbon atom is single bonded to an additional oxygen atom. The additional oxygen atom can be bonded to another entity. An O-acyl group can be described by the chemical formula: —O—C(=O)—$C_nH_{2n+1}$. Furthermore, depending on the carbon chain, length specific O-acyl groups may be termed an acetyl group (n=1), a propanoyl group (n=2), propoxycarbonyl group (n=3), a butoxycarbonyl group (n=4) etc.

The terms "carboxy group" and "carboxy", as used herein, refer to a molecule containing one atom of carbon bonded to an oxygen atom and a hydroxy group and having the formula —COOH. A carboxy group includes a deprotonated carboxy group, i.e., a carboxy ion, having the formula —$COO^-$. In its deprotonated form, a carboxy group may form a carboxy salt, for example, a sodium or potassium carboxy salt, or an organic carboxy salt. It is further to be understood that a carboxy group through its carbon atom may be chemically bonded to another entity. Furthermore, it is noted that an entity attached to a carboxy group may be referred to herein as a "carboxylated" entity, e.g., a carboxylated psilocybin derivative is a psilocybin derivative possessing a carboxy group.

The term "5-$HT_{2A}$ receptor", as used herein, refers to a subclass of a family of receptors for the neurotransmitter and peripheral signal mediator serotonin. 5-$HT_{2A}$ receptors can mediate a plurality of central and peripheral physiologic functions of serotonin. Central nervous system effects can include mediation of hallucinogenic effects of hallucinogenic compounds.

The term "modulating 5-$HT_{2A}$ receptors", as used herein, refers to the ability of a compound disclosed herein to alter the function of 5-$HT_{2A}$ receptors. A 5-$HT_{2A}$ receptor modulator may activate the activity of a 5-$HT_{2A}$ receptor, may activate or inhibit the activity of a 5-$HT_{2A}$ receptor depending on the concentration of the compound exposed to the 5-$HT_{2A}$ receptor, or may inhibit the activity of a 5-$HT_{2A}$ receptor. Such activation or inhibition may be contingent on the occurrence of a specific event, such as activation of a signal transduction pathway, and/or maybe manifest only in particular cell types. The term "modulating 5-$HT_{2A}$ receptors," also refers to altering the function of a 5-$HT_{2A}$ receptor by increasing or decreasing the probability that a complex forms between a 5-$HT_{2A}$ receptor and a natural binding partner to form a multimer. A 5-$HT_{2A}$ receptor modulator may increase the probability that such a complex forms between the 5-$HT_{2A}$ receptor and the natural binding partner, may increase or decrease the probability that a complex forms between the 5-$HT_{2A}$ receptor and the natural binding partner depending on the concentration of the compound exposed to the 5-$HT_{2A}$ receptor, and or may decrease the probability that a complex forms between the 5-$HT_{2A}$ receptor and the natural binding partner. It is further noted that the prenylated psilocybin derivatives may alter the function of a 5-$HT_{2A}$ receptor by acting as an agonist or antagonist of the 5-$HT_{1A}$ receptor, and that prenylated psilocybin derivatives according to the present disclosure may alter the function of a 5-$HT_{2A}$ receptor by directly interacting therewith or binding thereto, or by indirectly interacting therewith through one or more other molecular entities.

The term "5-$HT_{2A}$ receptor-mediated disorder", as used herein, refers to a disorder that is characterized by abnormal 5-$HT_{2A}$ receptor activity. A 5-$HT_{2A}$ receptor-mediated disorder may be completely or partially mediated by modulating 5-$HT_{2A}$ receptors. In particular, a 5-$HT_{2A}$ receptor-mediated disorder is one in which modulation of 5-$HT_{2A}$ receptors results in some effect on the underlying disorder e.g., administration of a 5-$HT_{2A}$ receptor modulator results in some improvement in at least some of the subjects being treated.

The term "5-$HT_{1A}$ receptor", as used herein, refers to a subclass of a family of receptors for the neurotransmitter and peripheral signal mediator serotonin. 5-$HT_{1A}$ receptors can mediate a plurality of central and peripheral physiologic functions of serotonin. Ligand activity at 5-HT$_{1A}$ is generally not associated with hallucination, although many hallucinogenic compounds are known to modulate 5-HT$_{1A}$ receptors to impart complex physiological responses (Inserra et al., 2020, Pharmacol Rev 73: 202).

The term "modulating 5-HT$_{1A}$ receptors", as used herein, refers to the ability of a compound disclosed herein to alter the function of 5-HT$_{1A}$ receptors. A 5-HT$_{1A}$ receptor modulator may activate the activity of a 5-HT$_{1A}$ receptor, may activate or inhibit the activity of a 5-HT$_{1A}$ receptor depending on the concentration of the compound exposed to the 5-HT$_{1A}$ receptor, or may inhibit the activity of a 5-HT$_{2A}$ receptor. Such activation or inhibition may be contingent on the occurrence of a specific event, such as activation of a signal transduction pathway, and/or maybe manifest only in particular cell types. The term "modulating 5-HT$_{1A}$ receptors," also refers to altering the function of a 5-HT$_{1A}$ receptor by increasing or decreasing the probability that a complex forms between a 5-HT$_{1A}$ receptor and a natural binding partner to form a multimer. A 5-HT$_{1A}$ receptor modulator may increase the probability that such a complex forms between the 5-HT$_{1A}$ receptor and the natural binding partner, may increase or decrease the probability that a complex forms between the 5-HT$_{1A}$ receptor and the natural binding partner depending on the concentration of the compound exposed to the 5-HT$_{1A}$ receptor, and or may decrease the probability that a complex forms between the 5-HT$_{1A}$ receptor and the natural binding partner. It is further noted that the prenylated psilocybin derivatives may alter the function of a 5-HT$_{1A}$ receptor by acting as an agonist or antagonist of the 5-HT$_{1A}$ receptor, and that prenylated psilocybin derivatives according to the present disclosure may alter the function of a 5-HT$_{1A}$ receptor by directly interacting therewith or binding thereto, or by indirectly interacting therewith through one or more other molecular entities.

The term "5-HT$_{1A}$ receptor-mediated disorder", as used herein, refers to a disorder that is characterized by abnormal 5-HT$_{1A}$ receptor activity. A 5-HT$_{1A}$ receptor-mediated disorder may be completely or partially mediated by modulating 5-HT$_{1A}$ receptors. In particular, a 5-HT$_{1A}$ receptor-mediated disorder is one in which modulation of 5-HT$_{1A}$ receptors results in some effect on the underlying disorder e.g., administration of a 5-HT$_{1A}$ receptor modulator results in some improvement in at least some of the subjects being treated.

The term "pharmaceutical formulation", as used herein, refers to a preparation in a form which allows an active inaredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject, and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The term "psilocybin biosynthetic enzyme complement", as used herein, refers to one or more polypeptides which alone or together are capable of facilitating the chemical conversion of: (i) a psilocybin derivative precursor compound, and form a prenylated psilocybin derivative compound and/or (ii) a prenylated psilocybin derivative compound and form another psilocybin derivative precursor compound. A psilocybin biosynthetic enzyme complement can include, for example, PsiD, PsiH, PsiK, PsiM, PsiP, Psi-ncAAAD and TrpB.

The term "PsiD", as used herein, refers to any and all enzymes comprising a sequence of amino acid residues which is (i) substantially identical to the amino acid sequences constituting any PsiD polypeptide set forth herein, including, for example, SEQ.ID NO: 2, or (ii) encoded by a nucleic acid sequence capable of hybridizing under at least moderately stringent conditions to any nucleic acid sequence encoding any PsiD set forth herein, but for the use of synonymous codons.

The term "PsiH", as used herein, refers to any and all enzymes comprising a sequence of amino acid residues which is (i) substantially identical to the amino acid sequences constituting any PsiH polypeptide set forth herein, including, for example, SEQ.ID NO: 4, or (ii) encoded by a nucleic acid sequence apable of hybridizing under at least moderately stringent conditions to any nucleic acid sequence encoding any PsiH set forth herein, but for the use of synonymous codons.

The term "PsiK", as used herein, refers to any and all enzymes comprising a sequence of amino acid residues which is (i) substantially identical to the amino acid sequences constituting any PsiK polypeptide set forth herein, including, for example, SEQ.ID NO: 6, or (ii) encoded by a nucleic acid sequence capable of hybridizing under at least moderately stringent conditions to any nucleic acid sequence encoding any PsiK set forth herein, but for the use of synonymous codons.

The term "PsiM", as used herein, refers to any and all enzymes comprising a sequence of amino acid residues which is (i) substantially identical to the amino acid sequences constituting any PsiM polypeptide set forth herein, including, for example, SEQ.ID NO: 8, or (ii) encoded by a nucleic acid sequence capable of hybridizing under at least moderately stringent conditions to any nucleic acid sequence encoding any PsiM set forth herein, but for the use of synonymous codons.

The term "Psi-ncAAAD", as used herein, refers to any and all enzymes comprising a sequence of amino acid residues which is (i) substantially identical to the amino acid sequences constituting any Psi-ncAAAD polypeptide et forth herein, including, for example, SEQ.ID NO: 10, or (ii) encoded by a nucleic acid sequence capable of hybridizing under at least moderately stringent conditions to any nucleic acid sequence encoding any Psi-ncAAAD set forth herein, but for the use of synonymous codons.

The term "TrpB", as used herein, refers to any and all enzymes comprising a sequence of amino acid residues which is (i) substantially identical to the amino acid sequences constituting any TrpB polypeptide set forth herein, including, for example, SEQ.ID NO: 12, or (ii) encoded by a nucleic acid sequence capable of hybridizing under at least moderately stringent conditions to any nucleic acid sequence encoding any TrpB set forth herein, but for the use of synonymous codons.

The term "prenyl transferase", as used herein, refers to any and all enzymes comprising a sequence of amino acid residues which is (i) substantially identical to the amino acid sequences constituting any prenyl transferase polypeptide set forth herein, including, for example, SEQ.ID NO: 14, or (ii) encoded by a nucleic acid sequence capable of hybridizing under at least moderately stringent conditions to any nucleic acid sequence encoding any prenyl transferase set forth herein, but for the use of synonymous codons.

The term "decarboxylase", as used herein, refers to any and all enzymes comprising a sequence of amino acid residues which is (i) substantially identical to the amino acid sequences constituting any decarboxylase polypeptide set forth herein, including, for example, SEQ.ID NO: 26, or (ii) encoded by a nucleic acid sequence capable of hybridizing under at least moderately stringent conditions to any nucleic acid sequence encoding any decarboxylase set forth herein, but for the use of synonymous codons.

The term "N-acetyl transferase", as used herein, refers to any and all enzymes comprising a sequence of amino acid residues which is (i) substantially identical to the amino acid sequences constituting any N-acetyl transferase polypeptide set forth herein, including, for example, SEQ.ID NO: 28, or (ii) encoded by a nucleic acid sequence capable of hybridizing under at least moderately stringent conditions to any nucleic acid sequence encoding any N-acetyl transferase set forth herein, but for the use of synonymous codons.

The term "acid phosphatase", as used herein, refers to any and all enzymes comprising a sequence of amino acid residues which is (i) substantially identical to the amino acid sequences constituting any acid phosphatase polypeptide set forth herein, including, for example, SEQ.ID NO: 30, or (ii) encoded by a nucleic acid sequence capable of hybridizing under at least moderately stringent conditions to any nucleic acid sequence encoding any acid phosphatase set forth herein, but for the use of synonymous codons.

The term "isopentenyl phosphate kinase", as used herein, refers to any and all enzymes comprising a sequence of amino acid residues which is (i) substantially identical to the amino acid sequences constituting any isopentenyl phosphate kinase polypeptide set forth herein, including, for example, SEQ.ID NO: 32, or (ii) encoded by a nucleic acid sequence capable of hybridizing under at least moderately stringent conditions to any nucleic acid sequence encoding any acid isopentenyl phosphate kinase set forth herein, but for the use of synonymous codons.

The terms "nucleic acid sequence encoding PsiD", and "nucleic acid sequence encoding a PsiD polypeptide", as may be used interchangeably herein, refer to any and all nucleic acid sequences encoding a PsiD polypeptide, including, for example, SEQ.ID NO: 1. Nucleic acid sequences encoding a PsiD polypeptide further include any and all nucleic acid sequences which (i) encode polypeptides that are substantially identical to the PsiD polypeptide sequences set forth herein; or (ii) hybridize to any PsiD nucleic acid sequences set forth herein under at least moderately stringent hybridization conditions or which would hybridize thereto under at least moderately stringent conditions but for the use of synonymous codons.

The terms "nucleic acid sequence encoding PsiH", and "nucleic acid sequence encoding a PsiH polypeptide", as may be used interchangeably herein, refer to any and all nucleic acid sequences encoding a PsiH polypeptide, including, for example, SEQ.ID NO: 3. Nucleic acid sequences encoding a PsiH polypeptide further include any and all nucleic acid sequences which (i) encode polypeptides that are substantially identical to the PsiH polypeptide sequences set forth herein; or (ii) hybridize to any PsiH nucleic acid sequences set forth herein under at least moderately stringent hybridization conditions or which would hybridize thereto under at least moderately stringent conditions but for the use of synonymous codons.

The terms "nucleic acid sequence encoding PsiK", and "nucleic acid sequence encoding a PsiK polypeptide", as may be used interchangeably herein, refer to any and all nucleic acid sequences encoding a PsiK polypeptide, including, for example, SEQ.ID NO: 5. Nucleic acid sequences encoding a PsiK polypeptide further include any and all nucleic acid sequences which (i) encode polypeptides that are substantially identical to the PsiK polypeptide sequences set forth herein; or (ii) hybridize to any PsiK nucleic acid sequences set forth herein under at least moderately stringent hybridization conditions or which would hybridize thereto under at least moderately stringent conditions but for the use of synonymous codons.

The terms "nucleic acid sequence encoding PsiM", and "nucleic acid sequence encoding a PsiM polypeptide", as may be used interchangeably herein, refer to any and all nucleic acid sequences encoding a PsiD polypeptide, including, for example, SEQ.ID NO: 7. Nucleic acid sequences encoding a PsiM polypeptide further include any and all nucleic acid sequences which (i) encode polypeptides that are substantially identical to the PsiM polypeptide sequences set forth herein; or (ii) hybridize to any PsiM nucleic acid sequences set forth herein under at least moderately stringent hybridization conditions or which would hybridize thereto under at least moderately stringent conditions but for the use of synonymous codons.

The terms "nucleic acid sequence encoding Psi-ncAAAD", and "nucleic acid sequence encoding a Psi-ncAAAD polypeptide", as may be used interchangeably herein, refer to any and all nucleic acid sequences encoding a PsiD polypeptide, including, for example, SEQ.ID NO: 9. Nucleic acid sequences encoding a Psi-ncAAAD polypeptide further include any and all nucleic acid sequences which (i) encode polypeptides that are substantially identical to the Psi-ncAAAD polypeptide sequences set forth herein; or (ii) hybridize to any Psi-ncAAAD nucleic acid sequences set forth herein under at least moderately stringent hybridization conditions or which would hybridize thereto under at least moderately stringent conditions but for the use of synonymous codons.

The terms "nucleic acid sequence encoding TrpB", and "nucleic acid sequence encoding a TrpB polypeptide", as may be used interchangeably herein, refer to any and all nucleic acid sequences encoding a TrpB polypeptide, including, for example, SEQ.ID NO: 11. Nucleic acid sequences encoding a TrpB polypeptide further include any and all nucleic acid sequences which (i) encode polypeptides that are substantially identical to the TrpB polypeptide sequences set forth herein; or (ii) hybridize to any TrpB nucleic acid sequences set forth herein under at least moderately stringent hybridization conditions or which would hybridize thereto under at least moderately stringent conditions but for the use of synonymous codons.

The terms "nucleic acid sequence encoding a prenyl transferase", and "nucleic acid sequence encoding a prenyl transferase polypeptide", as may be used interchangeably herein, refer to any and all nucleic acid sequences encoding a prenyl transferase polypeptide, including, for example, SEQ.ID NO: 13. Nucleic acid sequences encoding a prenyl transferase polypeptide further include any and all nucleic acid sequences which (i) encode polypeptides that are substantially identical to the prenyl transferase polypeptide sequences set forth herein; or (ii) hybridize to any prenyl transferase nucleic acid sequences set forth herein under at least moderately stringent hybridization conditions or which would hybridize thereto under at least moderately stringent conditions but for the use of synonymous codons.

The terms "nucleic acid sequence encoding tryptophan decarboxylase", and "nucleic acid sequence encoding a decarboxylase polypeptide", as may be used interchangeably herein, refer to any and all nucleic acid sequences encoding a decarboxylase, including, for example, SEQ.ID NO: 25. Nucleic acid sequences encoding a decarboxylase polypeptide further include any and all nucleic acid sequences which (i) encode polypeptides that are substantially identical to the decarboxylase polypeptide sequences set forth herein; or (ii) hybridize to any decarboxylase nucleic acid sequences set forth herein under at least moderately stringent hybridization conditions or which would hybridize thereto under at least moderately stringent conditions but for the use of synonymous codons.

The terms "nucleic acid sequence encoding N-acetyl transferase", and "nucleic acid sequence encoding an N-acetyl transferase polypeptide", as may be used interchangeably herein, refer to any and all nucleic acid sequences encoding an N-acetyl transferase, including, for example, SEQ.ID NO: 27. Nucleic acid sequences encoding an N-acetyl transferase polypeptide further include any and all nucleic acid sequences which (i) encode polypeptides that are substantially identical to the N-acetyl transferase polypeptide sequences set forth herein; or (ii) hybridize to any N-acetyl transferase nucleic acid sequences set forth herein under at least moderately stringent hybridization conditions or which would hybridize thereto under at least moderately stringent conditions but for the use of synonymous codons.

The terms "nucleic acid sequence encoding an acid phosphatase", and "nucleic acid sequence encoding an acid phosphatase polypeptide", as may be used interchangeably herein, refer to any and all nucleic acid sequences encoding an acid phosphatase, including, for example, SEQ.ID NO: 29. Nucleic acid sequences encoding an acid phosphatase further include any and all nucleic acid sequences which (i) encode polypeptides that are substantially identical to the acid phosphatase polypeptide sequences set forth herein; or (ii) hybridize to any acid phosphatase nucleic acid sequences set forth herein under at least moderately stringent hybridization conditions or which would hybridize thereto under at least moderately stringent conditions but for the use of synonymous codons.

The terms "nucleic acid sequence encoding isopentenyl phosphate kinase", and "nucleic acid sequence encoding an isopentenyl phosphate kinase polypeptide", as may be used interchangeably herein, refer to any and all nucleic acid sequences encoding an isopentenyl phosphate kinase, including, for example, SEQ.ID NO: 31. Nucleic acid sequences encoding an isopentenyl phosphate kinase polypeptide further include any and all nucleic acid sequences which (i) encode polypeptides that are substantially identical to the isopentenyl phosphate kinase polypeptide sequences set forth herein; or (ii) hybridize to any isopentenyl phosphate kinase nucleic acid sequences set forth herein under at least moderately stringent hybridization conditions or which would hybridize thereto under at least moderately stringent conditions but for the use of synonymous codons.

The terms "nucleic acid", or "nucleic acid sequence", as used herein, refer to a sequence of nucleoside or nucleotide monomers, consisting of naturally occurring bases, sugars and intersugar (backbone) linkages. The term also includes modified or substituted sequences comprising non-naturally occurring monomers or portions thereof. The nucleic acids of the present disclosure may be deoxyribonucleic nucleic acids (DNA) or ribonucleic acids (RNA) and may include naturally occurring bases including adenine, guanine, cytosine, thymidine, and uracil. The nucleic acids may also contain modified bases. Examples of such modified bases include aza and deaza adenine, guanine, cytosine, thymidine and uracil, and xanthine and hypoxanthine. A sequence of nucleotide or nucleoside monomers may be referred to as a polynucleotide sequence, nucleic acid sequence, a nucleotide sequence, or a nucleoside sequence.

The term "polypeptide", as used herein in conjunction with a reference SEQ.ID NO, refers to any and all polypeptides comprising a sequence of amino acid residues which is (i) substantially identical to the amino acid sequence constituting the polypeptide having such reference SEQ.ID NO, or (ii) encoded by a nucleic acid sequence capable of hybridizing under at least moderately stringent conditions to any nucleic acid sequence encoding the polypeptide having such reference SEQ.ID NO, but for the use of synonymous codons. A sequence of amino acid residues may be referred to as an amino acid sequence, or polypeptide sequence.

The term "nucleic acid sequence encoding a polypeptide", as used herein in conjunction with a reference SEQ.ID NO, refers to any and all nucleic acid sequences encoding a polypeptide having such reference SEQ.ID NO. Nucleic acid sequences encoding a polypeptide, in conjunction with a reference SEQ.ID NO, further include any and all nucleic acid sequences which (i) encode polypeptides that are substantially identical to the polypeptide having such reference SEQ.ID NO; or (ii) hybridize to any nucleic acid sequences encoding polypeptides having such reference SEQ.ID NO under at least moderately stringent hybridization conditions or which would hybridize thereto under at least moderately stringent conditions but for the use of synonymous codons.

By the term "substantially identical" it is meant that two amino acid sequences preferably are at least 70% identical, and more preferably are at least 85% identical and most preferably at least 95% identical, for example 96%, 97%, 98% or 99% identical. In order to determine the percentage of identity between two amino acid sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Mol. Biol., 1990: 215:403). A particularly preferred method for determining the percentage identity between two polypeptides involves the Clustal W algorithm (Thompson, J D, Higgines, D G and Gibson T J, 1994, Nucleic Acid Res 22(2): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.-16.6 (Log10 [Na+])+0.41(% (G+C)-60011), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5x sodium chloride/sodium citrate (SSC)/5xDenhardt's solution/1.0% SDS at Tm (based on the above equation) -5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts, and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "functional variant", as used herein in reference to polynucleotides or polypeptides, refers to polynucleotides or polypeptides capable of performing the same function as a noted reference polynucleotide or polypeptide. Thus, for example, a functional variant of the polypeptide set forth in SEQ.ID NO: 2, refers to a polypeptide capable of performing the same function as the polypeptide set forth in SEQ.ID NO: 2. Functional variants include modified a polypeptide wherein, relative to a noted reference polypeptide, the modification includes a substitution, deletion, or addition of one or more amino acids. In some embodiments, substitutions are those that result in a replacement of one amino acid with an amino acid having similar characteristics. Such substitutions include, without limitation (i) glutamic acid and aspartic acid; (i) alanine, serine, and threonine; (iii) isoleucine, leucine, and valine, (iv) asparagine and glutamine, and (v) tryptophan, tyrosine, and phenylalanine. Functional variants further include polypeptides having retained or exhibiting an enhanced psilocybin biosynthetic bioactivity.

The term "chimeric", as used herein in the context of nucleic acids, refers to at least two linked nucleic acids which are not naturally linked. Chimeric nucleic acids include linked nucleic acids of different natural origins. For example, a nucleic acid constituting a microbial promoter linked to a nucleic acid encoding a plant polypeptide is considered chimeric. Chimeric nucleic acids also may comprise nucleic acids of the same natural origin, provided they are not naturally linked. For example a nucleic acid constituting a promoter obtained from a particular cell-type may be linked to a nucleic acid encoding a polypeptide obtained from that same cell-type, but not normally linked to the nucleic acid constituting the promoter. Chimeric nucleic acids also include nucleic acids comprising any naturally occurring nucleic acids linked to any non-naturally occurring nucleic acids.

The terms "substantially pure" and "isolated", as may be used interchangeably herein describe a compound, e.g., a secondary metabolite, psilocybin or a psilocybin derivative, polynucleotide, or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "recovered", as used herein in association with an enzyme, protein, or a chemical compound, refers to a more or less pure form of he enzyme, protein, or chemical compound.

The term "in vivo", as used herein relation to a method of making a prenylated psilocybin compound, refers to a method involving contacting a psilocybin derivative precursor compound or a prenylated psilocybin derivative compound with an enzyme capable of converting the psilocybin derivative precursor compound or the prenylated psilocybin derivative compound within a cell, for example, a cell or a microorganism, cultivated, for example, in a growth medium, to convert the psilocybin derivative precursor compound or the prenylated psilocybin compound into a prenylated psilocybin derivative compound. The cell generally expresses the enzyme, such as a heterologously expressed renyl transferase, a decarboxylase, or an N-acetyl transferase, for example.

The term "in vitro", as used herein relation to a method of making a prenylated psilocybin compound, refers to a method involving contacting a psilocybin derivative precursor compound or a prenylated psilocybin derivative compound with an enzyme capable of converting the psilocybin derivative recursor compound or the prenylated psilocybin derivative compound outside a cell, for example, in a microwell plate, a tube, a flask, a beaker, a tank, a reactor, or the like, to convert the psilocybin derivative precursor compound or the prenylated psilocybin compound into a prenylated psilocybin derivative compound. The cell generally expresses the enzyme, such as a heterologously expressed a prenyl transferase, a decarboxylase, or an N-acetyl transferase, for example.

General Implementation

As hereinbefore mentioned, the present disclosure relates to psilocybin derivatives. In particular, the present disclosure provides novel prenylated psilocybin derivatives. In general, the herein provided compositions exhibit functional properties which deviate from the functional properties of psilocybin. Thus, for example, the prenylated psilocybin derivatives, can exhibit pharmacological properties which deviate from psilocybin. The prenylated psilocybin derivatives in this respect are useful in the formulation of pharmaceutical and recreation drug formulations. The practice of the method of the present disclosure avoids the extraction of psilocybin from mushrooms and the performance of subsequent chemical reactions to achieve prenylation. Furthermore, the growth of mushrooms can be avoided thus limiting the dependence on climate and weather, and potential legal and social challenges associated with the cultivation of mushrooms containing psychoactive compounds. The method can efficiently yield substantial quantities of prenylated psilocybin derivatives.

In what follows selected embodiments are described with reference to the drawings.

Initially various prenylated psilocybin derivatives will be described. Thereafter methods example methods of using and making the prenylated psilocybin derivatives will be described In at least one aspect, and in at least one example embodiment, the present disclosure provides a chemical compound having formula (I):

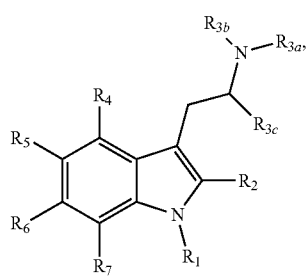

(I)

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and $R_{3b}$ each independently are a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

It is noted that in reference to the indole prototype structure shown in FIG. 2, carbon atoms $C_2$, $C_4$, $C_5$, $C_6$ and $C_7$ are bonded to $R_2$, $R_4$, $R_5$, $R_6$, and $R_7$, respectively, and nitrogen atom Ni is bonded to $R_1$. Furthermore, $R_{3a}$ and $R_{3b}$ reference chemical groups extending from the ethyl-amino group extending in turn from carbon atom $C_3$ of the prototype indole structure.

In one embodiment, referring to the chemical compound having formula (I), one of $R_1$, $R_2$, $R_4$, $R_5$, $R_6$, or $R_7$ can be a prenyl group, wherein each non-prenylated $R_1$, $R_2$, $R_5$, $R_6$, or $R_7$ is independently a hydrogen atom or an alkyl group, wherein $R_4$, when it is not prenylated, is an alkyl group, an O-alkyl group, an O-acyl group, a hydroxy group, a phosphate group, a glycosyloxy group, or a hydrogen atom, and wherein $R_{3a}$ and $R_{3b}$ are independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group (and, at the same time, $R_{3b}$ is a hydrogen atom, an alkyl group, acyl group or an aryl group), and wherein $R_{3c}$ is a hydrogen atom or a carboxy group.

Thus, referring to the chemical compound having formula (I), in accordance herewith, at least one of $R_1$, $R_2$, $R_4$, $R_5$, $R_6$, or $R_7$ is a prenyl group. Referring next to FIGS. 6A-6F, 7A-7F, 8A-8F, 9A-9F, 10A-10F, and 11A-11F, shown therein are example embodiments wherein $R_1$, $R_2$, $R_4$, $R_5$, $R_6$, or $R_7$, respectively, are a prenyl group. Having selected one of $R_1$, $R_2$, $R_4$, $R_5$, $R_6$, or $R_7$ as a prenyl group, additional further embodiments are included herein. In this respect, FIGS. 6A-6F and the following paragraph illustrate and describe various example embodiments wherein $R_1$ is a prenyl group, FIGS. 7A-7F and the paragraph thereafter illustrate and describe various example embodiments wherein $R_2$ is a prenyl group, and so forth.

Thus, in one embodiment, referring to the chemical compound having formula (I), $R_1$ can be a prenyl group, each of $R_2$, $R_5$, $R_6$, and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom, and wherein $R_{3a}$ and $R_{3b}$ are independently a hydrogen atom, an alkyl group, acyl group or an aryl group, or wherein $R_{3a}$ and $R_2$ together form an alkyl group and $R_{3b}$ is a hydrogen atom, an alkyl group, acyl group or an aryl group, and wherein $R_{3c}$ is a hydrogen atom or a carboxy group. Example compounds in this respect are shown in FIGS. 6A-6F. It is noted that in the example compounds shown in FIG. 6B-6F, one of $R_2$, $R_4$, $R_5$, $R_6$, and $R_7$ is a methyl group (see: FIGS. 6B, 6C, 6D, 6E, and 6F, respectively), while $R_2$, $R_4$, $R_5$, $R_6$, and $R_7$ which are not methylated are hydrogen atoms. In other embodiments, one of $R_2$, $R_4$, $R_5$, $R_6$, and $R_7$ can be an alkyl group other than a methyl group, e.g., an ethyl group, propyl group, or butyl group. In yet other embodiments, 2, 3, 4, or 5 of $R_2$, $R_4$, $R_5$, $R_6$, and $R_7$ can be alkylated. Furthermore included herein are embodiments, including, but not limited to those shown in FIGS. 6B-6F wherein $R_4$ instead of an alkyl group or hydrogen atom can be a O-alkyl group, an O-acyl group, a hydroxy group, a phosphate group, or a glycosyloxy group. Furthermore, in each of the foregoing example embodiments, including, but not limited to those shown in FIGS. 6A-6F, $R_{3a}$ and $R_{3b}$ can independently be a hydrogen atom, an alkyl group, acyl group or an aryl group, or $R_{3a}$ and $R_2$ can be joined together, along with the nitrogen atom to which $R_{3a}$ is attached, to form an optionally substituted heterocyclic ring, wherein the optional substituent on the heterocyclic ring is an alkyl group (and, at the same time, $R_{3b}$ is a hydrogen atom, an alkyl group, acyl group or an aryl group), and wherein $R_{3c}$ is a hydrogen atom or a carboxy group.

In one further embodiment, $R_2$ can be a prenyl group, each of $R_1$, $R_5$, $R_6$, and $R_7$ can be a hydrogen atom or an alkyl group, and $R_4$ can be an alkyl group O-alkyl group, an O-acyl group, a hydroxy group, a phosphate group, a glycosyloxy group, or a hydrogen atom. Example compounds in this respect are shown in FIGS. 7A-7F. It is noted that in the example compounds shown in FIG. 7B-7F, one of $R_1$, $R_4$, $R_5$, $R_6$, and $R_7$ is a methyl group (see: FIGS. 7B, 7C, 7D, 7E, and 7F, respectively), while $R_1$, $R_4$, $R_5$, $R_6$, and $R_7$ which are not methylated are hydrogen atoms. In other embodiments, one of $R_1$, $R_4$, $R_5$, $R_6$, and $R_7$ can be an alkyl group other than a methyl group, e.g., an ethyl group, propyl group, or butyl group. In yet other embodiments, 2, 3, 4, or 5 of $R_1$, $R_4$, $R_5$, $R_6$, and $R_7$ can be alkylated. Furthermore included herein are embodiments, including, but not limited to those shown in FIGS. 7B-7F wherein $R_4$ instead of an alkyl group or hydrogen atom can be a O-alkyl group, an O-acyl group, a hydroxy group, a phosphate group, or a glycosyloxy group. Furthermore, in each of the foregoing example embodiments, including, but not limited to those shown in FIGS. 7A-7F, $R_{3a}$ and $R_{3b}$ can independently be a hydrogen atom, an alkyl group, acyl group or an aryl group. However, as will be clear due to the prenylation of $R_2$, or $R_{3a}$ and $R_2$ together cannot form an alkyl group and $R_{3b}$ is a hydrogen atom, an alkyl group, acyl group or an aryl group, and wherein $R_{3c}$ is a hydrogen atom or a carboxy group.

In one further embodiment, $R_4$ can be a prenyl group, and each of $R_1$, $R_2$, $R_5$, $R_6$, and $R_7$ can independently be a hydrogen atom or an alkyl group. Example compounds in this respect are shown in FIGS. 8A-8F. It is noted that in the example compounds shown in FIG. 8B-8F, one of $R_1$, $R_2$, $R_5$, $R_6$, and $R_7$ is a methyl group (see: FIGS. 8B, 8C, 8D, 8E, and 8F, respectively), while $R_1$, $R_2$, $R_5$, $R_6$, and $R_7$ which are not methylated are hydrogen atoms. In other embodiments, one of $R_1$, $R_2$, $R_5$, $R_6$, and $R_7$ can be an alkyl group other than a methyl group, e.g., an ethyl group, propyl group, or butyl group. In yet other embodiments, 2, 3, 4, or 5 of $R_1$, $R_2$, $R_5$, $R_6$, and $R_7$ can be alkylated. Furthermore, in each of the foregoing example embodiments, including, but not limited to those shown in FIGS. 8A-8F, $R_{3a}$ and $R_{3b}$ can independently be a hydrogen atom, an alkyl group, acyl group or an aryl group, or $R_{3a}$ and $R_2$ can be joined together, along with the nitrogen atom to which $R_{3a}$ is attached, to form an optionally substituted heterocyclic ring, wherein the optional substituent on the heterocyclic ring is an alkyl group (and, at the same time, $R_{3b}$ is a hydrogen atom, an alkyl group, acyl group or an aryl group), and wherein $R_{3c}$ is a hydrogen atom or a carboxy group.

In one further embodiment, $R_5$ can be a prenyl group, each of $R_1$, $R_2$, $R_6$, and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. Example compounds in this respect are shown in FIGS. 9A-9F. It is noted that in the example compounds shown in FIG. 9B-9F, one of $R_1$, $R_2$, $R_4$, $R_6$, and $R_7$ is a methyl group (see: FIGS. 9B, 9C, 9D, 9E, and 9F, respectively), while $R_1$, $R_2$, $R_4$, $R_6$, and $R_7$ which are not methylated are hydrogen atoms. In other embodiments, one of $R_1$, $R_2$, $R_4$, $R_6$, and $R_7$ can be an alkyl group other than a methyl group, e.g., an ethyl group, propyl group, or butyl group. In yet other embodiments, 2, 3, 4, or 5 of $R_2$, $R_4$, $R_6$, and $R_7$ can be alkylated. Furthermore included herein are embodiments, including, but not limited to those shown in FIGS. 9B-9F wherein $R_4$ instead of an alkyl group or hydrogen atom can be a O-alkyl group, an O-acyl group, a hydroxy group, a phosphate group, or a glycosyloxy group. Furthermore, in each of the foregoing example embodiments, including, but not limited to those shown in FIGS. 9A-9F, $R_{3a}$ and $R_{3b}$ can independently be a hydrogen atom, an alkyl group, acyl group or an aryl group, or $R_{3a}$ and $R_2$ can be joined together, along with the nitrogen atom to which $R_{3a}$ is attached, to form an optionally substituted heterocyclic ring, wherein the optional substituent on the heterocyclic ring is an alkyl group (and, at the same time, $R_{3b}$ is a hydrogen atom, an alkyl group, acyl group or an aryl group), and wherein $R_{3c}$ is a hydrogen atom or a carboxy group.

In one further embodiment, $R_6$ can be a prenyl group, each of $R_1$, $R_2$, $R_5$, and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. Example compounds in this respect are shown in FIGS. 10A-10F. It is noted that in the example compounds shown in FIG. 10B-10F, one of $R_1$, $R_2$, $R_4$, $R_5$, and $R_7$ is a methyl group (see: FIGS. 10B, 10C, 10D, 10E, and 10F, respectively), while $R_1$, $R_2$, $R_4$, $R_5$, and $R_7$ which are not methylated are hydrogen atoms. In other embodiments, one of $R_1$, $R_2$, $R_4$, $R_5$, and $R_7$ can be an alkyl group other than a methyl group, e.g., an ethyl group, propyl group, or butyl group. In yet other embodiments, 2, 3, 4, or 5 of $R_1$, $R_2$, $R_4$, $R_5$, and $R_7$ can be alkylated. Furthermore included herein are embodiments, including, but not limited to those shown in FIGS. 10B-10F wherein $R_4$ instead of an alkyl group or hydrogen atom can be a O-alkyl group, an O-acyl group, a hydroxy group, a phosphate group, or a glycosyloxy group. Furthermore, in each of the foregoing example embodiments, including, but not limited to those shown in FIGS. 10A-10F, $R_{3a}$ and $R_{3b}$ can independently be a hydrogen atom, an alkyl group, acyl group or an aryl group, or $R_{3a}$ and $R_2$ can be joined together, along with the nitrogen atom to which $R_{3a}$ is attached, to form an optionally substituted heterocyclic ring, wherein the optional substituent on the heterocyclic ring is an alkyl group (and, at the same time, $R_{3b}$ is a hydrogen atom, an alkyl group, acyl group or an aryl group), and wherein $R_{3c}$ is a hydrogen atom or a carboxy group.

In one further embodiment, $R_7$ can be a prenyl group, each of $R_1$, $R_2$, $R_5$, and $R_6$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. Example compounds in this respect are shown in FIGS. 11A-11F. It is noted that in the example compounds shown in FIG. 11B-11F, one of $R_1$, $R_2$, $R_4$, $R_5$, and $R_6$ is a methyl group (see: FIGS. 11B, 11C, 11D, 11E, and 11F, respectively), while $R_1$, $R_2$, $R_4$, $R_5$, and $R_6$ which are not methylated are hydrogen atoms. In other embodiments, one of $R_1$, $R_2$, $R_4$, $R_6$, and $R_7$ can be an alkyl group other than a methyl group, e.g., an ethyl group, propyl group, or butyl group. In yet other embodiments, 2, 3, 4, or 5 of $R_1$, $R_2$, $R_4$, $R_5$, and $R_6$ can be alkylated. Furthermore included herein are embodiments, including, but not limited to those shown in FIGS. 11B-11F wherein $R_4$ instead of an alkyl group or hydrogen atom can be a O-alkyl group, an O-acyl group, a hydroxy group, a phosphate group, or a glycosyloxy group. Furthermore, in each of the foregoing example embodiments, including, but not limited to those shown in FIGS. 11A-11F, $R_{3a}$ and $R_{3b}$ can independently be a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group (and, at the same time, $R_{3b}$ is a hydrogen atom, an alkyl group, acyl group or an aryl group), and wherein $R_{3c}$ is a hydrogen atom or a carboxy group.

Thus, referring to the chemical compound having formula (I), it will now be clear that in accordance herewith in some embodiments one of $R_1$, $R_2$, $R_4$, $R_5$, $R_6$, or $R_7$ can a prenyl group.

In further embodiments, referring to the chemical compound having formula (I), two of $R_1$, $R_2$, $R_4$, $R_5$, $R_6$, or $R_7$ can be a prenyl group, wherein each non-prenylated $R_1$, $R_2$, $R_4$, $R_5$, $R_6$, or $R_7$ is independently a hydrogen atom or an alkyl group, and wherein $R_4$, when it is not prenylated, is an alkyl group, an O-alkyl group, an O-acyl group, a hydroxy group, a phosphate group, a glycosyloxy group, or a hydrogen atom, and wherein $R_{3a}$ and $R_{3b}$ are independently a hydrogen atom, an alkyl group, acyl group or an aryl group, or wherein $R_{3a}$ and $R_2$ together form an alkyl group and $R_{3b}$ is a hydrogen atom, an alkyl group, acyl group or an aryl group, and wherein $R_{3c}$ is a hydrogen atom or a carboxy group. Thus, in one embodiment, $R_1$ and $R_2$ can be prenyl groups, $R_5$, $R_6$ and $R_7$ can be independently a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_1$ and $R_4$ can be prenyl groups, and $R_2$, $R_5$ $R_6$ and $R_7$ can be independently a hydrogen atom or an alkyl group. In one embodiment, $R_1$ and $R_5$ can be prenyl groups, $R_2$, $R_6$ and $R_7$ can be independently a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_1$ and $R_6$ can be prenyl groups, $R_2$, $R_5$ and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_1$ and $R_7$ can be prenyl groups, $R_2$, $R_5$ and $R_6$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_2$ and $R_4$ can be prenyl groups, and $R_1$, $R_2$, $R_6$ and $R_7$ can independently be a hydrogen atom or an alkyl group. In one embodiment, $R_2$ and $R_5$ can be prenyl groups, $R_1$, $R_6$ and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_2$ and $R_6$ can be prenyl groups, $R_1$, $R_5$ and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_2$ and $R_7$ can be prenyl groups, $R_1$, $R_5$ and $R_6$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_4$ and $R_5$ can be prenyl groups, and $R_1$, $R_2$, $R_6$ and $R_7$ can independently be a hydrogen atom or an alkyl group. In one embodiment, $R_4$ and $R_6$ can be prenyl groups, and $R_1$, $R_2$, $R_5$ and $R_7$ can independently be a hydrogen atom or an alkyl group. In one embodiment, $R_4$ and $R_7$ can be prenyl groups, and $R_1$, $R_2$, $R_5$ and $R_6$ can independently be a hydrogen atom or an alkyl group. In one embodiment, $R_5$ and $R_6$ can be prenyl groups, $R_1$, $R_2$ and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_5$ and $R_7$ can be prenyl groups, $R_1$, $R_2$ and $R_6$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_6$ and $R_7$ can be prenyl groups, $R_1$, $R_2$ and $R_5$ can independently be a hydrogen atom or an alkyl group, and $R_4$ can be an alkyl group, an O-alkyl group, an O-acyl group, a hydroxy group, a phosphate group, a glycosyloxy group, or a hydrogen atom.

In further embodiments, referring to the chemical compound having formula (I), three of $R_1$, $R_2$, $R_4$, $R_5$, $R_6$, or $R_7$ can be a prenyl group, wherein each non-prenylated $R_1$, $R_2$, $R_5$, $R_6$, or $R_7$ is independently a hydrogen atom or an alkyl group, and wherein $R_4$ when it is not prenylated is an alkyl group, an O-alkyl group, an O-acyl group, a hydroxy group, a phosphate group, a glycosyloxy group, or a hydrogen atom, and wherein $R_{3a}$ and $R_{3b}$ are independently a hydrogen atom, an alkyl group, acyl group or an aryl group, or wherein $R_{3a}$ and $R_2$ together form an alkyl group and $R_{3b}$ is a hydrogen atom, an alkyl group, acyl group or an aryl group, and wherein $R_{3c}$ is a hydrogen atom or a carboxy group. Thus, in one embodiment $R_1$, $R_2$, and $R_4$ can be prenyl groups, $R_5$, $R_6$ and $R_7$ can independently be a hydrogen atom or an alkyl group. In one embodiment $R_1$, $R_2$, and $R_5$ can be prenyl groups, $R_6$ and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment $R_1$, $R_2$, and $R_6$ can be prenyl groups, $R_5$ and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_1$, $R_2$, and $R_7$ can be prenyl groups, $R_5$ and $R_6$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_1$, $R_4$, and $R_5$ can be prenyl groups, and $R_2$, $R_6$ and $R_7$ can independently be a hydrogen atom or an alkyl group. In one embodiment, $R_1$, $R_4$, and $R_6$ can be prenyl groups, and $R_2$, $R_5$ and $R_7$ can independently be a hydrogen atom or an alkyl group. In one embodiment $R_1$, $R_4$, and $R_7$ can be prenyl groups, and $R_2$, $R_5$ and $R_6$ can independently be a hydrogen atom or an alkyl group. In one embodiment, $R_1$, $R_5$, and $R_6$ can be prenyl groups, $R_2$ and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_1$, $R_5$, and $R_7$ can be prenyl groups, $R_2$ and $R_6$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_1$, $R_6$, and $R_7$ can be prenyl groups, $R_2$ and $R_5$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_2$, $R_4$, and $R_5$ can be prenyl groups, and $R_1$, $R_6$ and $R_7$ can independently be a hydrogen atom or an alkyl group. In one embodiment, $R_2$, $R_4$, and $R_6$ can be prenyl groups, and $R_1$, $R_5$ and $R_7$ can independently be a hydrogen atom or an alkyl group. In one embodiment, $R_2$, $R_4$, and $R_7$ can be prenyl groups, and $R_1$, $R_5$ and $R_6$ can independently be a hydrogen atom or an alkyl group. In one embodiment, $R_2$, $R_5$, and $R_6$ can be prenyl groups, $R_1$ and $R_7$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_2$, $R_5$, and $R_7$ can be prenyl groups, Ri and $R_6$ can independently be a hydrogen atom or an alkyl group, and $R_4$ can be an O-alkyl group, an O-acyl group, a hydroxy group, a phosphate group, a glycosyloxy group, or a hydrogen atom. In one embodiment, $R_2$, $R_6$, and $R_7$ can be prenyl groups, $R_1$ and $R_5$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_4$, $R_5$, and $R_6$ can be prenyl groups, and $R_1$, $R_2$ and $R_7$ can independently be a hydrogen atom or an alkyl group. In one embodiment, $R_4$, $R_5$, and $R_7$ can be prenyl groups, and $R_1$, $R_2$ and $R_6$ can independently be a hydrogen atom or an alkyl group. In one embodiment, $R_4$, $R_6$, and $R_7$ can a prenyl groups, and $R_1$, $R_2$ and $R_5$ can independently be a hydrogen atom or an alkyl group. In one embodiment, $R_5$, $R_6$, and $R_7$ can be prenyl groups, $R_1$ and $R_2$ can independently be a hydrogen atom or an alkyl group, and $R_4$ can be an alkyl group, an O-alkyl group, an O-acyl group, a hydroxy group, a phosphate group, a glycosyloxy group, or a hydrogen atom.

In further embodiments, referring to the chemical compound having formula (I), four of $R_1$, $R_2$, $R_4$, $R_5$, $R_6$, or $R_7$ can be a prenyl group, wherein each non-prenylated $R_1$, $R_2$, $R_5$, $R_6$, or $R_7$ is independently a hydrogen atom or an alkyl 30 group, and wherein $R_4$, when it is not prenylated, is an alkyl group, an O-alkyl group, an O-acyl group, a hydroxy group, a phosphate group, a glycosyloxy group, or a hydrogen atom, and wherein $R_{3a}$ and $R_{3b}$ independently are a hydrogen atom, an alkyl group, acyl group or an aryl group. Thus, in one embodiment, $R_1$, $R_2$, $R_4$ and $R_5$ can be prenyl groups, and $R_6$ and $R_7$ can independently be a hydrogen atom or an alkyl group. In one embodiment, $R_1$, $R_2$, $R_4$ and $R_6$ can be prenyl groups, and $R_5$ and $R_7$ can independently be a hydrogen atom or an alkyl group. In one embodiment, $R_1$, $R_2$, $R_4$ and $R_7$ can be prenyl groups, and $R_5$ and $R_6$ can independently be a hydrogen atom or an alkyl group. In one embodiment, $R_1$, $R_2$, $R_5$, and $R_6$ can be prenyl groups, $R_7$ can be a hydrogen atom or an alkyl group, and $R_4$ can be an alkyl group, an O-alkyl group, an O-acyl group, a hydroxy group, a phosphate group, a glycosyloxy group, ora hydrogen atom. In one embodiment, $R_1$, $R_2$, $R_5$, and $R_7$ can be prenyl groups, $R_6$ can be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_1$, $R_2$, $R_6$, and $R_7$ can be prenyl groups, $R_5$ can be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, Ri, $R_4$, $R_5$ and $R_6$ can be prenyl groups, and $R_2$ and $R_7$ can independently be a hydrogen atom or an alkyl group. In one embodiment, $R_1$, $R_4$, $R_6$ and $R_7$ can be prenyl groups, and $R_2$ and $R_5$ can independently be a hydrogen atom or an alkyl group. In one embodiment, $R_1$, $R_4$, $R_5$ and $R_7$ can be prenyl groups, and $R_2$ and $R_6$ can independently be a hydrogen atom or an alkyl group. In one embodiment, $R_1$, $R_5$, $R_6$, and $R_7$ can be prenyl groups, $R_2$ can independently be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_2$, $R_4$, $R_5$ and $R_6$ can be prenyl groups, and $R_1$ and $R_7$ can independently be a hydrogen atom or an alkyl group. In one embodiment, $R_2$, $R_4$, $R_5$ and $R_7$ can be a prenyl group, and $R_1$ and $R_6$ can independently be a hydrogen atom or an alkyl group. In one embodiment, $R_2$, $R_4$, $R_6$ and $R_7$ can be a prenyl group, and $R_1$ and $R_5$ can independently be a hydrogen atom or an alkyl group. In one embodiment, $R_2$, $R_5$, $R_6$, and $R_7$ can be a prenyl group, $R_1$ can be a hydrogen atom or an alkyl group, and $R_4$ can be an alkyl group, an O-alkyl group, an O-acyl group, a hydroxy group, a phosphate group, a glycosyloxy group, or a hydrogen atom. In one embodiment, $R_4$, $R_5$, $R_6$ and $R_7$ can be a prenyl group, and $R_1$ and $R_2$ can independently be a hydrogen atom.

In further embodiments, referring to the chemical compound having formula (I), five of $R_1$, $R_2$, $R_4$, $R_5$, $R_6$, or $R_7$ can be a prenyl group, wherein a non-prenylated $R_1$, $R_2$, $R_5$, $R_6$, or $R_7$ is a hydrogen atom or an alkyl group, and wherein $R_4$ when it is not prenylated is an alkyl group, an O-alkyl group, an O-acyl group, a hydroxy group, a phosphate group, a glycosyloxy group, or a hydrogen atom, and wherein $R_{3a}$ and $R_{3b}$ independently are a hydrogen atom, an alkyl group, acyl group or an aryl group, or wherein $R_{3a}$ and $R_2$ together form an alkyl group and $R_{3b}$ is a hydrogen atom, an alkyl group, acyl group or an aryl group, and wherein $R_{3c}$ is a hydrogen atom or a carboxy group. Thus, in one embodiment, $R_1$, $R_2$, $R_4$, $R_5$ and $R_6$ can be a prenyl group, and $R_7$ can be a hydrogen atom or an alkyl group. In one embodiment, $R_1$, $R_2$, $R_4$, $R_5$ and $R_7$ can be a prenyl group, and $R_6$ can be a hydrogen atom or an alkyl group. In one embodiment, $R_1$, $R_2$, $R_4$, $R_6$ and $R_7$ can be a prenyl group, and $R_5$ can be a hydrogen atom or an alkyl group. In one embodiment, $R_1$, $R_2$, $R_6$, $R_6$ and $R_7$ can be a prenyl group, and $R_4$ can be an alkyl group, a O-alkyl group, an O-acyl group, a hydroxy group, a phosphate group, a glycosyloxy group, ora hydrogen atom. In one embodiment, $R_1$, $R_4$, $R_5$, $R_6$ and $R_7$ can be a prenyl group, and $R_2$ can be a hydrogen atom or an alkyl group. In one embodiment, $R_2$, $R_4$, $R_5$, $R_6$ and $R_7$ can be a prenyl group, and $R_1$ can be a hydrogen atom or an alkyl group.

In yet further embodiments, referring to the chemical compound having formula (I), all six of $R_1$, $R_2$, $R_4$, $R_5$, $R_6$, and $R_7$ can be a prenyl group wherein $R_{3a}$ and $R_3B$ independently are a hydrogen atom, an alkyl group, acyl group or an aryl group, or wherein $R_{3a}$ and $R_2$ together form an alkyl group and $R_{3b}$ is a hydrogen atom, an alkyl group, acyl group or an aryl group, and wherein $R_{3c}$ is a hydrogen atom or a carboxy group.

It is noted that in a further aspect hereof, $R_{3a}$ and $R_{3b}$ can each independently be a hydrogen atom, an alkyl group, acyl group or an aryl group. Thus, $R_{3a}$ and $R_{3b}$ can each be a hydrogen atom, or $R_{3a}$ and $R_{3b}$ can each be an alkyl group, such as a methyl group, ethyl group, propyl group, or longer chain alkyl group, or $R_{3a}$ and $R_{3b}$ can be each be an acyl group, or $R_{3a}$ and $R_{3b}$ can each be an aryl group. Furthermore, one of $R_{3a}$ and $R_{3b}$ can be a hydrogen atom, and one of $R_{3a}$ and $R_{3b}$ can be an alkyl group. One of $R_{3a}$ and $R_{3b}$ can be a hydrogen atom, and one of $R_{3a}$ and $R_{3b}$ can be an acyl group. One of $R_{3a}$ and $R_{3b}$ can be a hydrogen atom, and one of $R_{3a}$ and $R_3$bcan be an aryl group. One of $R_{3a}$ and $R_{3b}$ can be an alkyl group, and one of $R_{3a}$ and $R_{3b}$ can be an aryl group. One of $R_{3a}$ and $R_{3b}$ can be an alkyl group, and one of $R_{3a}$ and $R_{3b}$ can be an acyl group. One of $R_{3a}$ and $R_{3b}$ can be an acyl group, and one of $R_{3a}$ and $R_{3b}$ can be an aryl group. In one further embodiment, $R_{3a}$ and $R_2$ are joined together, along with the nitrogen atom to which $R_{3a}$ is attached, to form an optionally substituted heterocyclic ring, wherein the optional substituents on the heterocyclic ring is an alkyl group (see: e.g., the compound having formula (VI)), and Rab can a hydrogen atom, an alkyl group, acyl group or an aryl group. In at least one embodiment, $R_{3a}$ and $R_2$ are joined together, along with the nitrogen atom to which $R_{3a}$ is attached, to form an optionally substituted 5-7-membered heterocyclic ring, wherein the optional substituent on the heterocyclic ring is an alkyl group. In one embodiment, the optionally substituted heterocyclic ring is an optionally substituted 6-membered heterocyclic ring. In one embodiment, the optional substituents are methyl, ethyl, or propyl.

It is noted that in a further aspect hereof, $R_{3c}$ can be a hydrogen atom or a carboxy group.

Furthermore, in one example embodiment, a prenylated psilocybin derivative according to the present disclosure can be a chemical compound having formula (IV):

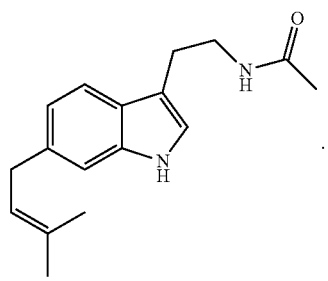

(IV)

Furthermore, in one example embodiment, a prenylated psilocybin derivative according to the present disclosure can be a chemical compound having formula (V):

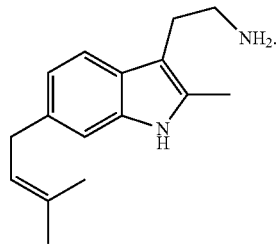

(V)

Furthermore, in one example embodiment, a prenylated psilocybin derivative according to the present disclosure can be a chemical compound having formula (VI):

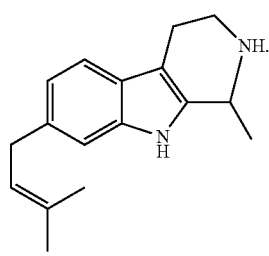

(VI)

Furthermore, in one example embodiment, a prenylated psilocybin derivative according to the present disclosure can be a chemical compound having formula (VII):

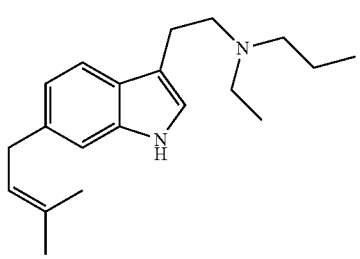

(VII)

Furthermore, in one example embodiment, a prenylated psilocybin derivative according to the present disclosure can be a chemical compound having ormula (VIII):

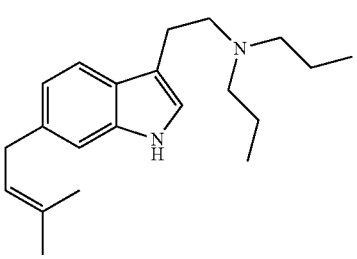

(VIII)

Furthermore, in one example embodiment, a prenylated psilocybin erivative according to the present disclosure can be a chemical compound having formula (IX):

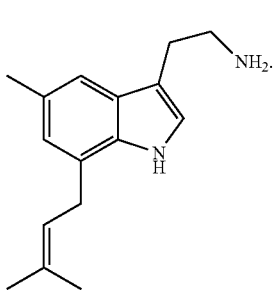

(IX)

Furthermore, in one example embodiment, a prenylated psilocybin derivative according to the present disclosure can be a chemical compound having formula (X):

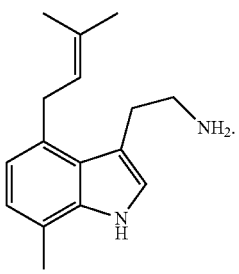

(X)

Furthermore, in one example embodiment, a prenylated psilocybin derivative according to the present disclosure can be a chemical compound having formula (XI):

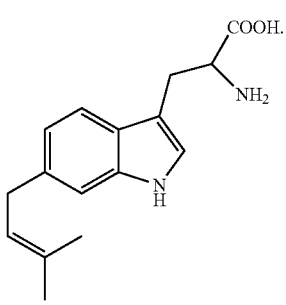

(XI)

Furthermore, in one example embodiment, a prenylated psilocybin derivative according to the present disclosure can be a chemical compound having formula (XII):

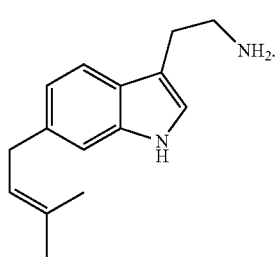

(XII)

Furthermore, in one example embodiment, a prenylated psilocybin derivative according to the present disclosure can be a chemical compound having formula (XIII):

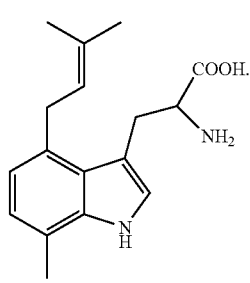

(XIII)

Furthermore, in one example embodiment, a prenylated psilocybin derivative according to the present disclosure can be a chemical compound having formula (XIV):

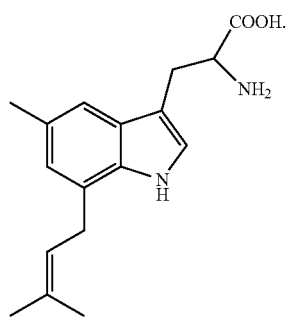

(XIV)

Furthermore, it is noted that the prenylated psilocybin derivatives of the present disclosure include salts thereof, including pharmaceutically acceptable salts. Thus, the nitrogen atom of the ethyl-amino group extending in turn from the $C_3$ atom may be protonated, and the positive charge may be balanced by, for example, chloride or sulfate ions, to thereby form a chloride salt or a sulfate salt. Furthermore, in compounds wherein $R_4$ is a phosphate group, the phosphate group may be de-protonated, and the negative charge may be balanced by, for example, sodium ions or potassium ions, to thereby form a sodium salt or a potassium salt.

Furthermore, it is noted that when $R_4$ is a phosphate group, the term prenylated psilocybin derivative also includes compounds having formula (XXIII):

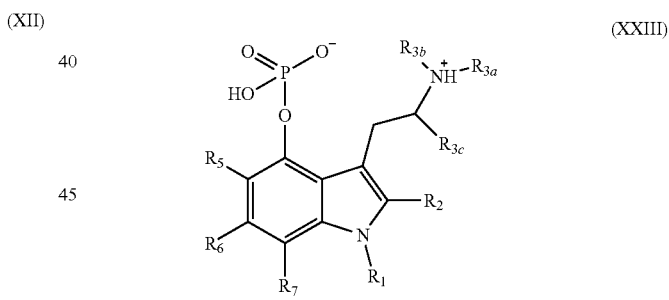

(XXIII)

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and $R_{3b}$ are independently a hydrogen atom, an alkyl group, acyl group or an aryl group, or, $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group. When $R_{3c}$ is a carboxy group, further included are compounds having formula (XXIV):

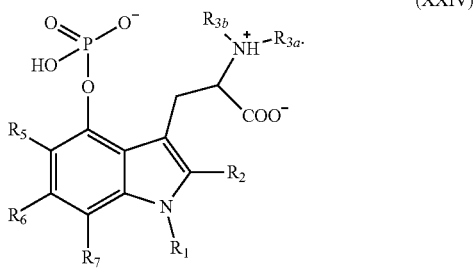

(XXIV)

Further included are salts of prenylated psilocybin derivatives having formula (XXIII) and (XXIV), such as a sodium salt, a potassium salt, etc.

Thus, to briefly recap, the present disclosure provides prenylated psilocybin derivatives. The disclosure provides, in particular, a chemical compound having formula (I):

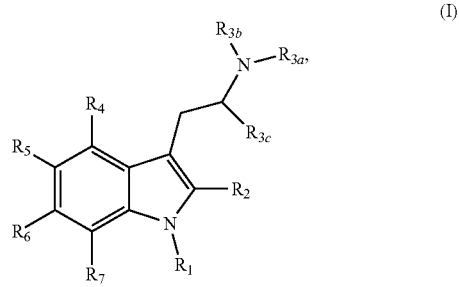

(I)

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$, is independently a hydrogen atom, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and $R_{3b}$ each independently are a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

In one embodiment, when $R_4$ is not prenylated, $R_4$ is a hydrogen atom, a $(C_1-C_{20})$-alkyl group, $(C_1-C_{20})$—O-alkyl group, or $(C_1-C_{20})$—O-acyl group a hydroxy group, a glycosyloxy group, or a phosphate group. In another embodiment, when $R_4$ is not carboxylated, $R_4$ is a hydrogen atom, a $(C_1-C_{10})$-alkyl group, a $(C_1-C_{10})$—O-alkyl group or $(C_1-C_{10})$—O-acyl group, a hydroxy group, a glycosyloxy group, or a phosphate group. In another embodiment, when $R_4$ is not carboxylated, $R_4$ is a hydrogen atom, a $(C_1-C_6)$—O-alkyl group, $(C_1-C_6)$—O-alkyl group or $(C_1-C_6)$—O-acyl group, a hydroxy group, a glycosyloxy group, or a phosphate group. In another embodiment, when $R_4$ is not carboxylated, $R_4$ is a hydrogen atom, a glycosyloxy group, a phosphate group, a methyl group, an ethyl group, a propyl group, an O-methyl group, an O-ethyl group, an O-propyl group, an acetyl group, a propanoyl group, propoxycarbonyl group, or a butoxycarbonyl group (n=4).

In one embodiment, when $R_1$, $R_2$, $R_4$, $R_5$, $R_6$, or $R_7$ is not a prenyl group, $R_1$, $R_2$, $R_5$, $R_6$, or $R_7$ are independently a hydrogen atom or a $(C_1-C_{20})$-alkyl group, or a $(C_1-C_{10})$-alkyl group, or a (01-06)-alkyl group, or a methyl group, an ethyl group, a propyl group, or a butyl group.

In another embodiment, $R_{3a}$ and $R_{3b}$ are a hydrogen atom, a $(C_1-C_{20})$-alkyl group, a $(C_6-C_{14})$-aryl group, or a —C(═O)$(C_1-C_{20})$-alkyl group. In another embodiment, $R_{3a}$ and $R_{3b}$ are a hydrogen atom, a $(C_1-C_{10})$-alkyl group, a $(C_6-C_{10})$-aryl group, or a —C(═O)$(C_1-C_{10})$-alkyl group. In another embodiment, $R_{3a}$ and $R_{3b}$ are a hydrogen atom, a $(C_1-C_6)$-alkyl group, a phenyl group, or a —C(═O)$(C_1-C_6)$-alkyl group. In another embodiment, $R_{3a}$ and $R_{3b}$ are a hydrogen atom, a methyl group, an ethyl group, a propyl group, a phenyl group, —C(═O)—$CH_3$, —O(═O)—$CH_2CH_3$, or —C(═O)—$CH_2CH_2CH_3$.

In another embodiment $R_{3a}$ and $R_2$ together form an alkyl group —$CH_2$— or $R_{3a}$ and $R_2$ together form an alkyl group an alkyl group —CH($C_nH_{2n+1}$)—, wherein n is an integer from 1-20, or from 1-10, or from 1-6, or a —CH($CH_3$)— group, a —CH($C_2H_5$)— group, or a CH($C_3H_7$)—group, and wherein $R_{3b}$ is a $(C_1-C_{20})$-alkyl group, a $(_6-C_{14})$-aryl group, or a —O(═O)$(C_1-C_{20})$-alkyl group; or $R_{3b}$ is a hydrogen atom, a $(C_1-C_{10})$-alkyl group, a $(C_6-C_{10})$-aryl group, or a —C(═O)$(C_1-C_{10})$-alkyl group; or $R_{3b}$ is a hydrogen atom, a $(C_1-C_6)$-alkyl group, a phenyl group, or a —C(═O)$(C_1-C_6)$-alkyl group. In another embodiment; or $R_{3b}$ is a hydrogen atom, a methyl group, an ethyl group, a propyl group, a phenyl group, —C(═O)—CH3, —O(═O)—$CH_2CH_3$, or —C(═O)—$CH_2CH_2CH_3$.

The prenylated psilocybin derivatives of the present disclosure may be used to prepare a pharmaceutical or recreational drug formulation. Thus, in one embodiment, the present disclosure further provides in another aspect, pharmaceutical and recreational drug formulations comprising prenylated psilocybin derivatives. Accordingly, in one aspect, the present disclosure provides in a further embodiment a pharmaceutical or recreational drug formulation comprising a chemical compound having formula (I):

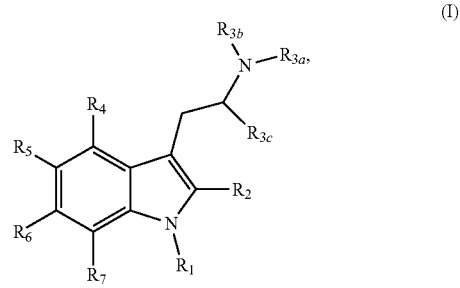

(I)

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and Rab are independently a hydrogen atom, an alkyl group, acyl group or an aryl group or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group, togetherwith a diluent, carrier, or excipient.

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated, or prophylaxis is conducted, on the mode of delivery of the compound, or on whether further active compounds are administered in addition to the compounds of the present disclosure. Representative doses of the present invention include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the prenylated psilocybin compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22$^{nd}$ Edition (Pharmaceutical Press and Philadelphia College of Pharmacy at the University of the Sciences, 2012).

The pharmaceutical and drug formulations comprising the prenylated psilocybin derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stealyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the prenylated psilocybin derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1 — Vol. 3, by CRC Press (2008).

The pharmaceutical and recreational drug formulations comprising the prenylated psilocybin derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the prenylated psilocybin derivatives of the present disclosure for parenteral administration may be formulated to be immediate and/or modified release. Modified release formulations include delayed-, sustained-, pulsed-, controlled-, targeted and programmed release. Thus, the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T.M., 1999 J. Pharm. Sci, 88 (10), 955-958).

Other means of topical administration include delivery by electroporation, iontophoresis, phonophoresis, sonophoresis and microneedle or needle-free (e.g., PowderjectTM, BiojectTM, etc.) injection.

Pharmaceutical and recreational drug formulations for inhalation or insufflation include solutions and suspensions in pharmaceutically acceptable aqueous or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

In further embodiments, in which the prenylated psilocybin compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound having formula (I):

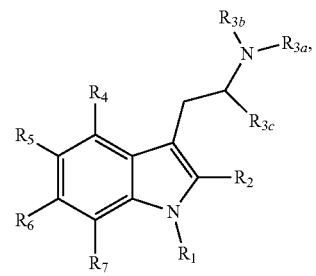

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and Rab are independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

Psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder, persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J Psychiatr Res 137: 273-282); substance-related disorders, such as alcohol-related disorders, cannabis related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder.

In an aspect, the compounds of the present disclosure may be used to be contacted with a 5-$HT_{2A}$ receptor to thereby modulate the 5-$HT_{2A}$ receptor. Such contacting includes bringing a compound of the present disclosure and 5-$HT_{2A}$ receptor together under in vitro conditions, for example, by introducing the compounds in a sample containing a 5-$HT_{2A}$ receptor, for example, a sample containing purified 5-$HT_{2A}$ receptors, or a sample containing cells comprising 5-$HT_{2A}$ receptors. In vitro conditions further include the conditions described in Example 1 hereof. Contacting further includes bringing a compound of the present disclosure and 5-$HT_{2A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the 5-$HT_{2A}$ receptor, the compound may activate the 5-$HT_{2A}$ receptor or inhibit the 5-$HT_{2A}$ receptor.

Thus, in a further aspect, the condition that may be treated in accordance herewith can be any 5-$HT_{2A}$ receptor mediated disorder. Such disorders include, but are not limited to schizophrenia, psychotic disorder, attention deficit hyperactivity disorder, autism, and bipolar disorder.

In an aspect, the compounds of the present disclosure may be used to be contacted with a 5-$HT_{1A}$ receptor to thereby modulate the 5-$HT_{1A}$ receptor. Such contacting includes bringing a compound of the present disclosure and 5-$HT_{1A}$ receptor together under in vitro conditions, for example, by introducing the compounds in a sample containing a 5-$HT_{1A}$ receptor, for example, a sample containing purified 5-$HT_{1A}$ receptors, or a sample containing cells comprising 5-$HT_{1A}$ receptors. In vitro conditions further include the conditions described in Example 1 hereof. Contacting further includes bringing a compound of the present disclosure and 5-$HT_{1A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the 5-$HT_{2A}$ receptor, the compound may activate the 5-$HT_{1A}$ receptor or inhibit the 5-$HT_{1A}$ receptor.

Thus, in a further aspect, the condition that may be treated in accordance herewith can be any 5-$HT_{1A}$ receptor mediated disorder. Such disorders include, but are not limited to schizophrenia, psychotic disorder, attention deficit hyperactivity disorder, autism, and bipolar disorder.

The chemical compounds of the present disclosure may also be used as a feedstock material for other psilocybin derivatives. Thus, in one embodiment, the chemical compounds of the present disclosure may be in used manufacture of a pharmaceutical or recreational drug formulation, wherein the manufacture may comprise derivatizing a chemical compound having formula (I):

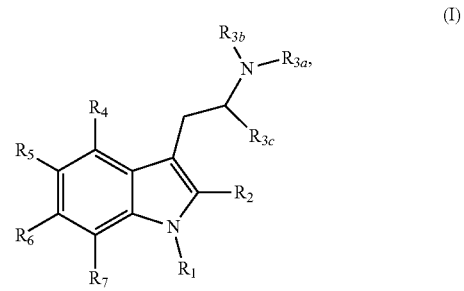

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and Rab are independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

Next, methods to make the prenylated compounds of the present disclosure will be discussed. In this respect, it is initially noted that the prenylated psilocybin compounds of the present disclosure may be prepared in any suitable manner, including by employing any organic chemical synthesis methods, biosynthetic methods, or combination thereof. In general terms, in an aspect hereof, in accordance with the teachings herein, the prenylated psilocybin derivatives of the present disclosure can be made by initially selecting and obtaining, providing, receiving, or preparing a psilocybin derivative precursor compound. By then modifying the obtained, provided, received, or prepared psilocybin derivative precursor compound source material, notably by combining the psilocybin derivative precursor compound with a prenyl compound, and chemically reacting the combined compounds, the prenylated psilocybin derivative compounds of the present disclosure can be made.

Next, initially suitable psilocybin precursor compounds and prenyl compounds will be discussed. Thereafter, suitable example methods to combine and react these two reactant compounds will be discussed, including methods to perform example chemical reactions involving enzymatic catalysis to facilitate chemical reaction between the reactants. The reactions may be conducted in vitro and/or in vivo.

In an aspect hereof, a variety of psilocybin derivative precursor compounds may be selected to make the psilocybin derivative compounds of the present disclosure. In general, suitable psilocybin derivative precursor compounds include compounds comprising an indole prototype structure (see: FIG. 2), including, for example, tryptophan, tryptamine, 4-hydroxyindole, 4-hydroxytryptophan, 4-hydroxytryptamine, norbaeocystin and baeocystin. Further suitable psilocybin derivative precursor compounds include psilocybin derivative precursor compounds having formula (XXII):

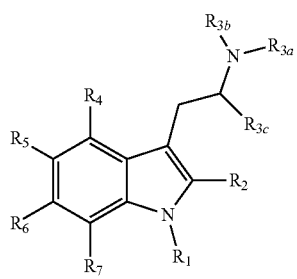

(XXII)

wherein each of $R_1$, $R_2$, $R_4$, $R_5$, $R_6$, or $R_7$ is independently a hydrogen atom or an alkyl group, wherein $R_4$ is an alkyl group, an O-alkyl group, an O-acyl group, a hydroxy group, a phosphate group, a glycosyloxy group, or a hydrogen atom, and wherein $R_{3a}$ and Rab are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

Referring further to chemical compounds having formula (XXII), suitable psilocybin derivative precursor compounds that further may be selected in accordance herewith further include compounds from the group having formula (XV); (XVI); (XVII); (XVIII); (XIX); (XX); and (XXI):

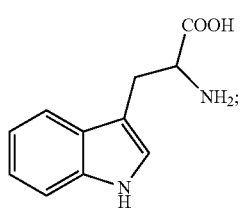

(XV)

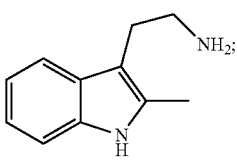

(XVI)

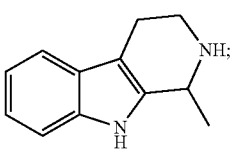

(XVII)

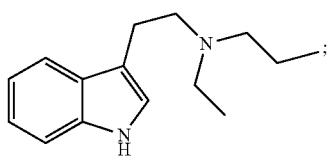

(XVIII)

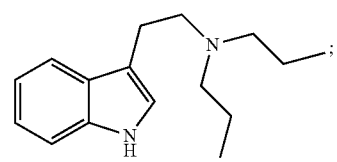

(XIX)

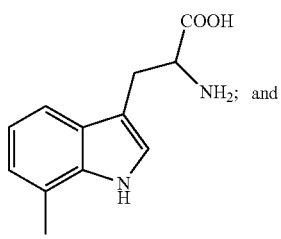

(XX)

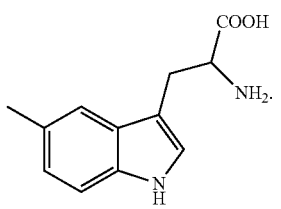

(XXI)

The psilocybin derivative precursor compounds may be obtained, received, prepared, or provided in a more or less chemically pure form or preparation, for example, in the form of a psilocybin derivative precursor compound preparation having a purity of at least about 95%, at least about 96%, at least about 97%, at least about 98%, at least about 99%, or at least 99.9%. The psilocybin derivative precursor compounds may be chemically or biosynthetically synthesized, or they may be purchased from a fine chemical manufacturer, for example.

Turning next to prenyl compounds that may be used in accordance herewith, in general any compound containing a prenyl group may be selected, and prepared, obtained or received for reaction with the psilocybin derivative precursor compounds. Particularly suitable prenyl compounds that may be selected include phosphorylated prenyl compounds, for example, geranyl pyrophosphate (GPP), dimethylallyl pyrophosphate (DMAPP), farnesyl pyrophosphate (FPP), or geranylgeranyl pyrophosphate (GGPP). The prenyl compounds may be provided in a more or less chemically pure form or preparation, for example, in the form of a prenyl compound preparation having a purity of at least about 95%, at least about 96%, at least about 97%, at least about 98%, at least about 99%, or at least 99.9%. The prenyl compounds may be chemically or biosynthetically synthesized, or purchased from a fine chemical manufacturer. Prenyl compounds also may be synthesized from $C_5$-OH compounds, such as dimethylallyl alcohol (DMAOH) and isopentenol, for example, using phosphatases, such as an *Xanthomanas translucens* acid phosphatase (PhoN$_{xt}$), and isopentyl phosphokinases (IPK), such as a *Methanococcus vannielii* IPK (IPK$_{Mv}$).

In at least one example embodiment, a suitable acid phosphatase, is an acid phosphatase encoded by a nucleic acid sequence selected from:
  (a) SEQ.ID NO: 29;
  (b) a nucleic acid sequence that is substantially identical to the nucleic acid sequence of (a);
  (c) a nucleic acid sequence that is substantially identical to the nucleic acid sequence of (a) but for the degeneration of the genetic code;
  (d) a nucleic acid sequence that is complementary to the nucleic acid sequence of (a);
  (e) a nucleic acid sequence encoding a polypeptide having an amino acid sequences set forth in SEQ.ID NO: 30;

(f) a nucleic acid sequence that encodes a functional variant of any one of the amino acid sequence set forth in SEQ.ID NO: 30; and (g) a nucleic acid sequence that hybridizes under stringent conditions to any one of the nucleic acid sequences set forth in (a), (b), (c), (d), (e) or (f).

In at least one example embodiment, a suitable isopentenyl phosphate kinase is an isopentenyl phosphate kinase encoded by a nucleic acid sequence selected from:

(a) SEQ.ID NO: 31;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 32;
(f) a nucleic acid sequence that encodes a functional variant of any one of the amino acid sequence set forth in SEQ.ID NO: 32; and
(g) a nucleic acid sequence that hybridizes under stringent conditions to any one of the nucleic acid sequences set forth in (a), (b), (c), (d), (e) or (f).

It is noted that, in general, an isopentenyl phosphate kinase and acid phosphatase together in the presence of adenosine tri-phosphate (ATP) can phosphorylate DMAOH to synthesize DMAPP. The synthesis reaction to form DMAPP may be conducted in vivo or in vitro, as desired. When the reaction is conducted in vivo, ATP may be endogenously provided by a host cell. When the reaction is conducted in vitro, ATP is one of the reagents included in the reaction mixture.

Next, referring to FIGS. 12A and 12B, several chemical reactions between example psilocybin derivative precursor compounds and prenyl compounds will be discussed. It is noted that these are example reactions. Having considered these example reactions, a person of skill in the art will readily be able to identify other reactions in accordance with the teachings of the present disclosure, and make prenylated psilocybin derivative compounds in accordance herewith, including, for example, the prenylated psilocybin derivative compounds shown in FIGS. 6A-6F, 7A-7F, 8A-8F, 9A-9F, 10A-10F, and 11A-11F.

Figure 12A:
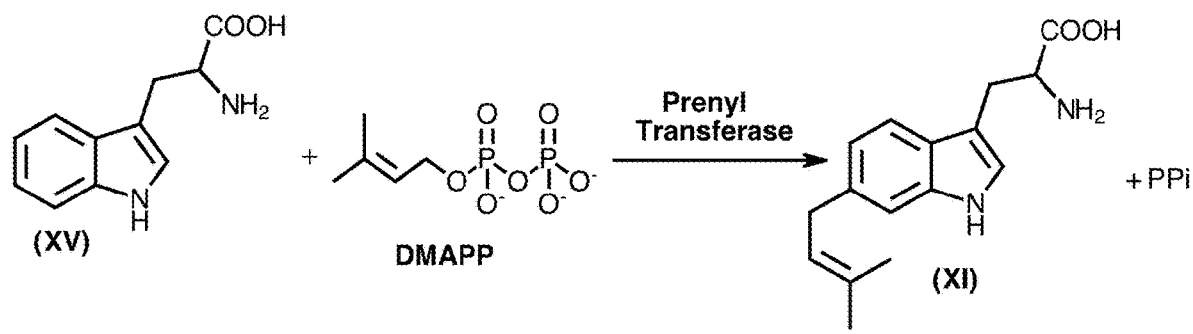
FIGS. 12A, 12B, 12C, 12D, 12E, 12F, and 12G depict certain example chemical reactions, catalyzed by a prenyl transferase that may be performed in accordance with example embodiments of the present disclosure to make example prenylated psilocybin derivative compounds, notably prenylated psilocybin derivative compounds having chemical formula (XI) (FIG. 12A); (V) (FIG. 12B); VI (FIG. 12C); (VII) (FIG. 12D); (VIII) (FIG. 12E); (XIII) (FIG. 12F); and (XIV) (FIG. 12G), which may be made from example precursor psilocybin derivative compounds having chemical formula (XV) (FIG. 12A); (XIV) (FIG. 12B); (XVII) (FIG. 12C); (XVIII) (FIG. 12D); (XIX) (FIG. 12E); (XX) (FIG. 12F); and (XXI) (FIG. 12G), respectively.

Thus, referring next to FIG. 12A, in an aspect, in one example embodiment, a psilocybin derivate precursor compound having formula (XV):

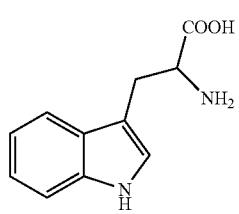

(XV)

may be combined and reacted with a prenyl compound to form a psilocybin derivative having formula (XI):

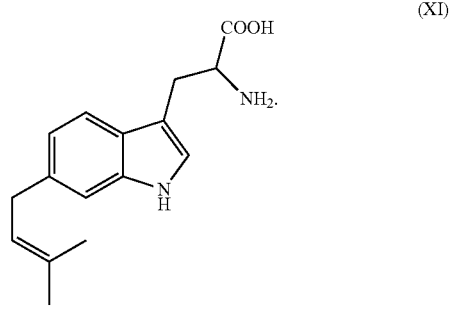 [SMILES: CC(C)=CCc1ccc2c(CC(N)C(=O)O)c[nH]c2c1]

(XI)

Figure 12B:
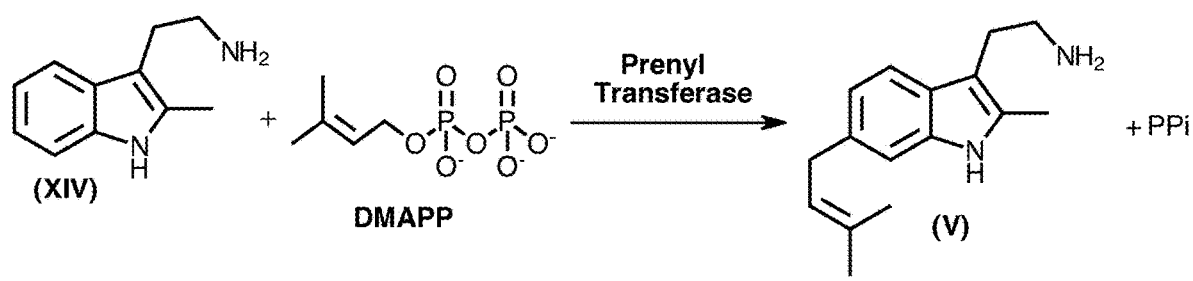

Referring next to FIG. 12B, in an aspect, in one example embodiment, a psilocybin derivate precursor compound having formula (XVI):

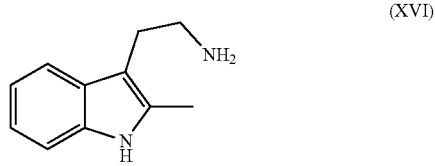

(XVI)

may be combined reacted with a prenyl compound to form a psilocybin derivative having formula (V):

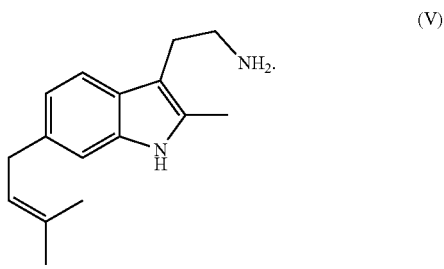 [SMILES: CC(C)=CCc1ccc2c(CCN)c(C)[nH]c2c1]

(V)

Figure 12C:
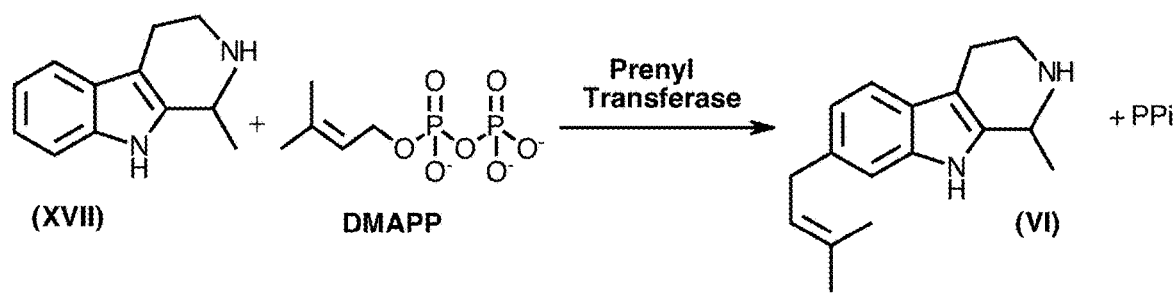

Referring next to FIG. 12C, in an aspect, in one example embodiment, a psilocybin derivate precursor compound having formula (XVII):

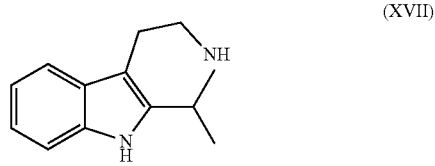

(XVII)

may be reacted with a prenyl compound to form a psilocybin derivative having formula (VI):

(XVI)

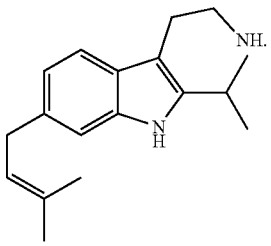

Figure 12D:
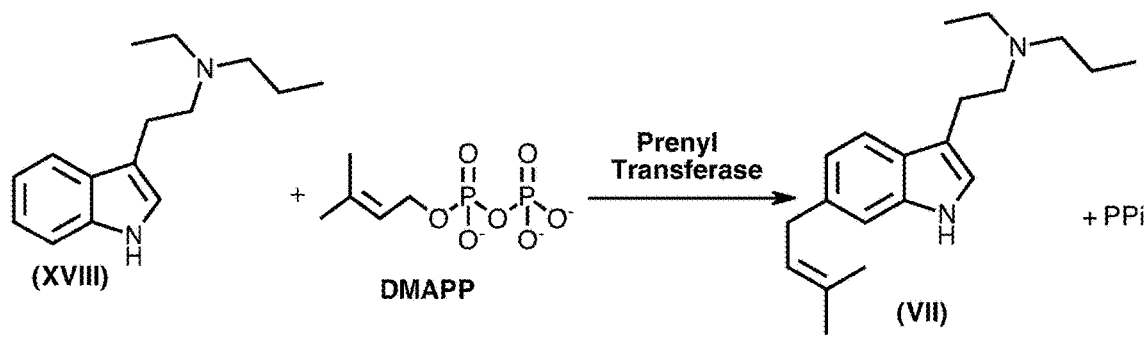

Referring next to FIG. 12D, in an aspect, in one example embodiment, a psilocybin derivate precursor compound having formula (XVIII):

(XVIII)

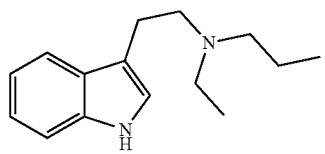

may be reacted with a prenyl compound to form a psilocybin derivative having formula (VII):

(VII)

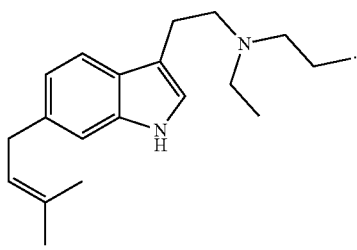

Figure 12E:
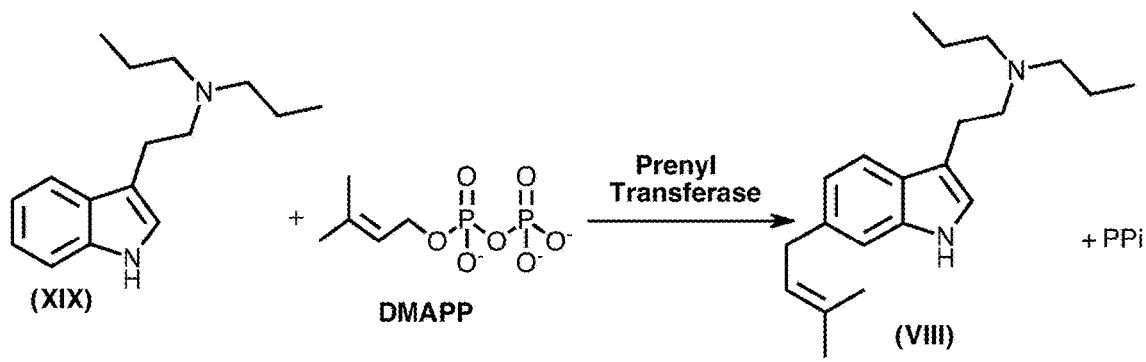

Referring next to FIG. 12E, in an aspect, in one example embodiment, a psilocybin derivate precursor compound having formula (XIX):

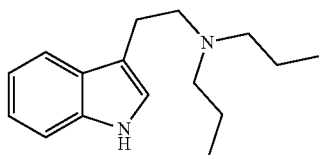 [SMILES: CCCN(CCC)CCc1c[nH]c2ccccc12]

may be reacted with a prenyl compound to form a psilocybin derivative having formula (VIII):

(VIII)

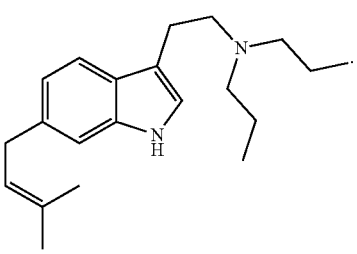

Figure 12F:
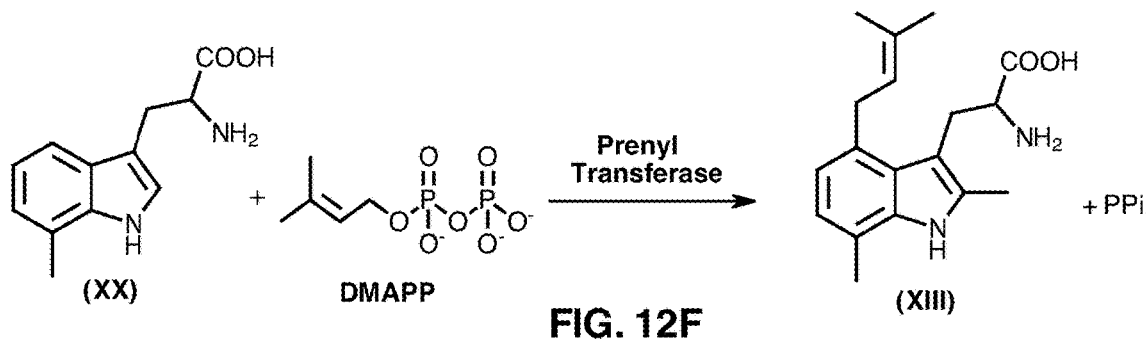

Referring next to FIG. 12F, in an aspect, in one example embodiment, a psilocybin derivate precursor compound having formula (XX):

(XX)

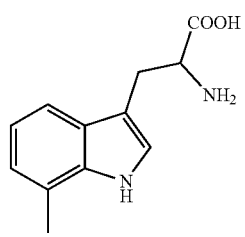

may be reacted with a prenyl compound to form a psilocybin derivative having formula (XIII):

(XIII)

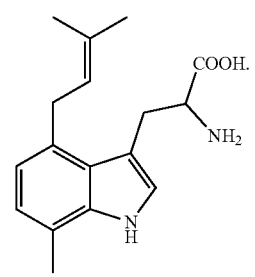

Figure 12G:
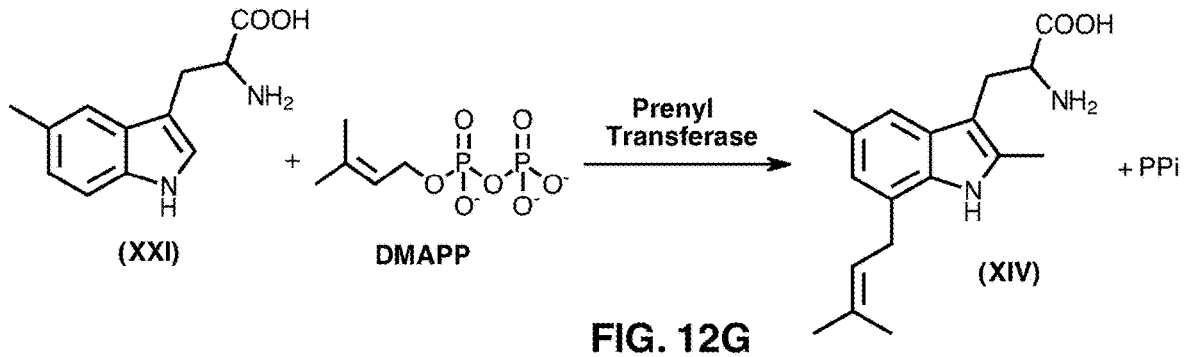

Referring next to FIG. 12G, in an aspect, in one example embodiment, a psilocybin derivate precursor compound having formula (XXI):

(XXI)

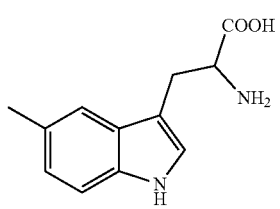

may be reacted with a prenyl compound to form a psilocybin derivative having formula (XIV):

(XIV)

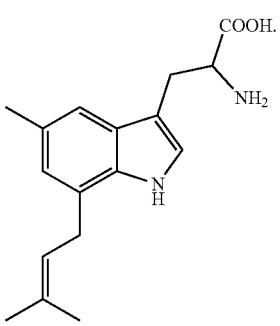

As already noted, any synthetic or biosynthetic method for reacting the psilocybin derivative precursor compound, including the example compounds set forth in FIGS. 12A-

12F, and prenyl compounds may be used. Next, example reaction conditions for performing reactions are discussed. In general, in order to prepare the prenylated psilocybin derivatives of the present disclosure, the reaction conditions are selected such that the psilocybin preservative precursor compound and prenyl compound can chemically react with one another, so that a prenylated psilocybin derivative compound can be formed.

In an aspect hereof, in one example embodiment, reactions can be enzymatically catalyzed, notably by combining and contacting the psilocybin derivative precursor compound and prenyl compound in the presence of a prenyl transferase. Thus, in one embodiment, in order to make the prenylated psilocybin derivatives of the present disclosure, a psilocybin derivative precursor compound can be contacted with sufficient quantities of a prenyl compound, as well a catalytic quantity of a prenyl transferase, under reaction conditions permitting an enzyme catalyzed conversion of the psilocybin derivative precursor compound to form the prenylated psilocybin compound, as shown by way of example in FIGS. 12A-12F.

In this respect, suitable prenyl transferases that may be used in accordance herewith include, for example, tryptophan 1-prenyl transferase (also known as CymD) (e.g., SEQ.ID NO: 14), tryptophan 4-prenyl transferase (also known as FgaPT2) (e.g., SEQ.ID NO: 16), tryptophan 5-prenyl transferase (also known as 5DMATS) (e.g., SEQ.ID NO: 18), tryptophan 6-prenyl transferase (also known as IptA) (SEQ.ID NO: 20), tryptophan 7-prenyl transferase (also known as 7DMATS) (SEQ.ID NO: 22), and a 6-prenyl transferase (also known as PriB) (SEQ.ID NO: 24), It is noted that these different prenyl transferase may exhibit different substrate specificities, notably with respect to the carbon atom on the indole moiety that may receive a prenyl group. Thus, referring to the indole structure in FIG. 2, for example, FgaPT2, can prenylate the $C_4$ carbon atom, and 7DMATS can prenylate the $C_7$ carbon atom. It will therefore be clear that by selecting one or more different prenyl transferases, different carbon atoms within the indole structure may be prenylated.

It is noted that prenyl transferases comprising amino acid sequences substantially similar to any of the aforementioned prenyl transferase sequences may be prepared and used to modulate the substrate specificity and/or the enzyme's catalytic efficiency. Thus, for example, prenyl transferases comprising amino acid sequences substantially similar to SEQ.ID NO: 14; SEQ.ID NO: 16; SEQ.ID NO: 18; SEQ.ID NO: 20, SEQ.ID NO: 22, and SEQ.ID NO: 24 may be prepared and used to obtain 1-prenyl, 4-prenyl, 5-prenyl, 6-prenyl or 7-prenyl tryptophan, or a prenyl transferase comprising amino acid sequences substantially similar to SEQ.ID NO: 14; SEQ.ID NO: 16; SEQ.ID NO: 18; SEQ.ID NO: 20, SEQ.ID NO: 22 and SEQ.ID NO: 24 may be prepared and used to prepare other non-prenylated psilocybin derivative precursor compounds, such as tryptamine, 4-hydroxyindole, 4-hydroxytryptophan, 4-hydroxytryptamine, norbaeocystin, baeocystin and a precursor psilocybin derivative compound having formula (XII), for example, to form prenylated forms thereof.

Accordingly, in one embodiment the prenyl transferase can be encoded by a nucleic acid selected from:
(a) SEQ.ID NO: 13, SEQ.ID NO: 15, SEQ. ID NO: 17, SEQ.ID NO: 19, SEQ.ID NO: 21 and SEQ.ID NO: 23;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 14, SEQ.ID NO: 16, SEQ. ID NO: 18, SEQ.ID NO: 20, SEQ.ID NO: 22 and SEQ.ID NO: 24;
(f) a nucleic acid sequence that encodes a functional variant of any one of the amino acid sequences set forth in SEQ.ID NO: 14, SEQ.ID NO: 16, SEQ. ID NO: 18, SEQ.ID NO: 20, SEQ.ID NO: 22 and SEQ.ID NO: 24; and
(g) a nucleic acid sequence that hybridizes under stringent conditions to any one of the nucleic acid sequences set forth in (a), (b), (c), (d), (e), or (f).

Prenyl transferase catalyzed reactions may be conducted under in vitro or in vivo reaction conditions, or a combination of in vitro and in vivo reaction conditions may, as herein after further described.

In Vitro Synthesis

In vitro synthesis, in general, involves initially providing the reagents, including the precursor psilocybin derivative compound and the prenyl compound, in a more or less pure form. Thus, the reactants may be provided as a particulate in a substantially pure form, or they may be dissolved, in a more or less pure form, in a suitable solvent or diluent, such as water or a buffer. The reagents can then be combined and contacted with one another in a suitable reaction vessel, such as a tube, beaker, flask, or the like, or, at a larger scale, in a tank or reactor, generally preferably in liquid form, which may be prepared by further including a diluent, such as water or a buffer, as necessary. The combined reagents may be mixed, by, in general gentle stirring, using a suitable stirring or mixing device, such as a laboratory size magnetic stirrer (e.g., as manufactured by Fisher Scientific®), or a handheld or industrial mixer, for example, to form a mixture. Relative quantities and absolute quantities of reagents may be selected as desired. Absolute quantities will typically depend on the scale one wishes to perform the reaction at, such as, for example, at a laboratory scale (e.g., at a less than 1 L, a less than 100 mL, a less than 10 mL, or a less than 1 mL scale), or, for example, at a commercial production scale (e.g., at a more than 100 L, a more than 1,000 L, or a more than 10,000 L scale). Relative quantities of the reagents may vary. Thus, for example, in one embodiment, stoichiometric quantities of each of a precursor psilocybin derivative and a prenyl compound can be combined and mixed with catalytic quantities of prenyl transferase enzymes. If desired, off-stoichiometric quantities of reagents, for example, a molar ratio of psilocybin precursor derivatives to prenyl compound of 1:0.95; 1:0.9; 1:0.75; or 1:1.05, 1:1.1 or 1:1.25, may be selected.

As will be understood by those of skill in the art, in molar quantity terms, small quantities of a prenyl transferase enzyme suffice to conduct the reaction, since the enzyme acts as a catalytic agent, and, unlike the precursor psilocybin derivatives and the prenyl compound, the enzyme is not consumed in the reaction. Thus, in general terms, catalytic quantities can be thought of as the at least minimal quantity of enzyme required to convert precursor psilocybin derivatives and the prenyl compound reagents, and form desirable quantities of prenylated psilocybin derivatives. Thus, for example, from 0.1 to 1,000 enzyme units (e.g., 0.1 enzyme unit, 1 enzyme unit, 10 enzyme units, 50 enzyme units, 100 enzyme units, 250 enzyme units, 500 enzyme units, or 1,000 enzyme units) may be included in a reaction mixture, wherein, as is known to those of skill in the art, 1 enzyme unit is an amount of enzyme that catalyzes 1 μmole of substrate (i.e., psilocybin precursor compound) per minute. Furthermore, in vitro reaction conditions may vary and may include temperatures ranging from, for example, between about 18° C. and about 37° C., and a pH in the range of about pH 5.0 to about pH 8.5. Furthermore, other agents may be included to facilitate catalysis, for example, a diluent (e.g., water ora buffer), salts, and pH modifying agents. The in vitro reaction conditions may be adjusted and optimized, for example, by preparing a plurality of samples, each being reacted at a different operating condition, e.g., at a different temperature, a different pH, including a different quantity of enzyme, including different relative quantities of reagents, and so forth, and detecting the formed prenylated psilocybin derivative.

In Vivo Synthesis

In one embodiment of the present disclosure the prenylated psilocybin derivatives may be formed in vivo in a host cell. Accordingly, the present disclosure further includes, in one embodiment, a method of making a prenylated psilocybin derivative the method comprising:

(a) contacting a psilocybin derivative precursor compound and a prenyl compound in a host cell, the host cell comprising a chimeric nucleic acid sequence comprising:
  (i) a nucleic acid sequence controlling expression in the host cell; and
  (ii) a nucleic acid sequence encoding a prenyl transferase; and
(b) growing the host cell to express the prenyl transferase and produce a prenylated psilocybin derivative compound having formula (I):

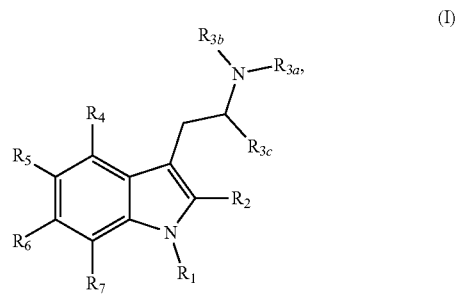

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and $R_{3b}$ are independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

Suitable chimeric nucleic acid sequences include any nucleic acid sequence comprising a nucleic acid sequence controlling expression in the host cell operably linked to a sequence encoding a prenyl transferase, Nucleic acid sequences capable of controlling expression of a nucleic acid sequence encoding a prenyl transferase in host cells that can be used herein include any transcriptional promoter capable of controlling expression of polypeptides in host cells. Generally, promoters obtained from bacterial cells are used when a bacterial host is selected in accordance herewith, while a fungal promoter will be used when a fungal host cell is selected, a plant promoter will be used when a plant cell is selected, and so on. Specific examples that can be used, for example for expression in yeast cells include a galactose inducible promoter, such as a Gal10/Gal 1 promoter, or for expression in Escherichia coli cells, a beta-galactosidase promoter. Further nucleic acid elements capable elements of controlling expression in a host cell include transcriptional terminators, enhancers, and the like, all of which may be included in the chimeric nucleic acid sequences of the present disclosure.

The chimeric nucleic acid sequences can be integrated into a recombinant expression vector which ensures good expression in the host cell, wherein the expression vector is suitable for expression in a host cell. The term "suitable for expression in a host cell" means that the recombinant expression vector comprises the chimeric nucleic acid sequence linked to genetic elements required to achieve expression in a cell. Genetic elements that may be included in the expression vector in this regard include a transcriptional termination region, one or more nucleic acid sequences encoding marker genes, one or more origins of replication and the like. In preferred embodiments, the expression vector further comprises genetic elements required for the integration of the vector or a portion thereof in the host cell's genome, for example. If a plant host cell is used the T-DNA left and right border sequences which facilitate the integration into the plant's nuclear genome.

Pursuant to the present disclosure, the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin, or an auxotrophic marker, for example, a leu marker (Sikorski and Hieter, 1989, Genetics 122(1): 19-27) or a ura marker (Rose and Winston, 1984, Mol. Gen. Genet. 193 (3): 557-560. Screenable markers that may be employed to identify transformants through visual inspection include β-glucuronidase (GUS) (U.S. Pat. Nos. 5,268,463 and 5,599,670) and green fluorescent protein (GFP) (Niedz et al., 1995, Plant Cell Rep., 14: 403).

A variety of host cells can be used in accordance herewith. The selected host cell may be able to naturally produce psilocybin compounds, or derivatives thereof or the cell may not be able to naturally produce psilocybin compounds or derivatives thereof. Host cells, upon the introduction of the chimeric nucleic acid sequence can be said to be able to heterologously express the prenyl transferase.

In some embodiments, the host cell can be a microbial cell, for example, bacterial cell or a yeast cell. An example bacterial cell that can be used in accordance herewith is an Escherichia coli cell. Example yeast cells that can be in accordance herewith are a Saccharomyces cerevisiae cell or a Yarrowia lipolytica cell.

In a further embodiment, the host cell can be a plant cell or an algal cell.

A variety of techniques and methodologies to manipulate host cells to introduce nucleic acid sequences, including expression vectors comprising the chimeric nucleic acid sequences of the current disclosure, in cells and attain expression exists and are well known to the skilled artisan. These methods include, for example, cation based methods, for example, lithium ion or calcium ion based methods, electroporation, biolistics, and glass beads based methods. As will be known to those of skill in the art, depending on the host cell selected, the methodology to introduce nucleic acid material in the host cell may vary, and, furthermore, methodologies may be optimized for uptake of nucleic acid material by the host cell, for example, by comparing uptake of nucleic acid material using different conditions. Detailed guidance can be found, for example, in Sambrook et al., Molecular Cloning, a Laboratory Manual, Cold Spring Harbor Laboratory Press, 2012, Fourth Ed. It is noted that the chimeric nucleic acid is a non-naturally occurring chimeric nucleic acid sequence and can be said to be heterologous to the host cell.

One example host cell that conveniently may be used is Escherichia coli. The preparation of the *E. coli* vectors may be accomplished using commonly known techniques such as restriction digestion, ligation, gel electrophoresis, DNA sequencing, the polymerase chain reaction (PCR) and other methodologies. A wide variety of cloning vectors is available to perform the necessary steps required to prepare a recombinant expression vector. Among the vectors with a replication system functional in *E. coli*, are vectors such as pBR$_{322}$, the pUC series of vectors, the M13 mp series of vectors, pBluescript etc. Suitable promoter sequences for use in E. coil include, for example, the T7 promoter, the T5 promoter, tryptophan (trp) promoter, lactose (lac) promoter, tryptophan/lactose (tac) promoter, lipoprotein app) promoter, and A phage PL promoter. Typically, cloning vectors contain a marker, for example, an antibiotic resistance marker, such as ampicillin or kanamycin resistance marker, allowing selection of transformed cells. Nucleic acid sequences may be introduced in these vectors, and the vectors may be introduced in E. coli by preparing competent cells, electroporation or using other well-known methodologies to a person of skill in the art. *E. coli* may be grown in an appropriate medium, such as Luria-Broth medium and harvested. Recombinant expression vectors may readily be recovered from cells upon harvesting and lysing of the cells.

Another example host cell that may be conveniently used is a yeast cell. Example yeast host cells that can be used are yeast cells belonging to the genus *Candida, Kluyveromyces, Saccharomyces, Schizosaccharomyces, Pichia, Hansenula*, and *Yarrowia*. In specific example embodiments, the yeast cell can be a *Saccharomyces cerevisiae* cell, a *Yarrowia lipolytica* cell, or *Pichia pastoris* cell.

A number of vectors exist for the expression of recombinant proteins in yeast host cells. Examples of vectors that may be used in yeast host cells include, for example. Yip type vectors, Yep type vectors, Yrp type vectors, Ycp type vectors, pGPD-2, pA)815, pGAPZ, pGAPZα, pHIL-D2, pHIL-S1, pPIC$_{3.5}$K, pPIC$_9$K, pPICZ, pPICZα, pPIC3K, pHWO10, pPUZZLE and 2 μm plasmids. Such vectors are known to the art and are, for example, described in Cregg et at., Mol Biotechnol. (2000) 16(1): 23-52. Suitable promoter sequences for use in yeast host cells are also known and described, for example, in Mattanovich et al., Methods Mol Biol., 2012, 824:329-58, and in Rornanos et al., 1992, Yeast 8: 423-488. Examples of suitable promoters for use in yeast host cells include promoters of glycolytic enzymes, like triosephosphate isomerase (TPI), phosphoglycerate kinase (PGI), glyceraldehyde-3-phosphate dehydrogenase (GAPDH or GAP) and variants thereof, lactase (LAC) and galactosidase (GAL), *P. pastoris* glucose-6-phosphate isomerase promoter (PPG), the 3-phosphoglycerate kinase promoter (PPGK), the glycerol aldehyde phosphate dehydrogenase promoter (PGAP), translation elongation factor promoter (PTEF), *S. cerevisiae* enolase (ENO-1), *S. cerevisiae* galactokinase (GAD), *S. cerevisiae* alcohol dehydrogenase/glyceraldehyde-3-phosphate dehydrogenase (ADH1, ADH2/GAP), *S. cerevisiae* triose phosphate isomerase (TPI), *S. cerevisiae* metallothionein (CUP1), and *S. cerevisiae* 3-phosphoglycerate kinase (PGK), and the maltase gene promoter (MAL). Marker genes suitable for use in yeast host cells are also known to the art. Thus, antibiotic resistance markers, such as ampicillin resistance markers, can be used in yeast, as well as marker genes providing genetic functions for essential nutrients, for example, leucine (LEU2), tryptophan (TRP1 and TRP2), uracil (URA3, URA5, URA6), histidine (HIS3), and the like. Methods for introducing vectors into yeast host cells can, for example, be found in S. Kawai et al., 2010, Bioeng. Bugs 1(6): 395-403.

Further, guidance with respect to the preparation of expression vectors and introduction thereof into host cells, including in *E. coli* cells, yeast cells, and other host cells, may be found in, for example: Sambrook et al., Molecular Cloning, a Laboratory Manual, Cold Spring Harbor Laboratory Press, 2012, Fourth Ed.

In accordance with the foregoing, the present disclosure, in a further include a host cell comprising a chimeric nucleic acid sequence comprising as operably linked components:

(i) a nucleic acid sequence controlling expression in the host cell; and (ii) a nucleic acid sequence encoding a prenyl transferase, the host cell capable of being grown to express the prenyl transferase and produce a prenylated psilocybin derivative compound having the formula (I):

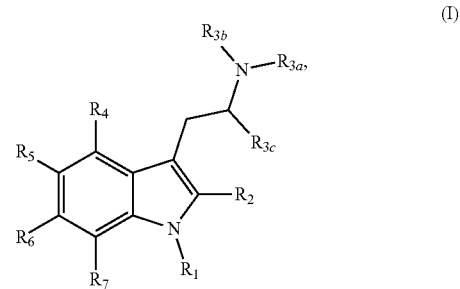

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein Ria and Rab are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group.

In one example embodiment, the prenyl transferase can be an enzyme heterologously expressed by the host cell wherein the prenyl transferase is an enzyme encoded by a nucleic acid selected from:

(a) SEQ.ID NO: 13, SEQ.ID NO: 15, SEQ. ID NO: 17, SEQ.ID NO: 19, SEQ.ID NO: 21 and SEQ.ID NO: 23;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 14, SEQ.ID NO: 16, SEQ. ID NO: 18, SEQ.ID NO: 20, SEQ.ID NO: 22 and SEQ.ID NO: 24;
(f) a nucleic acid sequence that encodes a functional variant of any one of the amino acid sequences set forth in SEQ.ID NO: 14, SEQ.ID NO: 16, SEQ. ID NO: 18, SEQ.ID NO: 20, SEQ.ID NO: 22, and SEQ.ID NO: 24; and
(g) a nucleic acid sequence that hybridizes under stringent conditions to any one of the nucleic acid sequences set forth in (a), (b), (c), (d), (e), or (f).

Thus, to briefly recap, a host cell comprising a chimeric nucleic acid comprising (i) a nucleic acid sequence controlling expression in a host cell and (ii) a nucleic acid sequence encoding a prenyl transferase, can be prepared in accordance with the present disclosure.

In accordance herewith, host cells are grown to multiply and to express a chimeric nucleic acid. Expression of the chimeric nucleic acid results in the biosynthetic production in the host cell of a psilocybin biosynthetic enzyme complement. Growth media and growth conditions can vary depending on the host cell that is selected, as will be readily appreciated to those of ordinary skill in the art. Growth media typically contain a carbon source, one or several nitrogen sources, essential salts including salts of potassium, sodium, magnesium, phosphate and sulphate, trace metals, water soluble vitamins, and process aids including but not limited to antifoam agents, protease inhibitors, stabilizers, ligands, and inducers, Example carbon sources are e.g., mono- or disaccharides, Example nitrogen sources are, e.g., ammonia, urea, amino acids, yeast extract, corn steep liquor and fully or partially hydrolyzed proteins. Example trace metals are e.g, Fe, Zn, Mn, Cu, Mo and $H_3BO_3$. Example water soluble vitamins are e biotin, pantothenate, niacin, thiamine, p- aminobenzoic acid, choline, pyridoxine, folic acid, riboflavin, and ascorbic acid. Further, specific example media include liquid culture media for the growth of yeast cells and bacterial cells including, Luria-Bertani (LB) broth for bacterial cell cultivation, and yeast extract peptone dextrose (YEPD or YPD), for yeast cell cultivation. Further media and growth conditions can be found in Sambrook et al., Molecular Cloning, a Laboratory Manual, Cold Spring Harbor Laboratory Press, 2012, Fourth Ed.

In order for the host cells to produce the prenylated psilocybin compounds, the cells are provided with a psilocybin derivative precursor compound and a prenyl compound. Thus, in accordance herewith, host cells may be contacted with a psilocybin derivative precursor compound and a prenyl compound. In some embodiments, a psilocybin derivative precursor compound and the prenyl compound can be exogenously supplied, for example, by including a psilocybin derivative precursor compound and prenyl compound in the growth medium of the host cells, and growing the host cells in a medium including the psilocybin derivative precursor compound and prenyl compound. The amounts of psilocybin derivative precursor compound or prenyl compound included in a host cell medium may vary, and can range, for example, from 0.05 gr/L to 10 gr/L, e.g., 0.05 gr/L, 0.1 gr/L, 0.5 gr/L, 1 gr/L, 2.5 gr/L, 5 gr/L, 7.5 gr/L or 10 gr/L. Specific amounts may be adjusted and optimized, for example, by in a series of experiments growing host cells in media comprising different concentrations of a psilocybin derivative precursor compound or prenyl compound, and evaluating the production of prenylated psilocybin derivative.

Figure 4:
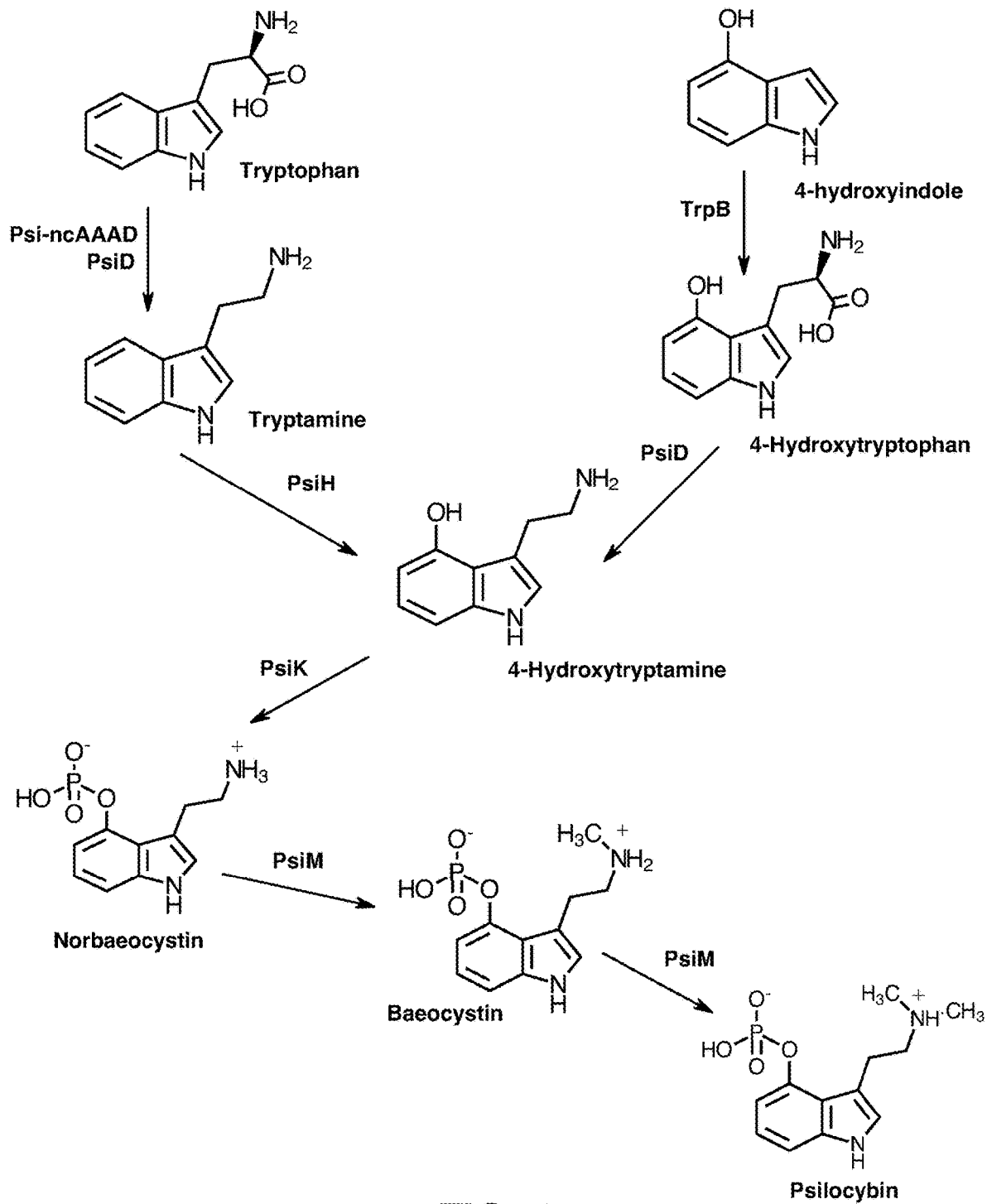
FIG. 4 depicts a biosynthesis pathway for the synthesis of psilocybin.

Referring next to FIG. 4, shown therein is an example natural biosynthetic pathway showing the conversion of example psilocybin derivative precursor compounds to form psilocybin. In some embodiments, the host cells may include a psilocybin biosynthetic enzyme complement. Thus, such cells endogenously can produce precursor psilocybin derivative compounds. Such precursor psilocybin derivative compound producing cells can be obtained in at least two ways. First, in some embodiments, host cells may be selected in which a psilocybin biosynthetic enzyme complement is naturally present. Generally, cells naturally producing psilocybin for example, cells of fungal species belonging to the genus psilocybe, are suitable in this respect. Second, in some embodiments, a host cell that not naturally produces psilocybin may be modulated to heterologously produce a psilocybin biosynthetic enzyme complement. Thus, for example, a nucleic acid sequence encoding a psilocybin biosynthetic enzyme complement may be introduced into a host cell, and upon cell growth the host cells can make the psilocybin biosynthetic enzyme complement. Techniques to introduce and nucleic acid sequences into host cells and express nucleic acid sequences hereinbefore described with respect to prenyl transferases, can readily be modulated by those of skill in the art to achieve the same for a psilocybin biosynthetic enzyme complement.

In some embodiments, the one or more enzymes constituting a psilocybin enzyme complement can be selected from by a nucleic acid sequence selected from the nucleic acid sequences consisting of:
(a) SEQ.ID NO: 1, SEQ.ID NO: 3, SEQ.ID NO: 5, SEQ.ID NO: 7, SEQ.ID NO: 9, and SEQ.ID NO 11;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 2, SEQ.ID NO: 4, SEQ.ID NO: 6, SEQ.ID NO: 8, SEQ.ID NO: 10, and SEQ.ID NO 12;
(f) a nucleic acid sequence that encodes a functional variant of any one of the amino acid sequences set forth in SEQ.ID NO: 2, SEQ.ID NO: 4, SEQ.ID NO: 6, SEQ.ID NO: 8, SEQ.ID NO: 10, and SEQ.ID NO 12; and
(g) a nucleic acid sequence that hybridizes under stringent conditions to any one of the nucleic acid sequences set forth in (a), (b), (c), (d), (e) or (f).

Thus, any of the nucleic acid sequences set forth in (a), (b), (c), (d), I, (f) or (g) may be selected and introduced into a host cell. It will be understood that by further including a nucleic acid sequence encoding a prenyl transferase into the host cell, and by including a prenyl compound in the cell's growth medium, prenylated psilocybin compounds can be produced by the host cells comprising a psilocybin biosynthetic enzyme complement.

Upon production by the host cells of the prenylated psilocybin compounds in accordance with the methods of the present disclosure, the prenylated psilocybin compounds may be extracted from the host cell suspension, and separated from other constituents within the host cell suspension, such as media constituents and cellular debris. Separation techniques will be known to those of skill in the art and include, for example, solvent extraction (e.g., butane, chloroform, ethanol), column chromatography based techniques, high-performance liquid chromatography (HPLC), for example, and/or countercurrent separation (CCS) based systems. The recovered prenylated psilocybin compounds may be obtained in a more or less pure form, for example, a preparation of prenylated psilocybin compounds of at least about 60% (w/v), about 70% (w/v), about 80% (w/v), about 90% (w/v), about 95% (w/v) or about 99% (w/v) purity may be obtained. Thus, in this manner, prenylated psilocybin derivatives in more or less pure form may be prepared.

Further Modification of Prenylated Psilocybin Derivative Compounds

In some embodiments, in accordance herewith, following an in vitro or in vivo production of a prenylated psilocybin derivative compound, as hereinbefore described, the prenylated psilocybin derivative compound may optionally be converted to form another prenylated psilocybin derivative compound, i.e., a second prenylated psilocybin derivative compound, and then, again optionally, the second prenylated psilocybin derivative compound may be converted into a third prenylated psilocybin derivative compound, a fourth prenylated psilocybin derivative compound, and so forth. Such modifications of an initial prenylated psilocybin compound may be conducted following an initial in vitro or an initial in vivo production of a prenylated psilocybin derivative compound, as herein before described, and the method to produce a second prenylated psilocybin derivative compound, or a third psilocybin derivative compound, or further psilocybin derivative compounds, may themselves be performed in vitro or in vivo. Thus, for example, the initially produced prenylated psilocybin derivative compound can be converted using one or more additional enzymes, such as a decarboxylase and an N-acetyl transferase, for example, to modify the initially produced prenylated psilocybin derivative, and produce another prenylated psilocybin derivative. In this manner, a final desired prenylated psilocybin derivative compound may be produced by performing multiple in vitro reactions, multiple in vivo reactions, or by performing a combination of in vitro and in vivo reactions.

In general, in order to modify an initially produced prenylated psilocybin derivative the in vivo or in vitro production methods hereinbefore described may be used and adjusted to be operable with enzymes, such a decarboxylase or an N-acetyl transferase, instead of a prenyl transferase, and using the initially produced prenylated psilocybin derivative as a starting point to conduct these further in vivo or in vitro reactions.

Thus, in an example embodiment, an initially produced prenylated psilocybin derivative compound having formula (XI):

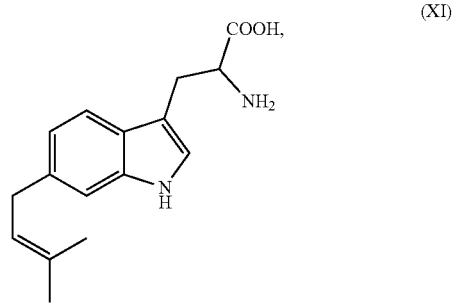 [SMILES: CC(C)=CCc1ccc2c(CC(N)C(=O)O)c[nH]c2c1]

formed in vitro or in vivo, can further be reacted, in vitro or in vivo, by contacting the prenylated psilocybin derivative compound having formula (XI) with a decarboxylase enzyme to form a second prenylated psilocybin derivative compound having formula (XII):

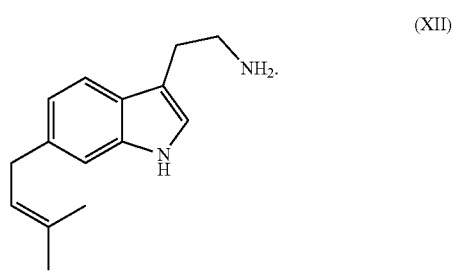 [SMILES: CC(C)=CCc1ccc2c(CCN)c[nH]c2c1]

In one embodiment, the decarboxylase can be an enzyme encoded by a nucleic acid selected from:

(a) SEQ.ID NO: 25;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 26;
(f) a nucleic acid sequence that encodes a functional variant of any one of the amino acid sequence set forth in SEQ.ID NO: 26; and
(g) a nucleic acid sequence that hybridizes under stringent conditions to any one of the nucleic acid sequences set forth in (a), (b), (c), (d), (e), or (f).

As will be understood, in vivo production of a second prenylated derivative compound, such as a compound having formula (XII), can involve the heterologous expression of the decarboxylase enzyme in a host cell, and may include the expression of the decarboxylase enzyme in the same host cell as the prenyl transferase enzyme.

In a further embodiment, the second prenylated psilocybin derivative compound having formula (XII) can then further be reacted, in vitro or in vivo, by contacting the second prenylated psilocybin derivative with an N-acetyl transferase to form a third prenylated psilocybin derivative compound having formula (IV):

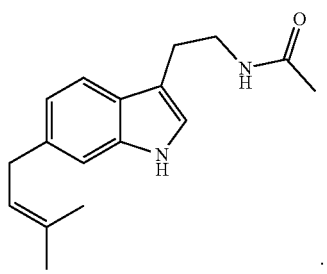

(IV)

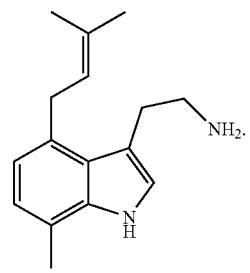

(X)

Figure 13A:
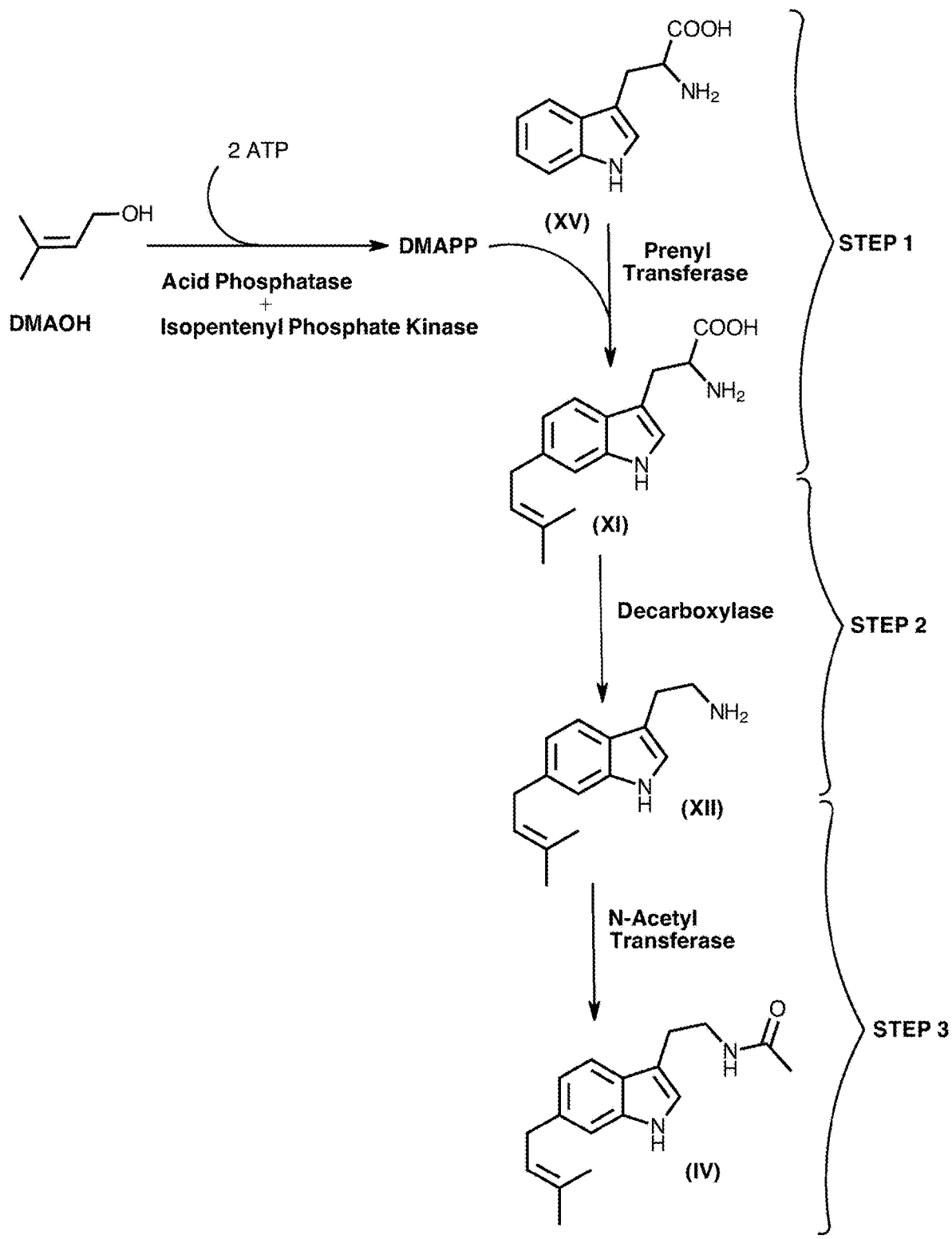
FIGS. 13A, 13B, and 13C depict certain example chemical reactions, catalyzed by a prenyl transferase and decarboxylase (FIGS. 13A, 13B, and 13C) and prenyl transferase, decarboxylase, and N-acetyl transferase (FIG. 13A) that may be performed in accordance with example embodiments of the present disclosure to make example prenylated psilocybin derivative compounds, notably prenylated psilocybin derivative compounds having chemical formula (XI), (XII), (IV) (FIG. 13A); (XIII), (X) (FIG. 13B); (XIV), and (IX) (FIG. 13C), which may be made from example precursor psilocybin derivative compounds having chemical formula (XV) (FIG. 13A), (XX) (FIG. 13B), and (XXI) (FIG. 13C).
Figure 13B:
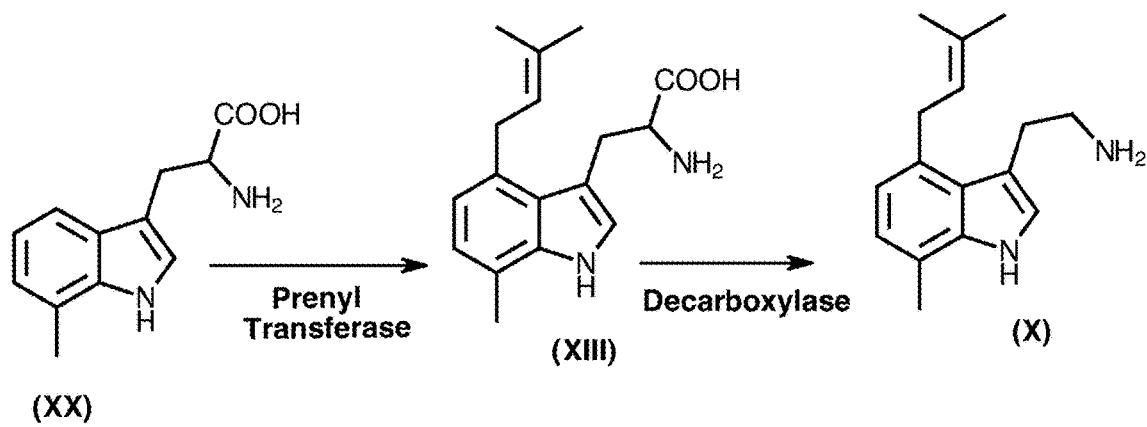

The foregoing is further illustrated in FIG. 13B.

In yet another embodiment, the prenylated psilocybin derivative having formula (XIV):

In one example embodiment, for example, the N-acetyl transferase can be an enzyme encoded by a nucleic acid selected from:

(a) SEQ.ID NO: 27;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 28;
(f) a nucleic acid sequence that encodes a functional variant of any one of the amino acid sequence set forth in SEQ.ID NO: 28; and
(g) a nucleic acid sequence that hybridizes under stringent conditions to any one of the nucleic acid sequences set forth in (a), (b), (c), (d), (e), or (f).

As will be understood, in vivo production of a third prenylated derivative compound, such as a compound having formula (IV), can involve the heterologous expression of the N-acetyl transferase enzyme in a host cell, and may include the expression of the N-acetyl transferase enzyme in the same host cell as the prenyl transferase enzyme and the decarboxylase.

The foregoing is further illustrated in FIG. 13A.

In another example embodiment, the prenylated psilocybin derivative having formula (XIII):

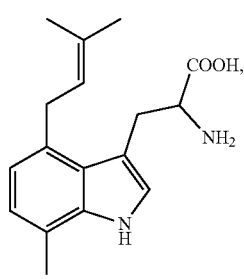

(XIII)

(made, for example, from a precursor psilocybin derivative having chemical formula (XX)) can further be reacted with a decarboxylase to form a second prenylated psilocybin derivative compound having formula (X):

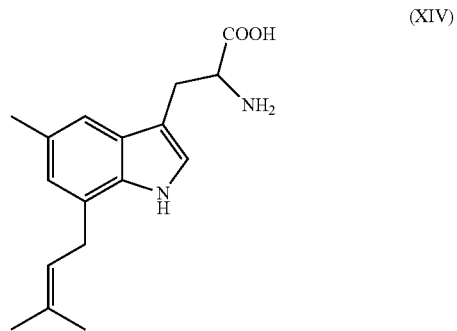 [SMILES: CC(C)=CCc1cc(C)cc2c(CC(N)C(=O)O)c[nH]c12]

(XIV)

(made, for example, from a precursor psilocybin derivative having chemical formula (XXI)) can further be reacted with a decarboxylase to form a second prenylated psilocybin compound derivative having formula (IX):

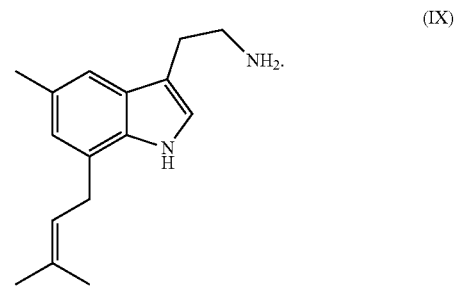 [SMILES: CC(C)=CCc1cc(C)cc2c(CCN)c[nH]c12]

(IX)

Figure 13C:
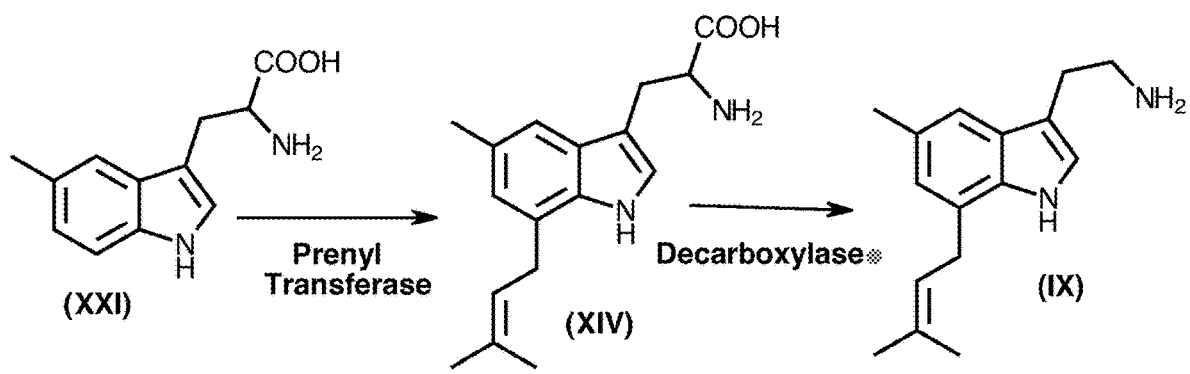

The foregoing is further illustrated in FIG. 13C.

In accordance with the foregoing, the present disclosure, in a further embodiment, includes a host cell comprising a chimeric nucleic acid sequence comprising as operably linked components:

(i) a nucleic acid sequence controlling expression in the host cell; and
(ii) a nucleic acid sequence encoding a prenyl transferase, the host cell capable of being grown to express the prenyl transferase and produce a prenylated psilocybin derivative compound having the formula (I):

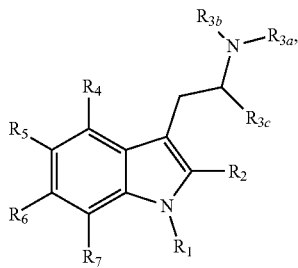

(I)

wherein at least one of $R_1$, $R_2$, $R_4$, $R_5$, $R_6$, or $R_7$ is a prenyl group, and wherein each non-prenylated $R_1$, $R_2$, $R_5$, $R_6$, or $R_7$ group, is independently a hydrogen atom or an alkyl group, wherein $R_4$, when not prenylated, is an alkyl group, an O-alkyl group, an O-acyl group, a hydroxy group, a phosphate group, a glycosyloxy group, or a hydrogen atom, and wherein $R_{3a}$ and $R_{3b}$ are each independently a hydrogen atom, an alkyl group, acyl group or an aryl group, or $R_{3a}$ and $R_2$ are joined together, along with the nitrogen atom to which $R_{3a}$ is attached, to form an optionally substituted heterocyclic ring, wherein the optional substituent on the heterocyclic ring is an alkyl group, and $R_{3c}$ is a hydrogen atom or a carboxy group, wherein the prenyl transferase is an enzyme heterologously expressed by the host cell wherein the prenyl transferase is an enzyme encoded by a nucleic acid selected from:
(a) SEQ.ID NO: 13, SEQ.ID NO: 15, SEQ. ID NO: 17, SEQ.ID NO: 19, SEQ.ID NO: 21 and SEQ.ID NO: 23;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 14, SEQ.ID NO: 16, SEQ. ID NO: 18, SEQ.ID NO: 20, SEQ.ID NO: 22 and SEQ.ID NO: 24;
(f) a nucleic acid sequence that encodes a functional variant of any one of the amino acid sequences set forth in SEQ.ID NO: 14, SEQ.ID NO: 16, SEQ. ID NO: 18, SEQ.ID NO: 20, SEQ.ID NO: 22, and SEQ.ID NO: 24; and
(g) a nucleic acid sequence that hybridizes under stringent conditions to any one of the nucleic acid sequences set forth in (a), (b), (c), (d), (e), or (f),
wherein the host cell further heterologously expresses:
(I) a decarboxylase encoded by a nucleic acid selected from:
(a) SEQ.ID NO: 25;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 26;
(f) a nucleic acid sequence that encodes a functional variant of any one of the amino acid sequence set forth in SEQ.ID NO: 26; and
(g) a nucleic acid sequence that hybridizes under stringent conditions to any one of the nucleic acid sequences set forth in (a), (b), (c), (d), (e) or (f); and/or
(II) an N-acetyl transferase encoded by a nucleic acid selected from:
(a) SEQ.ID NO: 27;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having an amino acid sequences set forth in SEQ.ID NO: 28;
(f) a nucleic acid sequence that encodes a functional variant of any one of the amino acid sequence set forth in SEQ.ID NO: 28; and
(g) a nucleic acid sequence that hybridizes under stringent conditions to any one of the nucleic acid sequences set forth in (a), (b), (c), (d), (e) or (f).

Thus, it will be clear from the foregoing that initially formed prenylated psilocybin derivative compounds may be used to form further prenylated psilocybin compounds.

It will now be clear form the foregoing that novel prenylated psilocybin derivatives are disclosed herein. The prenylated psilocybin compounds may be formulated for use as a pharmaceutical drug or recreational drug. The prenylated psilocybin compounds may also be used as a feedstock to produce other psilocybin derivatives.

Summary of Sequences

SEQ.ID NO: 1 sets forth a *Psilocybe cubensis* nucleic acid sequence encoding a PsiD polypeptide.

SEQ.ID NO: 2 sets forth a deduced amino acid sequence of a *Psilocybe cubensis* PsiD polypeptide.

SEQ.ID NO: 3 sets forth a *Psilocybe cubensis* nucleic acid sequence encoding a PsiH polypeptide.

SEQ.ID NO: 4 sets forth a deduced amino acid sequence of a *Psilocybe cubensis* PsiH polypeptide.

SEQ.ID NO: 5 sets forth a *Psilocybe cubensis* nucleic acid sequence encoding a PsiK polypeptide.

SEQ.ID NO: 6 sets forth a deduced amino acid sequence of a *Psilocybe cubensis* PsiK polypeptide.

SEQ.ID NO: 7 sets forth a *Psilocybe cubensis* nucleic acid sequence encoding a PsiM polypeptide.

SEQ.ID NO: 8 sets forth a deduced amino acid sequence of a *Psilocybe cubensis* PsiM polypeptide.

SEQ.ID NO: 9 sets forth a *Psilocybe cubensis* nucleic acid sequence encoding a Psi-ncAAAD polypeptide.

SEQ.ID NO: 10 sets forth a deduced amino acid sequence of a *Psilocybe cubensis* Psi-ncAAAD polypeptide.

SEQ.ID NO: 11 sets forth a *Psilocybe cubensis* nucleic acid sequence encoding a TrpB polypeptide.

SEQ.ID NO: 12 sets forth a deduced amino acid sequence of a *Psilocybe cubensis* TrpB polypeptide.

SEQ.ID NO: 13 sets forth a *Salinispora arenicola* nucleic acid sequence encoding tryptophan 1-prenyl transferase polypeptide.

SEQ.ID NO: 14 sets forth a deduced amino acid sequence of a Salinispora arenicola tryptophan 1-prenyl transferase polypeptide.

SEQ.ID NO: 15 sets forth an *Aspergillus fumigatus* nucleic acid sequence encoding a tryptophan 4-prenyl transferase polypeptide, named FgaPT2.

SEQ.ID NO: 16 sets forth a deduced amino acid sequence of an Aspergillus fumigatus tryptophan 4-prenyl transferase polypeptide, named FgaPT2.

SEQ.ID NO: 17 sets forth a Streptomyces coelicolor A3 nucleic acid sequence encoding a tryptophan 5-prenyl transferase polypeptide, named 5DMATS.

SEQ.ID NO: 18 sets forth a deduced amino acid sequence of a Streptomyces coelicolor A3 tryptophan 5-prenyl transferase polypeptide, named 5DMATS.

SEQ.ID NO: 19 sets forth a *Streptomyces* sp. RM-5-8 nucleic acid sequence encoding a tryptophan 6-prenyl transferase polypeptide, named IptA.

SEQ.ID NO: 20 sets forth a deduced amino acid sequence of a Streptomyces sp. RM-5-8 tryptophan 6-prenyl transferase polypeptide, named IptA.

SEQ.ID NO: 21 sets forth an *Aspergillus fumigatus* nucleic acid sequence encoding a tryptophan 7-prenyl transferase polypeptide, named 7DMATS.

SEQ.ID NO: 22 sets forth a deduced amino acid sequence of an *Aspergillus fumigatus* tryptophan 7-prenyl transferase polypeptide, named 7DMATS.

SEQ.ID NO: 23 sets forth a *Streptomyces* sp. RM-5-8 nucleic acid sequence encoding a 6-prenyl transferase polypeptide, named PriB.

SEQ.ID NO: 24 sets forth a deduced amino acid sequence of a *Streptomyces* sp. RM-5-8 6-prenyl transferase polypeptide, named PriB.

SEQ. ID NO: 25 sets forth a Bacillus atrophaeaus nucleic acid sequence encoding a decarboxylase polypeptide, named BaTDC.

SEQ.ID NO: 26 sets forth a deduced amino acid sequence of *Bacillus atrophaeaus* decarboxylase polypeptide, named BaTDC.

SEQ. ID NO: 27 sets forth a *Streptomyces griseofuscus* nucleic acid sequence encoding an N-acetyl transferase, named PmsF.

SEQ.ID NO: 28 sets forth a deduced amino acid sequence of a *Streptomyces griseofuscus* an N-acetyl polypeptide, named PmsF.

SEQ.ID NO: 29 sets forth a Xanthomonas translucens nucleic acid sequence encoding a PAP2 family phosphatase named PhoNxt.

SEQ.ID NO: 30 sets forth a deduced amino acid sequence of a *Xanthomonas translucens* PAP2 family phosphatase named PhoNxt.

SEQ.ID NO: 31 sets forth a *Methanolobus tindarius* nucleic acid sequence encoding an isopentyl phosphate kinase named IPKmt.

SEQ.ID NO: 32 sets forth a deduced amino acid sequence of a *Methanolobus tindarius* isopentyl phosphate kinase named IPKmt.

```
                          SEQUENCE LISTING

SEQ.ID NO: 1
ATGCAGGTGATACCCGCGTGCAACTCGGCAGCAATAAGATCACTATGTCCTACTCCCGA
GTCTTTTAGAAACATGGGATGGCTCTCTGTCAGCGATGCGGTCTACAGCGAGTTCATAG
GAGAGTTGGCTACCCGCGCTTCCAATCGAAATTACTCCAACGAGTTCGGCCTCATGCAA
CCTATCCAGGAATTCAAGGCTTTCATTGAAAGCGACCCGGTGGTGCACCAAGAATTTAT
TGACATGTTCGAGGGCATTCAGGACTCTCCAAGGAATTATCAGGAACTATGTAATATGT
TCAACGATATCTTTCGCAAAGCTCCCGTCTACGGAGACCTTGGCCCTCCCGTTTATATG
ATTATGGCCAAATTAATGAACACCCGAGCGGGCTTCTCTGCATTCACGAGACAAAGGTT
GAACCTTCACTTCAAAAAACTTTTCGATACCTGGGGATTGTTCCTGTCTTCGAAAGATT
CTCGAAATGTTCTTGTGGCCGACCAGTTCGACGACAGACATTGCGGCTGGTTGAACGAG
CGGGCCTTGTCTGCTATGGTTAAACATTACAATGGACGCGCATTTGATGAAGTCTTCCT
CTGCGATAAAAATGCCCCATACTACGGCTTCAACTCTTACGACGACTTCTTTAATCGCA
GATTTCGAAACCGAGATATCGACCGACCTGTAGTCGGTGGAGTTAACAACACCACCCTC
ATTTCTGCTGCTTGCGAATCACTTTCCTACAACGTCTCTTATGACGTCCAGTCTCTCGA
CACTTTAGTTTTCAAAGGAGAGACTTATTCGCTTAAGCATTTGCTGAATAATGACCCTT
TCACCCCACAATTCGAGCATGGGAGTATTCTACAAGGATTCTTGAACGTCACCGCTTAC
CACCGATGGCACGCACCCGTCAATGGGACAATCGTCAAAATCATCAACGTTCCAGGTAC
CTACTTTGCGCAAGCCCCGAGCACGATTGGCGACCCTATCCCGGATAACGATTACGACC
CACCTCCTTACCTTAAGTCTCTTGTCTACTTCTCTAATATTGCCGCAAGGCAAATTATG
TTTATTGAAGCCGACAACAAGGAAATTGGCCTCATTTTCCTTGTGTTCATCGGCATGAC
CGAAATCTCGACATGTGAAGCCACGGTGTCCGAAGGTCAACACGTCAATCGTGGCGATG
ACTTGGGAATGTTCCATTTCGGTGGTTCTTCGTTCGCGCTTGGTCTGAGGAAGGATTGC
AGGGCAGAGATCGTTGAAAAGTTCACCGAACCCGGAACAGTGATCAGAATCAACGAAGT
CGTCGCTGCTCTAAAGGCTTAG

SEQ.ID NO: 2
MQVIPACNSAAIRSLCPTPESFRNMGWLSVSDAVYSEFIGELATRASNRNYSNEFGLMQ
PIQEFKAFIESDPVVHQEFIDMFEGIQDSPRNYQELCNMFNDIFRKAPVYGDLGPPVYM
IMAKLMNTRAGFSAFTRQRLNLHFKKLFDTWGLFLSSKDSRNVLVADQFDDRHCGWLNE
RALSAMVKHYNGRAFDEVFLCDKNAPYYGFNSYDDFFNRRFRNRDIDRPVVGGVNNTTL
ISAACESLSYNVSYDVQSLDTLVFKGETYSLKHLLNNDPFTPQFEHGSILQGFLNVTAY
HRWHAPVNGTIVKIINVPGTYFAQAPSTIGDPIPDNDYDPPPYLKSLVYFSNIAARQIM
FIEADNKEIGLIFLVFIGMTEISTCEATVSEGQHVNRGDDLGMFHFGGSSFALGLRKDC
RAEIVEKFTEPGTVIRINEWAALKA

SEQ.ID NO: 3
ATGATCGCTGTACTATTCTCCTTCGTCATTGCAGGATGCATATACTACATCGTTTCTCG
TAGAGTGAGGCGGTCGCGCTTGCCACCAGGGCCGCCTGGCATTCCTATTCCCTTCATTG
GGAACATGTTTGATATGCCTGAAGAATCTCCATGGTTAACATTTCTACAATGGGGACGG
GATTACAGTCTGTCTTGCCGCGTTGACTTCTAATATATGAACAGCTAATATATTGTCAG
ACACCGATATTCTCTACGTGGATGCTGGAGGGACAGAAATGGTTATTCTTAACACGTTG
GAGACCATTACCGATCTATTAGAAAAGCGAGGGTCCATTTATTCTGGCCGGTGAGCTGA
TGTTGAGTTTTTTGCAATTGAATTTGTGGTCACACGTTTCCAGACTTGAGAGTACAATG
GTCAACGAACTTATGGGGTGGGAGTTTGACTTAGGGTTCATCACATACGGCGACAGGTG
GCGCGAAGAAAGGCGCATGTTCGCCAAGGAGTTCAGTGAGAAGGGCATCAAGCAATTTC
GCCATGCTCAAGTGAAAGCTGCCCATCAGCTTGTCCAACAGCTTACCAAAACGCCAGAC
CGCTGGGCACAACATATTCGCCAGTAAGTACTACTTGAGGAAAATAGCGTACGCTTCGC
TGACCGGTCCGTACATCAAAGTCAGATAGCGGCAATGTCACTGGATATTGGTTATGAA
```

```
TTGATCTTGCAGAAGACGACCCTTGGCTGGAAGCGACCCATTTGGCTAATGAAGGCCTC
GCCATAGCATCAGTGCCGGGCAAATTTTGGGTCGATTCGTTCCCTTCTCGTGAGCATCC
TTCTTCTATGTAGGAAGGGAAGGAGTCTAACAAGTGTTAGTAAAATACCTTCCTGCTTG
GTTCCCAGGTGCTGTCTTCAAGCGCAAAGCGAAGGTCTGGCGAGAAGCCGCCGACCATA
TGGTTGACATGCCTTATGAAACTATGAGGAAATTAGCAGTTAGTCAAATGCGTTCTCCC
CGTATTTTTTCAATACTCTAACTTCAGCTCACAGCCTCAAGGATTGACTCGTCCGTCGT
ATGCTTCAGCTCGTCTGCAAGCCATGGATCTCAACGGTGACCTTGAGCATCAAGAACAC
GTAATCAAGAACACAGCCGCAGAGGTTAATGTCGGTAAGTCAAAAGCGTCCGTCGGCAA
TTCAAAATTCAGGCGCTAAAGTGGGTCTTCTCACCAAGGTGGAGGCGATACTGTAAGGA
TTTCTCAATCGTTAGAGTATAAGTGTTCTAATGCAGTACATACTCCACCAACCAGACTG
TCTCTGCTATGTCTGCGTTCATCTTGGCCATGGTGAAGTACCCTGAGGTCCAGCGAAAG
GTTCAAGCGGAGCTTGATGCTCTGACCAATAACGGCCAAATTCCTGACTATGACGAAGA
AGATGACTCCTTGCCATACCTCACCGCATGTATCAAGGAGCTTTTCCGGTGGAATCAAA
TCGCACCCTCGCTATACCGCACAAATTAATGAAGGACGACGTGTACCGCGGGTATCTG
ATTCCCAAGAACACTCTAGTCTTCGCAAACACCTGGTGAGGCTGTCCATTCATTCCTAG
TACATCCGTTGCCCCACTAATAGCATCTTGATAACAGGGCAGTATTAAACGATCCAGAA
GTCTATCCAGATCCCTCTGTGTTCCGCCCAGAAAGATATCTTGGTCCTGACGGGAAGCC
TGATAACACTGTACGCGACCCACGTAAAGCGGCATTTGGCTATGGACGACGAAATTGGT
AAGTGCGCTTTCAGAACCCCCCCTTCCGTTGACTAGTGCCATGCGCGCATACAATATCG
CTATTGATCTGATATAACTTCCCTGCGGCATTTATTTTGGCATTCCTTTAGTCCCGGAA
TTCATCTAGCGCAGTCGACGGTTTGGATTGCAGGGGCAACCCTCTTATCAGCGTTCAAT
ATCGAGCGACCTGTCGATCAGAATGGGAAGCCCATTGACATACCGGCTGATTTTACTAC
AGGATTCTTCAGGTAGCTAATTTCCGTCTTTGTGTGCATAATACCCCTAACGACGCACG
TTTACCTTTTTGTAAAGACACCCAGTGCCTTTCCAGTGCAGGTTTGTTCCTCGAACAGA
GCAAGTCTCACAGTCGGTATCCGGACCCTGA

SEQ.ID NO: 4
MIAVLFSFVIAGCIYYIVSRRVRRSRLPPGPPGIPIPFIGNMFDMPEESPWLTFLQWGR
DYNTDILYVDAGGTEMVILNTLETITDLLEKRGSIYSGRLESTMVNELMGWEFDLGFIT
YGDRWREERRMFAKEFSEKGIKQFRHAQVKAAHQLVQQLTKTPDRWAQHIRHQIAAMSL
DIGYGIDLAEDDPWLEATHLANEGLAIASVPGKFWVDSFPSLKYLPAWFPGAVFKRKAK
VWREAADHMVDMPYETMRKLAPQGLTRPSYASARLQAMDLNGDLEHQEHVIKNTAAEVN
VGGGDTTVSAMSAFILAMVKYPEVQRKVQAELDALTNNGQIPDYDEEDDSLPYLTACIK
ELFRWNQIAPLAIPHKLMKDDVYRGYLIPKNTLVFANTWAVLNDPEVYPDPSVFRPERY
LGPDGKPDNTVRDPRKAAFGYGRRNCPGIHLAQSTVWIAGATLLSAFNIERPVDQNGKP
IDIPADFTTGFFRHPVPFQCRFVPRTEQVSQSVSGP

SEQ.ID NO: 5
ATGGCGTTCGATCTCAAGACTGAAGACGGCCTCATCACATATCTCACTAAACATCTTTC
TTTGGACGTCGACACGAGCGGAGTGAAGCGCCTTAGCGGAGGCTTTGTCAATGTAACCT
GGCGCATTAAGCTCAATGCTCCTTATCAAGGTCATACGAGCATCATCCTGAAGCATGCT
CAGCCGCACATGTCTACGGATGAGGATTTTAAGATAGGTGTAGAACGTTCGGTTTACGA
ATACCAGGCTATCAAGCTCATGATGGCCAATCGGGAGGTTCTGGGAGGCGTGGATGGCA
TAGTTTCTGTGCCAGAAGGCCTGAACTACGACTTAGAGAATAATGCATTGATCATGCAA
GATGTCGGGAAGATGAAGACCCTTTTAGATTATGTCACCGCCAAACCGCCACTTGCCGC
GGATATAGCCCGCCTTGTTGGGACAGAAATTGGGGGGTTCGTTGCCAGACTCCATAACA
TAGGCCGCGAGAGGCGAGACGATCCTGAGTTCAAATTCTTCTCTGGAAATATTGTCGGA
AGGACGACTTCAGACCAGCTGTATCAAACCATCATACCCAACGCAGCGAAATATGGCGT
CGATGACCCCTTGCTGCCTACTGTGGTTAAGGACCTTGTGGACGATGTCATGCACAGCG
AAGAGACCCTTGTCATGGCGGACCTGTGGAGTGGAAATATTCTTCTCCAGTTGGAGGAG
GGAAACCCATCGAAGCTGCAGAAGATATATATCCTGGATTGGGAACTTTGCAAGTACGG
CCCAGCGTCGTTGGACCTGGGCTATTTCTTGGGTGACTGCTATTTGATATCCCGCTTTC
AAGACGAGCAGGTCGGTACGACGATGCGGCAAGCCTACTTGCAAAGCTATGCGCGTACG
AGCAAGCATTCGATCAACTACGCCAAAGTCACTGCAGGTATTGCTGCTCATATTGTGAT
GTGGACCGACTTTATGCAGTGGGGAGCGAGGAAGAAAGGATAAATTTTGTGAAAAGG
GGGTAGCTGCCTTTCACGACGCCAGGGGCAACAACGACAATGGGAAATTACGTCTACC
TTACTGAAGGAATCATCCACTGCGTAA

SEQ.ID NO: 6
MHIRNPYRTPIDYQALSEAFPPLKPFVSVNADGTSSVDLTIPEAQRAFTAALLHRDFGL
TMTIPEDRLCPTVPNRLNYVLWIEDIFNYTNKTLGLSDDRPIKGVDIGTGASAIYPMLA
CARFKAWSMVGTEVERKCIDTARLNVVANNLQDRLSILETSIDGPILVPIFEATEEYEY
EFTMCNPPFYDGAADMQTSDAAKGFGFGVGAPHSGTVIEMSTEGGESAFVAQMVRESLK
LRTRCRWYTSNLGKLKSLKEIVGLLKELEISNYAINEYVQGSTRRYAVAWSFTDIQLPE
ELSRPSNPELSSLF

SEQ.ID NO: 7
ATGCATATCAGAAATCCTTACCGTACACCAATTGACTATCAAGCACTTTCAGAGGCCTT
CCCTCCCCTCAAGCCATTTGTGTCTGTCAATGCAGATGGTACCAGTTCTGTTGACCTCA
CTATCCCAGAAGCCCAGAGGGCGTTCACGGCCGCTCTTCTTCATCGTGACTTCGGGCTC
ACCATGACCATACCAGAAGACCGTCTGTGCCCAACAGTCCCCAATAGGTTGAACTACGT
TCTGTGGATTGAAGATATTTTCAACTACACGAACAAAACCCTCGGCCTGTCGGATGACC
GTCCTATTAAAGGCGTTGATATTGGTACAGGAGCCTCCGCAATTTATCCTATGCTTGCC
TGTGCTCGGTTCAAGGCATGGTCTATGGTTGGAACAGAGGTCGAGGAAGTGCATTGA
CACGGCCCGCCTCAATGTCGTCGCGAACAATCTCCAAGACCGTCTCTCGATATTAGAGA
CATCCATTGATGGTCCTATTCTCGTCCCATTTTCGAGGCGACTGAAGAATACGAATAC
GAGTTTACTATGTGTAACCCTCCATTCTACGACGGTGCTGCCGATATGCAGACTTCGGA
```

SEQUENCE LISTING

```
TGCTGCCAAAGGATTTGGATTTGGCGTGGGCGCTCCCCATTCTGGAACAGTCATCGAAA
TGTCGACTGAGGGAGGTGAATCGGCTTTCGTCGCTCAGATGGTCCGTGAGAGCTTGAAG
CTTCGAACACGATGCAGATGGTACACGAGTAACTTGGGAAAGCTGAAATCCTTGAAAGA
AATAGTGGGGCTGCTGAAAGAACTTGAGATAAGCAACTATGCCATTAACGAATACGTTC
AGGGGTCCACACGTCGTTATGCCGTTGCGTGGTCTTTCACTGATATTCAACTGCCTGAG
GAGCTTTCTCGTCCCTCTAACCCCGAGCTCAGCTCTCTTTTCTAG

SEQ.ID NO: 8
MHIRNPYRTPIDYQALSEAFPPLKPFVSVNADGTSSVDLTIPEAQRAFTAALLHRDFGL
TMTIPEDRLCPTVPNRLNYVLWIEDIFNYTNKTLGLSDDRPIKGVDIGTGASAIYPMLA
CARFKAWSMVGTEVERKCIDTARLNVVANNLQDRLSILETSIDGPILVPIFEATEEYEY
EFTMCNPPFYDGAADMQTSDAAKGFGFGVGAPHSGTVIEMSTEGGESAFVAQMVRESLK
LRTRCRWYTSNLGKLKSLKEIVGLLKELEISNYAINEYVQGSTRRYAVAWSFTDIQLPE
ELSRPSNPELSSLF

SEQ.ID NO: 9
ATGCCTTCCAGTCACCCTCACATTACTCATCGCTATCGGGTTCCTTCGAGTGACGACCA
TGAACGTATATCTGCTCTGTTCTTGGGTCCCAAAGCAGAAAATGCCGCATTTCTCCAGC
AATGGTTGACCACGGTCGTCGCACAGCAAAAGGCTGCCCGCGATGCATACTTCCCGGAT
GACAATGCTTTTATTACTACAGACATGCAAACTTCCCCCGCCTTTGCTCAGACTACTAA
AGTAATCGCCTCCAATCTCACCGAATTATTGACTGCACTCGGTGAAAGGTCGATTCCTT
TCTTCTCACCTCGGTACAGCGGCCATATGTCTGTGGACCAAAGTCTACCTGCCATTCTC
GGATTCTTATCGACCACATTTTATAATCCTAACAATGTTGCCTTCGAGGCTAGTCCATT
CACGACCCTCATCGAGGAAGAAGTTGGCTTGCAACTCTCTGAAATGCTGGGTTATATC
GGCTAAATAACACCGAGAAACCTCTCGCCTGGGGACATATTGCATCAGGTGGAACTGTT
GCAAACTTGGAAGCGATGTGGGCGGCGCGAAACCTCAAGTTTTACCCTCTCTCACTCCG
TGATGCTTCAGCCAAGGCGCAGAGATGGAATTCATTCGTGACACATTCTCCGTCAAAA
CCTGTGTTGGTGACAAAAAATTATTAAAGGATTGCAGCCCATGGGAACTCCTCAATTTG
CATGTTTCTACTATCTTAGACATGCCCGACCGTCTGCACGACGAGTACAATATTTCACC
TCAGTTCCTCGAAAAGGTTATGCGAAAGTATATCATCCAGTCTACCAACAAAGACACGT
TGATGCAGCGTTGGGGACTTACCCAACAACCTGTCGTTTTATCCCCGAGCACAAACCAT
TATTCCTGGCCAAAGGCTGCAGCTGTGCTCGGTATTGGCTCAGACAACCTTCGCAACGT
CCCAGTAGACATCCAAGCCCACATGGACATAAACGAACTCGATCGTATGTTAAAAATTT
GCTTGGACGAGGAGACGCCAGTATATCAAGTAGTTGCTGTTATCGGTACCACCGAAGAG
GGCGGTGTCGATCGCATTACGGAGATCCTGAAGCTGCGCCAAAAGTATGAAGCTTTGGG
GCTGTCTTTTGCCATCCATGCAGATGCTGCTTGGGGAGGCTATTTTGCAACCATGCTAC
CCAAAGATACATTGGGTCGAAACCGGACTAGGCTTCCCAAAGAGGACACTACCTCGGGC
TTTGTCCCTCACGTCGGTCTGCGCGAGGAGAGCGCGTTACAACTCAGCCATATAAAGTA
TGCCGATTCTATTACTATCGACCCGCACAAGGCAGGCTATGTTCCTTACCCCGCTGGGG
CACTCTGTTATCGCGACGGAAGAATGAGGTACCTGCTTACATGGTCCGCGCCCTACCTT
GCCCAAGGCAACGAGGGCCAAAGTATCGGAATATACGGGATCGAAGGAAGCAAACCTGG
TGCAGCAGCATCCGCGGTATTCATGGCGCACGAAACCATTGGCCTGACTCCTTCTGGAT
ACGGGAACCTTCTTGGCCAGGCAATGTTTACATGTCGCCGATACGCTGCTCACTGGTCT
GCAATGTCAACGGATACTACCAGTTTCACTGTCACCCCGTTCAATCCTATCCCTGCTGA
CATCGACCCCAACGCTGACCCCGCAAAGGTCGAAGAGCAAAAACAGTTCATCAGAGATC
GTATCTTGTTCAAATCGAACGAGGAAATATACAACGATTCTGAGGCTATGGAACTCTTG
CACCAACTTGGGTCCGATCTCAATATCAACGTTTTCGCATGCAACTTCCGCGACCGCGA
TAATAATCTCAACACCGACGTCGAGGAAGCCAACTGGCTCAATAACCGTATTTTCCAAC
GCTTTTCTGTTACAAGTGCTGAGGAGAACCCATTGGAAACGCCATTCTTCCTCAGCTCA
ACTACATTGAAACAATCCGAATACGGCGTCTGCGCAACCGAAGTAAAGAGACGCATGGG
ACTTGTTGGTGACCAGGATGTTATAGTCCTGAGGAACGTCGTTATGTCTCCATTTACTA
CAACGAACGACTTTGTGGGAACTCTGGCAAACACCTTCCAAAAGATCGTTGAGGAGGAG
GTCGAGTATGCACGGATCCGCAACGATATGAAACCTAGCATTCACACCTTCCTTCTTCA
TGGTTCAGGAGAGCAATACTATCTTGTCCACACCCCAACGATCCATATGGCCAGCGGCC
GTCGCCAAATCATCCTTTCAGTAAATGTTGAAGGCCAAGTTCGGCAGGCGATACATGCC
CATGAAAGAGTTGAAGCAGTGATTGTACATAAACACTGTGCCCCTCCGCCTTGACGAAAT
CGTTGACGGAGGATCATTTGACGGCATACTCACCATCGGAAAGAGGAAAACTAGTTTCA
AAGTGAAGATTTCAAACATTAAAGTAGTCAAGAAGCGCTCTCTGATGACTGAGGACCTG
GAATCTGCGTACCCATCGTTGATGCCATTCTATTTCTACGGGACTCAAGGACACGCTCA
TCTCGACCATGTCATTACTGTCGTTCCTAACATCCATCTGAGTGCTGGCGAAATACAGT
ACAAATTCGACGACGAGGTGTCAAGCGAGGACCTCGCCAAGGGCCTCATTGTTGTTGCT
GAGAACGTACACGAGGCATCCATGCAGCCCTTCCCGCTCATGAAAGATTTCAAGATCAC
CAACCAATTCTTCTTCAGCTCCGGCAAATACTCCGCGTCAAAGTGTACAGAGATCCAT
ACCCGGCATCGACAATGGATCCCATCCCTCTCCACGACATCAAGAACCAGCCCGTCGTG
ACACAAGGCACCATCACGCTCGTCGGAAATATTTACGTCGATTCTGATGCGCTCAACGT
CGCTTCCGAGCCTACTGCCGACGAAGACGCGGCGCATGTTCCTCACGCTCGCAACATGT
ACGGCGAGATGACCGCTGGAACGATCAAAGGCTGGCAAAACGCTGTTCGTCATTTCCAC
AACAAATTGGAGACTGTTGCTCCGACGAAGTAG

SEQ.ID NO: 10
MPSSHPHITHRYRVPSSDDHERISALFLGPKAENAAFLQQWLTTVVAQQKAARDAYFPD
DNAFITTDMQTSPAFAQTTKVIASNLTELLTALGERSIPFFSPRYSGHMSVDQSLPAIL
GFLSTTFYNPNNVAFEASPFTTLIEEEVGLQLSEMLGYNRLNNTEKPLAWGHIASGGTV
ANLEAMWAARNLKFYPLSLRDASAEGAEMEFIRDTFSVKTCVGDKKLLKDCSPWELLNL
HVSTILDMPDRLHDEYNISPQFLEKVMRKYIIQSTNKDTLMQRWGLTQQPVVLSPSTNH
YSWPKAAAVLGIGSDNLRNVPVDIQAHMDINELDRMLKICLDEETPVYQVVAVIGTTEE
GGVDRITEILKLRQKYEALGLSFAIHADAAWGGYFATMLPKDTLGRNRTRLPKEDTTSG
```

SEQUENCE LISTING

```
FVPHVGLREESALQLSHIKYADSITIDPHKAGYVPYPAGALCYRDGRMRYLLTWSAPYL
AQGNEGQSIGIYGIEGSKPGAAASAVFMAHETIGLTPSGYGNLLGQAMFTCRRYAAHWS
AMSTDTTSFTVTPFNPIPADIDPNADPAKVEEQKQFIRDRILFKSNEEIYNDSEAMELL
HQLGSDLNINVFACNFRDRDNNLNTDVEEANWLNNRIFQRFSVTSAEENPLETPFFLSS
TTLKQSEYGVCATEVKRRMGLVGDQDVIVLRNVVMSPFTTTNDFVGTLANTFQKIVEEE
VEYARIRNDMKPSIHTFLLHGSGEQYYLVHTPTIHMASGRRQIILSVNVEGQVRQAIHA
HERVEAVIVHNTVPLRLDEIVDGGSFDGILTIGKRKTSFKVKISNIKVVKKRSLMTEDL
ESAYPSLMPFYFYGTQGHAHLDHVITVVPNIHLSAGEIQYKFDDEVSSEDLAKGLIVVA
ENVHEASMQPFPLMKDFKITNQFFFSSGQILRVKVYRDPYPASTMDPIPLHDIKNQPVV
TQGTITLVGNIYVDSDALNVASEPTADEDAAHVPHARNMYGEMTAGTIKGWQNAVRHFH
NKLETVAPTK

SEQ.ID NO: 11
ATGGAGGCTATCAAAAAGGTTTTTGAGAACAAAAAGGCGGAGGGCATTCCTGTGTTGGT
GACCTTTGTTACTGCAGGATATCCTCGTCCCGAAGATACTGTTCCCATCTTGCTGGCCA
TGGAGGCCGGTGGTGCTGATATCATCGAGCTTGGTATGCCATTTTCAGACCCAATTGCA
GATGGTCCTGTCATCCAGGAAACGAACACAATCGCCGTTGCAAACCAGGTAGATTATAC
CACTGTTCTCGGACAACTTCGGGAAGCCCGCAAACAAGGGCTCAAGGCACCCGTTCTTC
TGATGGGATATTATAACCCCATATTGGCTTACGGAGAAGACAGATCTATTCAAGATGCG
GCTGAAGCTGGAGCCAATGGGTTTATTATGGTCGACCTTCCACCCGAGGAGGCTGTCGC
TTTTCGAGAGAAATGTATCAAATCCAACCTCTCATATGTTCCTCTAATTGCACCCTCAA
CGACTCTGTCGCGTATAAAGTTCCTCTCAACAATTGCAGACACGTTCATCTATGTCGTG
TCTAAAATGGGAACCACCGGATCCTCAGAGAAGGTTGCCATGAATAACGCCCTTCCCAC
CATCATCGATCGTATTCGCGAGTACGCTGAAGTTCCTTTAGCAGTCGGATTTGGAGTCG
CCACTCGGGCTCACTTCAACTACGTCGCCGATTCCGGTGCTGATGGTGTCGTTATTGGC
ACCAAACTCGTTAACGTTATTAAAGAGTCACCGCAAGGGGAAGCACCCAAAAATGTTGA
GGCATACTGCCGTGAGATGAGCCAAAAGGGAGAAACAAATCGCGTCAAATCTCCACCAA
CTGCCCGTGCTGCCAGCTCCGAATCAATTCCTGTTGTTGTTCCTTCTGTTCTCCCCGCA
CGTTTCGGAGAATTCGGAGGACAATACGTTCCCGAAGCTCTTGTCGATTGTCTGGTTGA
ACTAGAAGAAGCTCACAAATCTGCCATGGCTGATCCTGAATTCCAGAAGGAACTACAAT
CGCATGCCGATATGCAAATCGTCCTTCACAAATATACCTCGCCGAAAATCTCACCAAG
GATGCTGGGGGTGCAAATATTTGGTTGAAACGTGAAGATTTGAACCACACAGGTTCCCA
CAAAATCAATAACGCTTTGGGACAAATTCTGCTTGCCCGGAGAATCGGAAAGACCAGAA
TTATCGCAGAAACAGGTGCCGGCCAGCATGGTGTTGCAACAGCGACTGTTTGCGCTAAG
TTTGGAATGGAATGTGTTATCTACATGGGCGCAGAAGATGTGCGACGGCAAGCTCTAAA
TGTATTCAGGATTGAGATGCTAGGAGCAAAAGTTGTTCCTGTTACTTCAGGATCATGCA
CATTGAAGGACGCTGTAAACGAGGCCTTCCGTGACTGGGTGACAAACCTTTCTACGACG
CATTATTTGGTTGGCTCTGTAATTGGACCTCATCCCTTCCCCACCATTGTCCGAGATTT
CCAAAAGGTCATTGGTCAAGAGATCAAGGCTCAGATGTTGGCCGCCCGCGGCAAACTTC
CTGATGTCGTCGTCGCTTGTGTTGGTGGAGGAAGCAATGCTATCGGTACGTTCTATGAT
TTTATTGGCGACAAGAGTGTACGTCTAGTTGGGGTGGAAGCAGGAGGAGAAGGTATTGA
CGGAGACCGACATAGCGCCACACTTTCGATGGGGCAACCGGGAGTACTTCACGGTGTTA
GAACATATATTCTACAAGACAAGGCCGGTCAAATCATCGAGACGCACTCAATCAGCGCT
GGATTGGATTATCCCGGCGTTGGACCAGAACATGCTTGGCTAAAGGACTCTAAAAGAGC
AGAATATGTTGTCGCCACAGACGAAGAAGCACTTCGCGGTTTCCGTATGCTAACACAAA
GGGAGGGAATTATTCCTGCCCTTGAATCTTCCCATGCGATCTGGGAGGCTGTCAGGATT
GCCCGCACCATGTCGAAGGACCAGGATCTTGTTGTGTGTTTGTCTGGCCGAGGTGATAA
AGACGTTGAGCAAATTTCTCAACTTCTTCCCAAGTGGGCGGATATTCTAGACTGGCATG
TTTCTTCCCATGCCGTTGGACACACAACAAAATTCTAA

SEQ.ID NO: 12
MEAIKKVFENKKAEGIPVLVTFVTAGYPRPEDTVPILLAMEAGGADIIELGMPFSDPIA
DGPVIQETNTIAVANQVDYTTVLGQLREARKQGLKAPVLLMGYYNPILAYGEDRSIQDA
AEAGANGFIMVDLPPEEAVAFREKCIKSNLSYVPLIAPSTTLSRIKFLSTIADTFIYVV
SKMGTTGSSEKVAMNNALPTIIDRIREYAEVPLAVGFGVATRAHFNYVADSGADGVVIG
TKLVNVIKESPQGEAPKNVEAYCREMSQKGETNRVKSPPTARAASSESIPVVVPSVLPA
RFGEFGGQYVPEALVDCLVELEEEAHKSAMADPEFQKELQSHAGYANRPSQIYLAENLTK
DAGGANIWLKREDLNHTGSHKINNALGQILLARRIGKTRIIAETGAGQHGVATATVCAK
FGMECVIYMGAEDVRRQALNVFRIEMLGAKVVPVTSGSCTLKDAVNEAFRDWVTNLSTT
HYLVGSVIGPHPFPTIVRDFQKVIGQEIKAQMLAARGKLPDVVVACVGGGSNAIGTFYD
FIGDKSVRLVGVEAGGEGIDGDRHSATLSMGQPGVLHGVRTYILQDKAGQIIETHSISA
GLDYPGVGPEHAWLKDSKRAEYVVATDEEALRGFRMLTQREGIIPALESSHAIWEAVRI
ARTMSKDQDLVVCLSGRGDKDVEQISQLLPKWADILDWHVSSHAVGHTTKF

SEQ.ID NO: 13
ATGACCGAGGAGTTGACGACGGTCCGAGACGCCTGCGCCAGAACGTTGGAGAACACGGC
ACGGACACTGCACCTGGGAGCCAGCGGTACGGAATTCGTCGCGGCGTTCCGGGCCATGA
CCGACCACTGGGCGCCGCCCGCCCCCACGATCTACCCCTGTCGGACGTGTCACCCGAC
GGGTCGCCGGTGGAGTACGCCGTCGACCTCGGCGGGCTCGCGCCCGCACTCCAGTTCGC
CATGGAGCCGCTGACCGCGGGCGTGCCGGCTCGTGATCCCCTCGCGGCGCGGGCCATCA
TGCCGCTGCTGGCCGGGCGGTACGGCGCGACGCGACCCGGTGGTCGGCCCTCGCGGAC
CGGCTCCTGCCAGACGACGCGCACGGCCCGCACGTCTCCATGTACGGCGCCGAGGTTCG
GGCGGGTGCCCCGATCCGGTTCAAGGCCTGGTTCTACCTGAACGTGACCGGCCCGGACG
GCGCCTTCAACCTGCTGTACTCCGCCTTGGAACGGATGGGTACGACGCACCTGTGGCCG
GTCGTCCAAGCGCACGTGCACCGCGCTGGGGAGGACGTGCCGTTCCTGCTGTCGCTGGA
CCTGTCGGACGACCCGGCGGCCCGGGTGAAGGTGTACTTCCGGCACTTCGCGGCGGATG
TCGAGGAGGTCGCGGCCGTGCTCAAGGCGTACCCAGGTTTCGAGCCGGGCGAGGTGCGG
```

```
GCCTTCTGCAAGGTCATGATGGGCGGTCGGCGCCGCTTCAGCGACCAGCCGGCCGTCAC
CTGCGTATCACTGCTCGACGCGCAGACCTTCGATCGCACTGCGGCCACCCTCTACGTTC
CGCTGTGGACGTACGCCGAGCACGACGGCGAAGTGCGGCAGCGGGTGCACCGGACCCTG
GCTGCGTGGCCGGAGGCGCTGTACCGCTACGACAGCGTGCTCGCCGGCATCGCGCACCG
CGGGCTGGACGCCGGAACCGGGATCCACAACTACATCTCCTGGCAACCCGGCCGGACCC
GCCCGCGGATGAAGGTCTACCTGTCACCGGAGATGCACGACGTCACTCCTCCGCCGCTC
GGCGTAAGCCAACAGCATCACCTCAGTGGCCAGACCACTGCGAGAGGGAGAACCGAATG
A

SEQ.ID NO: 14
MTEELTTVRDACARTLENTARTLHLGASGTEFVAAFRAMTDHWGAARPHDLPLSDVSPD
GSPVEYAVDLGGLAPALQFAMEPLTAGVPARDPLAARAIMPLLAGRYGADATRWSALAD
RLLPDDAHGPHVSMYGAEVRAGAPIRFKAWFYLNVTGPDGAFNLLYSALERMGTTHLWP
VVQAHVHRAGEDVPFLLSLDLSDDPAARVKVYFRHFAADVEEVAAVLKAYPGFEPGEVR
AFCKVMMGGRRRFSDQPAVTCVSLLDAQTFDRTAATLYVPLWTYAEHDGEVRQRVHRTL
AAWPEALYRYDSVLAGIAHRGLDAGTGIHNYISWQPGRTRPRMKVYLSPEMHDVTPPPL
GVSQQHHLSGQTTARGRTE

SEQ.ID NO: 15
ATGAAGGCAGCCAATGCCTCCAGTGCGGAGGCCTATCGAGTTCTTAGTCGCGCCTTTAG
ATTCGATAATGAAGATCAGAAGCTGTGGTGGCACAGCACTGCCCCGATGTTTGCAAAAA
TGCTGGAAACTGCCAACTACACCACCTTGTCAGTATCAATACCTCATCACCTATAAG
GAGTGCGTAATTCCCAGTCTCGGATGCTATCCGACCAACAGCGCCCCCGCTGGTTGAG
CATCCTCACTCGATACGGCACTCCGTTCGAATTGAGCCTAAATTGCTCTAATTCAATAG
TGAGATACACATTCGAGCCGATCAATCAACATACCGGAACAGATAAAGACCCATTCAAT
ACGCACGCCATCTGGGAGAGCCTGCAGCACCTGCTTCCACTGGAGAAGAGCATTGATCT
GGAGTGGTTCCGCCACTTCAAGCACGATCTCACCCTCAACAGTGAAGAATCTGCTTTTC
TGGCTCATAATGATCGCCTCGTGGGCGGCACTATCAGGACGCAGAACAAGCTCGCGCTC
GATCTGAAGGATGGCCGCTTTGCACTTAAGACGTACATATACCCGGCTCTCAAAGCTGT
CGTCACCGGCAAGACAATTCATGAGTTGGTCTTTGGCTCAGTCCGCCGGCTGGCAGTGA
GGGAGCCCCGAATCTTGCCCCCACTCAACATGCTGGAGGAATACATCCGATCACGCGGT
TCCAAGAGCACTGCCAGTCCCCGCCTAGTGTCCTGTGATCTGACCAGTCCTGCCAAGTC
GAGAATCAAGATCTACCTGCTGGAGCAGATGGTTTCACTAGAAGCCATGGAGGACCTGT
GGACTCTGGGCGGACGGCGCCGAGACGCTTCCACTTTAGAGGGGCTCTCTCTGGTGCGT
GAGCTTTGGGATCTGATCCAACTGTCGCCGGGATTGAAGTCCTATCCGGCGCCGTATCT
GCCTCTCGGGGTTATCCCAGACGAGAGGCTGCCGCTTATGGCCAATTTCACCCTGCACC
AGAATGACCCGGTCCCAGAGCCGCAAGTATATTTCACAACCTTCGGCATGAACGACATG
GCGGTGGCGGATGCCCTGACGACGTTCTTCGAGCGCCGGGGTTGGAGTGAAATGGCCTG
CACCTACGAAACTACTTTGAAGTCGTACTACCCCATGCGGATCATGACAAACTTAACT
ACCTCCACGCCTACATATCCTTCTCCTACAGGGACCGTACCCCTTATCTGAGTGTCTAT
CTTCAATCCTTCGAGACAGGGGACTGGGCAGTTGCAAACTTATCCGAATCAAAGGTCAA
GTGTCAGGATGCGGCCTGTCAACCCACAGCTTTACCTCCAGATCTGTCAAAGACAGGGG
TATATTATTCCGGTCTCCACTGA

SEQ.ID NO: 16
MKAANASSAEAYRVLSRAFRFDNEDQKLWWHSTAPMFAKMLETANYTTPCQYQYLITYK
ECVIPSLGCYPTNSAPRWLSILTRYGTPFELSLNCSNSIVRYTFEPINQHTGTDKDPFN
THAIWESLQHLLPLEKSIDLEWFRHFKHDLTLNSEESAFLAHNDRLVGGTIRTQNKLAL
DLKDGRFALKTYIYPALKAVVTGKTIHELVFGSVRRLAVREPRILPPLNMLEEYIRSRG
SKSTASPRLVSCDLTSPAKSRIKIYLLEQMVSLEAMEDLWTLGGRRRDASTLEGLSLVR
ELWDLIQLSPGLKSYPAPYLPLGVIPDERLPLMANFTLHQNDPVPEPQVYFTTFGMNDM
AVADALTTFFERRGWSEMARTYETTLKSYYPHADHDKLNYLHAYISFSYRDRTPYLSVY
LQSFETGDWAVANLSESKVKCQDAACQPTALPPDLSKTGVYYSGLH

SEQ.ID NO: 17
ATGAGGGCCGCGTCGACGGGCGCGGACCCGCAGGACGCATCCACGCTCGGCTCTTTCAC
CGGCGGCCAGTTGCGAAGACTCGGCTCGGTCGCCGGTCTGTCCCGCGCCGACGTCGAGA
CCTACGCACAGGTCCTGACCGACGCATTGGGCCCGGTGGCCCAGCGGCCGCTGAGCCTG
GCGCCGCCCACCCGCACCTTCCTGTCGGACGACCACACCCCCGTGGAGTTCTCCCTCTC
CTTCCGGCCCGGGGCGGCGCCCGCCATGCGGGTCCTCGTGGAACCGGGCTGCGGTGCGA
CCAGCCTGGCCGACAACGGCCGTGCCGGTCTTGAGGCGGTCCGCACGATGGCGCGGCGC
TGGCACTTCACCACCGACGCCCTCGACGAACTCCTGGACCTGTTCCTGCCGCCCGCTCC
GCAGGGCCCCCTCGCCCTGTGGTGCGCCCTGGAACTCAGGCCCGGGGTGTACCGGGCG
TCAAGGTCTATCTGAAACCCTGCGGTGGGCGGGAGGAACGTTCCGCCGCGACGGTGCCG
GAGGCCCTGCGCCGGCTCGGGCACCACCAGGCCTTCGACAGCCTCCCCCAGGGCAGTGG
ATACCCGTTCCTCGCCCTGGACCTCGGGAACTGGACGGAGCCCCGGGCGAAGGTCTACC
TGCGCCACGACAACCTCACGGCCGGTCGGGCCGCACGGCTGTCCCGACGGACTCGGGC
CTCGTGCCGACCGCGGTCGAGGGTTTCTTCCGCACCGCCGCGGGTCCCGGCTCCGACGC
GGGTGGGCTCGACGGGCGGCTGCTCAGTCCTGCCACTCCTTCACCGACCCCGGCGGG
AGCGGCCGAGCGGCTTCACCCTGTACATCCCGGTTCGTGACTACGTCCGGCATGACGGG
GAGGCCCTGGCGCGGGCGTCCACCGTGCTGCACCACCACGGCATGGACGCCTCCGTGCT
CCACCGCGCCCTGGCCGCCCTCACCGAGCGGCGGCCCGAGGACGGGGTGGGCCTGATCG
CCTACCTGGCCCTCGCCGGCCAACGGGACCAGCCGCCGCGGGTGACGGCCTACCTCTCC
TCGGAGGCCTACACGGTCCGGCCGCCGGTCGTGGAGACCGTCCGCCAACCGCTGTCGGT
CGGCTGA
```

SEQUENCE LISTING

SEQ.ID NO: 18
MRAASTGADPQDASTLGSFTGGQLRRLGSVAGLSRADVETYAQVLTDALGPVAQRPLSL
APPTRTFLSDDHTPVEFSLSFRPGAAPAMRVLVEPGCGATSLADNGRAGLEAVRTMARR
WHFTTDALDELLDLFLPPAPQGPLALWCALELRPGGVPGVKVYLNPAVGGEERSAATVR
EALRRLGHHQAFDSLPQGSGYPFLALDLGNWTEPRAKVYLRHDNLTAGRAARLSRTDSG
LVPTAVEGFFRTAAGPGSDAGGLDGRPAQSCHSFTDPGAERPSGFTLYIPVRDYVRHDG
EALARASTVLHHHGMDASVLHRALAALTERRPEDGVGLIAYLALAGQRDQPPRVTAYLS
SEAYTVRPPVVETVRQPLSVG

SEQ.ID NO: 19
ATGGGAGGTCCGATGAGCGGTTTCCATTCGGGGGAGGCGCTGCTCGGTGACCTCGCCAC
CGGTCAGCTGACCAGGCTGTGCGAGGTGGCGGGGCTGACCGAGGCCGACACGGCGGCCT
ACACGGGGGTGCTGATCGAAAGTCTGGGGACGTCGGCCGGACGGCCGTTGTCCCTGCCA
CCCCCGTCGCGGACCTTTCTCTCCGACGACCACACCCCCGTGGAGTTCTCCCTGGCCTT
CCTGCCGGGACGCGCACCGCACCTGCGGGTCCTGGTGGAACCGGGCTGCTCCAGCGGCG
ACGACCTGGCGGAAAACGGCCGGGCCGGTCTGCGGGCGGTCCACACCATGGCGGACCGC
TGGGGATTCTCCACCGAGCAACTCGACCGGCTGGAGGACCTGTTCTTCCCCTCCTCCCC
CGAGGGCCCGCTGGCCCTGTGGTGCGCCCTGGAGCTCCGCTCCGGTGGGGTGCCGGGGG
TGAAGGTCTACCTCAACCCCGCGGCGAATGGCGCCGACCGGGCCGCCGAGACGGTACGC
GAGGCGCTGGCCAGGCTGGGCCACCTGCAGGCGTTCGACGCGCTGCCCCGGGCGGACGG
CTTCCCGTTCCTCGCCCTGGACCTCGCGACTGGGACGCCCCGCGGGTGAAGATCTACC
TCAAACACCTCGGCATGTCCGCCGCCGACGCGGGCTCCCTCCCCCGGATGTCGCCCGCA
CCGAGCCGGGAGCAGCTGGAGGAGTTCTTCCGCACCGCCGGTGACCTCCCGGCCCCGGG
AGACCCGGGGCCCACCGAGGACACCGGCCGGCTCGCCGGGCGCCCCGCCCTCACCTGCC
ACTCCTTCACGGAGACGGCGACCGGGCGGCCCAGCGGCTACACCCTCCACGTGCCGGTC
CGCGACTACGTCCGGCACGACGGCGAGGCACGGGACCGGGCGGTGGCCGTGCTGCGCGA
ACATGACATGGACAGTGCGGCACTGGACCGGGCGCTGGCCGCCGTGAGCCCCCGCCCGC
TGAGTGACGGGGTGGGCCTGATCGCCTATCTGGCACTGGTCCACCAGCGGGCCGGCCG
ACACGGGTGACCGTCTACGTCTCCTCCGAGGCGTACGAGGTGCGGCCGCCCCGCGAGAC
GGTCCCCACCCGCGACCGGGCGCGGGCACGGCTGTGA

SEQ.ID NO: 20
MGGPMSGFHSGEALLGDLATGQLTRLCEVAGLTEADTAAYTGVLIESLGTSAGRPLSLP
PPSRTFLSDDHTPVEFSLAFLPGRAPHLRVLVEPGCSSGDDLAENGRAGLRAVHTMADR
WGFSTEQLDRLEDLFFPSSPEGPLALWCALELRSGGVPGVKVYLNPAANGADRAAETVR
EALARLGHLQAFDALPRADGFPFLALDLGDWDAPRVKIYLKHLGMSAADAGSLPRMSPA
PSREQLEEFFRTAGDLPAPGDPGPTEDTGRLAGRPALTCHSFTETATGRPSGYTLHVPV
RDYVRHDGEARDRAVAVLREHDMDSAALDRALAAVSPRPLSDGVGLIAYLALVHQRGRP
TRVTVYVSSEAYEVRPPRETVPTRDRARARL

SEQ.ID NO: 21
ATGTCCATCGGAGCCGAGATCGATTCGCTGGTTCCTGCTCCACCGGGCCTCAACGGCAC
CGCTGCGGGCTATCCAGCCAAGACGCAGAAGGAGTTAAGCAACGGAGACTTTGACGCGC
ACGATGGTCTTTCTCTTGCACAACTGACACCGTACGATGTCTTGACGGCTGCACTTCCG
CTGCCGGCTCCGGCTTCGAGCACAGGGTTCTGGTGGCGGGAGACGGGCCCTGTTATGAG
CAAGCTTTTGGCCAAGGCGAACTACCCTCTTTACACTCATTACAAGTACCTTATGTTAT
ACCATACCCATATTCTCCCATTGTTGGGACCTCGACCGCCGCTCGAGAACTCGACGCAC
CCGTCGCCGAGTAACGCGCCGTGGAGGTCCTTCCTGACAGACGACTTCACTCCGCTCGA
GCCGAGCTGGAACGTGAACGGGAACTCGGAAGCACAGAGCACAATCCGTCTTGGTATTG
AACCTATAGGCTTTGAAGCCGGGGCTGCAGCGGACCCATTCAACCAAGCTGCCGTGACG
CAGTTCATGCACTCATACGAGGCAACCGAAGTCGGTGCCACGCTGACGCTGTTCGAGCA
CTTCCGCAACGACATGTTTGTTGGCCCAGAAACGTACGCTGCGTTAAGAGCGAAGATAC
CAGAAGGCGAGCATACCACACAGAGTTTCCTGGCGTTCGACCTGGACGCGGGTCGTGTC
ACCACAAAGGCGTACTTTTTCCCGATTCTCATGTCGTTGAAAACTGGACAGAGCACAAC
AAAGGTGGTCTCTGATTCCATTCTGCATCTAGCGCTGAAGAGTGAGGTGTGGGGTGTGC
AGACCATCGCCGCGATGTCGGTCATGGAGGCGTGATAGGTAGCTACAGGTGGCGCGGCA
AAGACGGAGATGATCAGCGTCGATTGCGTGAACGAGGCAGACTCTCGGATCAAGATATA
CGTGCGGATGCCACATACATCCTTGCGGAAGGTAAAAGAGGCGTACTGCTTAGGTGGGC
GGTTGACAGACGAGAACACAAAGGAGGGCCTGAAGCTGCTGGACGAGCTGTGGAGGACG
GTCTTCGGCATCGACGACGAGGACGCGGAGCTGCCACAGAATAGCCATCGCACCGCAGG
CACAATATTCAATTTCGAGCTGAGGCCAGGGAAATGGTTCCCCGAGCCCAAGGTATACC
TGCCCGTCCGACACTACTGTGAAAGTGATATGCAGATTGCTAGTCGGCTACAAACGTTC
TTTGGAAGGCTCGGATGGCACAACATGGAGAAAGATTATTGCAAGCATCTGGAAGATTT
GTTTCCCCATCATCCACTGTCCTCGTCAACGGGCACACACACCTTTCTCTCATTTTCGT
ATAAGAAGCAGAAGGGGGTCTATATGACCATGTATTATAATCTCCGGGTGTACAGCACC
TAA

SEQ.ID NO: 22
MSIGAEIDSLVPAPPGLNGTAAGYPAKTQKELSNGDFDAHDGLSLAQLTPYDVLTAALP
LPAPASSTGFWWRETGPVMSKLLAKANYPLYTHYKLMLYHTHILPLLGPRPPLENSTH
PSPSNAPWRSFLTDDFTPLEPSWNVNGNSEAQSTIRLGIEPIGFEAGAAADPFNQAAVT
QFMHSYEATEVGATLTLFEHFRNDMFVGPETYAALRAKIPEGEHTTQSFLAFDLDAGRV
TTKAYFFPILMSLKTGQSTTKVVSDSILHLALKSEVWGVQTIAAMSVMEAWIGSYGGAA
KTEMISVDCVNEADSRIKIYVRMPHTSLRKVKEAYCLGGRLTDENTKEGLKLLDELWRT
VFGIDDEDAELPQNSHRTAGTIFNFELRPGKWFPEPKVYLPVRHYCESDMQIASRLQTF
FGRLGWHNMEKDYCKHLEDLFPHHPLSSSTGTHTFLSFSYKKQKGVYMTMYYNLRVYST

SEQUENCE LISTING

SEQ.ID NO: 23
ATGGGAGGTCCGATGAGCGGTTTCCATTCGGGGAGGCGCTGCTCGGTGACCTCGCCAC
CGGTCAGCTGACCAGGCTGTGCGAGGTGGCGGGGCTGACCGAGGCCGACACGGCGGCCT
ACACGGGGGTGCTGATCGAAAGTCTGGGGACGTCGGCCGGACGGCCGTTGTCCCTGCCA
CCCCCGTCGCGGACCTTTCTCTCCGACGACCACACCCCCGTGGAGTTCTCCCTGGCCTT
CCTGCCGGGACGCGCACCGCACCTGCGGGTCCTGGTGGAACCGGGCTGCTCCAGCGGCG
ACGACCTGGCGGAAAACGGCCGGGCCGGTCTGCGGGCGGTCCACACCATGGCGGACCGC
TGGGGATTCTCCACCGAGCAACTCGACCGGCTGGAGGACCTGTTCTTCCCCTCCTCCCC
CGAGGGCCCGCTGGCCCTGTGGTGCGCCCTGGAGCTCCGCTCCGGTGGGGTGCCGGGGG
TGAAGGTCTACCTCAACCCCGCGGCGAATGGCGCCGACCGGGCCGCCGAGACGGTACGC
GAGGCGCTGGCCAGGCTGGGCCACCTGCAGGCGTTCGACGCGCTGCCCCGGGCGGACGG
CTTCCCGTTCCTCGCCCTGGACCTCGGCGACTGGGACGCCCCGCGGGTGAAGATCTACC
TCAAACACCTCGGCATGTCCGCCGCCGACGCGGGCTCCCTCCCCCGGATGTCGCCCGCA
CCGAGCCGGGAGCAGCTGGAGGAGTTCTTCCGCACCGCCGGTGACCTCCCGGCCCCGGG
AGACCCGGGGCCCACCGAGGACACCGGCCGGCTCGCCGGGCGCCCCGCCCTCACCTGCC
ACTCCTTCACGGAGACGGCGACCGGGCGGCCCAGCGGCTACACCCTCCACGTGCCGGTC
CGCGACTACGTCCGGCACGACGGCGAGGCACGGGACCGGGCGGTGGCCGTGCTGCGCGA
ACATGACATGGACAGTGCGGCACTGGACCGGGCGCTGGCCGCCGTGAGCCCCCGCCCGC
TGAGTGACGGGGTGGGCCTGATCGCCTATCTGGCACTGGTCCACCAGCGCGGCCGGCCG
ACACGGGTGACCGTCTACGTCTCCTCCGAGGCGTACGAGGTGCGGCCGCCCCGCGAGAC
GGTCCCCACCCGCGACCGGGCGCGGGCACGGCTGTGA

SEQ.ID NO: 24
MGGPMSGFHSGEALLGDLATGQLTRLCEVAGLTEADTAAYTGVLIESLG
TSAGRPLSLPPPSRTFLSDDHTPVEFSLAFLPGRAPHLRVLVEPGCSSGDDLAENGRAG
LRAVHTMADRWGFSTEQLDRLEDLFFPSSPEGPLALWCALELRSGGVPGVKVYLNPAAN
GADRAAETVREALARLGHLQAFDALPRADGFPPFLALDLGDWDAPRVKIYLKHLGMSAAD
AGSLPRMSPAPSREQLEEFFRTAGDLPAPGDPGPTEDTGRLAGRPALTCHSFTETATGR
PSGYTLHVPVRDYVRHDGEARDRAVAVLREHDMDSAALDRALAAVSPRPLSDGVGLIAY
LALVHQRGRPTRVTVYVSSEAYEVRPPRETVPTRDRARARL

SEQ.ID NO: 25
ATGTCTGAAAATTTGCAATTGTCAGCTGAAGAAATGAGACAATTGGGTTACCAAGCAGT
TGATTTGATCATCGATCACATGAACCATTTGAAGTCTAAGCCAGTTTCAGAAACAATCG
ATTCTGATATCTTGAGAAATAAGTTGACTGAATCTATCCCAGAAAATGGTTCAGATCCA
AAGGAATTGTTGCATTTCTTGAACAGAAACGTTTTTAATCAAATTACACATGTTGATCA
TCCACATTTCTTGGCTTTTGTTCCAGGTCCAAATAATTACGTTGGTGTTGTTGCAGATT
TCTTGGCTTCTGGTTTTAATGTTTTTCCAACTGCATGGATTGCTGGTGCAGGTGCTGAA
CAAATCGAATTGACTACAATTAATTGGTTGAAATCTATGTTGGGTTTTCCAGATTCAGC
TGAAGGTTTATTTGTTTCTGGTGGTTCAATGGCAAATTTGACAGCTTTGACTGTTGCAA
GACAGGCTAAGTTGAACAACGATATCGAAAATGCTGTTGTTTACTTCTCTGATCAAACA
CATTTCTCAGTTGATAGAGCATTGAAGGTTTTAGGTTTTAAACATCATCAAATCTGTAG
AATCGAAACAGATGAACATTTGAGAATCTCTGTTTCAGCTTTGAAGAAACAAATTAAAG
AAGATAGAACTAAGGGTAAAAAGCCATTCTGTGTTATTGCAAATGCTGGTACTACAAAT
TGTGGTGCTGTTGATTCTTTGAACGAATTAGCAGATTTGTGTAACGATGAAGATGTTTG
GTTGCATGCTGATGGTTCTTATGGTGCTCCAGCTATCTTGTCTGAAAAGGGTTCAGCTA
TGTTGCAAGGTATTCATAGAGCAGATTCTTTGACTTTAGATCCACATAAGTGGTTGTTC
CAACCATACGATGTTGGTTGTGTTTTGATCAGAAACTCTCAATATTTGTCAAAGACTTT
TAGAATGATGCCAGAATACATCAAGGATTCAGAAACTAACGTTGAAGGTGAAATTAATT
TCGGTGAATGTGGTATCGAATTGTCAAGAAGATTCAGAGCTTTGAAGGTTTGGTTGTCT
TTTAAAGTTTTCGGTGTTGCTGCTTTTAGACAAGCAATCGATCATGGTATCATGTTAGC
AGAACAAGTTGAAGCATTTTTGGGTAAAGCAAAAGATTGGGAAGTTGTTACACCAGCTC
AATTGGGTATCGTTACTTTTAGATACATTCCATCTGAATTGGCATCAACAGATACTATT
AATGAAATTAATAAGAAATTGGTTAAGGAAATCACACATAGAGGTTTCGCTATGTTATC
TACTACAGAATTGAAGGAAAAGGTTGTTATTAGATTGTGTTCAATTAATCCAAGAACTA
CAACTGAAGAAATGTTGCAAATCATGATGAAGATTAAAGCATTGGCTGAAGAAGTTTCT
ATTTCATACCCATGTGTTGCTGAACATCATCATCATCATCATTAA

SEQ.ID NO: 26
MSENLQLSAEEMRQLGYQAVDLIIDHMNHLKSKPVSETIDSDILRNKLTESIPENGSDP
KELLHFLNRNVFNQITHVDHPHFLAFVPGPNNYVGVVADFLASGFNVFPTAWIAGAGAE
QIELTTINWLKSMLGFPDSAEGLFVSGGSMANLTALTVARQAKLNNDIENAVVYFSDQT
HFSVDRALKVLGFKHHQICRIETDEHLRISVSALKKQIKEDRTKGKKPFCVIANAGTTN
CGAVDSLNELADLCNDEDVWLHADGSYGAPAILSEKGSAMLQGIHRADSLTLDPHKWLF
QPYDVGCVLIRNSQYLSKTFRMMPEYIKDSETNVEGEINFGECGIELSRRFRALKVWLS
FKVFGVAAFRQAIDHGIMLAEQVEAFLGKAKDWEVVTPAQLGIVTFRYIPSELASTDTI
NEINKKLVKEITHRGFAMLSTTELKEKVVIRLCSINPRTTTEEMLQIMMKIKALAEEVS
ISYPCVAEHHHHHH

SEQ.ID NO: 27
ATGAACACCTTCAGAACAGCCACTGCCAGAGACATACCTGATGTAGCAGCAACTCTTAC
GGAAGCCTTCGCAACTGATCCACCCACGCAGTGGGTGTTCCCCGACGGTACTGCCGCCG
TCAGCAGGTTCTTTACACATGTTGCAGATAGGGTTCACACGGCCGGTGGTATTGTTGAG
CTACTACCAGACAGAGCCGCCATGATTGCATTGCCACCACACGTGAGGCTGCCAGGAGA
AGCTGCCGACGAAGGCAGGCGGAAATTCAGAGAAGGCTGGCAGACAGGCACCCGCTGA
CACCTCACTACTACCTGCTGTTTTACGGAGTTAGAACGGCACACCAGGGTTCGGGATTG

-continued

SEQUENCE LISTING

```
GGCGGAAGAATGCTGGCCAGATTAACTAGCAGAGCTGATAGGGACAGGGTGGGTACATA
TACTGAGGCATCCACCTGGCGTGGCGCTAGACTGATGCTGAGACATGGATTCCATGCTA
CAAGGCCACTAAGATTGCCAGATGGACCCAGCATGTTTCCACTTTGGAGAGATCCAATC
CATGATCATTCTGATCTCGAGCACCACCACCACCACCACTGA

SEQ.ID NO: 28
MNTFRTATARDIPDVAATLTEAFATDPPTQWVFPDGTAAVSRFFTHVADRVHTAGGIVE
LLPDRAAMIALPPHVRLPGEAADGRQAEIQRRLADRHPLTPHYYLLFYGVRTAHQSGSL
GGRMLARLTSRADRDRVGTYTEASTWRGARLMLRHGFHATRPLRLPDGPSMFPLWRDPI
HDHSD

SEQ.ID NO: 29
ATGACACACACGCTGCCGGCCTCAACCTCGACCAGTACCAGCACTCCGGCAACGGCAGC
AGCTGCTGCGGGCAAAGCATCGGGTTACCTGGCACCGGCGGCAATTCCAGCTAGCCTGC
AGTTACTGCCGCCCCCACCAGCGGAAGGCTCACCGGGACAAGCTTTAGACCTGGCGGTA
AATCGTGAGGCGCTGGCGATGCGCGGCTCTGCTCGCTGGCAACAAGCAACACGTGACGC
CGACTTAAGCTTCCCGGCAGGTGCCGGTCATTTCGCTTGCGCGCTTGGTGTGGCAATTG
ACGCCCAACGTACTCCTCACTTATACGCTTTACTTGAACGTTCACGCATTGACGCTTCG
GCAGCGACTAAGGCCGCAAAGAATCATTACCGCCGTCCACGCCCTTTCATGCTGAACCA
ACAACCGAGCTGCACCCCTCAGGACGAAGAACAATTACGCCATAACGGTTCATATCCCT
CGGGGCATTCGGCTATTGGTTGGACATGGGCTCTTATTCTTAGCGAGATCGCGCCAGAC
CGTGCAGATGCCTTGATTTTACGTGGGCGTAGTTTCAGTGAGTCGCGCCTGGTGTGCAA
TGTTCATTGGCACAGCGATGTGTTAGCGGGCCGCCTGATGGGCGCGGCGACAGTTGCCC
GTCTGCACGCGGATCCTACCTTTCGTGCCGATTTGGATGCAGCCCGTGGGGAAATTGCA
CGTGCGCAGGCCCAGGGCGCGATGCCTGGAGAGGACTGCGCTGCGCAAGCACAGACGCT
CCAAGTCCGTCCAGCGAGTGCATTATAA

SEQ.ID NO: 30
MTHTLPASTSTSTSTPATAAAAAGKASGYLAPAAIPASLQLLPPPPAEGSPGQALDLAV
NREALAMRGSARWQQATRDADLSFPAGAGHFACALGVAIDAQRTPHLYALLERSRIDAS
AATKAAKNHYRRPRPFMLNQQPSCTPQDEEQLRHNGSYPSGHSAIGWTWALILSEIAPD
RADALILRGRSFSESRLVCNVHWHSDVLAGRLMGAATVARLHADPTFRADLDAARGEIA
RAQAQGAMPGEDCAAQAQTLQVRPASAL

SEQ.ID NO: 31
ATGGATAATAACAACATCACAATTTTGAAGATTGGTGGAAGCGTGATCACCGATAAGTC
TGCCGATGACGGCACCGCTAGACTCTCGGAGATAGAAAGAATCGCAGCTGAAATCTCCG
GTTTTGAGGGCAAACTTATCATCGTTCATGGTGCCGGTTCTTTCGGACACCCTCAAGTT
AAAAGATTCGGCCTGACCGGGAAATTTGACCACGAGGGCAGCATCATCACACACATGTC
TGTGCGAAAATTGAACACTATGGTGGTGGAAACTTTAAACAGTGCTGGTATCAATGCTT
TACCAGTCCACCCTATGGCGTGCGCTATTTCAAGTAATTCACGCATTAAGAGTATGTTT
CGGGAGCAAATAGAGGAAATGTTAGCCAATGGATTTGTTCCGGTATTACACGGCGACAT
GGTTATGGATACTGACCTTGGGACGTCTGTACTTAGCGGCGACCAGATCGTGCCGTACC
TGGCAATACAAATGAAAGCCTCAAGAATCGGTATCGGCAGTGCCGAGGAAGGAGTTCTG
GATGATAAGGGCGGTGTTATCCCTCTGATAAATAACGAGAACTTCGATGAGATTAAGGC
TTATCTGTCCGGTTCCGCAAACACTGATGTTACGGGTGGGATGTTAGGGAAAGTTTTAG
AATTATTGGAGTTGAGCGAGCAAAGTAACAGTACCTCATACATATTTAATGCTGGTAAC
ACCGGTAACATTAGTGATTTCCTTTCCGGCAAGAATATCGGGACCGCTATTGGCGCCGG
CACGATATAA

SEQ.ID NO: 32
MDNNNITILKIGGSVITDKSADDGTARLSEIERIAAEISGFEGKLIIVHGAGSFGHPQV
KRFGLTGKFDHEGSIITHMSVRKLNTMVVETLNSAGINALPVHPMACAISSNSRIKSMF
REQIEEMLANGFVPVLHGDMVMDTDLGTSVLSGDQIVPYLAIQMKASRIGIGSAEEGVL
DDKGGVIPLINNENFDEIKAYLSGSANTDVTGGMLGKVLELLELSEQSNSTSYIFNAGN
TGNISDFLSGKNIGTAIGAGTI
```

EXAMPLES

Example 1

Synthesis of a First, Second, and Third Example Prenylated Psilocybin Derivative Referring to FIG. 13A, shown therein is a schematic diagram, illustrating three steps used in the synthesis of a first, second and third prenylated psilocybin derivative having chemical formula (IV):

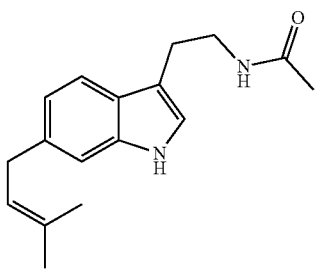

(IV)

Referring further to FIG. 13A, Step 1 was conducted in vitro using biocatalytic conversion. Three recombinant enzymes, the prenyl transferase PriB (SEQ.ID NO: 24), in addition to PhoNxt (SEQ.ID NO: 30), and IPKmt (SEQ.ID NO: 32) were individually expressed in *E. coli* using the following plasmids, respectively: pET26b(+)-PriB, pET28a(+)-IPKmt, and pET21(+)-PhoNxt. Prenyl transferase PriB (SEQ.ID NO: 24) catalyzes the stereospecific 6-prenylation of tryptophan with dimethylallyl pyrophosphate (DMAPP) as the prenyl-donor. A cDNA encoding PriB enzyme (SEQ.ID NO: 23) was synthesized and cloned into pET26b(+) vector by service provider GenScript (www.genscript.com) in-frame with a vector-encoded, N-terminal HIS epitope tag. PhoNxt (SEQ.ID NO: 30) is a non-specific acid phosphatase, while IPKmt (SEQ.ID NO: 32) is an isopentenyl phosphate kinase. Together, these two enzymes can use dimethylallyl alcohol (DMAOH) (www.sigmaaldrich.com) as the starting substrate to produce DMAPP, which in turn is a required co-substrate for PriB. cDNAs encoding IPkmt (SEQ.ID NO: 31) and PhoNxt (SEQ.ID NO: 29) were synthesized and cloned into *E.coli* expression vectors pET28a(+) and pET21(+), respectively using the Clonal Genes service of Twist Bioscience. Specifically, IPKmt was cloned between the NdeI and XhoI sites of pET28a(+) thus enabling an in-frame, N-terminal HIS tag in the corresponding protein. PhoNxt was cloned between the BamHI and XhoI sites of pET21(+) thus enabling an in-frame, C-terminal HIS tag in the corresponding protein. Each *E.coli* expression construct was transformed into Rosetta (DE3) competent *E.coli* cells. Transformed Rosetta (DE3) *E.coli* cells were grown in LB media at 30° C. for overnight and then transferred into TB (terrific broth) media to grow at 37° C. until optical density ($OD_{600}$) reached 0.6-1.5. The cell culture was then transferred to a 16° C. incubator with the addition of IPTG at 0.2 mM to initiate recombinant protein expression. After 20 hours the cells were harvested by centrifugation at 5,000×g for 6 minutes and the cell pellet was stored in −80° C. before protein extraction. For extraction and purification of PriB, PhoNxt, and IPKmt recombinant proteins respectively, E.coli cells were resuspended in a buffer containing 50 mM sodium phosphate (pH 7.0) and 300 mM NaCl and then sonicated for 5-10 minutes to break the cells. The cell lysate was centrifuged at 12,000 g for 30 minutes to collect the supernatant containing soluble crude protein. The supernatant was applied to cobalt resin (TALON Superflow™, Cytiva) to isolate HIS-tagged target protein. Purified protein was stored at −80° C. in a buffer containing 50 mM Tris-HCl (pH 7.0), 100 mM NaCl, and 10% glycerol. A one-pot biocatalysis system containing PriB, PhoNxt and IPKmt was devised, using tryptophan (www.sigmaaldrich.com) and DMAOH as substrates for the production of 6-dimethylallyl-tryptophan. This one-pot biocatalysis system contained the following ingredients: 25 mM Tris-HCl (pH 8.0), 2.5 mM $MgCl_2$, 50 mM DMAOH, 50 mM ATP (pH 6.5), 5 mM tryptophan, 62 pg/mL of PhoNxt, 200 μg/mL of IPKmt, and 392 μg/mL of PriB. The reaction, normally comprising 5 mL total volume, was carried out at 30° C. for 20 hours. In a typical 5 mL-reaction, tryptophan would be completely converted to 6-dimethylallyl-tryptophan (a first prenylated psilocybin derivative compound having chemical formula (XI)) as examined by routine LC-MS procedures. Thus, in each 5 mL-reaction, 5.7 mg of 6-dimethylallyl-tryptophan could be made, representing a production titer of 1.1 g/L. Multiple 5 mL reactions were conducted to achieve sufficient product for the next step.

Continuing to refer to FIG. 13A, Step 2 was conducted in vitro using biocatalytic conversion. In this case, the interim product 6-dimethylallyl-tryptophan from the first step was decarboxylated to 6-dimethylallyl-tryptamine by the addition of recombinant BaTDC (tryptophan decarboxylase) enzyme (SEQ.ID NO: 26) to the previous one-pot assay mixture. A cDNA encoding BaTDC enzyme was synthesized (SEQ.ID NO: 25) and cloned into pET26b(+) vector by service provider GenScript (www.genscript.com) in-frame with a vector-encoded, N-terminal HIS epitope tag. E. coli transformation of resulting pET26b(+)-BaTDC vector, recombinant protein production, and purification was carried out in the same manner as described for enzymes of the first step. Because 6-dimethylallyl-tryptophan is not soluble at a concentration of 1.1 g/L, the previous 5 mL reaction was first diluted to 40 mL and then adjusted to pH 6 to increase the solubility of 6-dimethylallyl-tryptophan. Five milligrams of BaTDC protein were then added to the diluted reaction to enable decarboxylation, wherein 80-100% of the 6-dimethylallyl-tryptophan was converted to 6-dimethylallyl-tryptamine ((a second example prenylated psilocybin derivative compound having chemical formula (XII)).

Continuing to refer to FIG. 13A, Step 3 was conducted in vivo using an *E. coli* culture expressing recombinant PsmF enzyme (SEQ.ID NO: 28). PsmF is a promiscuous tryptamine N-acetyltransferase. cDNA encoding PsmF (SEQ.ID NO: 27) was synthesized and cloned into *E.coli* expression vector pET28a(+) using the Clonal Genes service of Twist Bioscience. Specifically, the gene was cloned between the NdeI and XhoI sites of pET28a(+) thus enabling an in-frame, N-terminal HIS tag in the corresponding protein. *E. coli* transformation of resulting pET28a(+)-PsmF vector, recombinant protein production, and purification was carried out in the same manner as described for enzymes of the first step. The whole reaction mixture from step 2 (containing 6-dimethylallyl-tryptamine) was then added to 100 mL of *E.coli* culture expressing PsmF. The culture was incubated at 30° C. for overnight to complete the N-acetylation of 6-dimethylallyl-tryptamine to the final product of 6-dimethylallyl, N-acetyl-tryptamine. The culture was centrifuged at 5000 g for 10 minutes. The cell pellet was washed in 20× volume acidic water (HCl, pH 5.0) three times. The supernatants were combined and saved at −80° C. until further purification. Approximately 200 mL of combined supernatant was then extracted by ethyl acetate (4×150 ml). The organic layer was washed with brine and dried over $Na_2SO_4$, followed by concentration under reduced pressure. The residue was purified by flash chromatography on silica gel (1% methanol in dichloromethane), to afford the compound as an off white solid (8 mg). The product was determined to be 95% pure. $^1H$ NMR (400 MHz, $CDCl_3$): δ=1.78 (s, 6H), 1.93 (s, 3H), 2.97 (t, J=6.7 Hz, 2H), 3.47 (d, J=7.4 Hz, 2H), 3.61 (dt, 7.6, 6.1 Hz, 2H), 5.41 (m, 1H), 5.61 (br. s, 1H), 6.97 (m, 2H), 7.19 (br. s, 1H), 7.55 (d, 8.0 Hz, 1H), 8.24 (br. s, 1H). $^{13}C$ NMR (100 MHz, $CD_3Cl_3$): δ=17.8, 23.3, 25.3, 25.8, 34.5, 39.79, 110.5, 112.7, 118.5, 120.5, 121.6, 123.9, 125.5, 123.1, 136.2, 136.9, 170.1, HRMS (ESI) m/z: calcd. for $C_{17}H_{22}N_2O$ $[M+H]^+$ 271.1805, found 271.1803. It is noted that this product corresponds with a third example prenylated psilocybin derivative compound having chemical formula (IV), noted above.

Figure 14A:
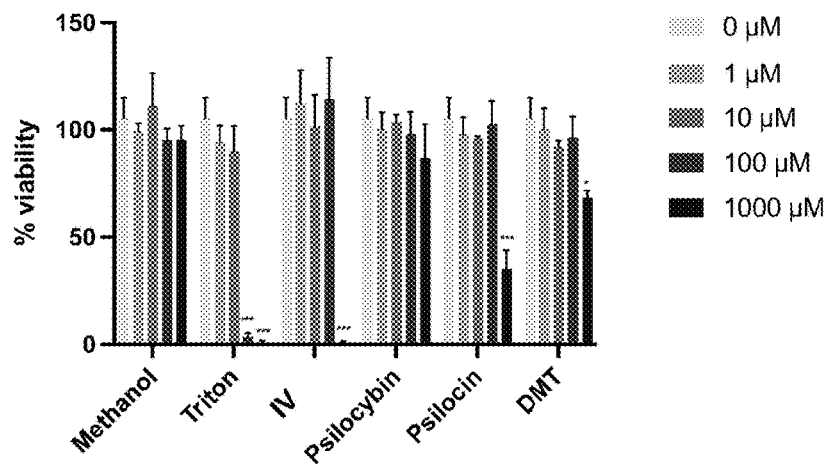
FIGS. 14A, 14B, 14C, 14D, 14E, 14F, 14G, 14H, 14I, 14J, 14K, 14L, 14M, 14N, and 14O depict various graphs, obtained in the performance of experimental assays to evaluate the efficacy of an example prenylated psilocybin derivative having the chemical formula (IV) set forth herein, notably a cell viability assay for an aminated psilocybin derivative having the chemical formulae (IV) (FIG. 14A); a saturation binding assay for [$^3$H]ketanserin at the 5-HT$_{2A}$ receptor (FIG. 14B); a competition assay for psilocin as a positive control (binding) (FIG. 14C); a competition assay for tryptophan as a negative control (no binding) (FIG. 14D); a competition assay for a prenylated psilocybin derivative compound with formula (IV), designated "IV" (FIGS. 14E; 14F, plotted with two different Y-axes, for clarity); a luminescence assay in +5HT$_{1A}$ and −5HT$_{1A}$ cell cultures at various forskolin concentrations (FIG. 14G); a luminescence assay in +5HT$_{1A}$ and −5HT$_{1A}$ cell cultures in the presence of constant (4 μM) forskolin but with decreasing serotonin concentration (FIG. 14H); another luminescence assay in +5HT$_{1A}$ and −5HT$_{1A}$ cell cultures in the presence of constant (4 μM) forskolin but with decreasing serotonin concentration (FIG. 14I); a luminescence assay in +5HT$_{1A}$ cell cultures in the presence of constant (4 μM) forskolin but with decreasing DMT concentration (FIG. 14J); another luminescence assay in +5HT$_{1A}$ cell cultures in the presence of constant (4 μM) forskolin but with decreasing DMT concentration (FIG. 14K); a cAMP assay in the presence of constant (4 μM) forskolin but with increasing concentration of prenylated psilocybin compound having formula (IV), designated "IV" in +5HT$_{1A}$ cells and −5HT$_{1A}$ cells (FIG. 14L); a luminescence assay in the presence of constant (4 μM) forskolin and 10 μM serotonin, but with decreasing concentration of prenylated psilocybin compound having formula (IV), designated "IV" in +5HT$_{1A}$ cells and −5HT$_{1A}$ cells (FIG. 14M); a cAMP assay in the presence of constant (4 μM) forskolin and 10 μM serotonin, but with decreasing concentration of prenylated psilocybin compound having formula (IV), designated "IV" in +5HT$_{1A}$ cells and −5HT$_{1A}$ cells (FIG. 14N); and mass spectrometry data in the form of a chromatogram, notably a chromatogram obtained in the performance of an experiment to synthesize an example prenylated psilocybin derivative compound having the chemical formula (IV) set forth herein (FIG. 14O).
Figure 14B:
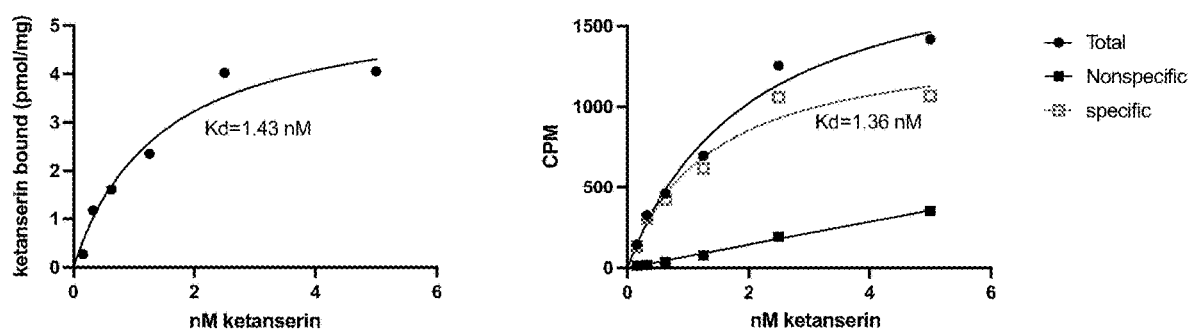
Figure 14C:
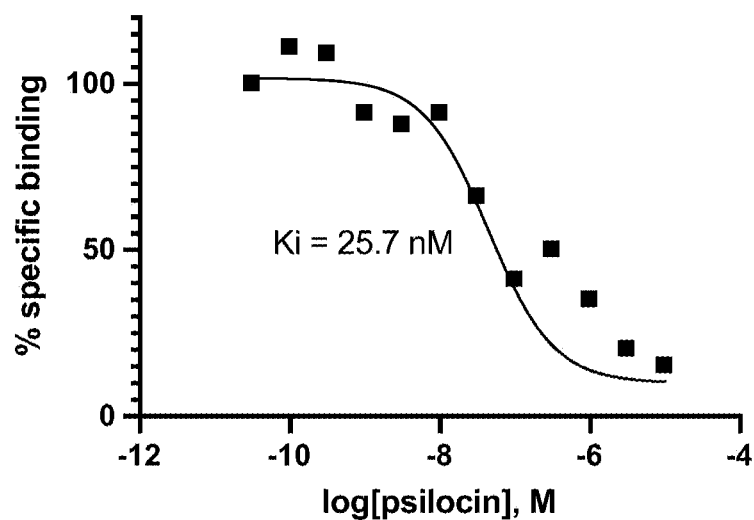

As part of routine procedure, further analysis was carried out using high-resolution LC-HESI-LTQ-Orbitrap-XL MS (Thermo Fisher Scientific), employing a modified version of a method described previously (Chang et al., 2015, Plant Physiol. 169: 1127-1140), with the exception that liquid chromatography was carried out using an UltiMate 3000 HPLC (Thermo Fisher Scientific) equipped with a Poroshell 120 SB-$C_{18}$ column (Agilent Technologies) instead of an Accela HPLC system (Thermo Fisher Scientific) equipped with a Zorbax C18 column (Agilent Technologies). Briefly, 100 microliters of culture media were dried and resuspended in 100 microliters of DMSO. One tenth (10 microliters) of this suspension was injected at a flow rate of 0.5 mL/min and a gradient of solvent A (water with 0.1% of formic acid) and solvent B (ACN with 0.1% formic acid) as follows: 100% to 0% (v/v) solvent A over 5 min; isocratic at 0% (v/v) for 1 min; 0% to 100% (v/v) over 0.1 min; and isocratic at 100% (v/v) for 1.9 min. Total run time was 8 minutes. Heated ESI source and interface conditions were operated in positive ion mode as follows: vaporizer temperature, 400° C., source voltage, 3 kV; sheath gas, 60 au, auxiliary gas, 20 au; capillary temperature, 380° C.; capillary voltage, 6 V; tube lens, 45 V. Instrumentation was performed as a single, HR scan event using Orbitrap detection of m/z in the range of 100-500 m/z. Ion injection time was 300 ms with scan time of 1 s. External and internal calibration procedures ensured <2 ppm error to facilitate elemental formulae predictions. Singly protonated product with exact m/z and expected elemental formula matching the singly protonated form of N-(2-(6-[3-methyl-1-butenyl]-1H-indol-3-yl)ethyl)acetamide having chemical formula (IV) eluted at 3.8 minutes (EIC, see: FIG. 14O).

Assessment of Cell Viability Upon Treatment of Prenylated Psilocybin Derivative

To establish suitable ligand concentrations for competitive binding assays, PrestoBlue assays were first performed. The PrestoBlue assay measures cell metabolic activity based on tetrazolium salt formation, and is a preferred method for routine cell viability assays (Terrasso et al., 2017, J Pharmacol Toxicol Methods 83: 72). Results of these assays were conducted using both control ligands (e.g., psilocybin, psilocin, DMT) and novel derivative, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Drug-induced changes in cell health within simple in vitro systems such as the HepG2 cell line are commonly adopted as first-line screening approaches in the pharmaceutical industry (Weaver et al., 2017, Expert Opin Drug Metab Toxicol 13: 767). HepG2 is a human hepatoma that is most commonly used in drug metabolism and hepatotoxicity studies (Donato et al., 2015, Methods Mol Biol 1250: 77). Herein, HepG2 cells were cultured using standard procedures using the manufacture's protocols (ATCC, HB-8065). Briefly, cells were cultured in Eagle's minimum essential medium supplemented with 10% fetal bovine serum and grown at 37° C. in the presence of 5% $CO_2$. To test the various compounds with the cell line, cells were seeded in a clear 96-well culture plate at 20,000 cells per well. After allowing cells to attach and grow for 24 hours, compounds were added at 1 μM, 10 μM, 100 μM, and 1 mM. Methanol was used as vehicle, at concentrations 0.001, 0.01, 0.1, and 1%. As a positive control for toxicity, TritonX concentrations used were 0.0001, 0.001, 0.01 and 0.1%. Cells were incubated with compounds for 48 hours before accessing cell viability with the PrestoBlue assay following the manufacture's protocol (ThermoFisher Scientific, P50200). PrestoBlue reagent was added to cells and allowed to incubate for 1 hour before reading. Absorbance readings were performed at 570 nm with the reference at 600 nm on a SpectraMax iD3 plate reader. Non-treated cells were assigned 100% viability. Bar graphs show the mean+/−SD, n=3. Significance was determined by 2-way ANOVA followed by Dunnett's multiple comparison test and is indicated by *($P<0.0001$), ($P<0.001$), *($P<0.005$). Data acquired for the derivative having chemical formula (IV) is displayed as "IV" on the x-axis of FIG. 14A.

Radioligand Receptor Binding Assays.

Evaluation of drug binding is an essential step to characterization of all drug-target interactions (Fang 2012, Exp Opin Drug Discov 7:969). The binding affinity of a drug to a target is traditionally viewed as an acceptable surrogate of its in vivo efficacy (Núñez et al., 2012, Drug Disc Today 17: 10). Competition assays, also called displacement or modulation binding assays, are a common approach to measure activity of a ligand at a target receptor (Flanagan 2016, Methods Cell Biol 132: 191). In these assays, standard radioligands acting either as agonists or antagonists are ascribed to specific receptors. In the case of G protein-coupled receptor 5-$HT_{2A}$, [$^3$H]ketanserin is a well-established antagonist used routinely in competition assays to evaluate competitive activity of novel drug candidates at the 5-$HT_{2A}$ receptor (Maguire et al., 2012, Methods Mol Biol 897: 31). Thus, to evaluate activity of novel psilocybin derivatives at the 5-$HT_{2A}$ receptor, competition assays using [$^3$H]ketanserin were employed as follows. SPA beads (RPNQ0010), [$^3$H] ketanserin (NET1233025UC), membranes containing 5-$HT_{2A}$ (ES-313-M400UA), and isoplate-96 microplate (6005040) were all purchased from PerkinElmer. Radioactive binding assays were carried out using Scintillation Proximity Assay (SPA). For saturation binding assays, mixtures of 10 ug of membrane containing 5-$HT_{2A}$ receptor was pre-coupled to 1 mg of SPA beads at room temperature in a tube rotator for 1 hour in binding buffer (50 mM Tris-HCl pH7.4, 4 mM $CaCl_2$, 1 mM ascorbic acid, 10 μM pargyline HCl). After pre-coupling, the beads and membrane were aliquoted in an isoplate-96 microplate with increasing amounts of [$^3$H]ketanserin (0.1525 nM to 5 nM) and incubated for two hours at room temperature in the dark with shaking. After incubation, the samples were read on a MicroBeta 2 Microplate Counter (Perkin Elmer). Determination of non-specific binding was carried out in the presence of 20 μM of spiperone (S7395-250MG, Sigma). Equilibrium binding constants for ketanserin ($K_d$) were determined from saturation binding curves using the 'one-site saturation binding analysis' method of GraphPad PRISM software (Version 9.2.0). Competition binding assays were performed using fixed (1 nM) [$^3$H]ketanserin and different concentrations of tryptophan (3 nM to 1 mM), psilocin (30 pM to 10 μM) or unlabeled test compound (3 nM to 1 mM) similar to the saturation binding assay. $K_i$ values were calculated from the competition displacement data using the competitive binding analysis from GraphPad PRISM software. Tryptophan was included as a negative control as it has no activity at the 5-$HT_{2A}$ receptor. In contrast, psilocin was used as a positive control since it has established binding activity at the 5-$HT_{2A}$ receptor (Kim et al., 2020, Cell 182: 1574). FIG. 14B depicts the saturation binding curves for [$^3$H]ketanserin at the 5-$HT_{2A}$ receptor. The panel on the left hand shows the specific saturation ligand binding of [$^3$H]ketanserin (from 0.1525 nM to 5 nM) to membranes containing 5-$HT_{2A}$ receptor, which was obtained after subtracting non-specific binding values (shown in the panel on the right hand). Specific binding in counts per minute (cpm) was calculated by subtracting non-specific binding from total binding. Specific binding (pmol/mg) was calculated from pmol of [$^3$H]ketanserin bound per mg of protein in the assay. The $K_d$ was calculated by fitting the data with the one-site binding model of PRISM software (version 9.2.0). FIG. 14C shows the competition binding curve for psilocin as a positive control (binding).

Figure 14D:
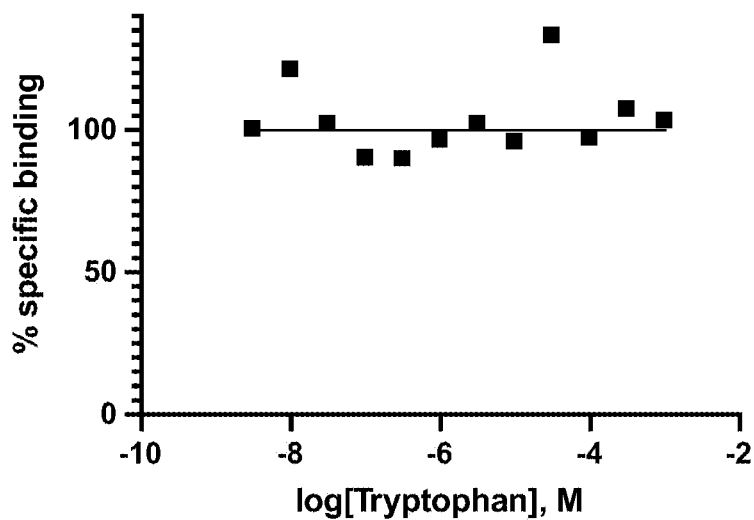
Figure 14E:
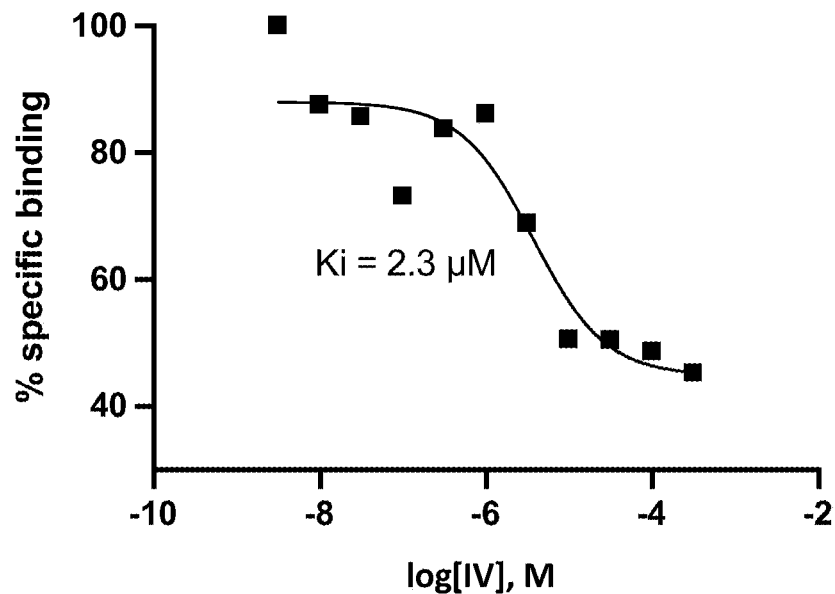
Figure 14F:
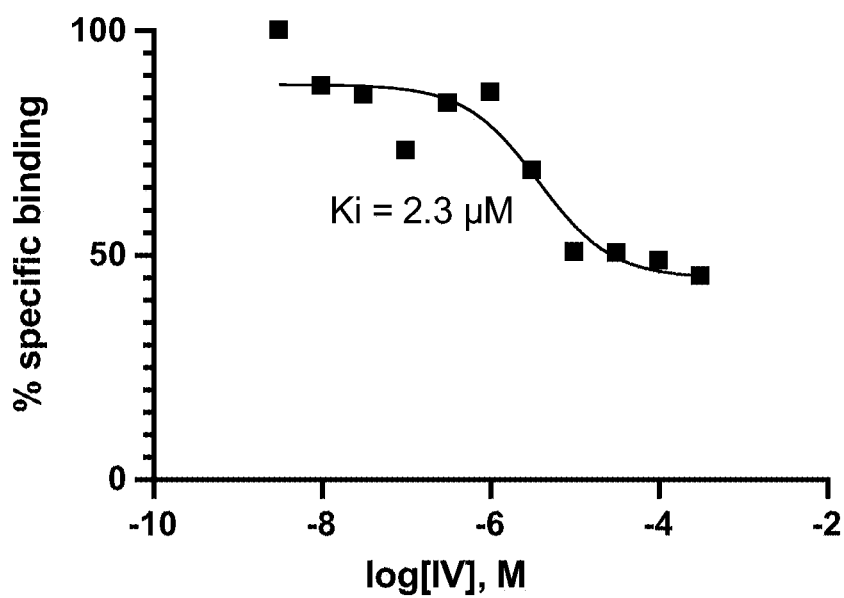

FIG. 14D shows the competition binding curve for tryptophan as a negative control (no binding). FIGS. 14E, 14F show competition binding curve for compound with formula (IV), designated "IV" in the figure. Notably, competition of compound (IV) for 5-$HT_{2A}$ sites occupied by [$^3$H]ketanserin does not appear complete, as suggested by only ~50% specific binding (refer to data of FIG. 14E, which replots data of FIG. 14F with a reformatted y-axis for clarity). It is known that ketanserin binds both primary sites normally occupied by agonist (e.g. serotonin) in addition to other sites of 5-$HT_{2A}$ (Sleight et al., 1996, Biochem Pharmacol 51: 71); thus, incomplete competition by compound (IV) implies this derivative competes for a particular subset (i.e., fraction) of the total sites bound by ketanserin.

Cell Lines and Control Ligands Used to Assess Activity at 5-HT1A.

CHO-K1/G$\alpha_{15}$ (GenScript, M00257) (−5-$HT_{1A}$) and CHO-K1/5-$HT_{1A}$/G$\alpha_{15}$ (GenScript, M00330) (+5-$HT_{1A}$) cells lines were used. Briefly, CHO-K1/G$\alpha_{15}$ is a control cell line that constitutively expresses G$\alpha_{15}$ which is a promiscuous $G_q$ protein. This control cell line lacks any transgene encoding 5-$HT_{1A}$ receptors, but still responds to forskolin; thus, cAMP response to forskolin should be the same regardless of whether or not 5-$HT_{1A}$ agonists are present. Conversely, CHO-K1/5-$HT_{1A}$/G$\alpha_{15}$ cells stably express 5-$HT_{1A}$ receptor in the CHO-K1 host background. Notably, G$\alpha_{15}$ is a promiscuous G protein known to induce calcium flux response, present in both control and 5-$HT_{1A}$ cell lines. In+5-$HT_{1A}$ cells, G$\alpha_{15}$ may be recruited in place of $G_{\alpha i/o}$, which could theoretically dampen cAMP response (Rojas and Fiedler 2016, Front Cell Neurosci 10: 272). Thus, we included two known 5-$HT_{1A}$ agonists, DMT (Cameron and Olson 2018, ACS Chem Neurosci 9: 2344) and serotonin (Rojas and Fiedler 2016, Front Cell Neurosci 10: 272) as positive controls to ensure sufficient cAMP response was observed, thereby indicating measurable recruitment of $G_{\alpha i/o}$ protein to activated 5-$HT_{1A}$ receptors. Cells were maintained in complete growth media as recommended by supplier (GenScript) which is constituted as follows: Ham's F12 Nutrient mix (HAM's F12, GIBCO #11765-047) with 10% fetal bovine serum (FBS) (Thermo Scientific #12483020), 200 µg/ml zeocin (Thermo Scientific #R25005) and/or 100 µg/ml hygromycin (Thermo Scientific #10687010). The cells were cultured in a humidified incubator with 37° C. and 5% $CO_2$. Cells maintenance was carried out as recommended by the cell supplier. Briefly, vials with cells were removed from the liquid nitrogen and thawed quickly in 37° C. water bath. Just before the cells were completely thawed the vial's outside was decontaminated by 70% ethanol spray. The cell suspension was then retrieved from the vial and added to warm (37° C.) complete growth media, and centrifuged at 1,000 rpm for 5 minutes. The supernatant was discarded, and the cell pellet was then resuspended in another 10 ml of complete growth media, and added to the 10 cm cell culture dish (Greiner Bio-One #664160). The media was changed every third day until the cells were about 90% confluent. The ~90% confluent cells were then split 10:1 for maintenance or used for experiment.

Evaluation of 5-HT1A Receptor Modulation

Figure 14G:
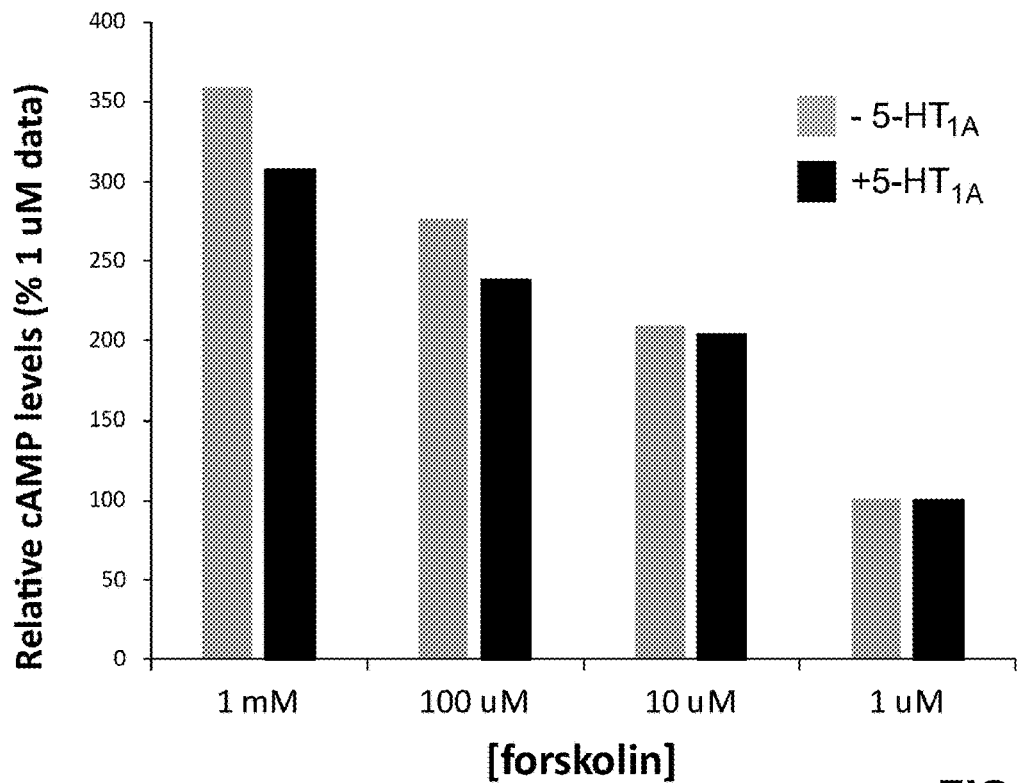
Figure 14H:
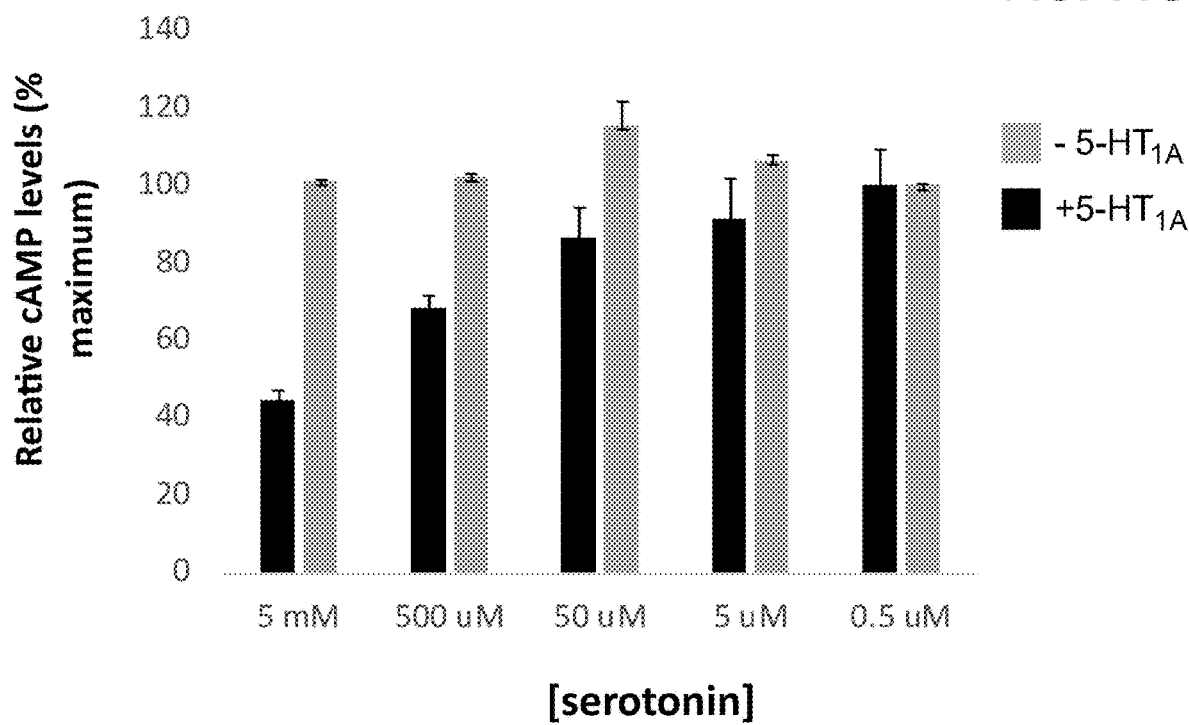
Figure 14I:
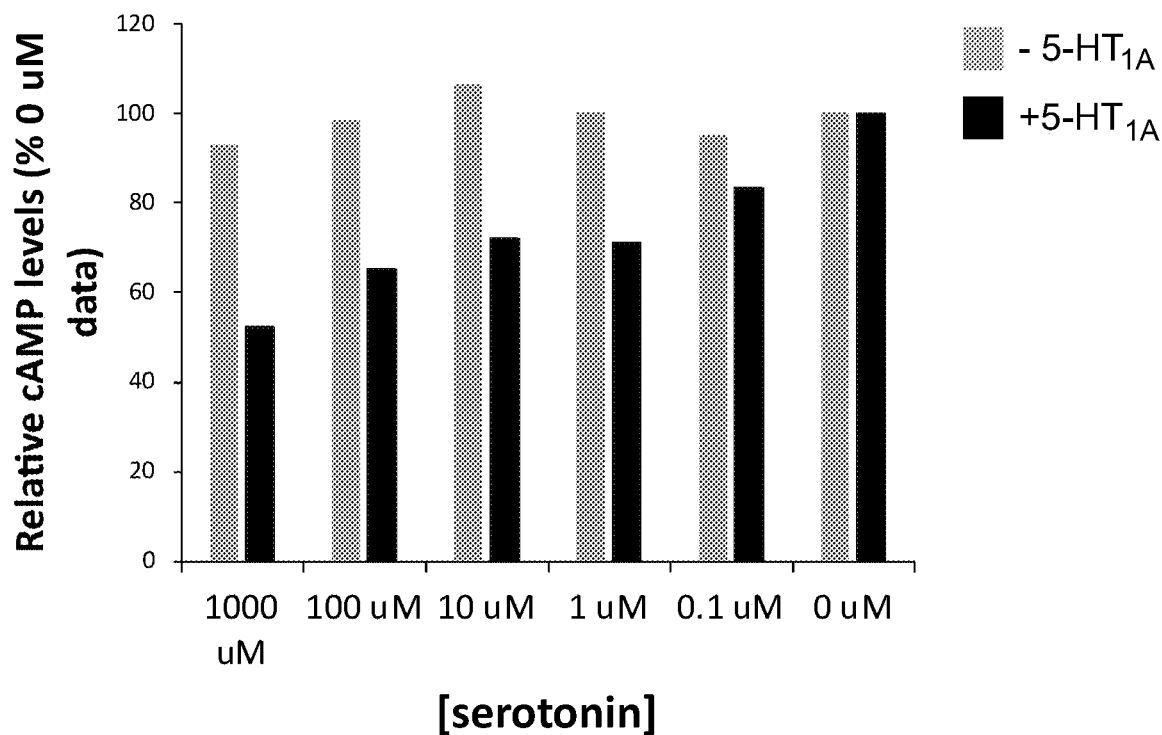
Figure 14J:
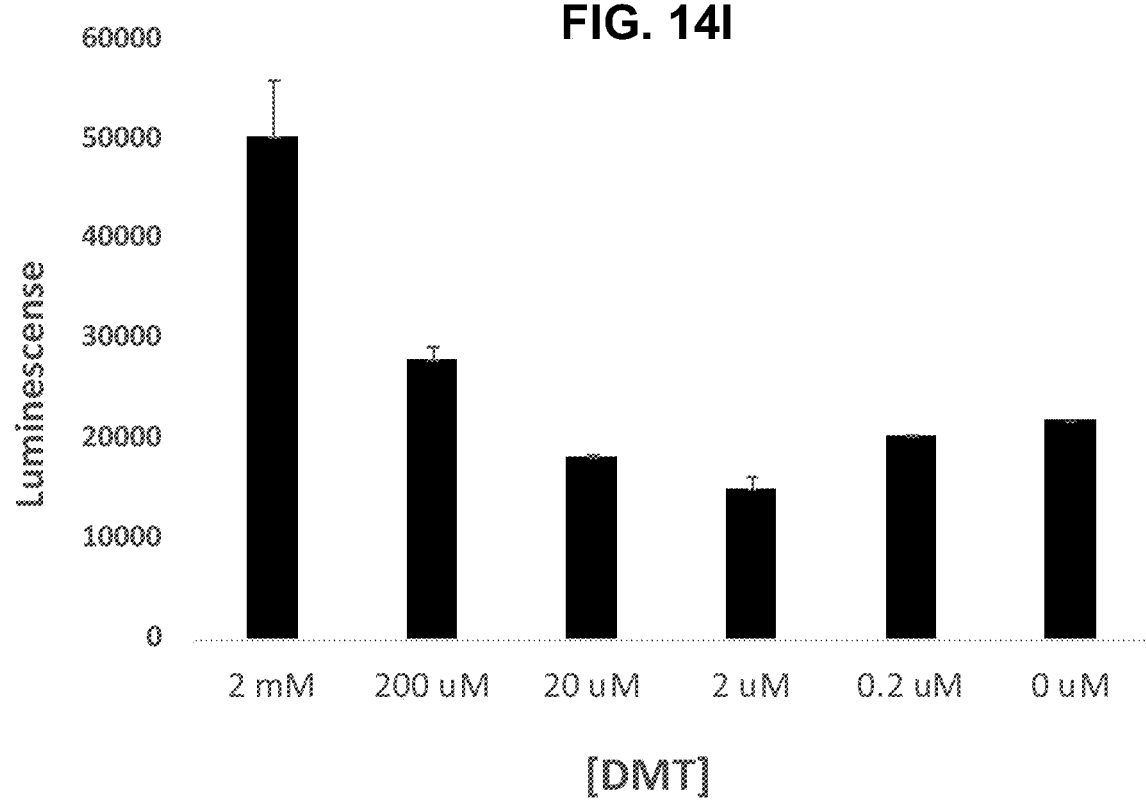
Figure 14K:
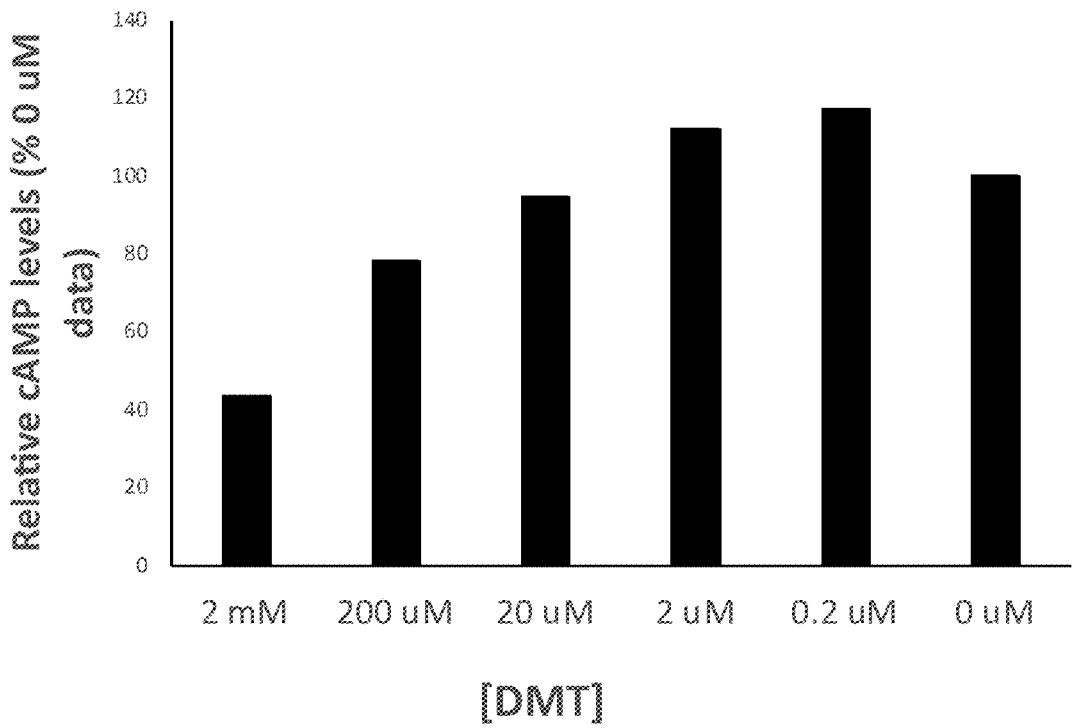
Figure 14L:
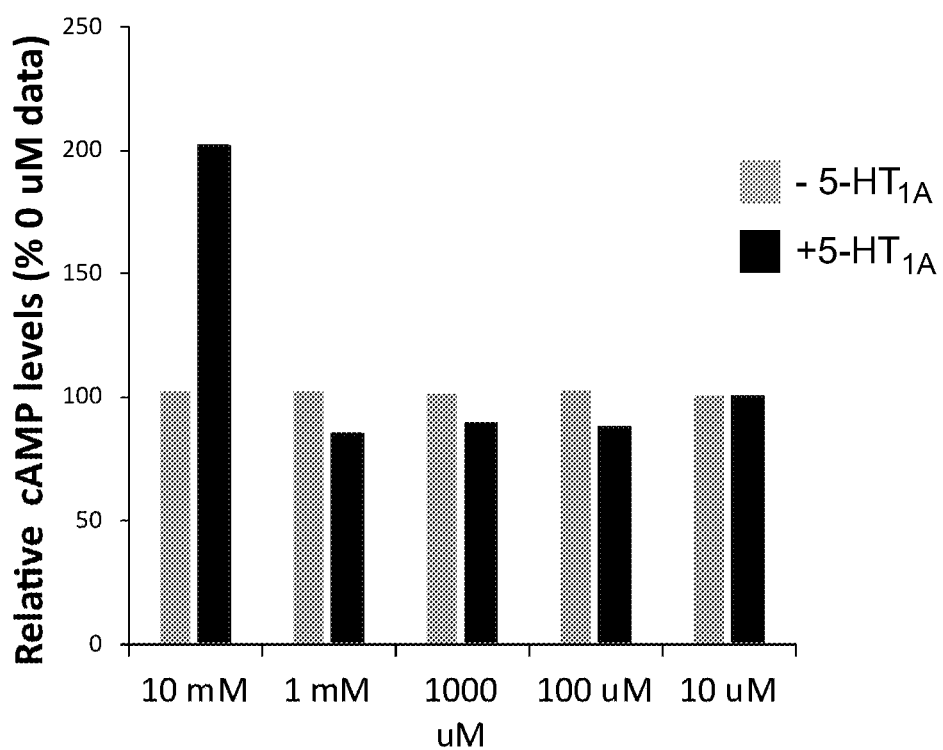
Figure 14M:
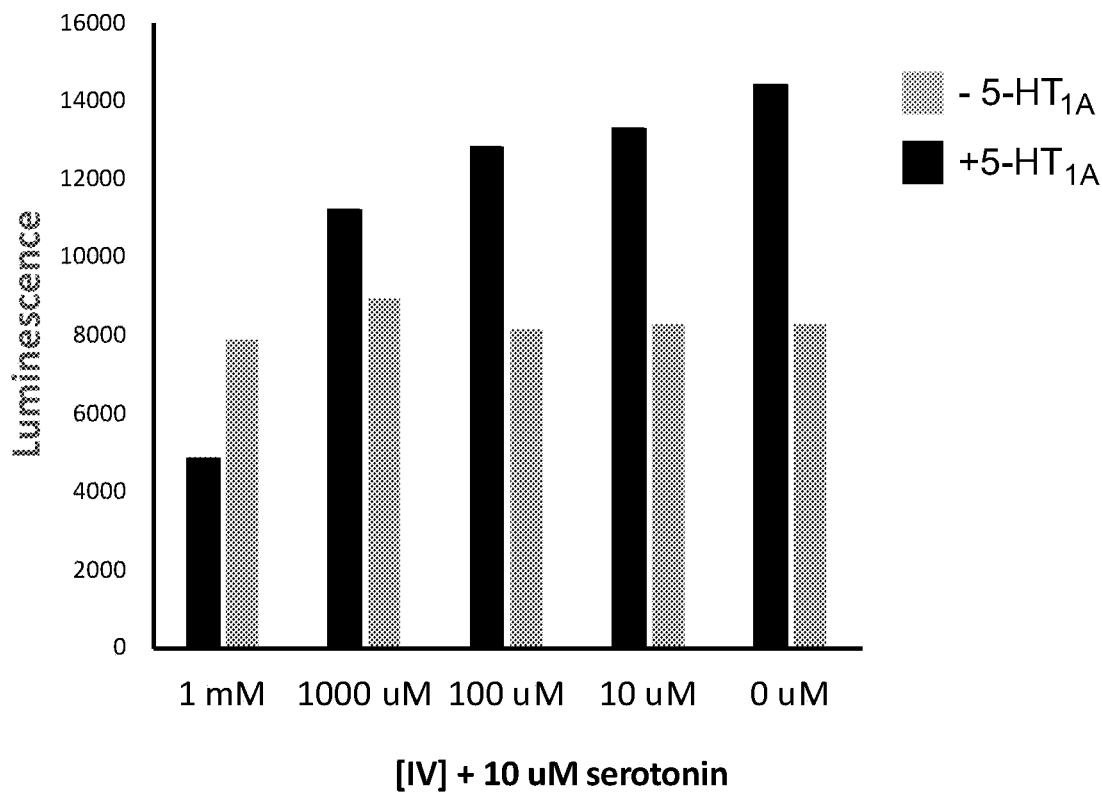
Figure 14N:
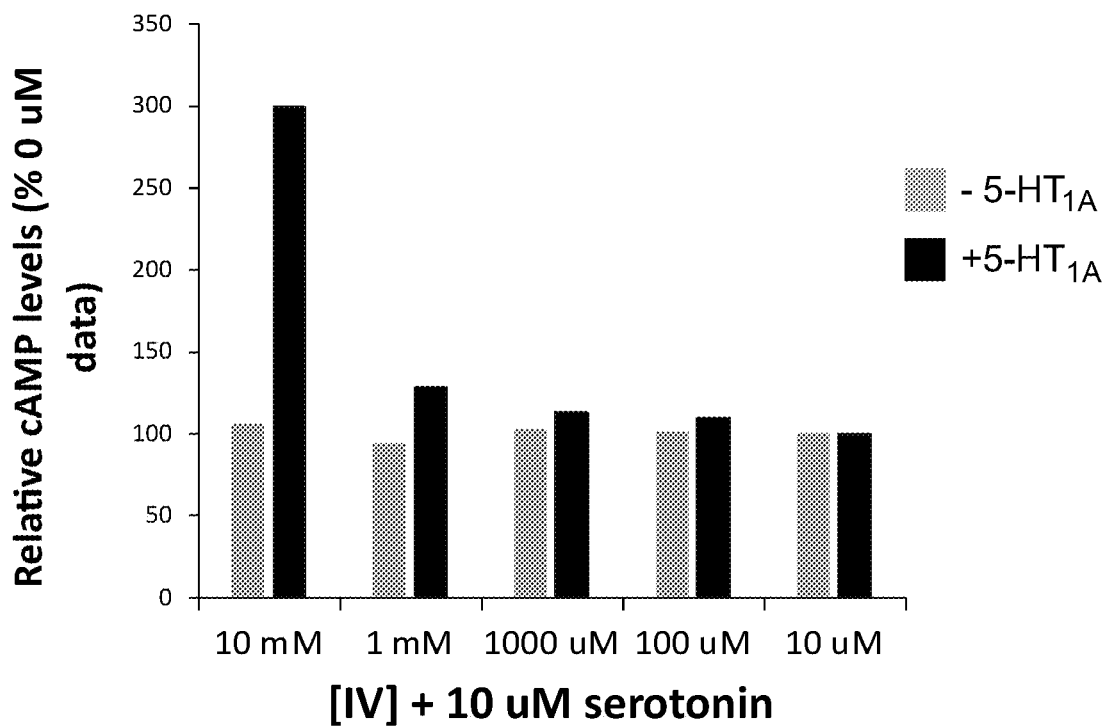
Figure 14O:
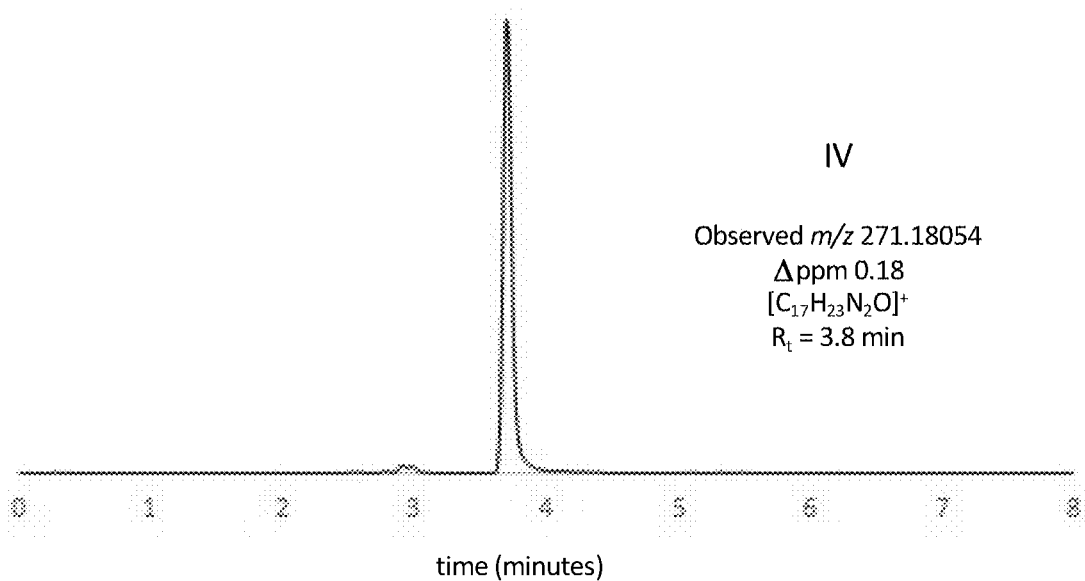

As 5-$HT_{1A}$ activation inhibits cAMP formation, the agonist activity of test molecules on 5-$HT_{1A}$ was measured via the reduction in the levels of cAMP produced due to application of 4 µM forskolin. The change in intracellular cAMP levels due to the treatment of novel molecules was measured using cAMP-Glo Assay kit (Promega #V1501). Briefly, +5-$HT_{1A}$ cells were seeded on 1-6 columns and base −5-$HT_{1A}$ cells were seeded on columns 7-12 of the white walled clear bottom 96-well plate (Corning, #3903). Both cells were seeded at the density of 30,000 cells/well in 100 µl complete growth media and cultured 24 hrs in humidified incubator at 37° C. and 5% $CO_2$. On the experiment day, the media of cells was replaced with serum/antibiotic free culture media. Then the cells were treated for minutes with test molecules dissolved in induction medium (serum/antibiotic free culture media containing 4 µM forskolin, 500 µM IBMX (isobutyl-1-methylxanthine, Sigma-Aldrich, Cat. #17018) and 100 µM (RO 20-1724, Sigma-Aldrich, Cat. #68279)). Forskolin induced cAMP formation whereas IBMX and RO 20-1724 inhibited the degradation of cAMP. PKA was added to the lysate, mixed, and subsequently the substrate of the PKA was added. PKA was activated by cAMP, and the amount of ATP consumed due to PKA phosphorylation directly corresponded to cAMP levels in the lysate. Reduced ATP caused reduced conversion of luciferin to oxyluciferin, conferring diminished luminescence as the result of 5-$HT_{1A}$ activation. FIG. 14G shows decreased cAMP resulting from decreased dosages of forskolin in both +5$HT_{1A}$ and −5$HT_{1A}$ cell cultures. FIGS. 14H and 14I illustrate increased cAMP in the presence of fixed (4 µM) forskolin as dosages of serotonin decrease, revealing 5-$HT_{1A}$ binding activity of serotonin in two separate experiments, respectively. Conversely, this trend of increasing % cAMP levels with decreasing serotonin is not observed in −5$HT_{1A}$ cell cultures. FIG. 14J illustrates decreasing luminescence (alternatively plotted as increased % cAMP levels in FIG. 14K) in the presence of fixed (4 µM) forskolin as dosages of DMT decrease, revealing 5-$HT_{1A}$ activity of DMT in +5$HT_{1A}$ cell cultures. FIG. 14L illustrates decreased % cAMP levels in the presence of fixed (4 µM) forskolin as dosages of compound (IV) decrease, revealing 5-$HT_{1A}$ modulation activity in +5$HT_{1A}$ cell cultures. Conversely, this trend of decreasing % cAMP levels with decreasing compound (IV) is not observed in -5-$HT_{1A}$ cell cultures. Note that compound (IV) is shown simply as (IV) along the x-axis. FIG. 14M and FIG. 14N (y-axis plotted as luminescence and corresponding % cAMP levels, respectively) show results of an experiment conducted under identical conditions, except with inclusion of 10 uM serotonin in the assays. Notably, the usual impact of serotonin on +5-$HT_{1A}$ cell cultures is modulated by the presence of compound (IV) in a concentration-dependent manner. Significantly, this modulation effect is not notable in −5-$HT_{1A}$ cell cultures. Data showing error bars represent results of three experiments (n=3).

Example 2

Synthesis of a Fourth Example Prenylated Psilocybin Derivative

Synthesis of a fourth prenylated psilocybin derivative was accomplished using PriB enzyme and the following in vitro procedure. Purified, recombinant PriB enzyme (SEQ.ID NO: 24) was raised in *E. coli* and isolated as described in Example 1. The tryptamine derivative 2-(2-methyl-1 H-indol-3-yl)ethylamine (Enamine, https://enamine.net) and DMAPP (www.sigmaaldrich.com) were used as co-substrates in the reaction. Briefly, reactions were set up as follows: 50 mM Tris-HCl (pH 8.0), 180 µM DMAPP, 2 mM tryptamine derivative, and 392 µg/mL of PriB were added together and the reaction proceeded at 37° C. for 2 hours. Equal volume of MeOH was added to quench the reaction and precipitate the protein. The sample was then centrifuged at 13,000 g for 20 minutes, allowing removal of the supernatant which contained the desired product. Product analysis was carried out using high-resolution, LC-HESI-LTQ-Orbitrap-XL MS (Thermo Fisher Scientific) procedures as described in Example 1. Singly protonated product with exact m/z and expected elemental formula matching the singly protonated form of 2-(6-[3-methyl-1-butenyl]-2-methyl-1H-indol-3-yl)ethylamine having chemical formula (V):

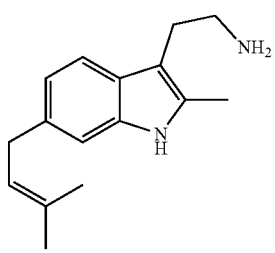

Figure 15:
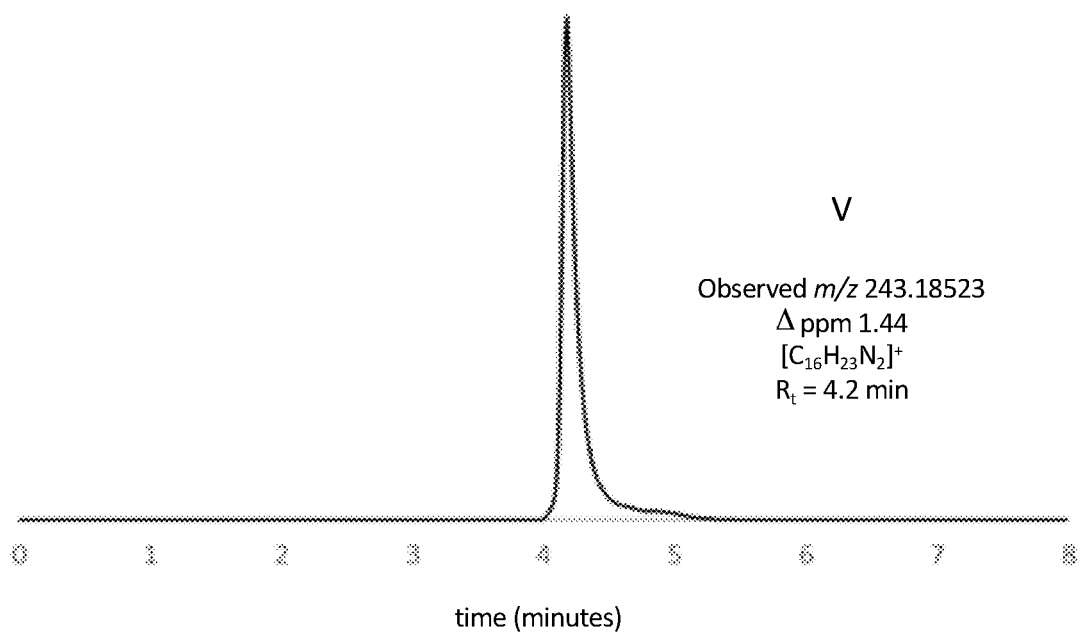
FIG. 15 depicts a representation of further mass spectrometry data in the form of a chromatogram, notably a chromatogram obtained in the performance of an experiment to synthesize an example prenylated psilocybin derivative compound having the chemical formula (V) set forth herein.

(V)

eluted at 4.2 minutes (EIC, see: FIG. 15).

Example 3

Synthesis of a Fifth Example Prenylated Psilocybin Derivative

Synthesis of a fifth prenylated psilocybin derivative was accomplished using PriB enzyme and the in vitro procedure described in Example 2, with the exception that 1-methyl-2,3,4,9-tetrahydro-1H-13-carboline (https://www.oakwood-chemical.com) was used in place of 2-(2-methyl-1H-indol-3-yl)ethylamine. Product analysis was carried out using high-resolution, LC-HESI-LTQ-Orbitrap-XL MS (Thermo Fisher Scientific) procedures as described in Example 1. Singly protonated product with exact m/z and expected elemental formula matching the singly protonated form of 1-methyl-7-(3-methyl-2-butenyl)-2,3,4,9-tetrahydro-1H-13-carboline having chemical formula (VI):

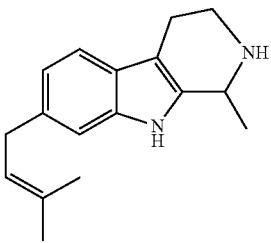

(VI)

Figure 16A:
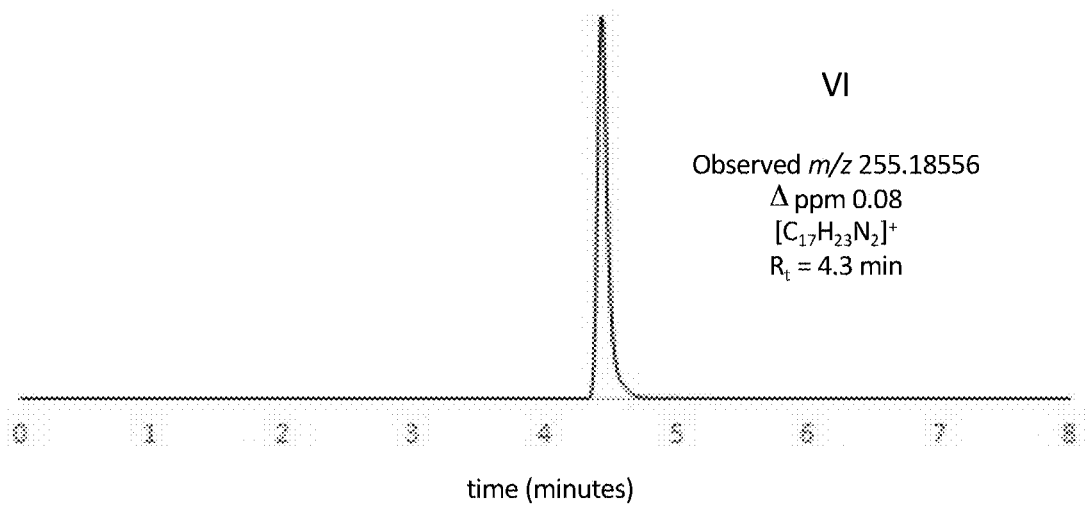
FIGS. 16A and 16B depict a representation of further mass spectrometry data in the form of a chromatogram, notably a chromatogram obtained in the performance of an experiment to synthesize an example prenylated psilocybin derivative compound having the chemical formula (VI) set forth herein (FIG. 16A); and a representation of mass spectrometry data in the form of a further mass spectrometry spectrum obtained in the performance of an experiment to identify a prenylated psilocybin derivative compound having the chemical formula (VI) set forth herein (FIG. 16B).
Figure 16B:
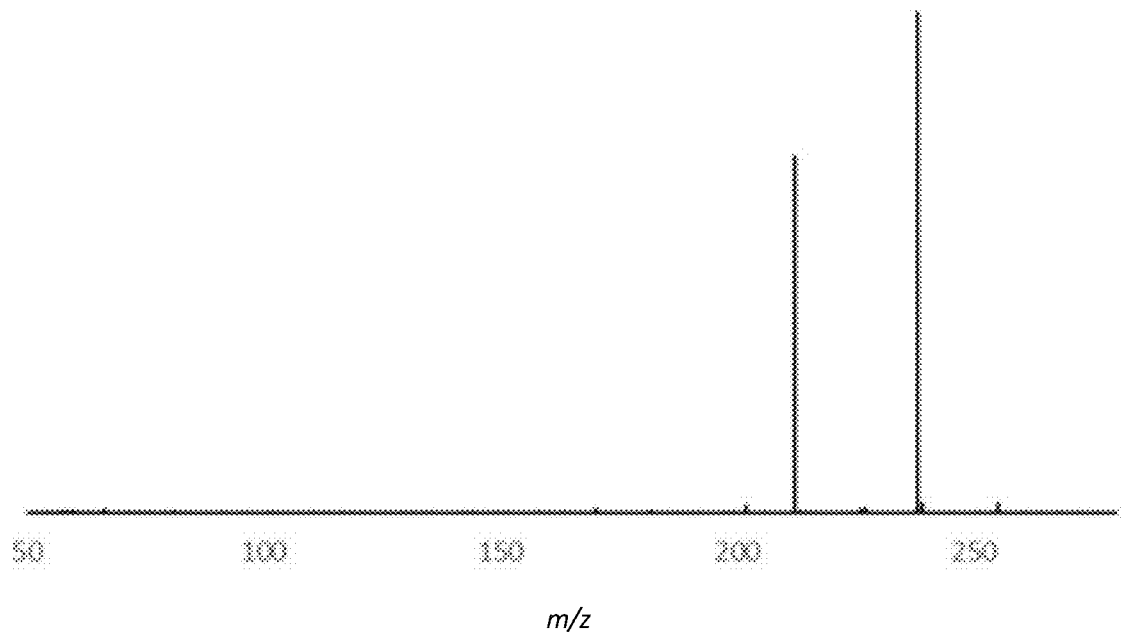

Eluted at 4.3 minutes (EIC, see: FIG. 16A), As per standard procedures (Menendez-Perdomo et al., 2021, Mass Spectrom 56: 34683) further analysis using high energy collisions (HOD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted prenylated psilocybin derivative with formula (VI) as follows (FIG. 16B, Table I) (Servillo L, etal., 2013, J. Agric. Chem. 61: 5156-5162).

TABLE 1

| m/z | % Relative abundance | Ionic species | Δ ppm |
|---|---|---|---|
| 238.15881 | 100 | $[M + H - NH_3]^+$ | 0.92 |
| 212.14327 | 72 | $[M + H - NH_2C_2H_3]^+$ | 0.52 |
| 239.16211 | 2.0 | | |
| 255.18537 | 1.9 | $[M + H]^+$ | 0.83 |
| 201.88868 | 1.5 | | |
| 227.16209 | 1.0 | | |
| 238.16287 | 0.9 | | |
| 170.09627 | 0.8 | | |
| 226.16497 | 0.7 | | |
| 59.50852 | 0.6 | | |

Example 4

Synthesis of a Sixth Example Prenylated Psilocybin Derivative

Synthesis of a sixth prenylated psilocybin derivative was accomplished using PriB enzyme and the in vitro procedure described in Example 2, with the exception that N-ethyl[2-(1H-indol-3-yl)ethyl]propylamine (https://theindoleshop.com) was used in place of 2-(2-methyl-1H-indol-3-yl)ethylamine. Product analysis was carried out using high-resolution, LC-HESI-LTQ-Orbitrap-XL MS (Thermo Fisher Scientific) procedures as described in Example 1. Singly protonated product with exact m/z and expected elemental formula matching the singly protonated form of N-ethyl(2-[6-(3-methyl-2-butenyl)-1H-indol-3-yl]ethyl)propylamine, having chemical formula (VII):

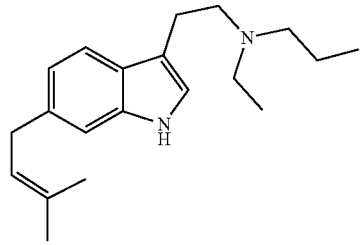

Figure 17A:
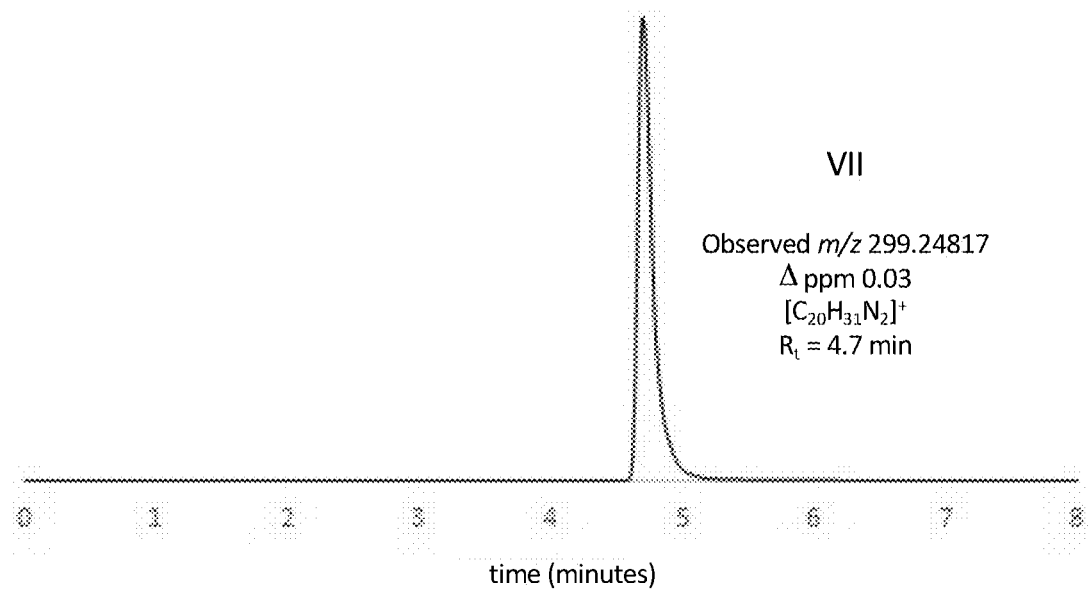
FIGS. 17A and 17B depict a representation of further mass spectrometry data in the form of a chromatogram, notably a chromatogram obtained in the performance of an experiment to synthesize an example prenylated psilocybin derivative compound having the chemical formula (VII) set forth herein (FIG. 17A); and a representation of mass spectrometry data in the form of a further mass spectrometry spectrum obtained in the performance of an experiment to identify a prenylated psilocybin derivative compound having the chemical formula (VII) set forth herein (FIG. 17B).
Figure 17B:
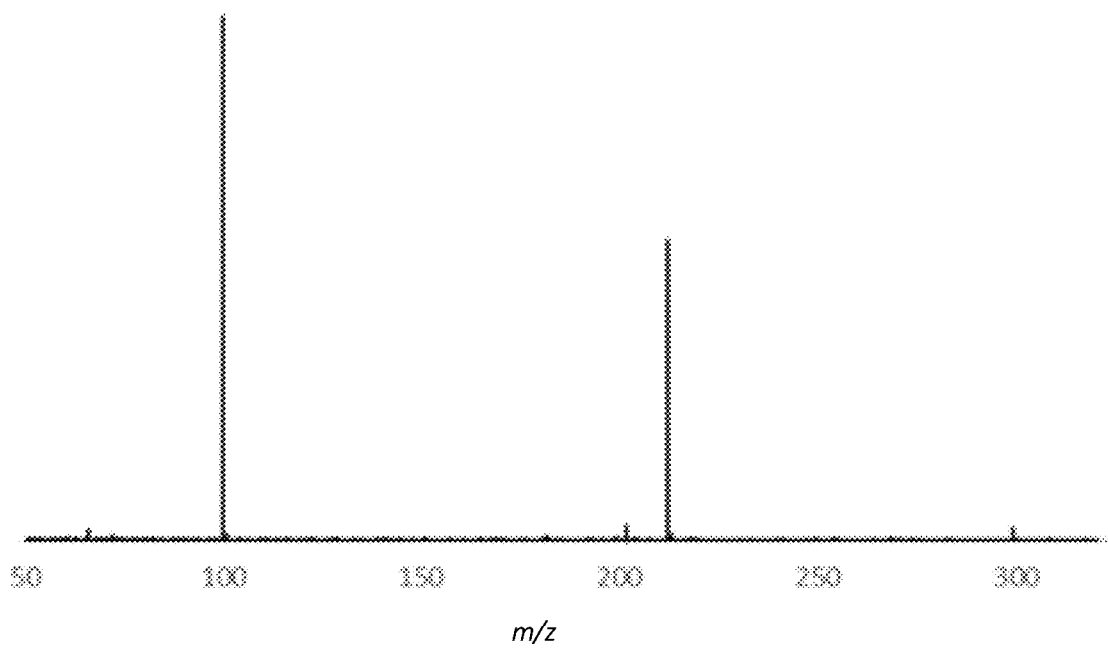

(VII)

eluted at 4.7 minutes (EIC, see: FIG. 17A). As per standard procedures (Menendez-Perdomo et al., 2021, Mass Spectrom 56: 34683) further analysis using high energy collisions (HOD) was achieved in a dedicated, post-LTQ, nitrogen collision cell, Orbitrap-based, HR fragment detection was employed (normalized collision energy, NCE 35), enabling opportunity to assign elemental formulae to subsequent diagnostic ion species characteristic of the targeted prenylated psilocybin derivative with formula (VII) as follows (FIG. 17B, Table II) (Servillo L. et at., 2013, J. Agric. Chem. 61: 5156-5162).

TABLE II

| m/z | % Relative abundance | Ionic species | Δ ppm |
|---|---|---|---|
| 100.11171 | 100 | $[C_6H_{13}N + H]^+$ | 3.7 |
| 212.14336 | 57 | $[M + H - NHC_2H_5C_3H_7]^+$ | 0.09 |
| 299.79168 | 2.0 | | |
| 66.12271 | 2.0 | | |
| 213.14673 | 1.2 | | |

TABLE II-continued

| m/z | % Relative abundance | Ionic species | Δ ppm |
|---|---|---|---|
| 101.11493 | 1.1 | | |
| 72.08039 | 1.0 | | |
| 181.73363 | 0.9 | | |
| 199.41150 | 0.7 | | |

Example 5

Synthesis of a Seventh Example Prenylated Psilocybin Derivative

Synthesis of a seventh prenylated psilocybin derivative was accomplished using PriB enzyme and the in vitro procedure described in Example 2, with the exception that [2-(1H-Indol-3-yl)ethyl]dipropylamine (https://theindoleshop.com) was used in place of 2-(2-methyl-1H-indol-3-yl)ethylamine. Product analysis was carried out using high-resolution, LC-HESI-LTQ-Orbitrap-XL MS (Thermo Fisher Scientific) procedures as described in Example 1. Singly protonated product with exact m/z and expected elemental formula matching the singly protonated form of (2-[6-(3-methyl-2-butenyl)-1 H-indol-3-yl]ethyl)dipropylamine, having chemical formula (VIII):

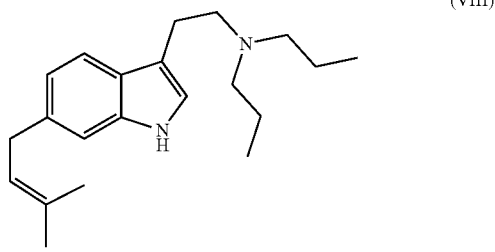

Figure 18A:
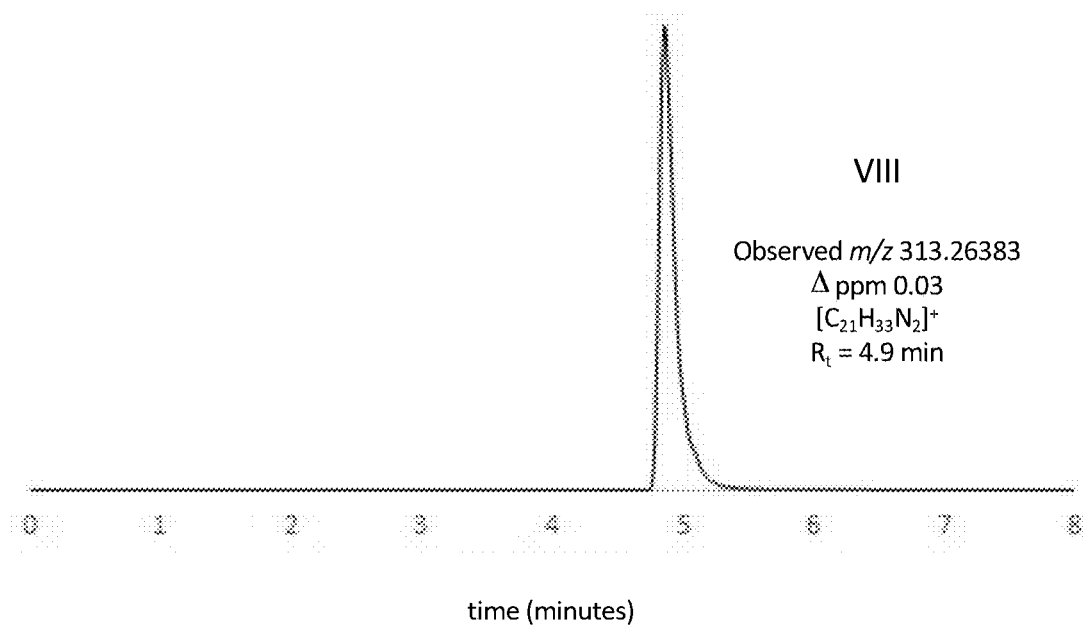
FIGS. 18A and 18B depict a representation of further mass spectrometry data in the form of a chromatogram, notably a chromatogram obtained in the performance of an experiment to synthesize an example prenylated psilocybin derivative compound having the chemical formula (VIII) set forth herein (FIG. 18A); and a representation of mass spectrometry data in the form of a further mass spectrometry spectrum obtained in the performance of an experiment to identify a prenylated psilocybin derivative compound having the chemical formula (VIII) set forth herein (FIG. 18B).
Figure 18B:
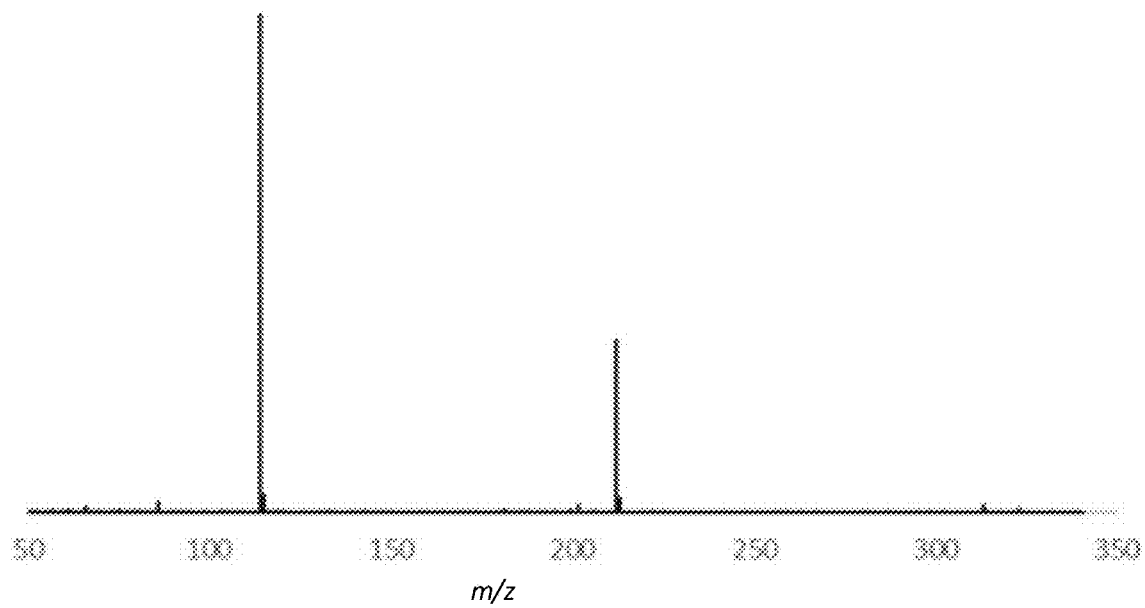

(VIII)

eluted at 4.9 minutes (EIC, see: FIG. 18A). As per standard procedures (Menendez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted prenylated psilocybin derivative with formula (VIII) as follows (FIG. 18B, Table Ill) (Servillo L. et al., 2013, J. Agric. Chem. 61:5156-5162).

TABLE III

| m/z | % Relative abundance | Ionic species | Δ ppm |
|---|---|---|---|
| 114.12742 | 100 | $[C_{6.5}H_{13}N + H]^+$ | 2.72 |
| 212.14337 | 34 | $[M + H - NH-C_6H_{14}]^+$ | 0.05 |
| 115.13069 | 3.5 | $[C_{6.5}H_{13}N + H]^+$ | |
| 213.14673 | 2.8 | | |
| 86.09608 | 2.0 | | |
| 201.78611 | 1.6 | | |
| 313.26408 | 1.4 | $[M + H]^+$ | 0.80 |
| 66.12277 | 1.1 | | |
| 181.73375 | 0.5 | | |

Example 6

Synthesis of an Eighth and Ninth Example Prenylated Psilocybin Derivative

Referring to FIG. 13B, synthesis of an eighth and ninth prenylated psilocybin derivative was accomplished using 7DMATS (SEQ.ID NO: 22) and BaTDC (SEQ.ID NO: 26) enzymes in the following in vitro procedure. cDNA encoding the tryptophan 7-prenyltransferase enzyme 7DMATS (SEQ.ID NO: 21) was synthesized and subcloned at GenScript (www.genscript.com) using Nde1 and Xho1 sites to pET26b(+) plasmid. The final plasmid pET26b(+)-7DMATS encoded an in-frame, C-terminal HIS tag fusion of 7DMATS. The procedure for the production and purification of 7DMATS was identical to that described for enzymes in Example 1. The construction of pET26b(+)-BaTDC, in addition to the procedure for the production and purification of recombinant BaTDC enzyme are described in Example 1. The tryptophan derivative 2-amino-3-(5-methyl-1H-indol-3-yl)propionic acid (www.sigmaaldrich.com) and DMAPP (www.sigmaaldrich.com) were used as initial co-substrates in the reaction. Briefly, 100 µl reactions were set up as follows: 50 mM Tris-HCl (pH 8.0), 360 µM DMAPP, 2 mM tryptophan derivative, and 200 µg/mL of 7DMATS. The reaction was carried out at 37° C. for 2 hours. This reaction yielded an eighth prenylated psilocybin derivative compound having chemical formula (XIV). Thereafter, an equal volume of water was added to the reaction followed by a negligibly small volume of purified BaTDC to a final concentration of 250 µg/mL. The reaction was carried out at 37° C. overnight. Equal volume of MeOH was added to quench the reaction and precipitate the protein. The sample was then centrifuged at 13,000 g for 20 minutes, allowing removal of the supernatant which contained the desired product. Product analysis was carried out using high-resolution, LC-HESI-LTQ-Orbitrap-XL MS (Thermo Fisher Scientific) procedures as described in Example 1. Singly protonated product with exact m/z and expected elemental formula matching the singly protonated form of 2-[5-methyl-7-(3-methyl-2-butenyl)-1H-indol-3-yl]ethylamine, a ninth prenylated psilocybin derivative compound having chemical formula (IX):

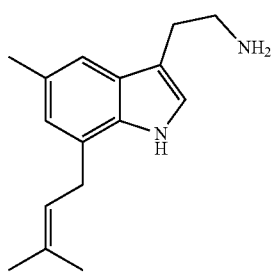

Figure 19A:
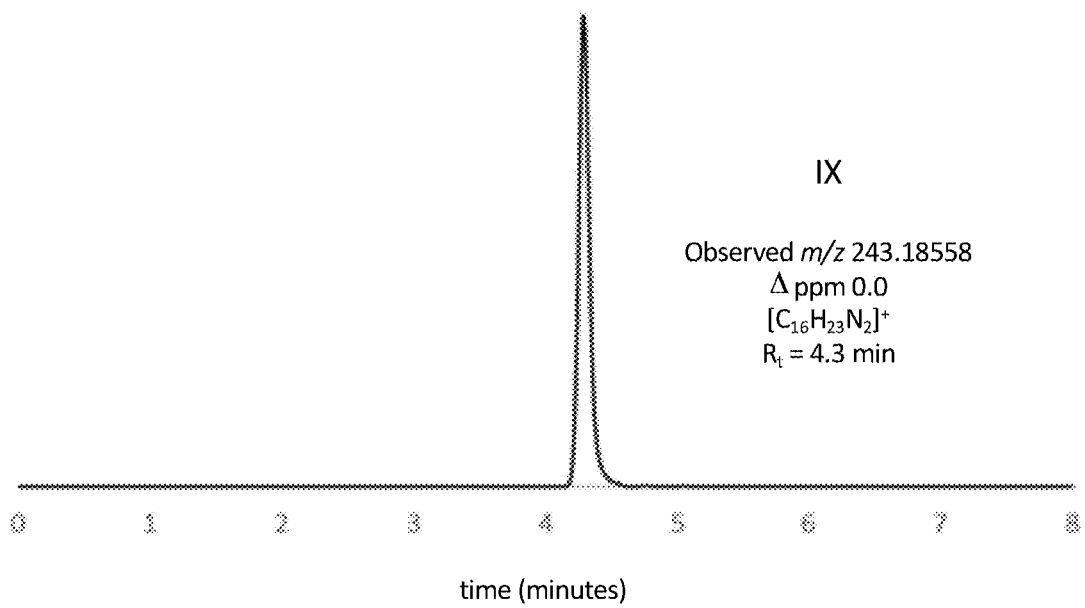
FIGS. 19A and 19B depict a representation of further mass spectrometry data in the form of a chromatogram, notably a chromatogram obtained in the performance of an experiment to synthesize an example prenylated psilocybin derivative compound having the chemical formula (IX) set forth herein (FIG. 19A); and a representation of mass spectrometry data in the form of a further mass spectrometry spectrum obtained in the performance of an experiment to identify a prenylated psilocybin derivative compound having the chemical formula (IX) set forth herein (FIG. 19B).
Figure 19B:
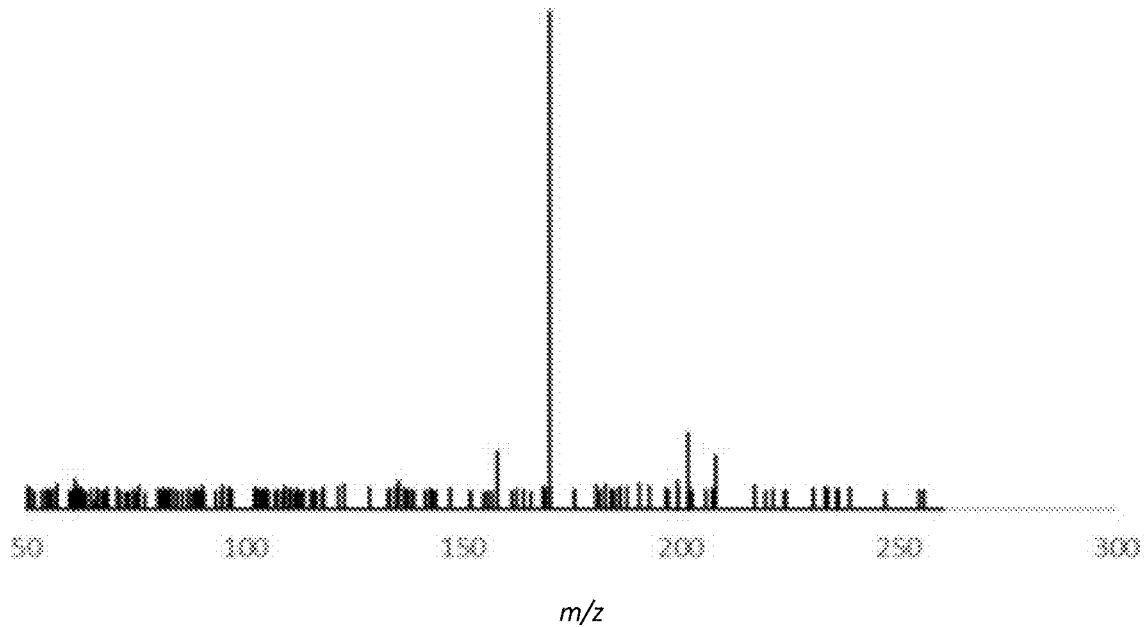

(IX)

eluted at 4.3 minutes (EIC, see: FIG. 19A). As per standard procedures (Menendez-Perdomo et al., 2021, Mass Spectrom 56: 34683) further analysis using high energy collisions (HOD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted prenylated psilocybin derivative with formula (IX) as follows (FIG. 19B, Table IV) (Servillo L. et al., 2013, J. Agric. Chem. 61: 5156-5162).

TABLE IV

| m/z | % Relative abundance | Ionic species | Δ ppm |
|---|---|---|---|
| 170.09635 | 100 | $[M + H - NH_3 - C_4H_8]^+$ | 0.47 |
| 158.09638 | 12 | $[M + H - NH_3 - C_5H_8]^+$ | 0.32 |
| 208.16955 | 11 | | |
| 199.47105 | 5.9 | | |
| 135.45978 | 5.7 | | |
| 190.66194 | 5.1 | | |
| 56.98435 | 5.1 | | |

Example 7

Synthesis of a Tenth and Eleventh Example Prenylated Psilocybin Derivative

Referring to FIG. 13C, synthesis of a tenth and eleventh prenylated psilocybin derivative was accomplished using the in vitro procedure described in Example 6, except that (1) the tryptophan 4-prenyltransferase FgaPT2 (SEQ.ID NO: 16) was used in place of 7DMATS, and (2) the tryptophan derivative 2-amino-3-(7-methyl-1H-indol-3-yl) propionic acid (www.sigmaaldrich.com) was used in place of 2-amino-3-(5-methyl-1H-indol-3-yl)propionic acid. cDNA encoding FgaPT2 (SEQ.ID NO: 15) was synthesized and subcloned at GenScript (www.genscript.com) using NdeI and XhoI sites to pET26b(+) plasmid. The final plasmid pET26b(+)-FgaPT2 encoded an in-frame, C-terminal HIS tag fusion of FgaPT2. The initial product obtained was a prenylated psilocybin derivative having chemical formula (XIII). Upon reaction thereof with BatDC, the obtained reaction product was analyzed using high-resolution, LC-HESI-LTQ-Orbitrap-XL MS (Thermo Fisher Scientific) procedures as described in Example 1. Singly protonated product with exact m/z and expected elemental formula matching the singly protonated form of 2-[7-methyl-4-(3-methyl-2-butenyl)-1H-indol-3-yl]ethylamine having chemical formula (X):

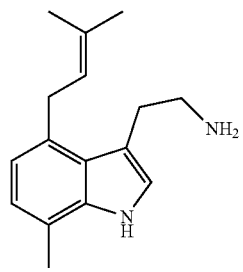

(X)

Figure 20A:
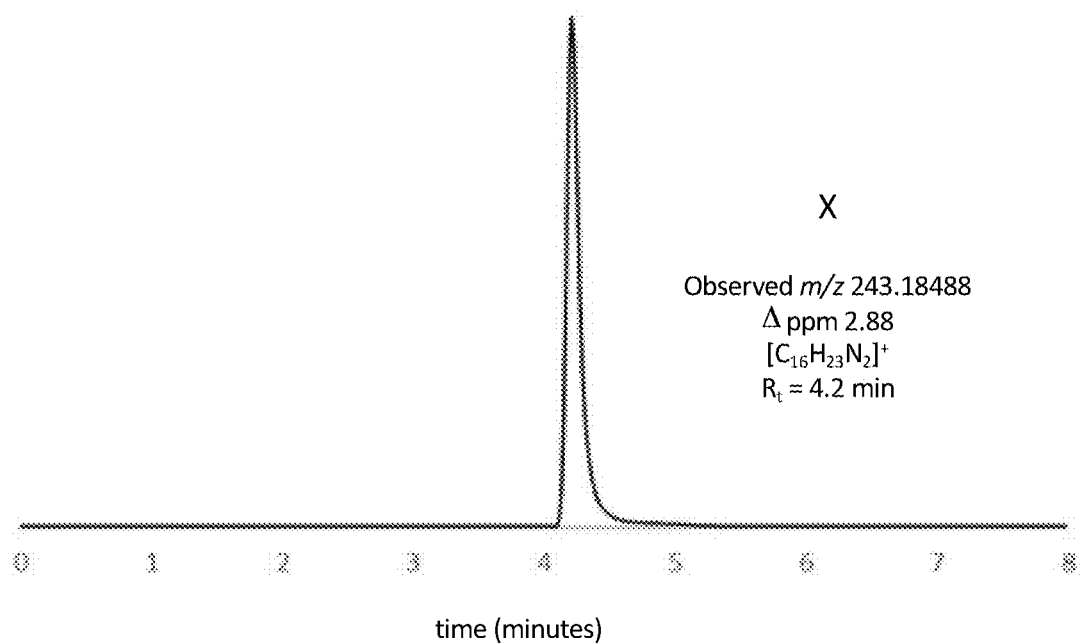
FIGS. 20A and 20B depict a representation of further mass spectrometry data in the form of a chromatogram, notably a chromatogram obtained in the performance of an experiment to synthesize an example prenylated psilocybin derivative compound having the chemical formula (X) set forth herein (FIG. 20A); and a representation of mass spectrometry data in the form of a further mass spectrometry spectrum obtained in the performance of an experiment to identify a prenylated psilocybin derivative compound having the chemical formula (X) set forth herein (FIG. 20B).
Figure 20B:
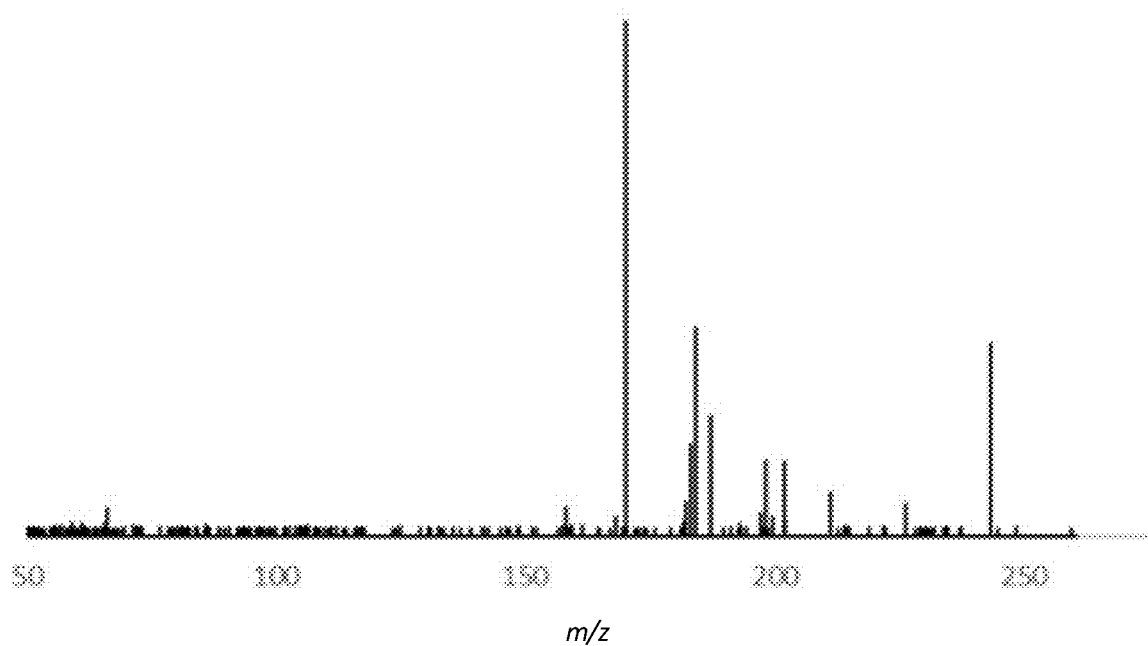

Eluted at 4.2 minutes (EIC, see: RG. 20A). As per standard procedures (Menendez-Perdomo et al., 2021, Mass Spectrom 56: 34683) further analysis using high energy collisions (HCD) was achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of the targeted prenylated psilocybin derivative with formula (X) as follows (FIG. 20B, Table V) (Servillo L. et al., 2013, J. Agric. Chem. 61: 5156-5162).

TABLE V

| m/z | % Relative abundance | Ionic species | Δ ppm |
|---|---|---|---|
| 170.09611 | 100 | $[M + H - NH_3 - C_4H_8]^+$ | 1.88 |
| 184.11175 | 40 | $[M + H - CH_2 - NH_2C_2H_5]$ | 1.79 |
| 243.18531 | 38 | $[M + H]^+$ | 1.11 |
| 187.12269 | 24 | $[M + H - CH_2 - C_3H_6]^+$ | 1.55 |
| 183.10395 | 18 | | |
| 198.12732 | 15 | | |
| 211.13525 | 8.7 | | |
| 182.09595 | 6.6 | | |
| 226.15493 | 6.3 | | |
| 158.09601 | 5.7 | | |

The invention claimed is:

1. A chemical compound or salt thereof having formula (I):

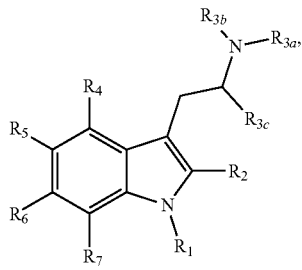

wherein, $R_6$, is a prenyl group, and wherein $R_4$, $R_5$, and $R_7$ are a hydrogen atom, wherein $R_1$ is a hydrogen atom, and $R_2$ is a hydrogen atom or an alkyl group, and wherein $R_{3a}$ is a hydrogen atom, and $R_{3b}$ is an acyl group and $R_{3c}$ is a hydrogen atom or a carboxy group.

2. A chemical compound according to claim 1, wherein $R_{3b}$ is a —(C=O)($C_1$-$C_6$)-alkyl group.

3. A chemical compound according to claim 1, wherein $R_{3b}$ is a —(C=O)($C_1$-$C_3$)-alkyl group.

4. A chemical compound according to claim 1, wherein $R_2$ is a $C_1$-$C_6$-alkyl group.

5. A chemical compound according to claim 1, wherein $R_2$ is a $C_1$-$C_3$-alkyl group.

6. A chemical compound according to claim 1, wherein $R_{3c}$ is a carboxy group.

7. A chemical compound according to claim 1, wherein the chemical compound is compound (IV):

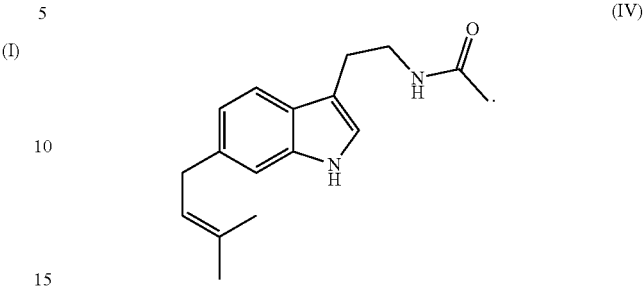

8. A chemical compound according to claim 1, wherein the compound is at least about 95% (w/w) pure.

9. A pharmaceutical or recreational drug formulation comprising an effective amount of a chemical compound according to claim 1, together with a pharmaceutically acceptable excipient, diluent, or carrier.

10. A method for treating a psychiatric disorder, the method comprising administering to a subject having said psychiatric disorder a pharmaceutical formulation comprising a chemical compound according to claim 1, wherein the pharmaceutical formulation is administered in an effective amount to treat the psychiatric disorder in the subject.

11. A chemical compound according to claim 7, wherein the compound is at least about 95% (w/w) pure.

12. A pharmaceutical or recreational drug formulation comprising an effective amount of a chemical compound according to claim 7, together with a pharmaceutically acceptable excipient, diluent, or carrier.

* * * * *